United States Patent
Cha et al.

(10) Patent No.: US 11,672,172 B2
(45) Date of Patent: *Jun. 6, 2023

(54) HETEROCYCLIC COMPOUND COMPRISING AROMATIC AMINE GROUP AND ORGANIC LIGHT-EMITTING DIODE INCLUDING THE SAME

(71) Applicant: SFC CO., LTD., Cheongju (KR)

(72) Inventors: Soon-Wook Cha, Goyang (KR); Seok-Bae Park, Geumsan-gun (KR); Hee-Dae Kim, Miryang (KR); Yu-rim Lee, Chuncheon (KR); Sang-Woo Park, Seoul (KR); Ju-man Song, Mokpo (KR)

(73) Assignee: SFC CO., LTD., Cheongju (KR)

( * ) Notice: Subject to any disclaimer, the term of this patent is extended or adjusted under 35 U.S.C. 154(b) by 249 days.

This patent is subject to a terminal disclaimer.

(21) Appl. No.: 15/306,867

(22) PCT Filed: May 7, 2015

(86) PCT No.: PCT/KR2015/004552
§ 371 (c)(1),
(2) Date: Oct. 26, 2016

(87) PCT Pub. No.: WO2015/174682
PCT Pub. Date: Nov. 19, 2015

(65) Prior Publication Data
US 2017/0062729 A1 Mar. 2, 2017

(30) Foreign Application Priority Data

May 13, 2014 (KR) .................. 10-2014-0056951
Jun. 16, 2014 (KR) .................. 10-2014-0072710

(51) Int. Cl.
*H01L 51/00* (2006.01)
*C09K 11/06* (2006.01)
(Continued)

(52) U.S. Cl.
CPC ........ *H01L 51/0061* (2013.01); *C07C 211/61* (2013.01); *C07D 209/94* (2013.01);
(Continued)

(58) Field of Classification Search
CPC ................ C09K 2211/1074; C09K 2211/1044
See application file for complete search history.

(56) References Cited

U.S. PATENT DOCUMENTS

2007/0247059 A1† 10/2007 Cho
2012/0104940 A1* 5/2012 Shin ...................... C09K 11/06
313/504

(Continued)

FOREIGN PATENT DOCUMENTS

CN 102046598 A 5/2011
CN 102558121 A 7/2012
(Continued)

OTHER PUBLICATIONS

European Search Report from European Patent Office, dated Oct. 16, 2017.
(Continued)

*Primary Examiner* — Sean M DeGuire
(74) *Attorney, Agent, or Firm* — STIP Law Group, LLC

(57) ABSTRACT

The present invention relates to a heterocyclic compound containing an aromatic amine group and an organic light-emitting device comprising the same and, more specifically, to a heterocyclic compound and an organic light-emitting device comprising the same, the heterocyclic compound being excellent in brightness and excellent light emission efficiency and being able to exhibit long life and excellent device characteristics when being used as an organic light-emitting material.

17 Claims, 1 Drawing Sheet

(51) Int. Cl.

| | | |
|---|---|---|
| C07D 405/14 | (2006.01) | |
| C07D 493/04 | (2006.01) | |
| C07C 211/61 | (2006.01) | |
| C07D 209/94 | (2006.01) | |
| C07D 307/77 | (2006.01) | |
| C07D 493/10 | (2006.01) | |
| C07D 495/10 | (2006.01) | |
| C07F 7/08 | (2006.01) | |
| H01L 51/50 | (2006.01) | |

(52) U.S. Cl.
CPC ......... *C07D 307/77* (2013.01); *C07D 405/14* (2013.01); *C07D 493/04* (2013.01); *C07D 493/10* (2013.01); *C07D 495/10* (2013.01); *C07F 7/0812* (2013.01); *C09K 11/06* (2013.01); *H01L 51/006* (2013.01); *H01L 51/0052* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/0094* (2013.01); *C07C 2603/94* (2017.05); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/0056* (2013.01); *H01L 51/0058* (2013.01); *H01L 51/5012* (2013.01)

(56) References Cited

U.S. PATENT DOCUMENTS

| | | | | |
|---|---|---|---|---|
| 2012/0112174 A1* | 5/2012 | Lee | ...................... | C07D 307/93 257/40 |
| 2012/0168734 A1* | 7/2012 | Park | ...................... | C09K 11/06 257/E51.026 |
| 2014/0054559 A1† | 2/2014 | Kim | | |
| 2015/0144937 A1 | 5/2015 | Park et al. | | |
| 2017/0062732 A1* | 3/2017 | Jatsch | .................. | C07D 401/04 |

FOREIGN PATENT DOCUMENTS

| | | | | |
|---|---|---|---|---|
| EP | 02450975 | A2 | | 5/2012 |
| JP | 2012028548 | A | * | 2/2012 |
| KR | 1020110000006 | | | 1/2011 |
| KR | 1020120009761 | | | 2/2012 |
| KR | 1020120047706 | | | 5/2012 |
| KR | 1020120047706 | A | | 5/2012 |
| KR | 2014-0045153 | A | † | 4/2014 |
| KR | 1020140045153 | A | | 4/2014 |
| KR | 1020140046303 | | | 4/2014 |
| KR | 1020160118366 | A | | 10/2016 |
| WO | WO2006080640 | A1 | | 8/2006 |
| WO | WO2009122445 | A2 | | 10/2009 |
| WO | 2013105747 | A1 | | 7/2013 |
| WO | 2014010910 | A1 | | 1/2014 |
| WO | 2014058124 | A1 | | 4/2014 |
| WO | WO2014058124 | A1 | | 4/2014 |
| WO | WO2015124255 | A1 | | 8/2015 |

OTHER PUBLICATIONS

Japanese Office Action from Japan Patent Office, dated Aug. 22, 2017.
Third-party submission filed in USPTO, Jun. 30, 2017.
Office Action from Chinese Patent Office, dated Feb. 26, 2018, pp. 1-13.
"339997-35-2", Registry, STN on the web, Jun. 7, 2001, pp. 1-2.
"58475-52-8", Registry, STN on the web, Nov. 16, 1984, pp. 1-3.
International Search Report, dated Aug. 6, 2015 (English Translation).
Office Action from Korean Intellectual Property Office of 10-2014-007271, dated Oct. 21, 2018.

\* cited by examiner
† cited by third party

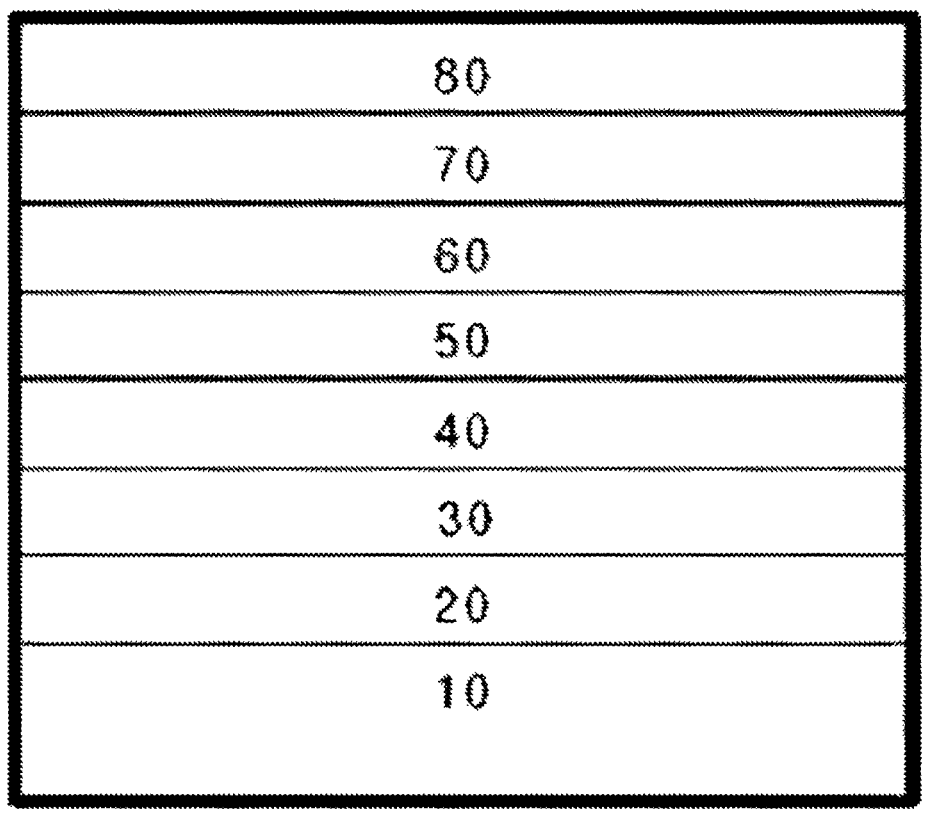

HETEROCYCLIC COMPOUND COMPRISING AROMATIC AMINE GROUP AND ORGANIC LIGHT-EMITTING DIODE INCLUDING THE SAME

CROSS-REFERENCE TO RELATED APPLICATIONS

This application is the U.S. National Phase under 35 U.S.C. § 371 of International Application No. PCT/KR2015/004552 filed on May 7, 2015, which in turn claims the benefit of Korean Applications No. 10-2014-0056951, filed on May 13, 2014, and No. 10-2014-0072710, filed on Jun. 16, 2014, the disclosures of which are incorporated by reference into the present application.

TECHNICAL FIELD

The present disclosure relates to a heterocyclic compound containing an aromatic amine group and an organic light-emitting device comprising the same. More particularly, the present disclosure relates to a heterocyclic compound that is superior in luminance and light emission efficiency when used as an organic light-emitting material and that secures a long lifetime and excellent properties for organic light-emitting devices, and to an organic light-emitting device containing the same.

BACKGROUND ART

Organic light-emitting diodes (OLEDs), based on self-luminescence, are used to create digital displays having the advantage of being able to be made thinner and lighter than liquid crystal displays (LCDs). In addition, an OLED display exhibits a much faster response time than an LCD. Accordingly, organic light-emitting diodes find applications in the illumination field as well as the full-color display field.

In general, the term organic light-emitting phenomenon refers to a phenomenon in which electric energy is converted to light energy by means of an organic material. An organic light-emitting device using the organic light-emitting phenomenon has a structure usually comprising an anode, a cathode, and an organic material layer interposed therebetween. In this regard, the organic material layer may be of a multilayer structure consisting of different materials, for example, a hole injection layer, a hole transport layer, a light-emitting layer, an electron transport layer, and an electron injection layer, in order to improve efficiency and stability of the organic light emitting device. In the organic light-emitting device having such a structure, when a voltage is applied between the two electrodes, a hole injected from the anode migrates to the organic layer while an electron is released from the cathode and moves toward the organic layer. In the luminescent zone, the hole and the electron recombine to produce an exciton. When the exciton returns to the ground state from the excited state, the molecule of the organic layer emits light. Such an organic light emitting device is known to have characteristics such as self-luminescence, high luminance, high efficiency, low driving voltage, wide viewing angle, high contrast and high-speed response.

The materials used as organic layers in organic light-emitting diodes may be divided into luminescent materials and charge-carrying materials, for example, a hole injection material, a hole transport material, an electron injection material, and an electron transport material. As for the luminescent materials, there are two main families of OLED: those based on small molecules and those employing polymers. The light-emitting mechanism allows the luminescent materials to be classified as fluorescent and phosphorescent materials, which use excitons in singlet and triplet states, respectively. Further, luminescent materials may be divided according to color into blue, green, and red light-emitting materials. Further, yellow and reddish yellow light-emitting materials have been developed in order to achieve more natural colors.

Meanwhile, when a single material is employed as the luminescent material, intermolecular actions cause the maximum luminescence wavelength to shift toward a longer wavelength, resulting in a reduction in color purity and light emission efficiency. In this regard, a host-dopant system may be used as a luminescent material so as to increase the color purity and the light emission efficiency through energy transfer.

This is based on the principle whereby, when a dopant is smaller in energy band gap than a host accounting for the light-emitting layer(, the addition of a small amount of the dopant to the host generates excitons from the light-emitting layer so that the excitons are transported to the dopant, emitting light at high efficiency. Here, light of desired wavelengths can be obtained depending on the kind of dopant because the wavelength of the host moves to a wavelength range of the dopant.

With regard to related arts pertaining to dopant compounds in the light-emitting layer, reference may be made to Korean Unexamined Patent Application Publication No. 10-2008-0015865 (Feb. 20, 2008), which describes an organic light-emitting device using an arylamine-coupled indenofluorene derivative, and Korean Unexamined Patent Application Publication No. 10-2012-0047706 (May 14, 2012), which describes an organic photoelectric device using a compound in which dibenzofuran or dibenzothiophene coexists with fluorene or carbazole.

In spite of enormous effort, there is still continued need to develop novel organic light-emitting materials that exhibit excellent luminance, light emission efficiency, and lifetime compared to those developed based on conventional technology.

DISCLOSURE

Technical Problem

Therefore, it is an object of the present disclosure to provide a novel organic light-emitting material, available for use in a light-emitting layer of an organic light-emitting diode (OLED) exhibiting high luminance, light emission efficiency, and longevity.

It is another object of the present disclosure to provide an organic light-emitting diode (OLED) containing the organic light-emitting material.

Technical Solution

In accordance with an aspect thereof, the present disclosure provides an amine compound represented by the following Chemical Formula A or B.

[Chemical Formula A]

[Chemical Formula B]

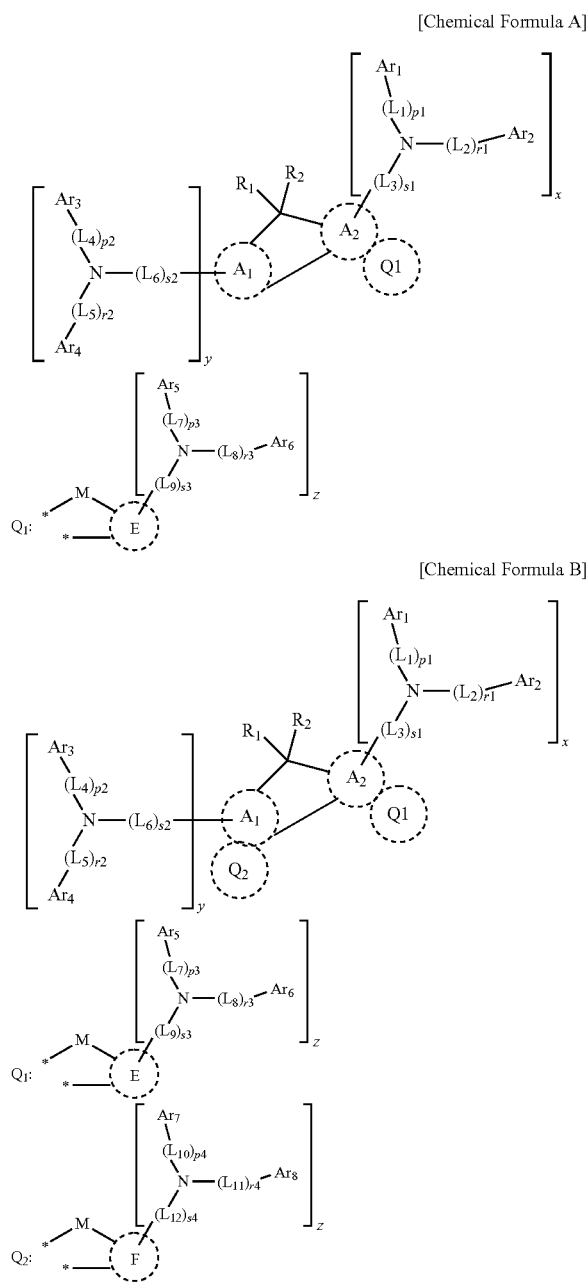

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms, wherein two adjacent carbon atoms of the aromatic ring $A_1$ and two adjacent carbon atoms of the aromatic ring $A_2$ form a 5-membered fused ring together with a carbon atom to which substitutents $R_1$ and $R_2$ are bonded;

linkers $L_1$ to $L_{12}$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among $N-R_3$, $CR_4R_5$, $SiR_6R_7$, $GeR_8R_9$, O, S, and Se;

$R_1$ to $R_9$, and $Ar_1$ to $Ar_8$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkylgermanium of 1 to 30 carbon atoms, a substituted or unsubstituted arylgermanium of 1 to 30 carbon atoms, a cyano, a nitro, and a halogen, with the proviso that $R_1$ and $R_2$ together may form a mono- or polycyclic aliphatic or aromatic ring that may be a heterocyclic ring containing a heteroatom selected from among N, O, P, Si, S, Ge, Se, and Te as a ring member;

p1 to p4, $R_1$ to $R_4$, and s1 to s4 are each independently an integer of 1 to 3, with the proviso that when any of them is 2 or greater, the corresponding linkers may be the same or different, x is an integer of 1 or 2, and y and z may be the same or different and are each independently an integer of 0 to 3; and $Ar_1$ may form a ring with $Ar_2$, $Ar_3$ may form a ring with $Ar_4$, $Ar_5$ may form a ring with $Ar_6$, and $Ar_7$ may form a ring with $Ar_8$, two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions of structural Formula $Q_2$ to form a fused ring.

In accordance with another aspect thereof, the present disclosure provides an organic light-emitting diode, comprising: a first electrode; a second electrode facing the first electrode; and an organic layer interposed between the first electrode and the second electrode, wherein the organic layer comprises at least one of the organic light-emitting compounds represented by Chemical Formula A or B.

Advantageous Effects

Exhibiting excellent luminance, light emission efficiency and longevity compared to conventional materials, the amine compound of the present disclosure, represented by Chemical Formula A or B, is available for use in organic light-emitting diodes having improved properties.

DESCRIPTION OF DRAWINGS

FIG. 1 is a schematic cross-sectional view of the structure of an organic light-emitting diode according to some embodiments of the present disclosure.

BEST MODE

Below, a detailed description will be given of the present disclosure.

The present invention provides a novel organic light-emitting material represented by Chemical Formula A or B, which is available for use in a light-emitting layer of an organic light-emitting diode (OLED).

[Chemical Formula A]

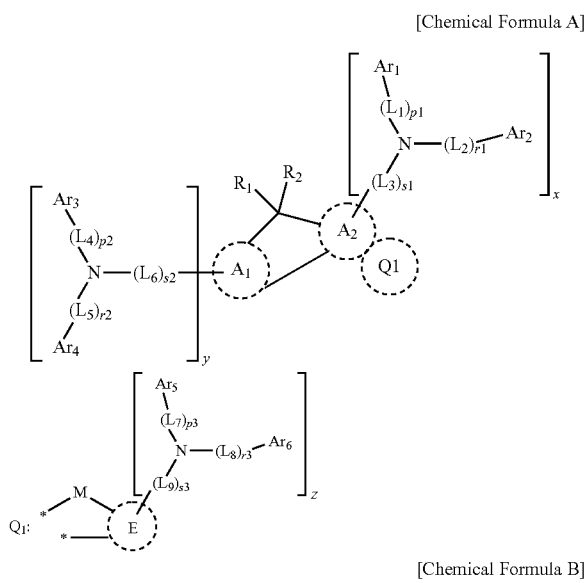

[Chemical Formula B]

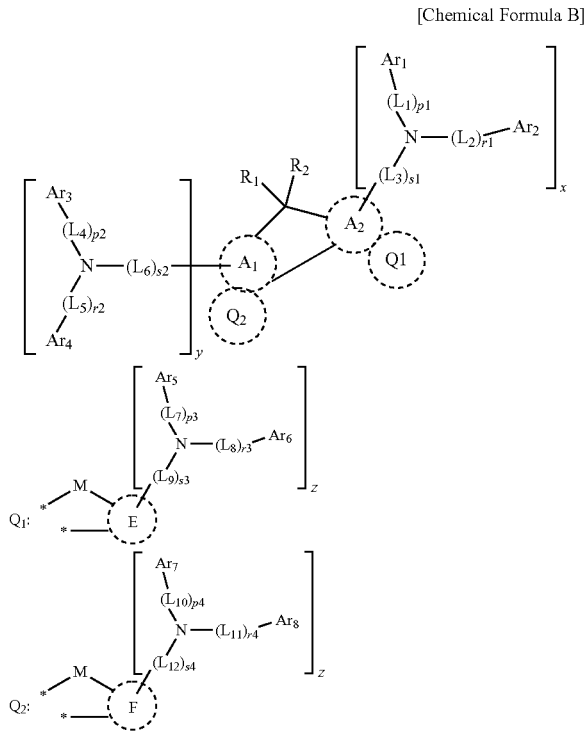

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_1$ and two adjacent carbon atoms of the aromatic ring $A_2$ form a 5-membered fused ring together with a carbon atom to which substitutents $R_1$ and $R_2$ are bonded;

linkers $L_1$ to $L_{12}$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$, and $Ar_1$ to $Ar_8$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkylgermanium of 1 to 30 carbon atoms, a substituted or unsubstituted arylgermanium of 1 to 30 carbon atoms, a cyano, a nitro, and a halogen, with the proviso that $R_1$ and $R_2$ together may form a mono- or polycyclic aliphatic or aromatic ring that may be a heterocyclic ring containing a heteroatom selected from among N, O, P, Si, S, Ge, Se, and Te as a ring member;

p1 to p4, $R_1$ to $R_4$, and s1 to s4 are each independently an integer of 1 to 3, with the proviso that when any of them is 2 or greater, the corresponding linkers may be the same or different, x is an integer of 1 or 2, and y and z may be the same or different and are each independently an integer of 0 to 3; and $Ar_1$ may form a ring with $Ar_2$, $Ar_3$ may form a ring with $Ar_4$, $Ar_6$ may form a ring with $Ar_6$, and $Ar_7$ may form a ring with $Ar_8$, two adjacent carbon atoms of the $A_2$ ring moiety of Chemical Formula A may occupy respective positions of Structural Formula $Q_4$ to form a fused ring, and two adjacent carbon atoms of the $A_1$ ring moiety of Chemical Formula B may occupy respective positions of structural Formula $Q_2$ to form a fused ring, wherein the term 'substituted' in the expression 'substituted or unsubstituted' means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 1 to 24 carbon atoms, a hetero arylamino of 1 to 24 carbon atoms, an alkylsilyl of 1 to 24 carbon atoms, an arylsilyl of 1 to 24 carbon atoms, and an aryloxy of 1 to 24 carbon atoms.

The amine compound represented by Chemical Formula A or B used in the present disclosure is characterized by a structure in which the moiety of Chemical Formula $Q_1$ in Chemical Formula A is connected to the ring $A_2$ while an amine moiety containing both $Ar_1$ and $Ar_2$ is bonded to the ring $A_2$, or in which the moieties of Chemical Formula s $Q_2$ and $Q_1$ in Chemical Formula B are respectively connected to the rings $A_1$ and $A_2$ while an amine moiety containing both $Ar_1$ and $Ar_2$ is bonded to the ring $A_2$.

The expression for a number of carbon atoms such as in "a substituted or unsubstituted alkyl of 1 to 30 carbon atoms", "a substituted or unsubstituted aryl of 6 to 50 carbon atoms", etc. means the total number of carbon atoms in, for example, the alkyl or aryl radical or moiety alone, exclusive of the number of carbon atoms of the substituent. For instance, a phenyl group with a butyl at the para position falls within the scope of an aryl of 6 carbon atoms, even if it is substituted with a butyl radical of 4 carbon atoms.

As used herein, the term "aryl" means an aromatic system composed of hydrocarbon containing one or more rings. Further, the aromatic system may include a fused ring that is formed by adjacent substituents on the aryl radical.

Examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, at least one hydrogen atom of which may be substituted by a deuterium atom, a halogen atom, a hydroxy, a nitro, a cyano, a silyl, an amino (—$NH_2$, —NH(R), —N(R') (R") wherein R' and R" are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms containing one to three heteroatoms selected from among N, 0, P, Si, S, Ge, Se, and Te. In the aromatic system, two or more rings may be fused. One or more hydrogen atoms on the heteroaryl may be substituted by the same substituents as on the aryl.

As used herein, the term "heteroaromatic ring" refers to an aromatic hydrocarbon ring containing as a ring member at least one heteroatom selected from among N, O, P, Si, S, Ge, Se, and Te.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the silyl useful in the present disclosure are trimethylsilyl, triethylsilyl, triphenylsilyl, trimethoxysilyl, dimethoxyphenylsilyl, diphenylmethylsilyl, silyl, diphenylvinylsilyl, methylcyclobutylsilyl, and dimethylfurylsilyl. One or more hydrogen atoms of the silyl may be substituted by the same substituent as in the aryl.

According to one embodiment, $A_1$, $A_2$, E, and F in Chemical Formula A or B may be the same or different and may each be independently a substituted or unsubstituted aromatic hydrocarbon ring of 6 to 50 carbon atoms.

When $A_1$, $A_2$, E, and F in Chemical Formula A or B are each independently a substituted or unsubstituted aromatic hydrocarbon ring of 6 to 50 carbon atoms, the aromatic hydrocarbon ring moieties may each be independently any one selected from among [Structural Formula 10] to [Structural Formula 21].

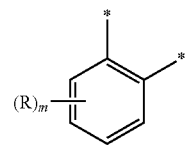

[Structural Formula 10]

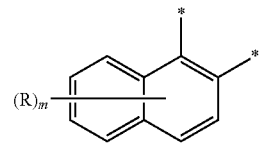

[Structural Formula 11]

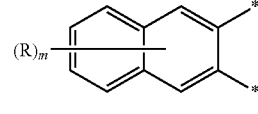

[Structural Formula 12]

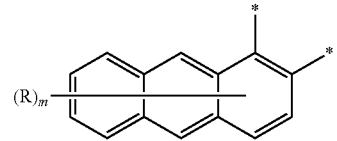

[Structural Formula 13]

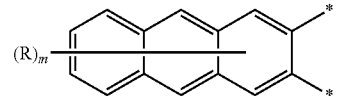

[Structural Formula 14]

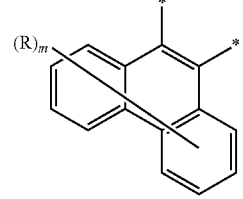

[Structural Formula 15]

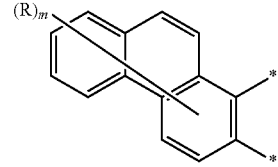

[Structural Formula 16]

-continued

[Structural Formula 17]
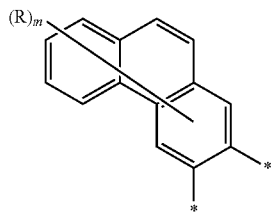

[Structural Formula 18]
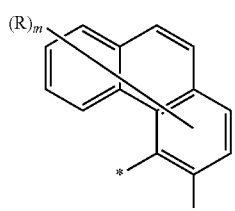

[Structural Formula 19]
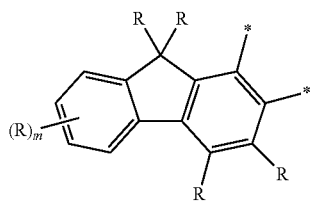

[Structural Formula 20]
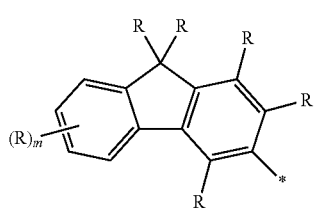

[Structural Formula 21]
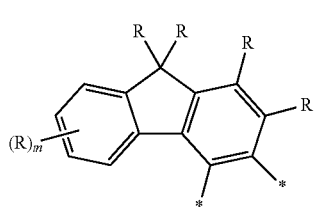

wherein,

"-*" denotes a bonding site for forming a 5-membered ring containing the carbon atom connected to both the substituents $R_1$ and $R_2$, or a bonding site for forming a 5-membered ring containing M of the structural Formula $Q_1$ and $Q_2$ with moiety $A_1$ or $A_2$, when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring; and R's are the same as defined above for $R_1$ and $R_2$, m is an integer of 1 to 8, with the proviso that when m is 2 or greater or two or more R's exist, the corresponding R's may be the same or different.

According to one embodiment, $A_1$, $A_2$, E, and F in Chemical Formula A or B may be the same or different and may each be independently a substituted or unsubstituted heteroaromatic ring of 2 to 30 carbon atoms.

When $A_1$, $A_2$, E, and F in Chemical Formula A or B are each independently a substituted or unsubstituted heteroaromatic ring of 2 to 30 carbon atoms, the aromatic hydrocarbon ring moieties may each be independently any one selected from among [Structural Formula 31] to [Structural Formula 40].

[Structural Formula 31]

[Structural Formula 32]

[Structural Formula 33]
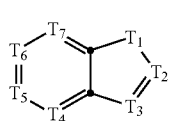

[Structural Formula 34]
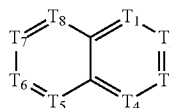

[Structural Formula 35]
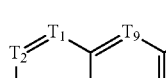

[Structural Formula 36]
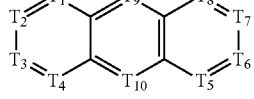

[Structural Formula 37]
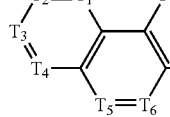

[Structural Formula 38]
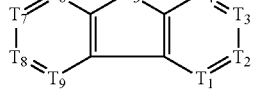

[Structural Formula 39]
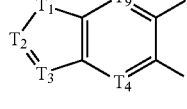

[Structural Formula 40]
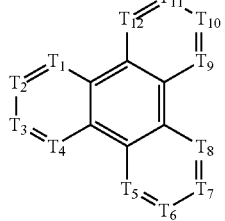

wherein $T_1$ to $T_{12}$ may be the same or different and may each be independently selected from among $C(R_{41})$, $C(R_{42})(R_{43})$, N, N($R_{44}$), O, S, Se, Te, Si($R_{45}$)($R_{46}$) and Ge($R_{47}$)($R_{48}$), with the proviso that not all of $T_1$ to $T_{12}$ are simultaneously carbon atoms, $R_{41}$ to $R_{48}$ are as defined in $R_1$ and $R_2$, and two adjacent ones of $T_1$ to $T_{12}$ within the aromatic rings contain a single bond for forming a five-membered ring containing a carbon atom connected to the substituent $R_1$ and $R_2$ or for forming a five-membered ring containing an oxygen atom of Structural Formula s $Q_1$ and $Q_2$; and when one of the heteroaromatic rings of [Structural Formula 31] to [Structural Formula 40] for $A_1$ or $A_2$ is bonded to Structural Formula $Q_1$ or Structural Formula $Q_2$, two adjacent carbon atoms of $T_1$ to $T_{12}$ occupy respective positions * of Structural Formula $Q_1$ or $Q_2$ to form a fused ring.

In addition, the compound of [Structural Formula 33] may include the compound represented by the following [Structural Formula 33-1] due to a resonance structure based on delocalized electrons.

[Structural Formula 33-1]

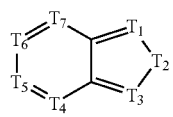

wherein, $T_1$ to $T_7$ are as defined for $T_1$ to $T_{12}$ in [Structural Formula 31] to [Structural Formula 40].

According to some embodiments of the present disclosure, [Structural Formula 31] to [Structural Formula 40] may be selected from among the hetero rings represented by the following [Structural Formula 41]:

[Structural Formula 41]

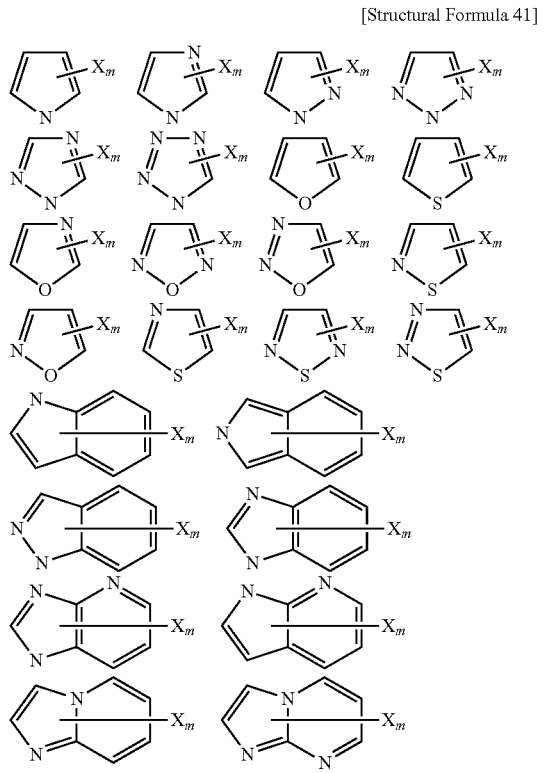

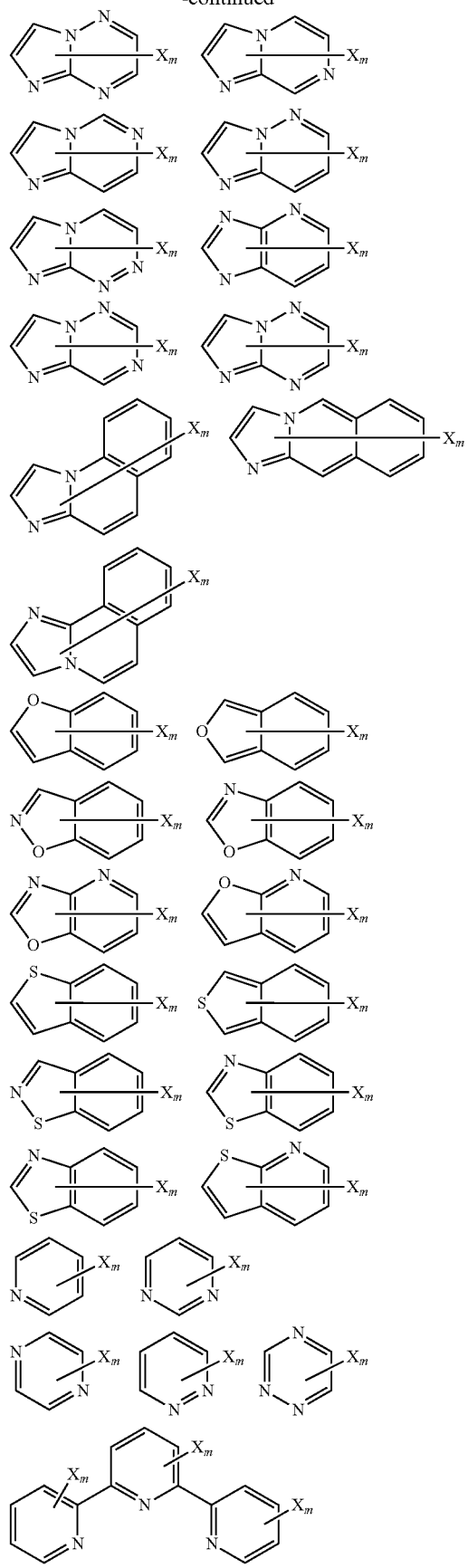

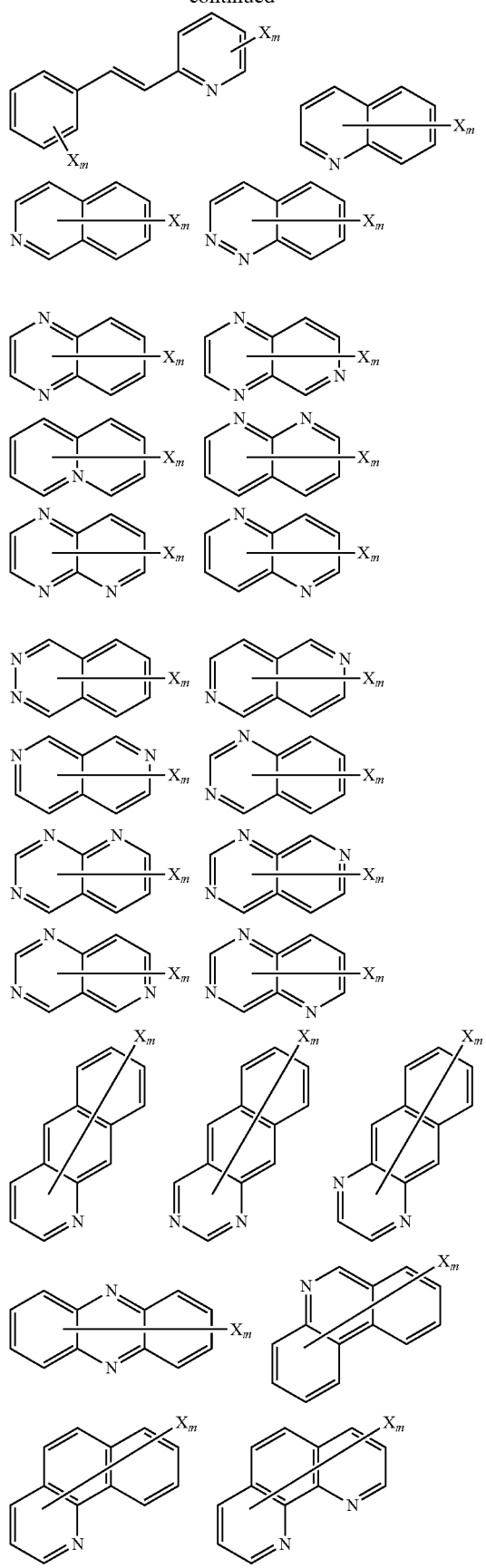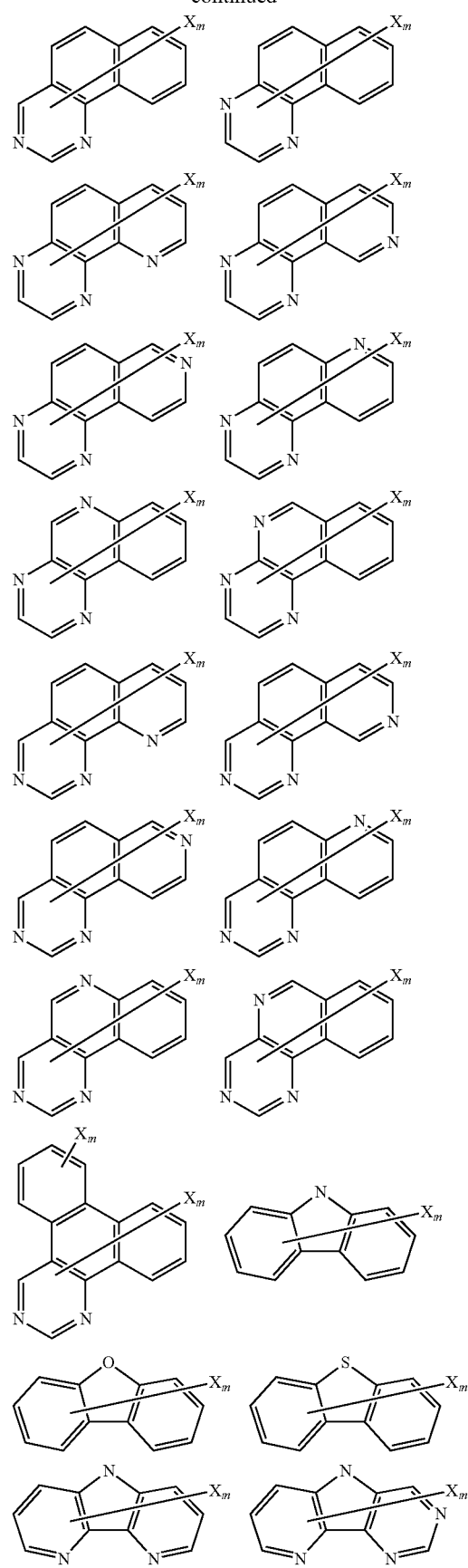

-continued

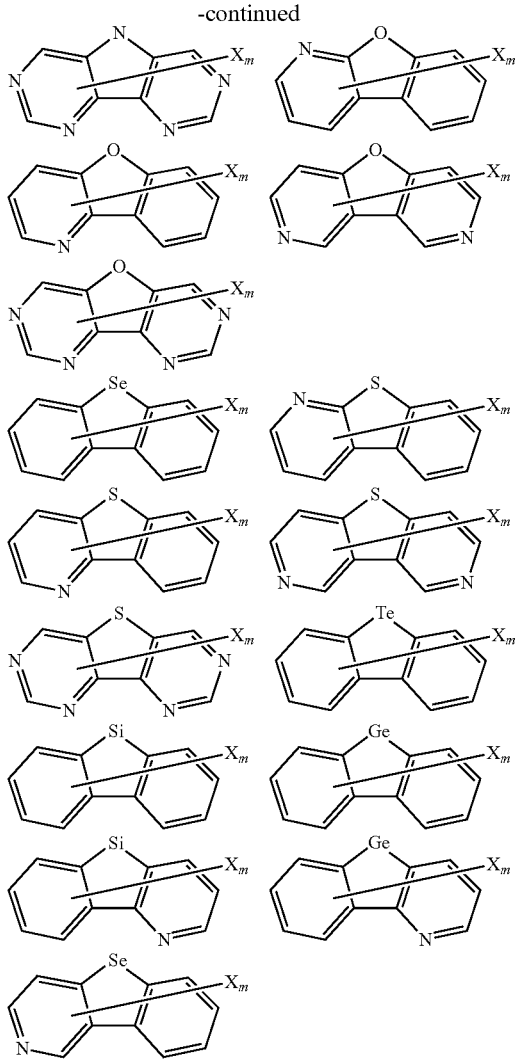

wherein,

X is as defined above for $R_1$ and $R_2$, and m is an integer of 1 to 11 with the proviso that when m is 2 or greater, R's are the same or different;

two adjacent carbon atoms within an aromatic ring form a 5-membered ring containing a carbon atom connected to both the substituents $R_1$ and $R_2$ or a 5-membered ring containing an oxygen atom of Structural Formula $Q_1$ and $Q_2$; and when one of the heteroaromatic rings of [Structural Formula 41] for $A_1$ or $A_2$ is bonded to Structural Formula $Q_1$ or Structural Formula $Q_2$, two adjacent carbon atoms of the aromatic ring occupy respective positions * of Structural Formula $Q_1$ or $Q_2$ to form a fused ring.

In one embodiment of the present disclosure, linkers $L_1$ to $L_{12}$ in Chemical Formula A or Chemical Formula B may each be a single bond, or any one selected from among a substituted or unsubstituted arylene of 6 to 20 carbon atoms, and a substituted or unsubstituted heteroarylene of 2 to 20 carbon atoms.

In this regard, the linkers $L_1$ to $L_{12}$ may each be a single bond, or any one selected from the following [Structural Formula 22] to [Structural Formula 30], p1 to p4, $r_1$ to $r_4$, and s1 to s4 may each be 1 or 2, and x may be 1:

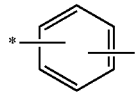
[Structural Formula 22]

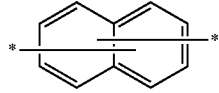
[Structural Formula 23]

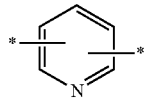
[Structural Formula 24]

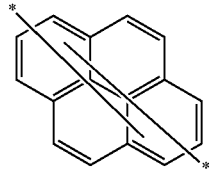
[Structural Formula 25]

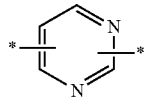
[Structural Formula 26]

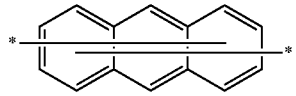
[Structural Formula 27]

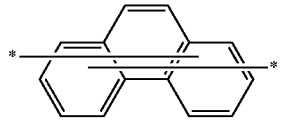
[Structural Formula 28]

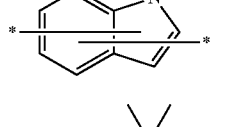
[Structural Formula 29]

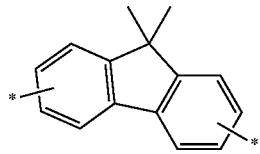
[Structural Formula 30]

In the linker, each of the unsubstituted carbon atoms of the aromatic ring moiety is bound with a hydrogen atom or a deuterium atom.

In this case, y may be 1 and z may be 0.

In particular embodiments of the present disclosure, the substituents $R_1$ and $R_2$ of Chemical Formula A or Chemical Formula B, which is the same or different, may each be independently a substituted or unsubstituted aryl of 6 to 24 carbon atoms, and may be connected to each other to form a ring or may be not.

According to a specific embodiment of the present disclosure, $R_1$ to $R_9$, and $Ar_1$ to $Ar_8$ may be the same or different and may each be independently any one selected from among hydrogen, deuterium, a substituted or unsubstituted aryl of 6 to 20 carbon atoms, a substituted or unsubstituted cycloalkyl of 3 to 30 carbon atoms, a substituted or unsubstituted heteroaryl of 2 to 20 carbon atoms containing at least one heteroatom selected from among O, N, S, and Si, a cyano, and a halogen.

In the amine compound of Chemical Formula A or B according to some embodiments of the present disclosure, $A_1$, $A_2$, E, F, $Ar_1$ to $Ar_8$, $L_1$ to $L_{12}$, $R_1$ to $R_9$ may have as a substituent any one selected from the group consisting of a cyano, a halogen, an alkyl of 1 to 6 carbon atoms, an aryl of 6 to 18 carbon atoms, an arylalkyl of 6 to 18 carbon atoms, a heteroaryl of 3 to 18 carbon atoms, an alkylsilyl of 1 to 12 carbon atoms, and an arylsilyl of 6 to 18 carbon atoms.

The amine compound of the present disclosure may be selected from compounds represented by the following [Chemical Formula 1] to [Chemical Formula 239].

<Chemical Formula 1>

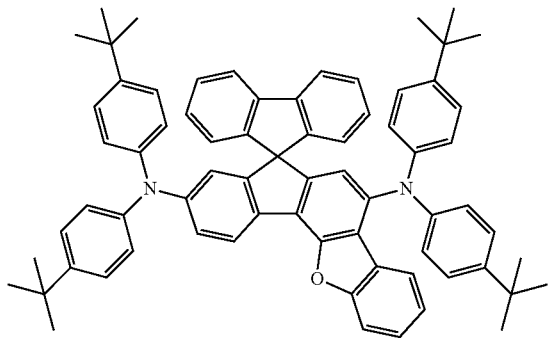

<Chemical Formula 2>

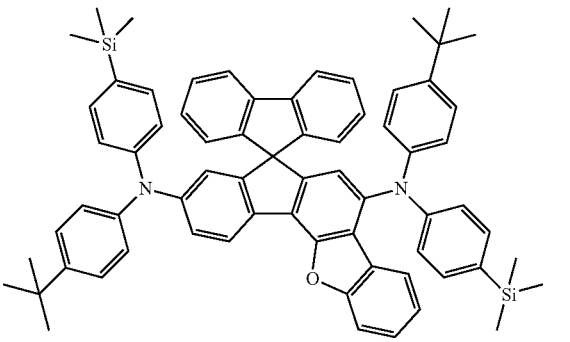

<Chemical Formula 3>

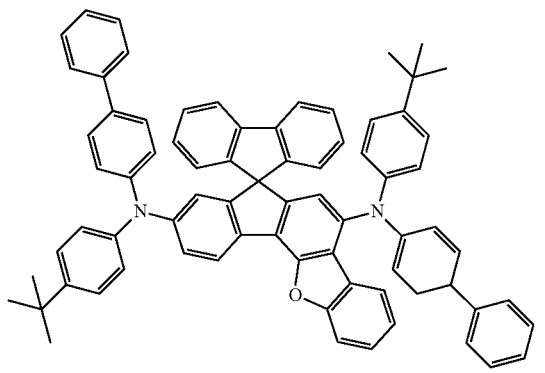

<Chemical Formula 4>

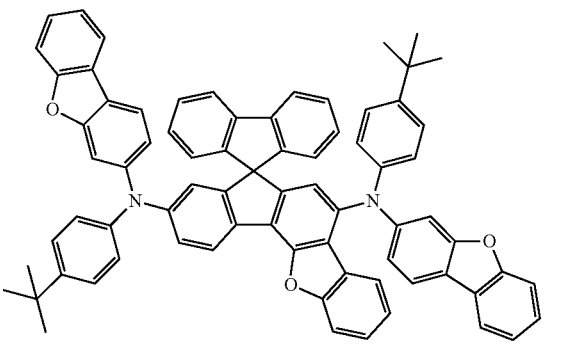

<Chemical Formula 5>

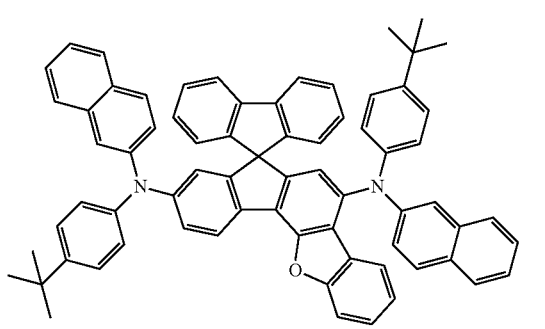

<Chemical Formula 6>

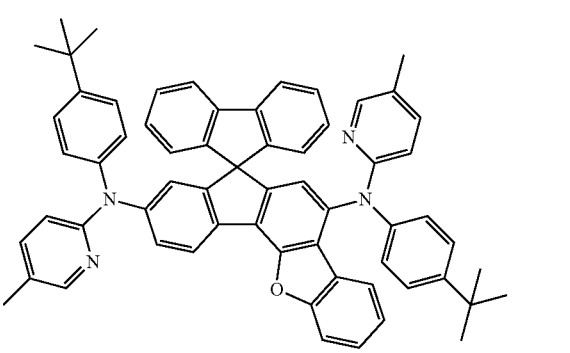

<Chemical Formula 7>

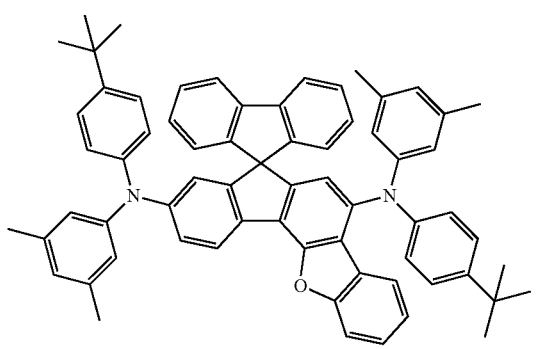

<Chemical Formula 8>

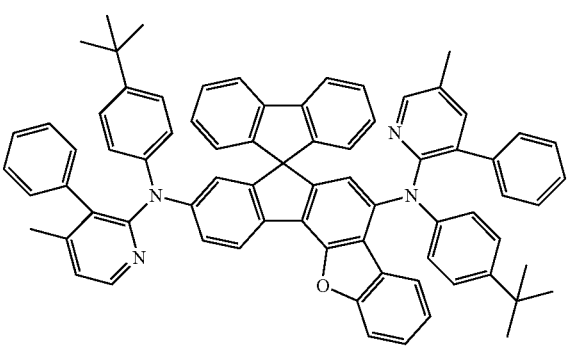

<Chemical Formula 9>
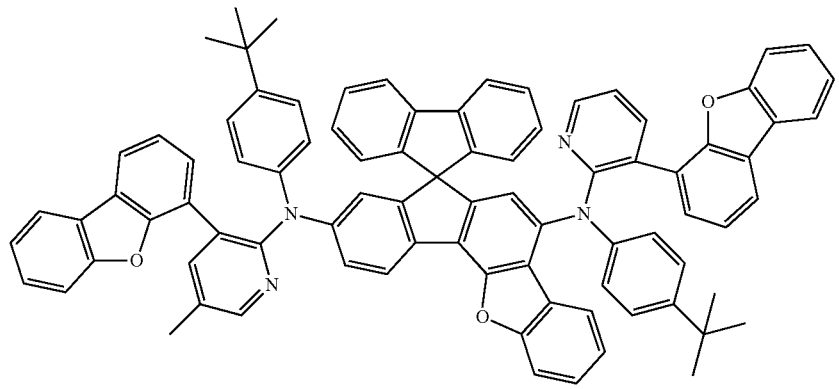
<Chemical Formula 10>
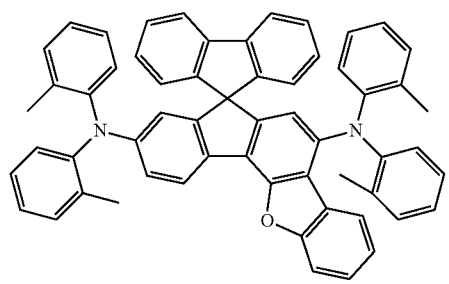
<Chemical Formula 11>
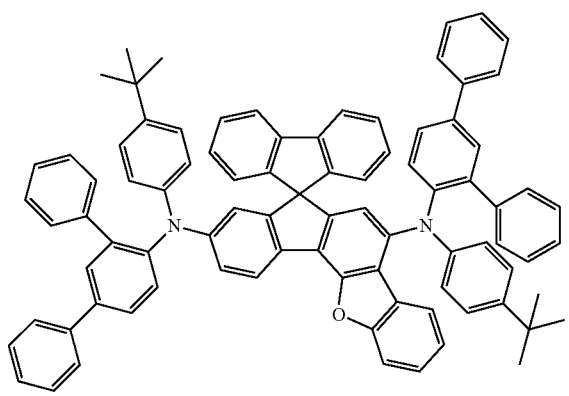
<Chemical Formula 12>
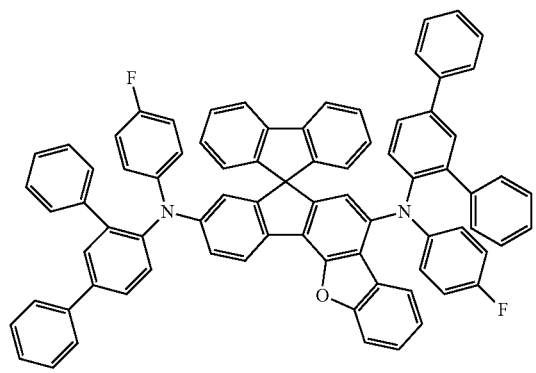
<Chemical Formula 13>
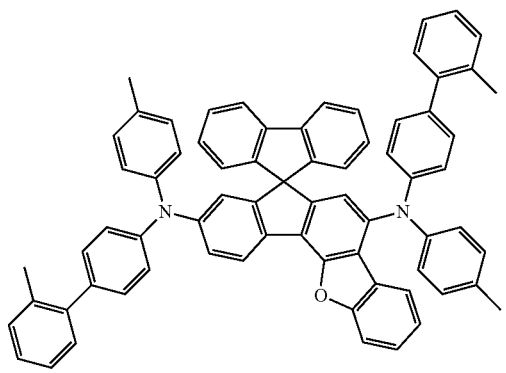

-continued
<Chemical Formula 14>
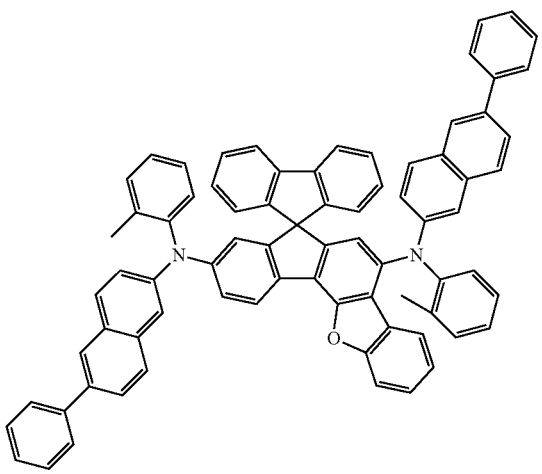
<Chemical Formula 15>
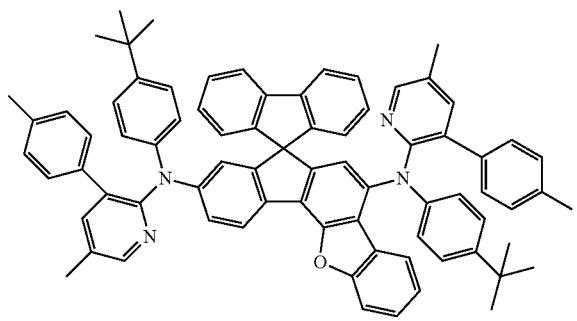
<Chemical Formula 16>
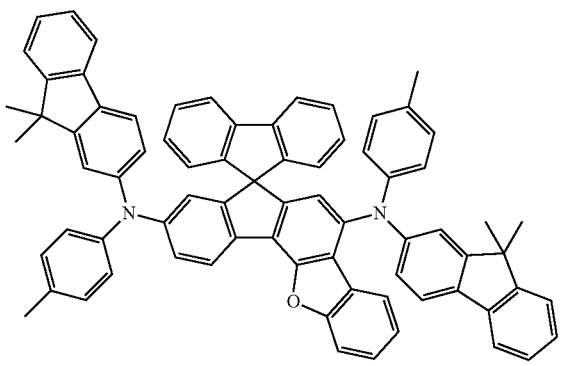
<Chemical Formula 17>
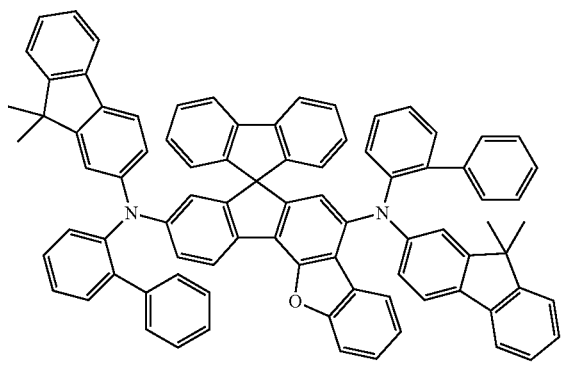
<Chemical Formula 18>
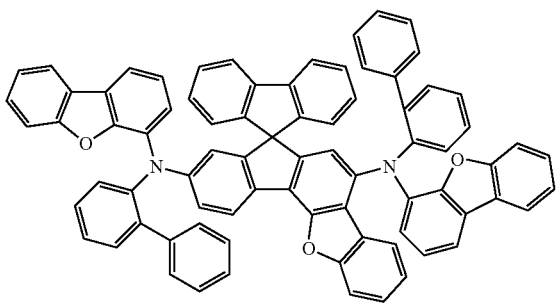
<Chemical Formula 19>
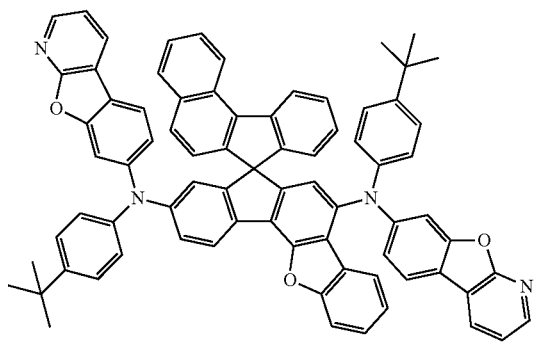

<Chemical Formula 20>
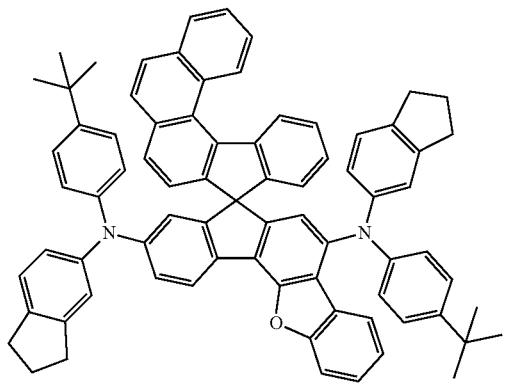
<Chemical Formula 21>
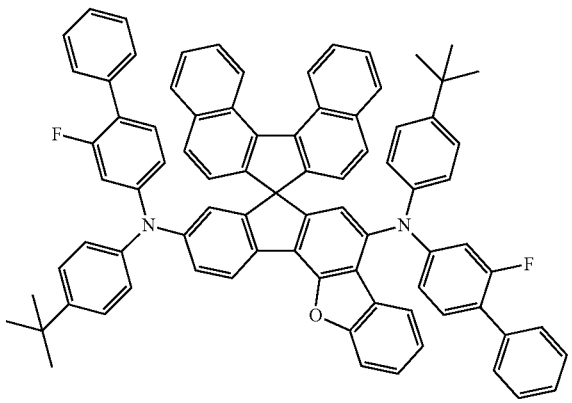
<Chemical Formula 22>
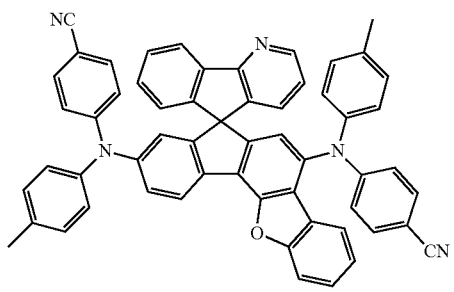
<Chemical Formula 23>
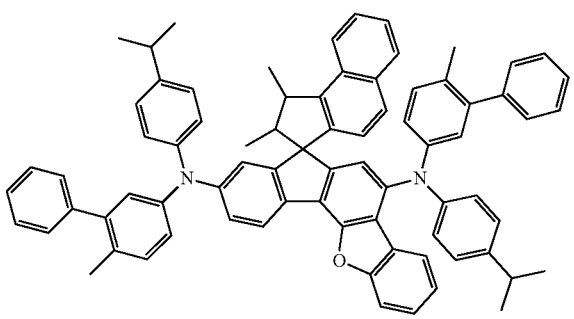
<Chemical Formula 24>
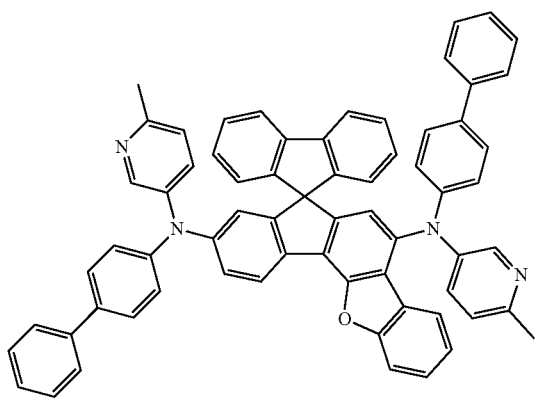
<Chemical Formula 25>
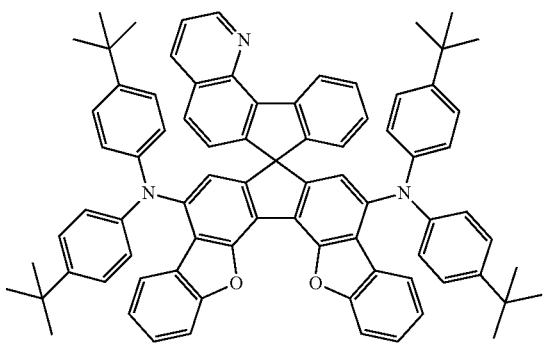

<Chemical Formula 26>
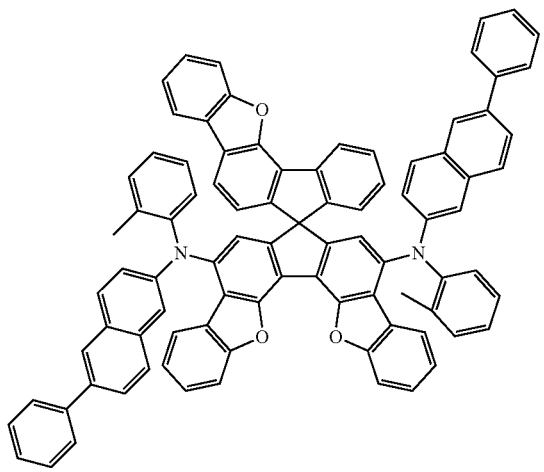
<Chemical Formula 27>
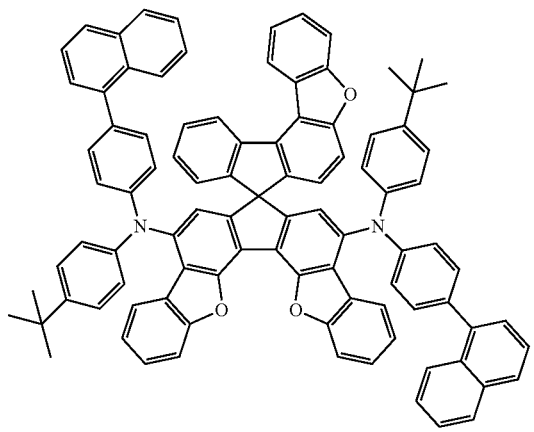
<Chemical Formula 28>
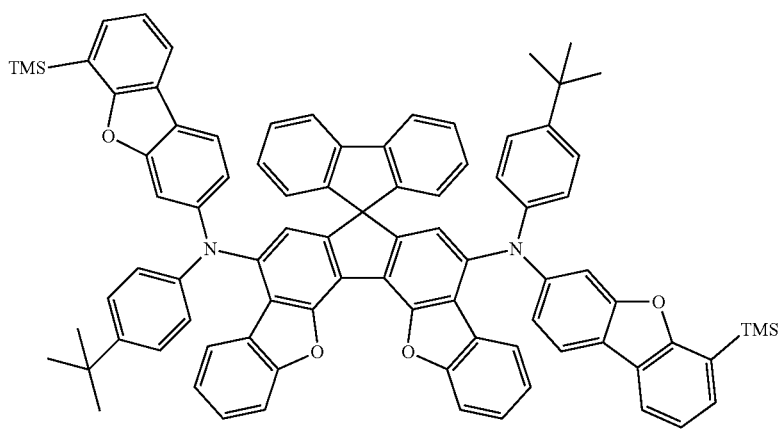
<Chemical Formula 29>
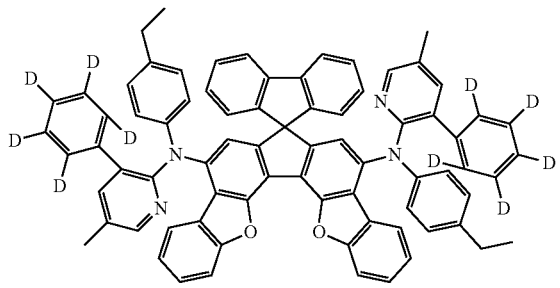
<Chemical Formula 30>
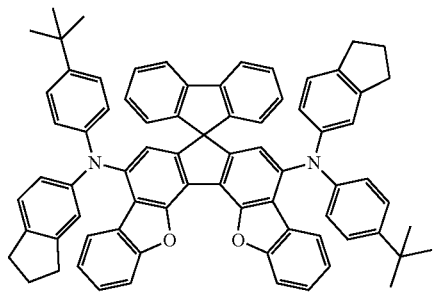
<Chemical Formula 31>
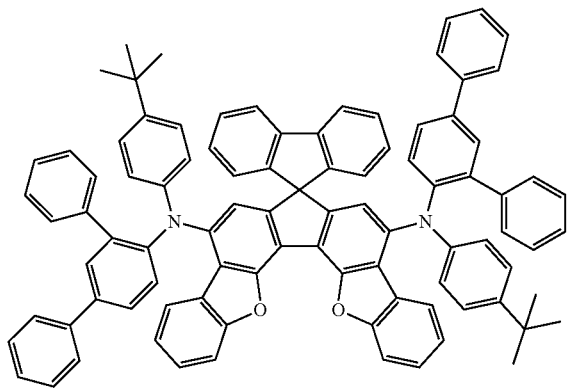

<Chemical Formula 32>
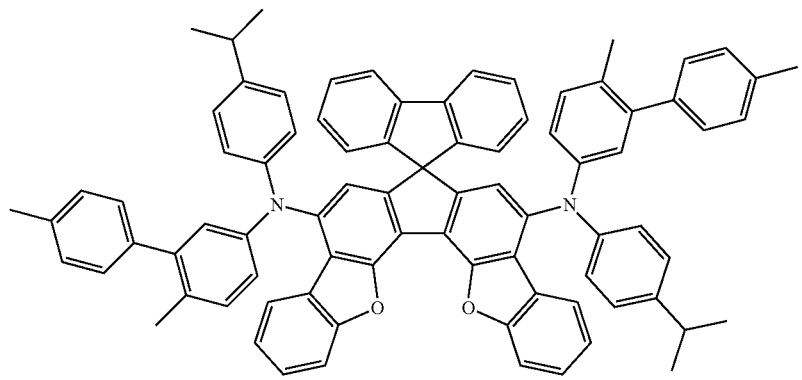
<Chemical Formula 33>
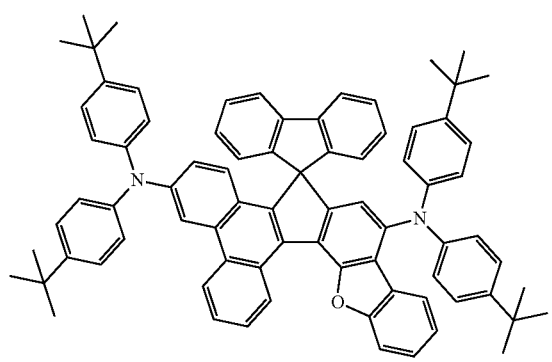
<Chemical Formula 34>
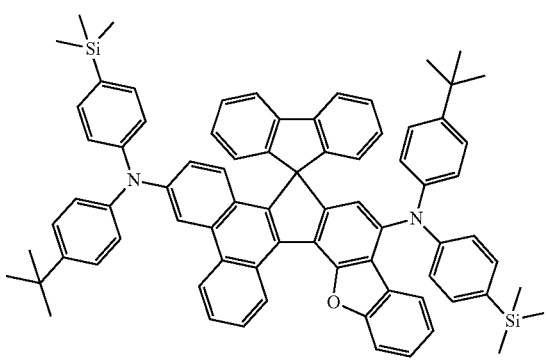
<Chemical Formula 35>
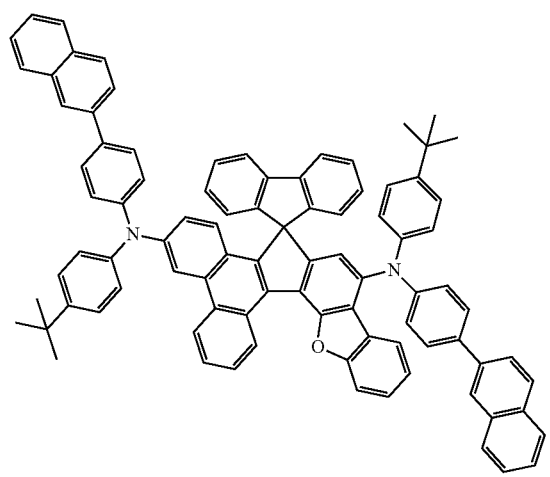
<Chemical Formula 36>
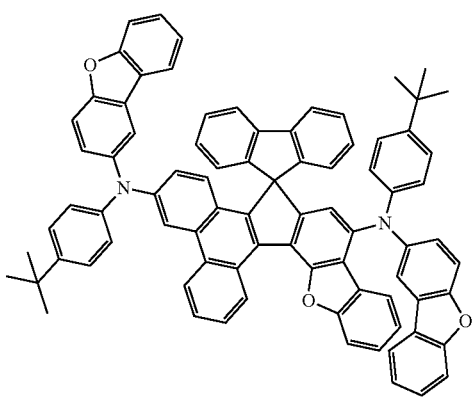
<Chemical Formula 37>
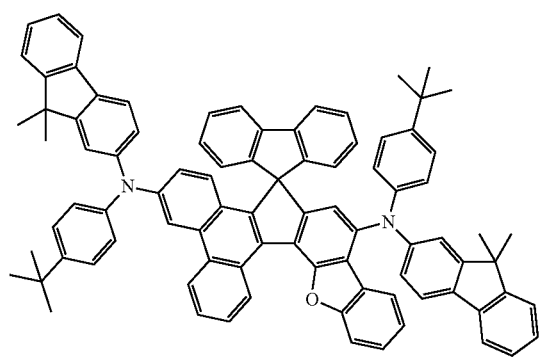
<Chemical Formula 38>
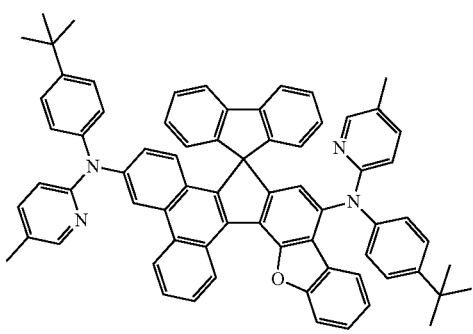

-continued
<Chemical Formula 39>
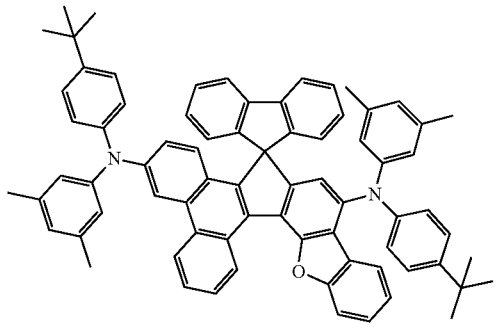
<Chemical Formula 40>
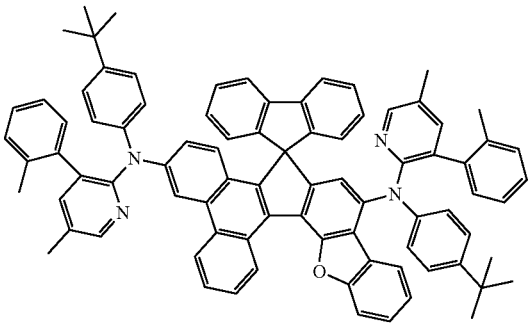
<Chemical Formula 41>
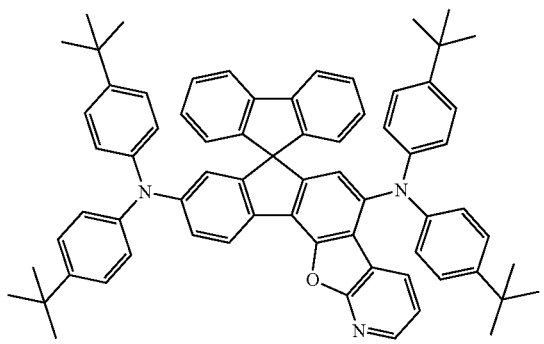
<Chemical Formula 42>
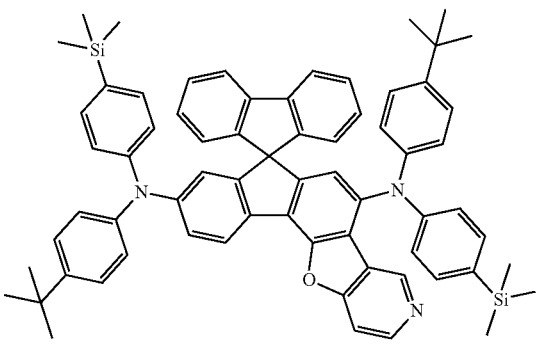
<Chemical Formula 43>
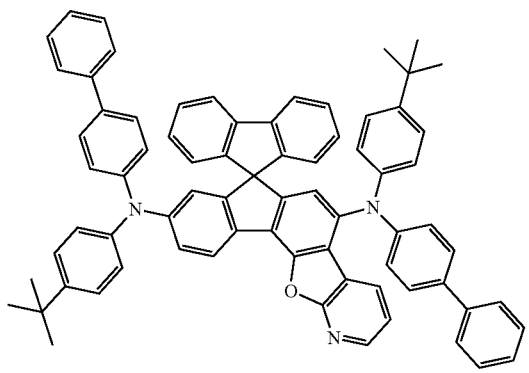
<Chemical Formula 44>
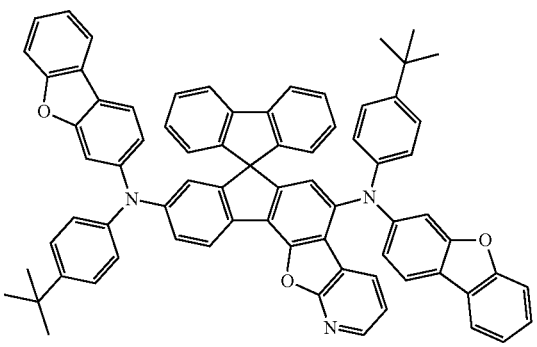
<Chemical Formula 45>
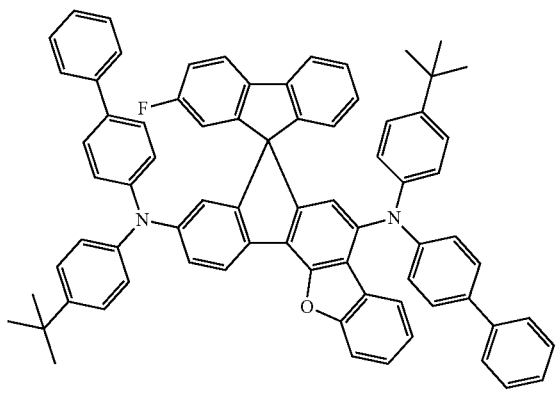
<Chemical Formula 46>
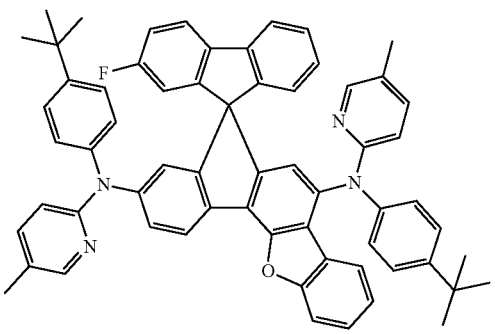

-continued
<Chemical Formula 47>
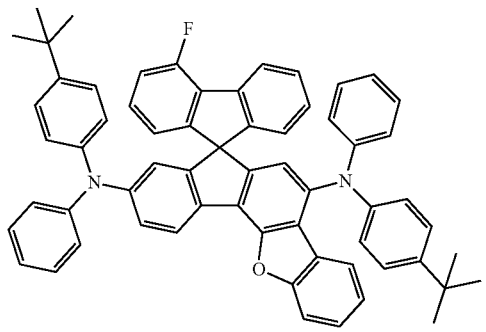
<Chemical Formula 48>
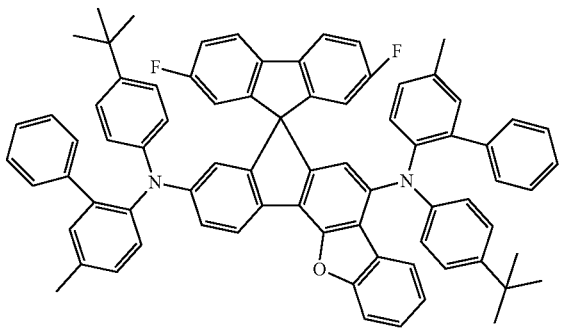
<Chemical Formula 49>
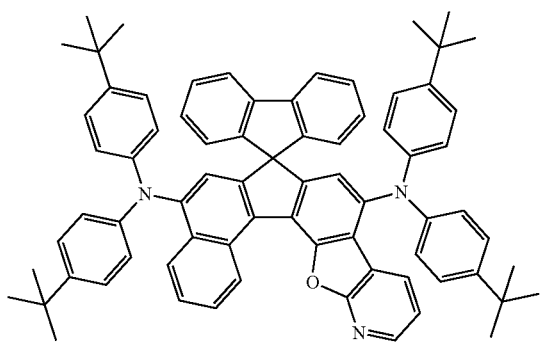
<Chemical Formula 50>
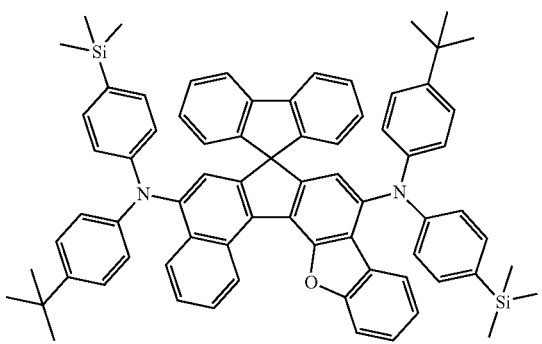
<Chemical Formula 51>
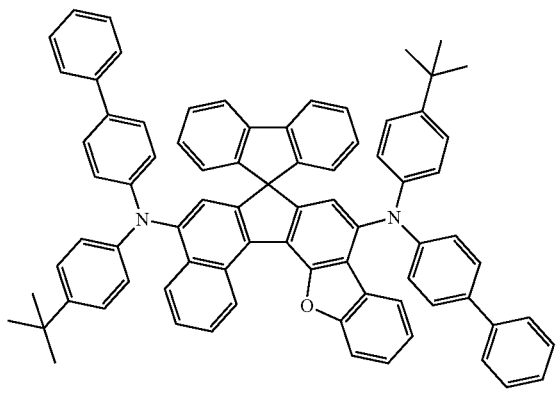
<Chemical Formula 52>
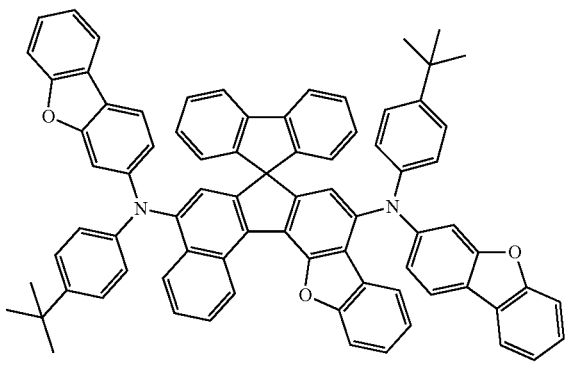
<Chemical Formula 53>
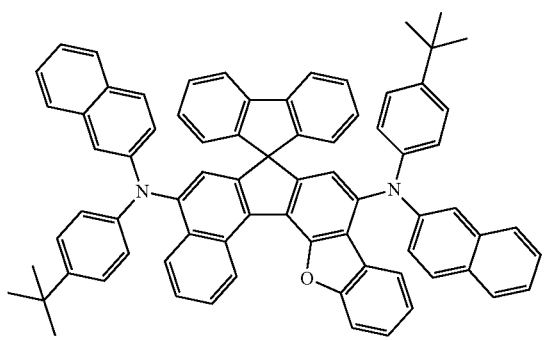
<Chemical Formula 54>
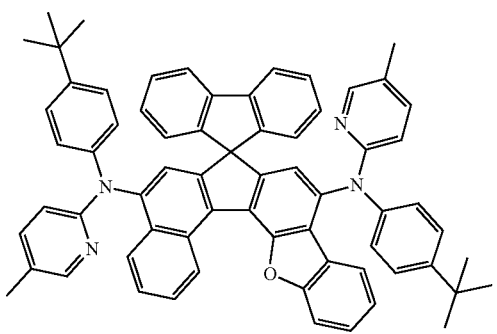

-continued
<Chemical Formula 55>
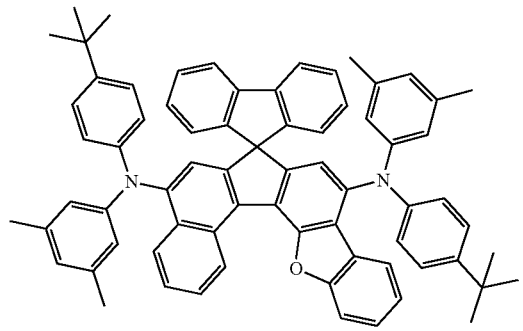
<Chemical Formula 56>
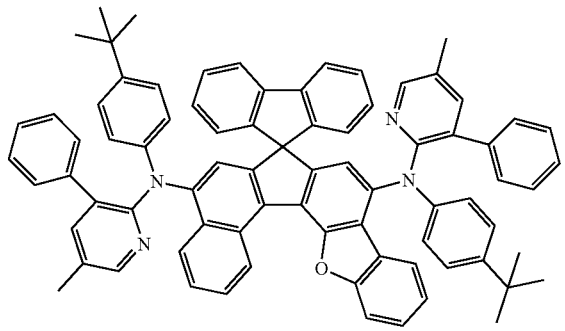
<Chemical Formula 57>
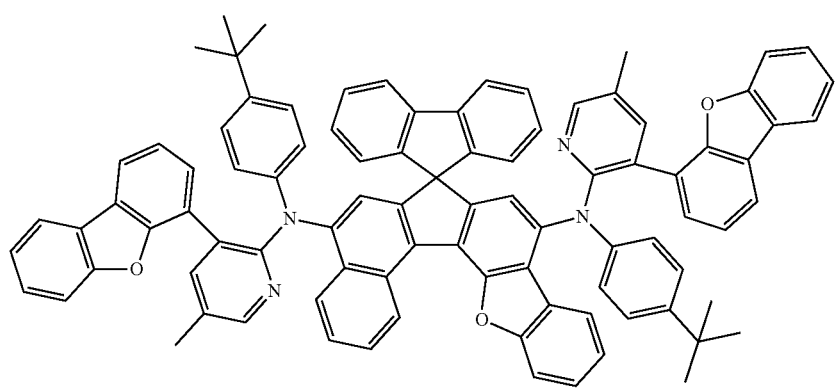
<Chemical Formula 58>
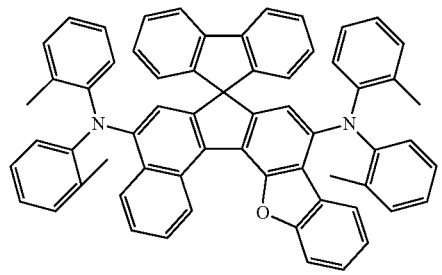
<Chemical Formula 59>
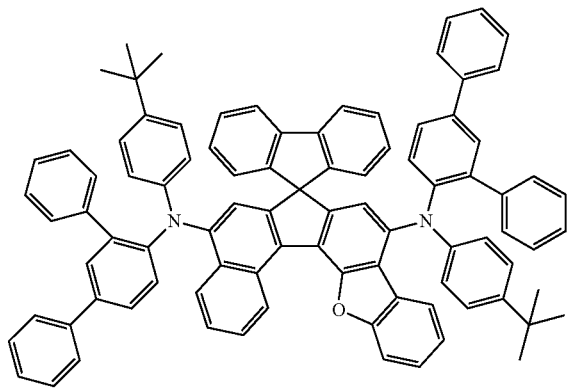
<Chemical Formula 60>
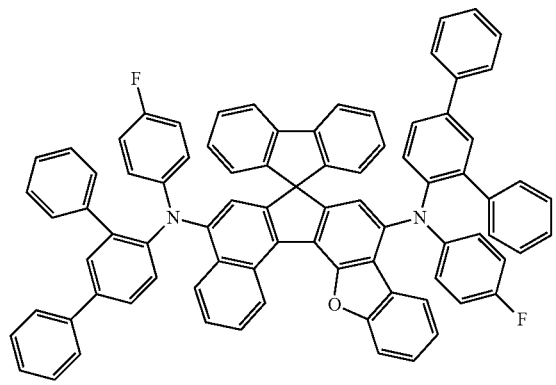
<Chemical Formula 61>
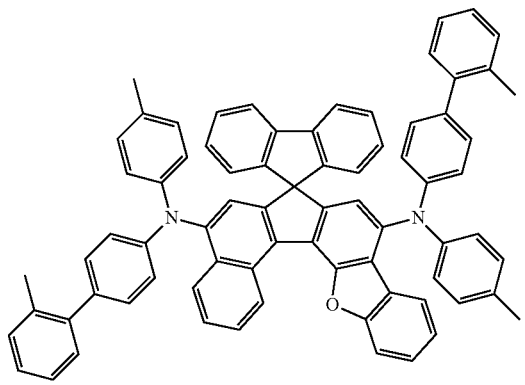

<Chemical Formula 62>
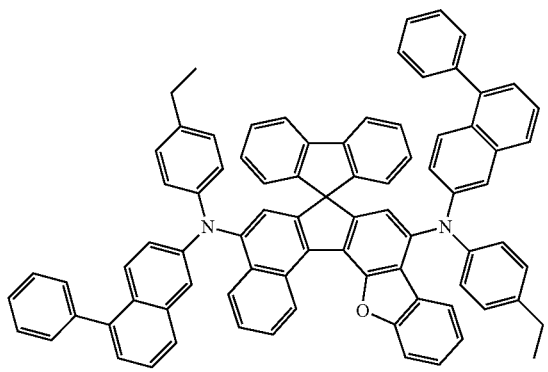
<Chemical Formula 63>
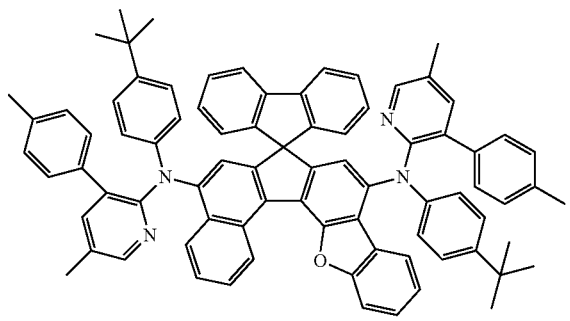
<Chemical Formula 64>
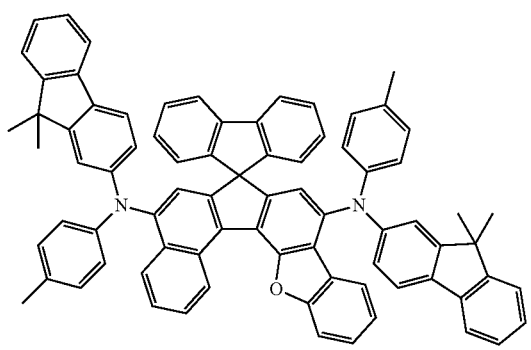
<Chemical Formula 65>
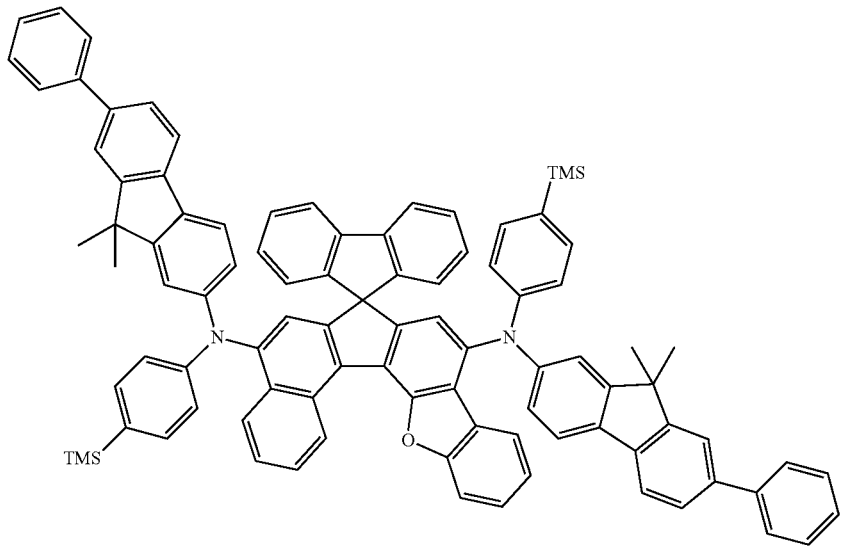
<Chemical Formula 66>
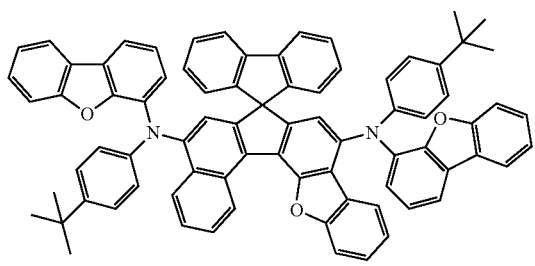
<Chemical Formula 67>
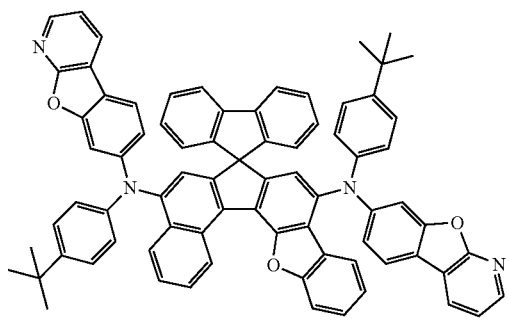

-continued
<Chemical Formula 68>
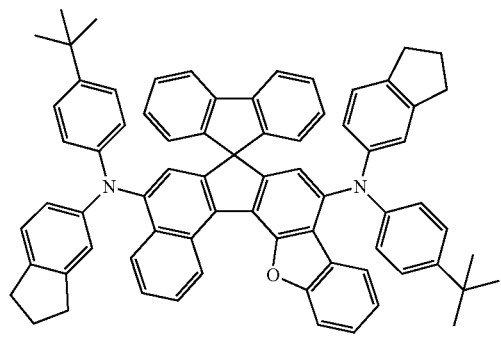
<Chemical Formula 69>
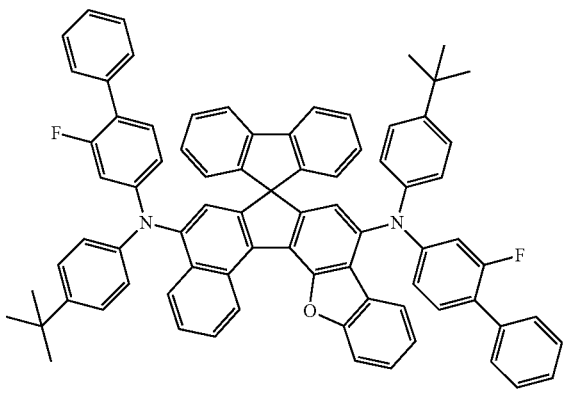
<Chemical Formula 70>
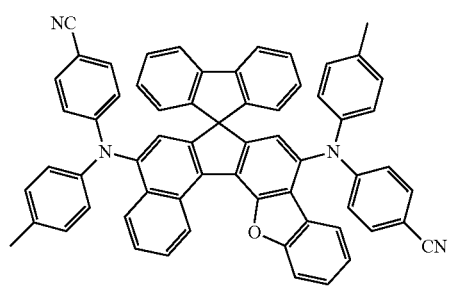
<Chemical Formula 71>
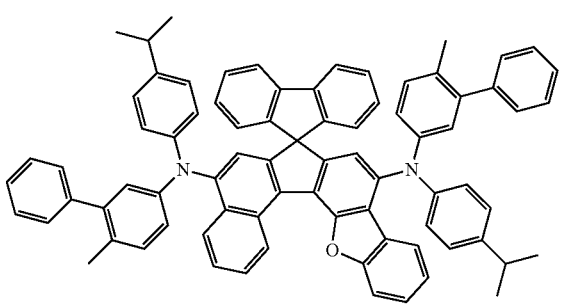
<Chemical Formula 72>
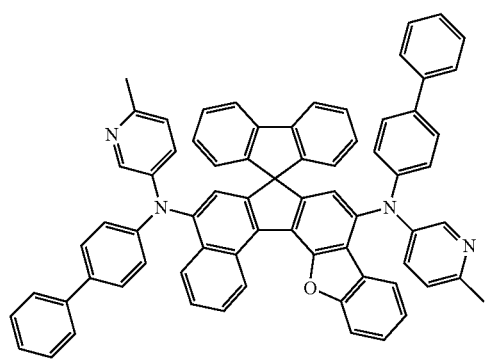
<Chemical Formula 73>
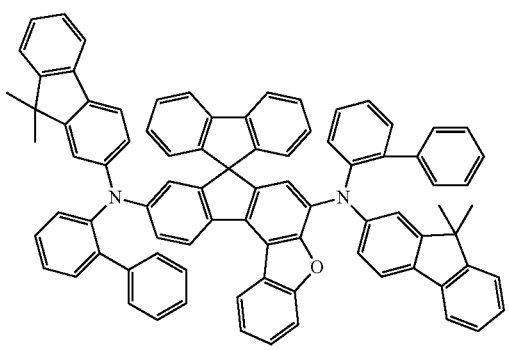
<Chemical Formula 74>
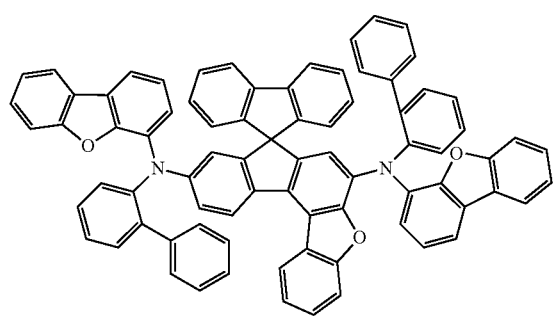
<Chemical Formula 75>
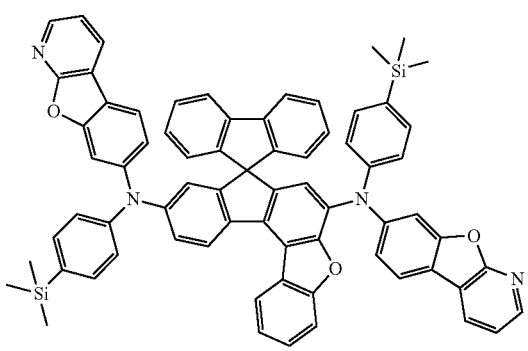

<Chemical Formula 76>
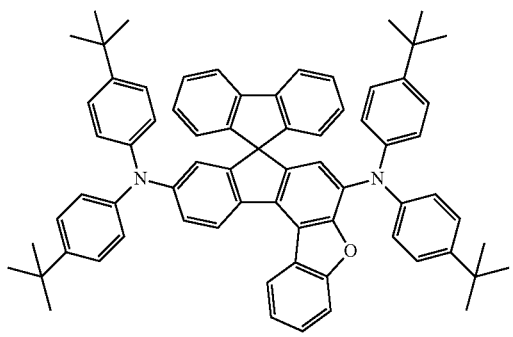
<Chemical Formula 77>
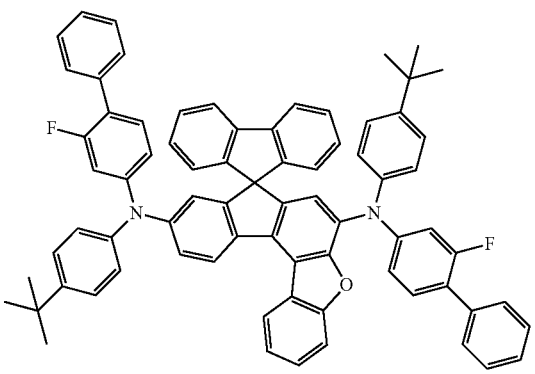
<Chemical Formula 78>
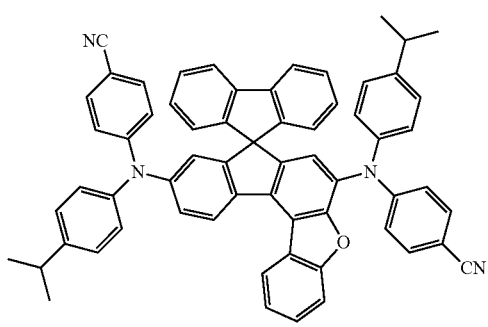
<Chemical Formula 79>
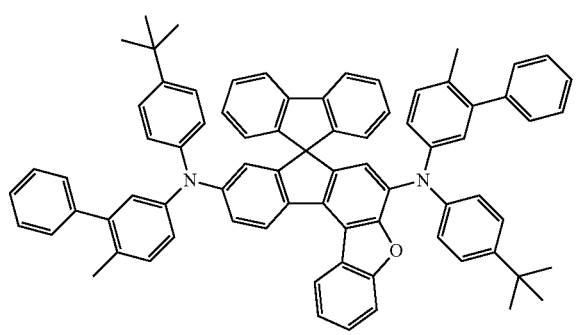
<Chemical Formula 80>
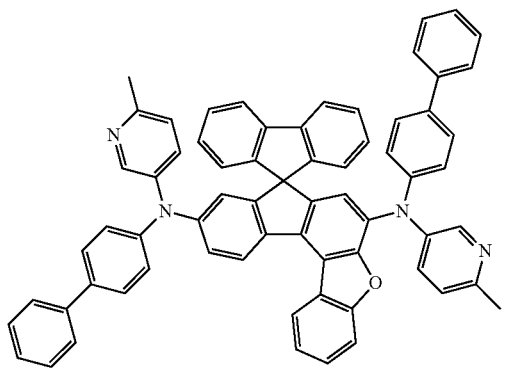
<Chemical Formula 81>
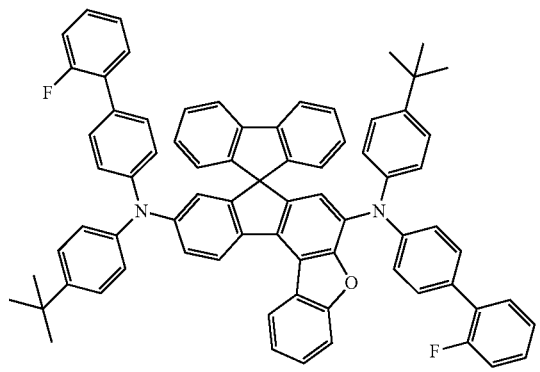
<Chemical Formula 82>
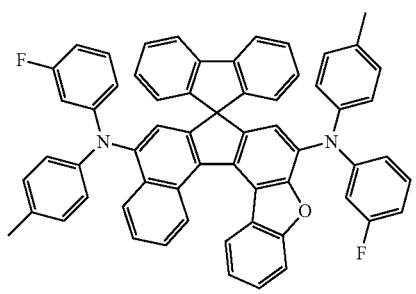
<Chemical Formula 83>
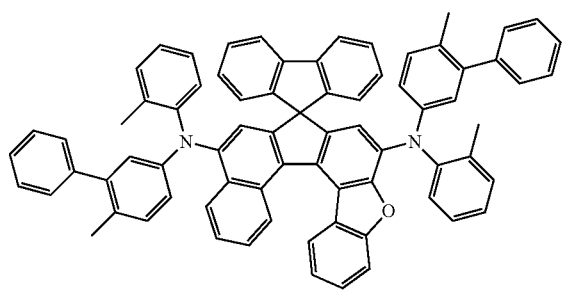

<Chemical Formula 84>
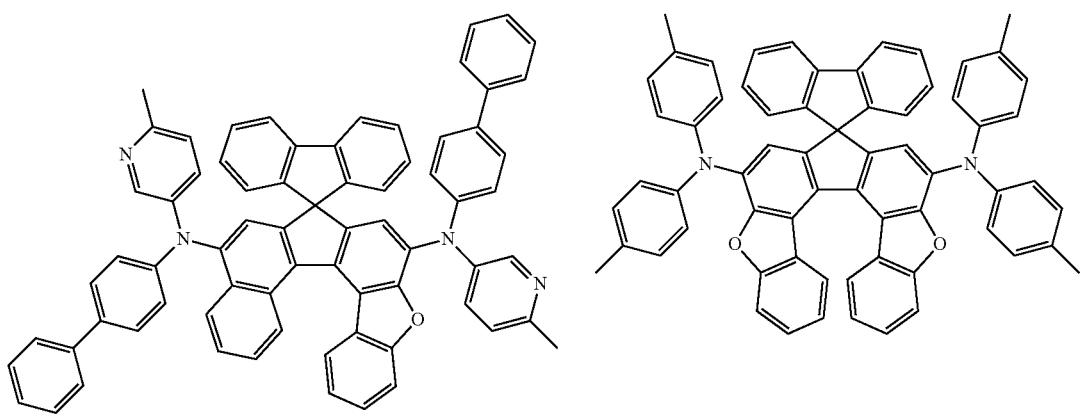
<Chemical Formula 85>
<Chemical Formula 86>
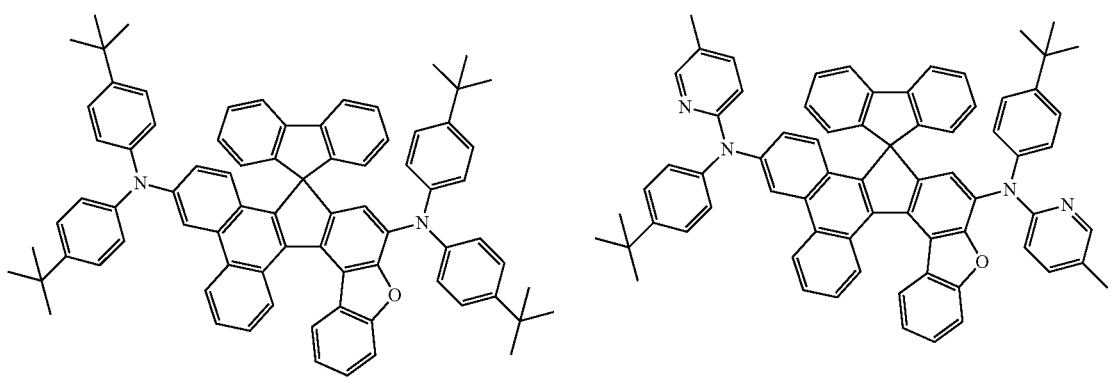
<Chemical Formula 87>
<Chemical Formula 88>
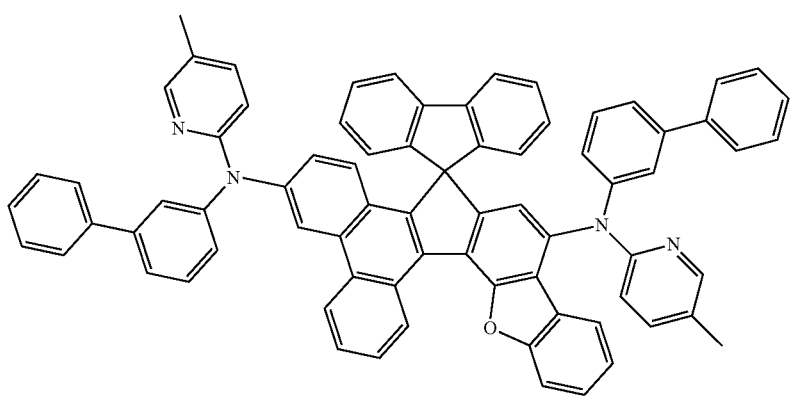
<Chemical Formula 89>
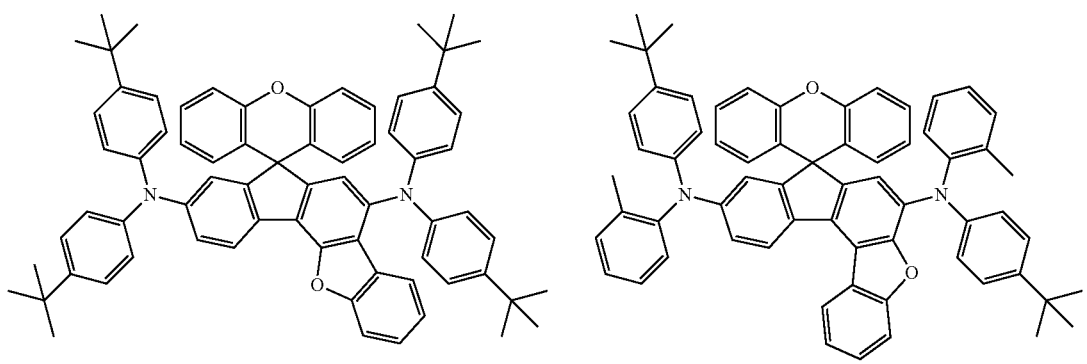
<Chemical Formula 90>

-continued
<Chemical Formula 91>
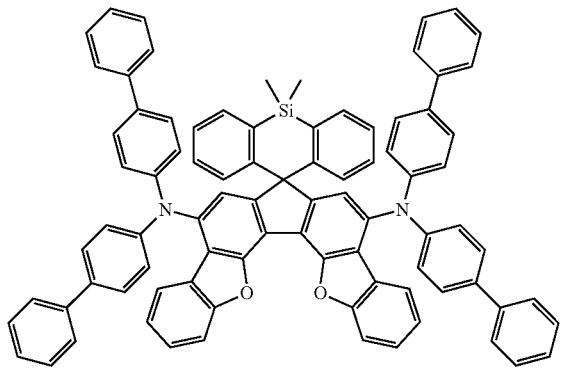
<Chemical Formula 92>
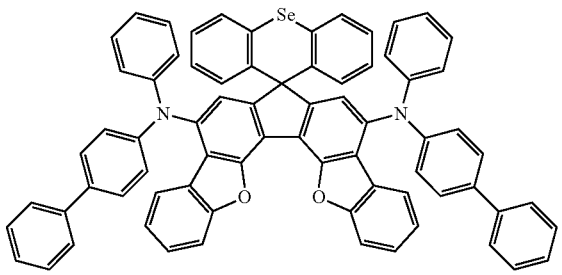
<Chemical Formula 93>
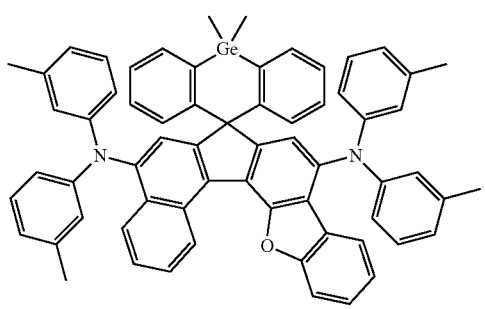
<Chemical Formula 94>
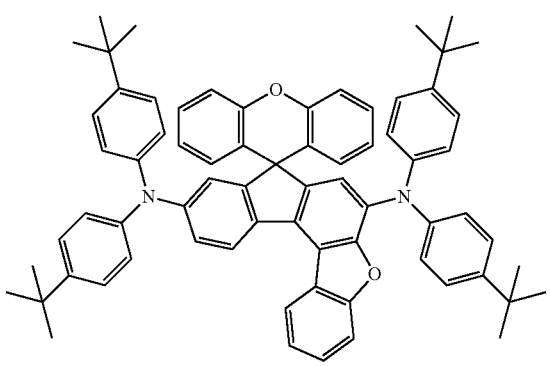
<Chemical Formula 95>
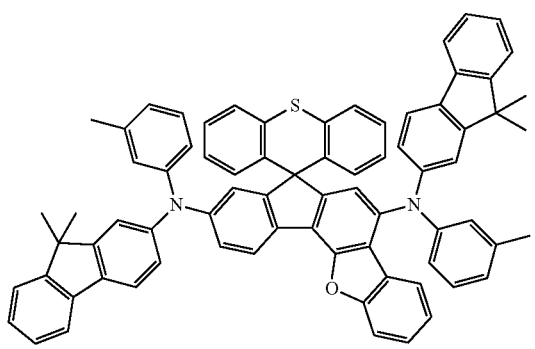
<Chemical Formula 96>
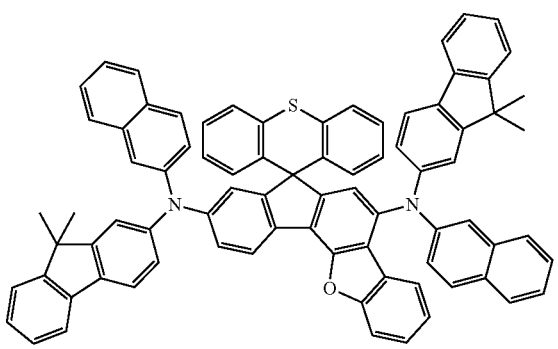
<Chemical Formula 97>
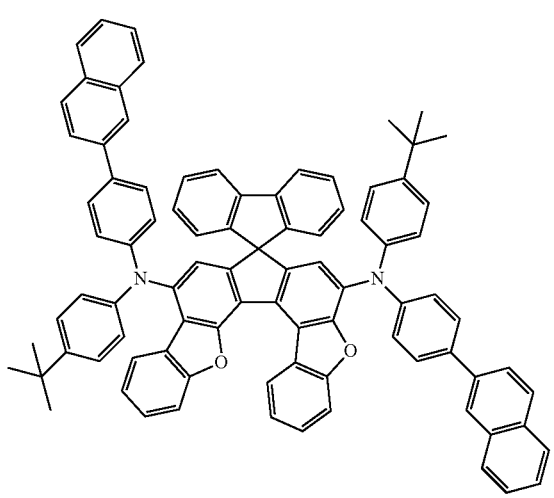
<Chemical Formula 98>
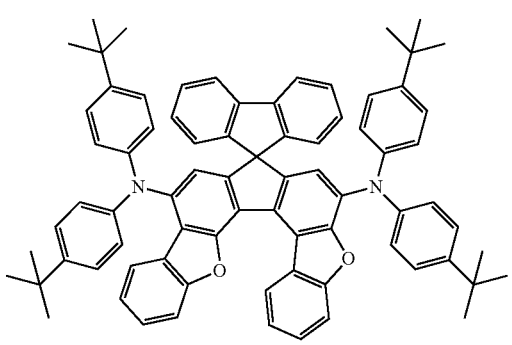

-continued
<Chemical Formula 99>
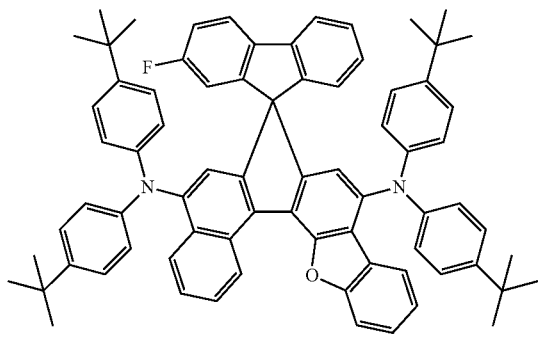
<Chemical Formula 100>
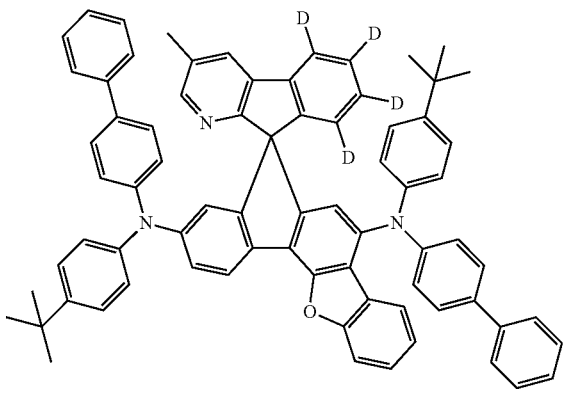
<Chemical Formula 101>
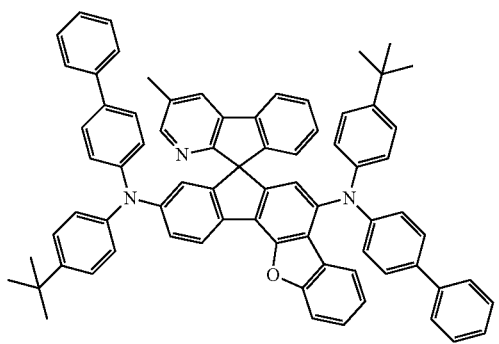
<Chemical Formula 102>
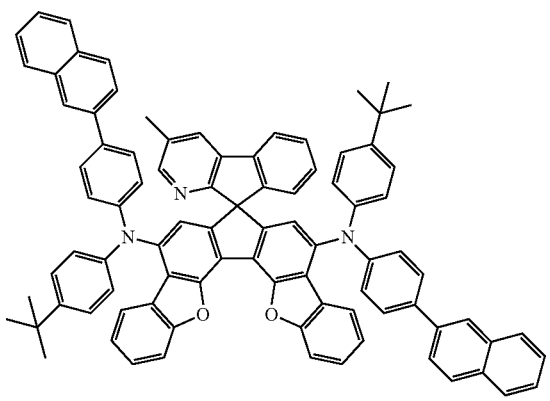
<Chemical Formula 103>
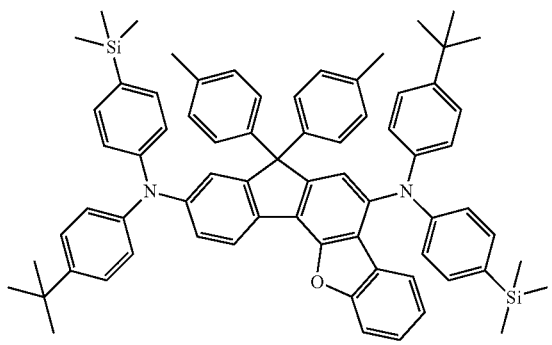
<Chemical Formula 104>
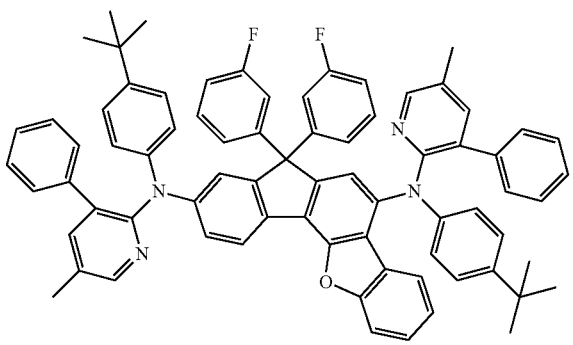
<Chemical Formula 105>
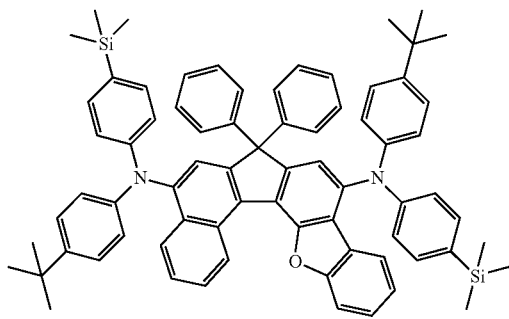
<Chemical Formula 106>
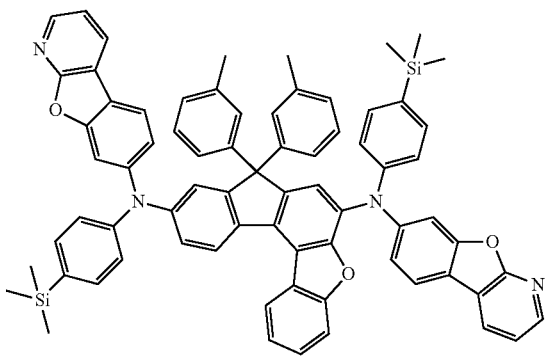

-continued
<Chemical Formula 107>
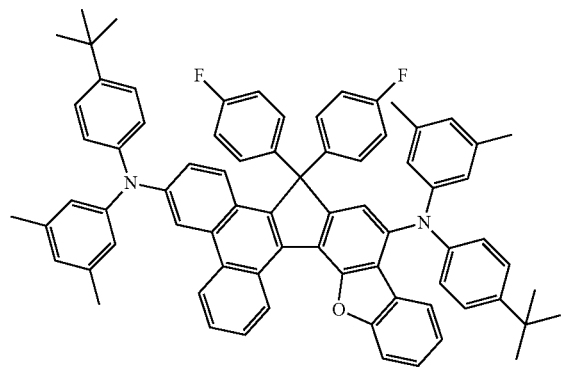
<Chemical Formula 108>
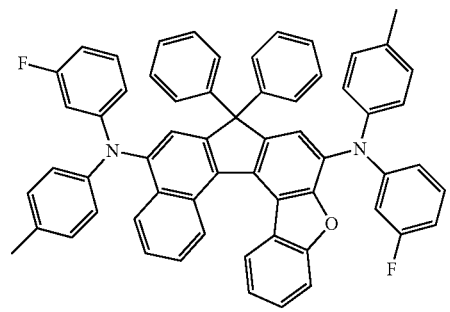
<Chemical Formula 109>
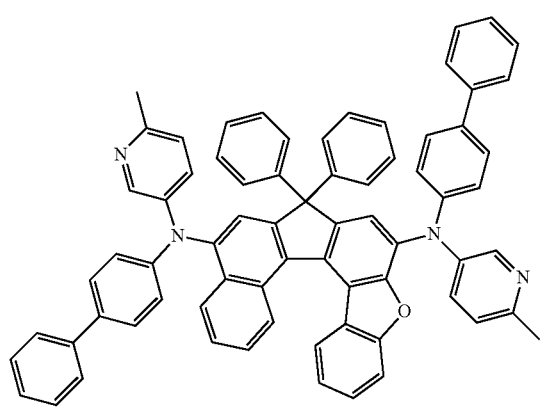
<Chemical Formula 110>
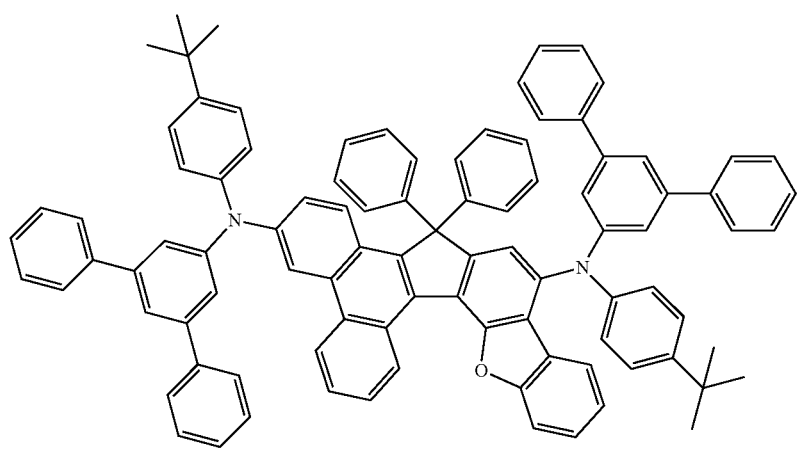

-continued
<Chemical Formula 111>
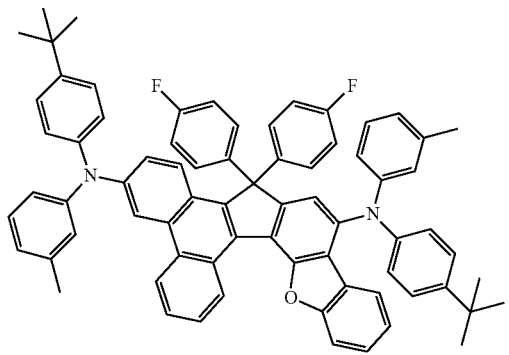
<Chemical Formula 112>
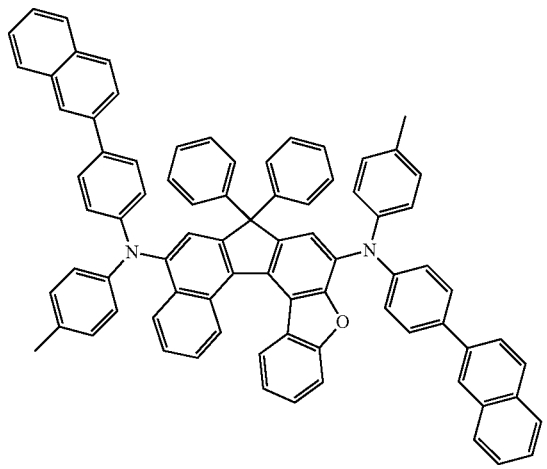
<Chemical Formula 113>
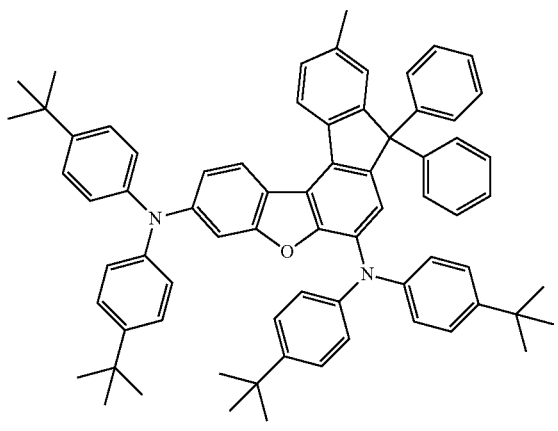
<Chemical Formula 114>
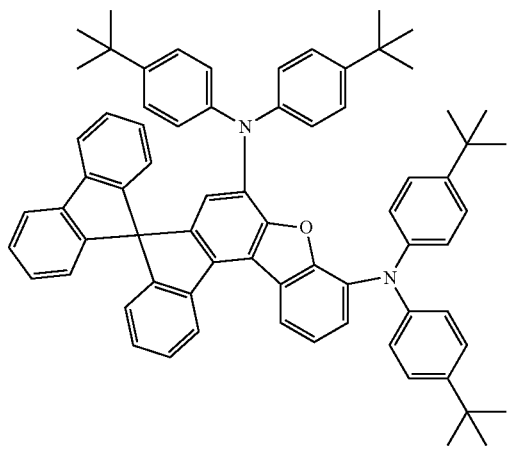
<Chemical Formula 115>
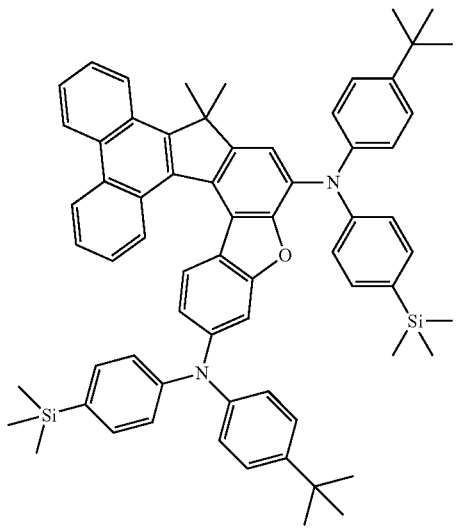
<Chemical Formula 116>
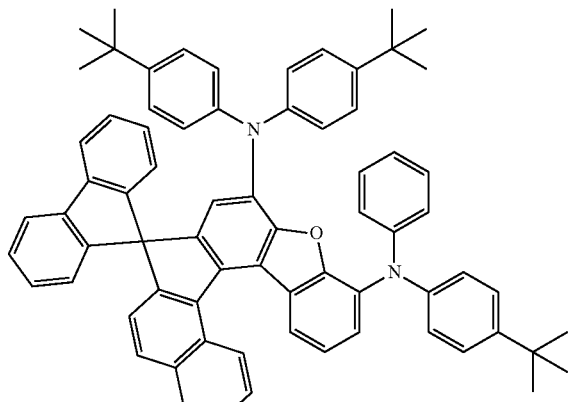

<Chemical Formula 117>
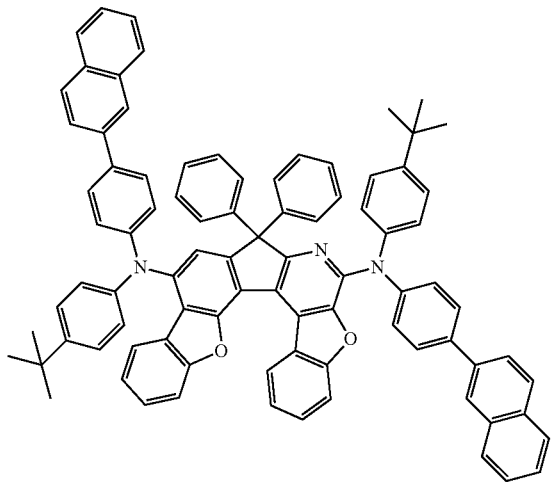
<Chemical Formula 118>
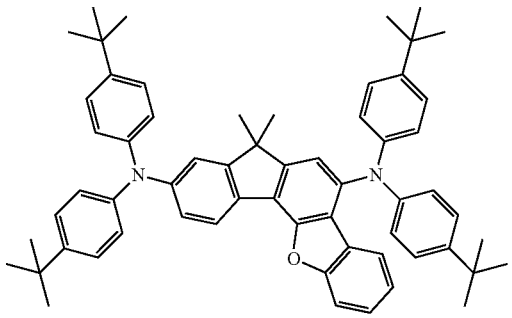
<Chemical Formula 119>
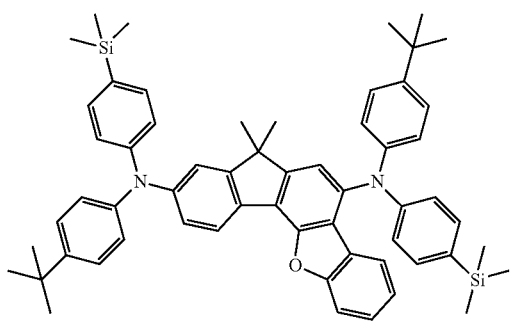
<Chemical Formula 120>
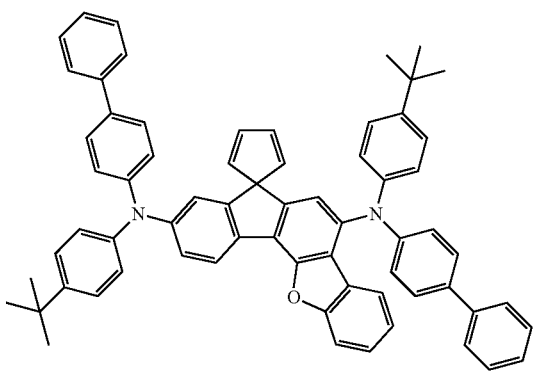
<Chemical Formula 121>
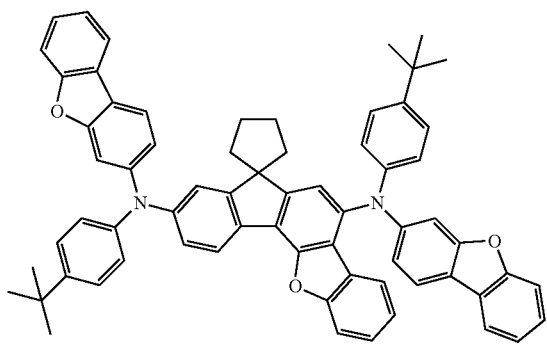
<Chemical Formula 122>
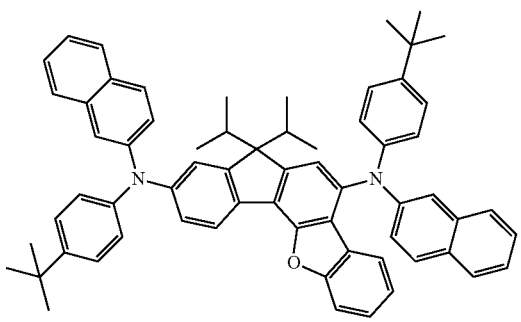
<Chemical Formula 123>
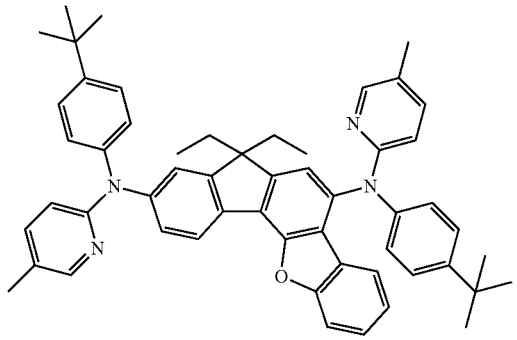
<Chemical Formula 124>
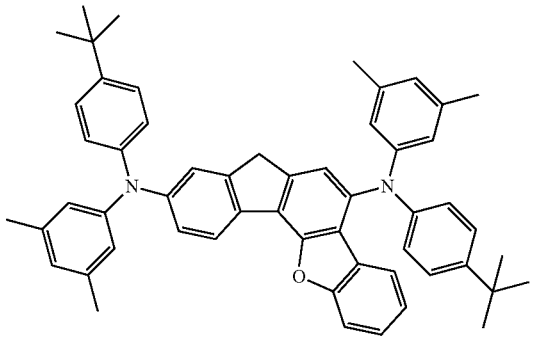

<Chemical Formula 125>
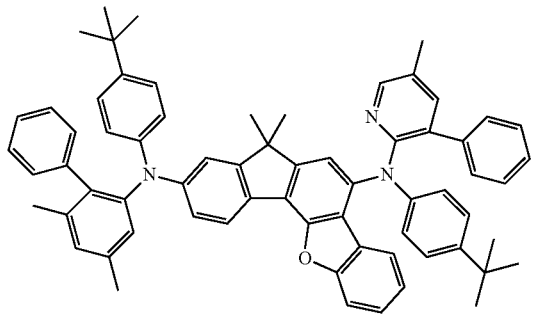
<Chemical Formula 126>
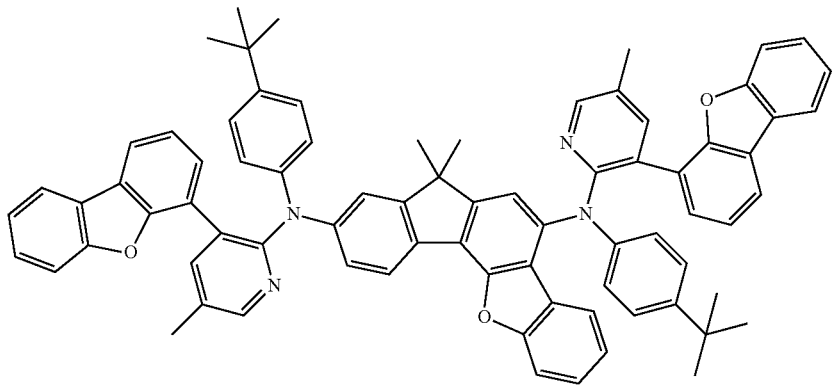
<Chemical Formula 127>
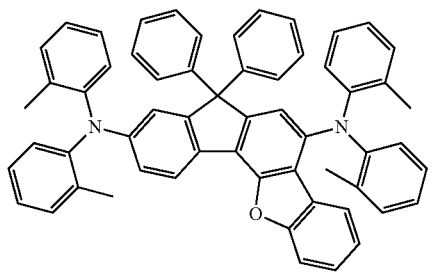
<Chemical Formula 128>
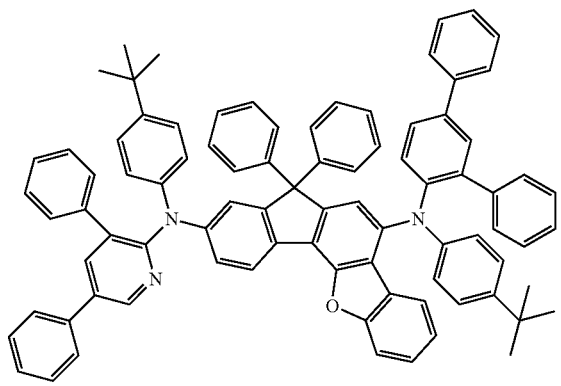
<Chemical Formula 129>
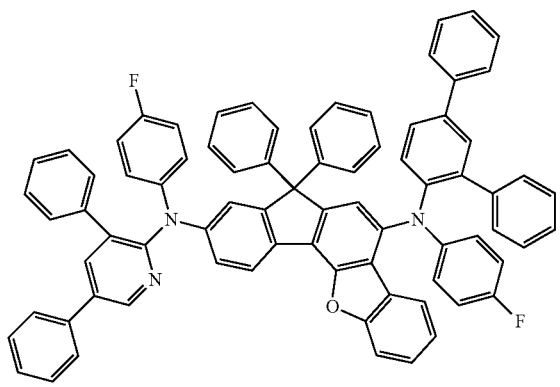
<Chemical Formula 130>
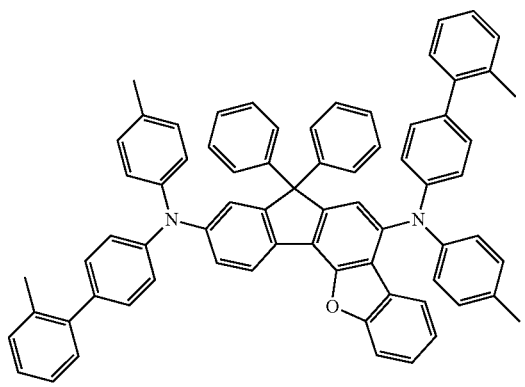

<Chemical Formula 131>
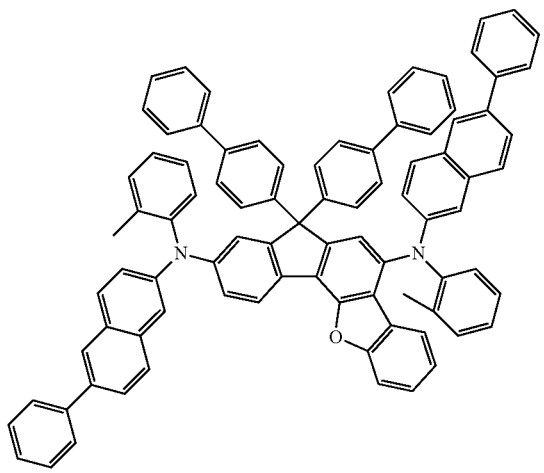
<Chemical Formula 132>
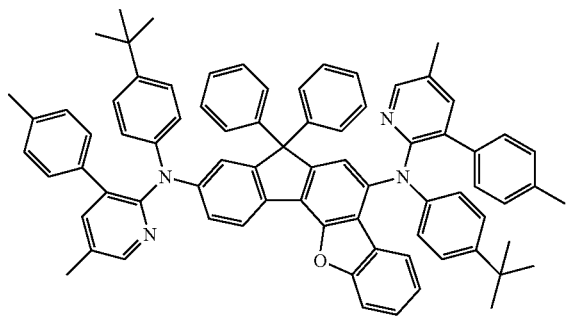
<Chemical Formula 133>
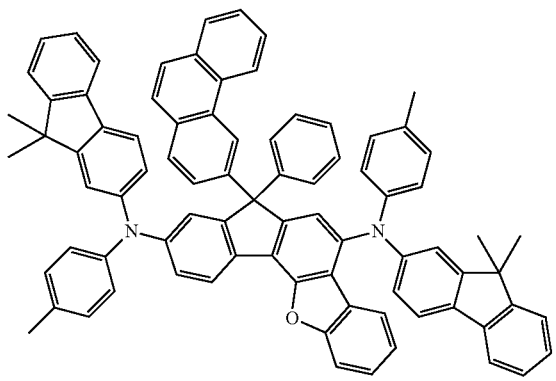
<Chemical Formula 134>
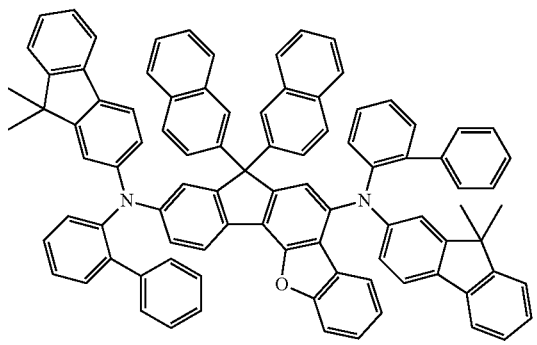
<Chemical Formula 135>
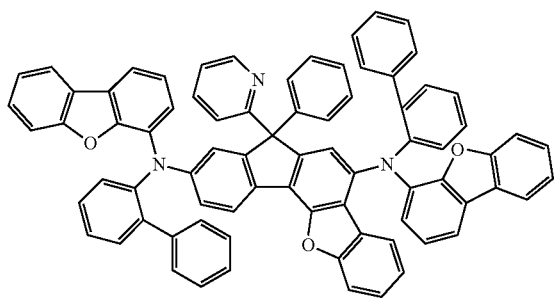
<Chemical Formula 136>
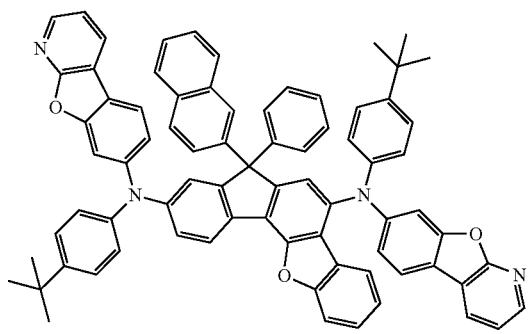
<Chemical Formula 137>
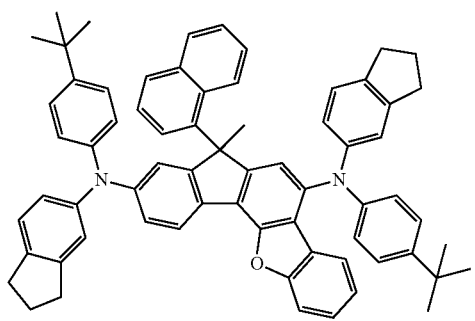
<Chemical Formula 138>
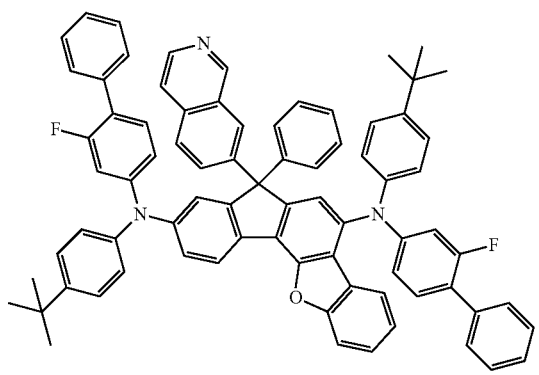

<Chemical Formula 139>
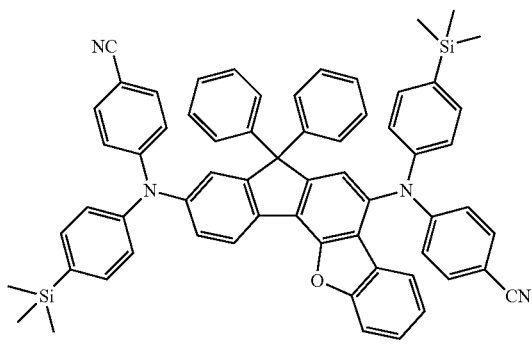
<Chemical Formula 140>
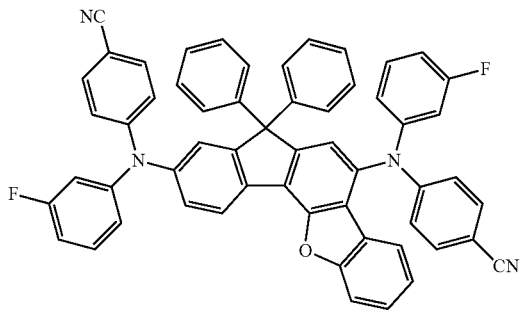
<Chemical Formula 141>
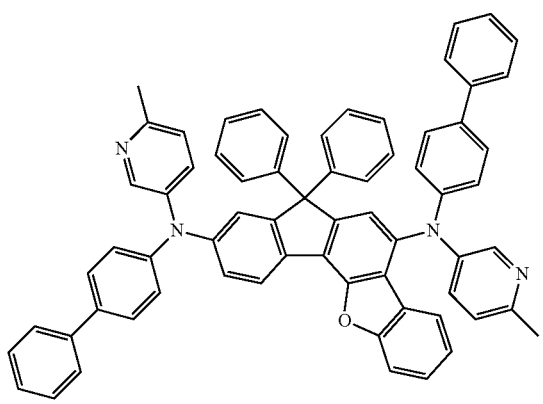
<Chemical Formula 142>
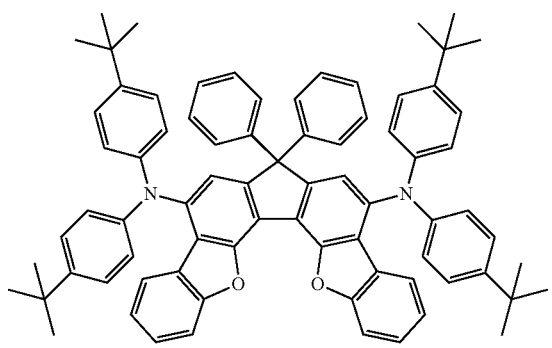
<Chemical Formula 143>
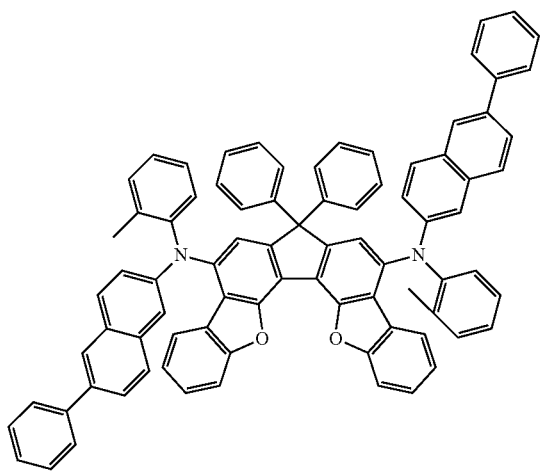
<Chemical Formula 144>
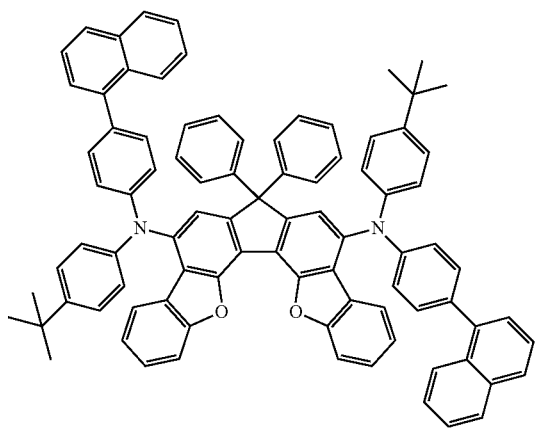

<Chemical Formula 145>
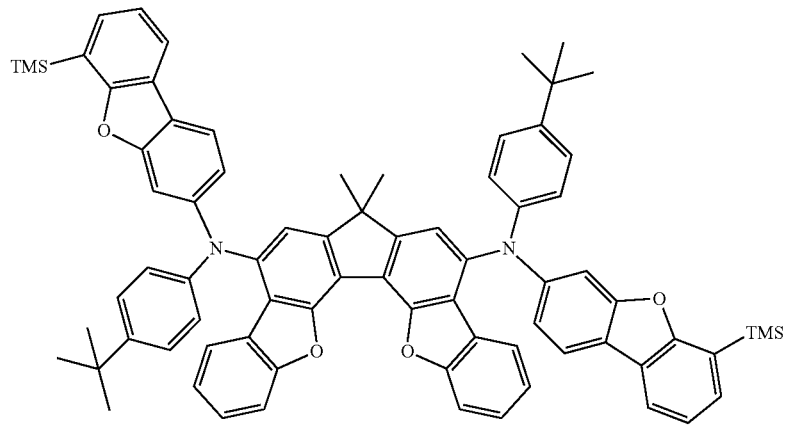
<Chemical Formula 146>
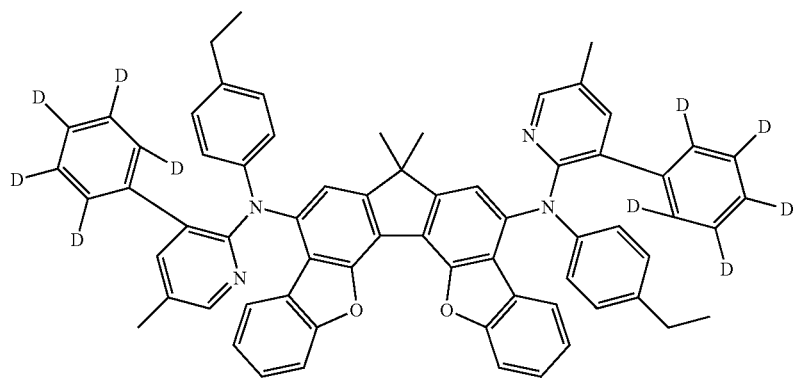
<Chemical Formula 147>
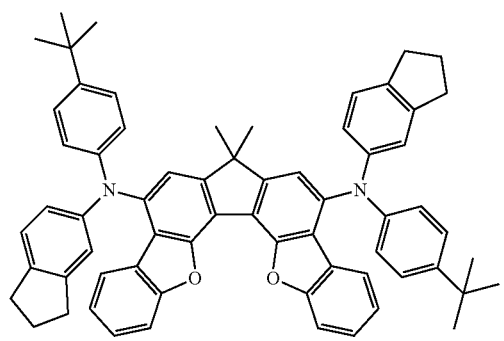
<Chemical Formula 148>
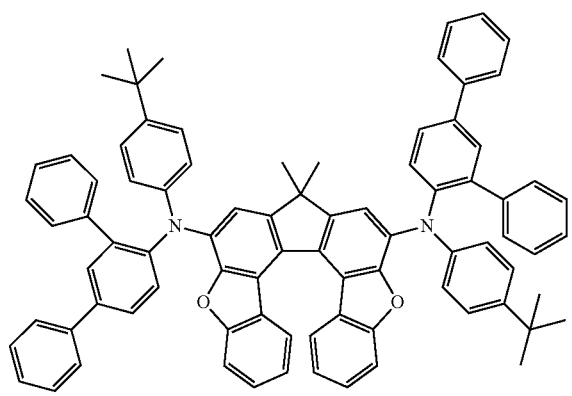
<Chemical Formula 149>
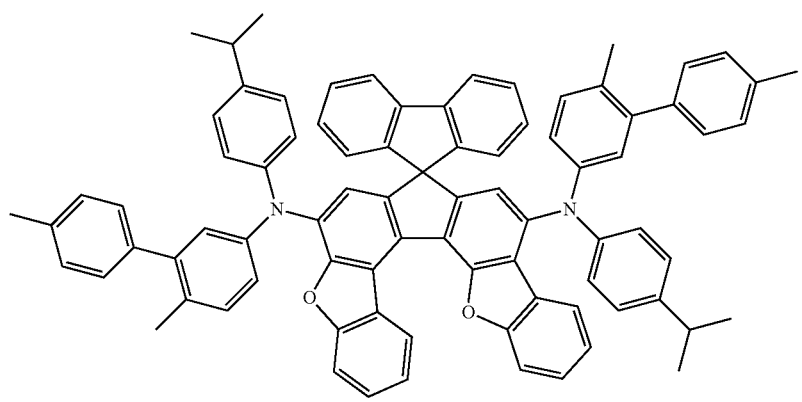

<Chemical Formula 150>
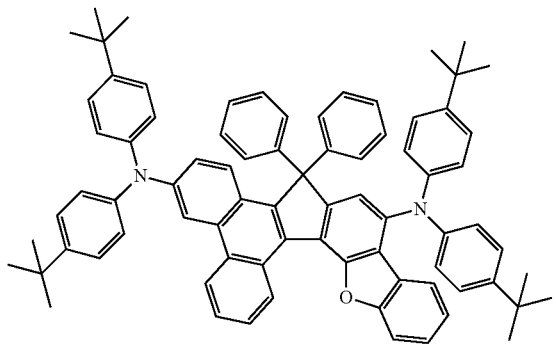
<Chemical Formula 151>
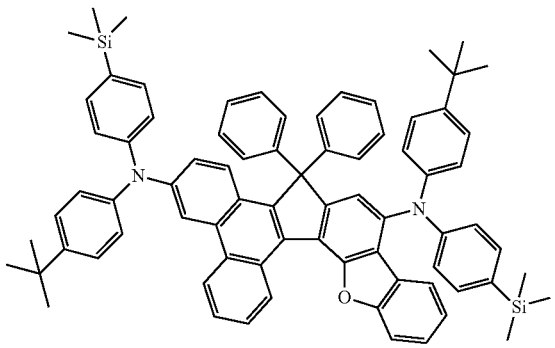
<Chemical Formula 152>
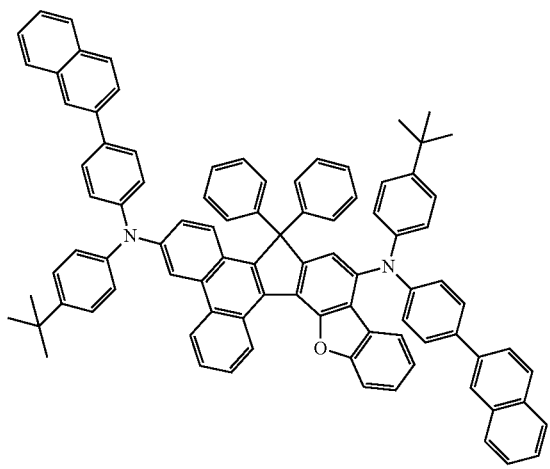
<Chemical Formula 153>
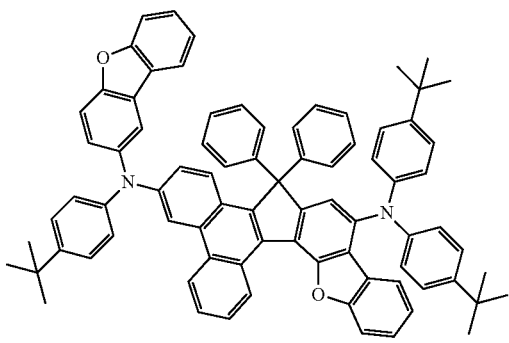
<Chemical Formula 154>
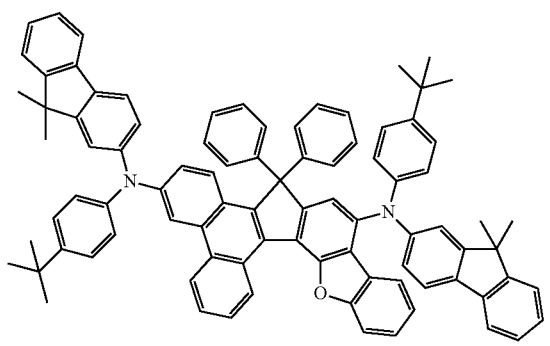
<Chemical Formula 155>
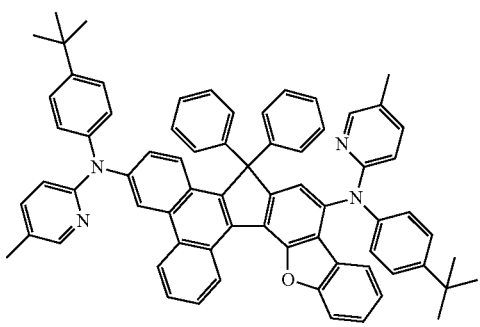
<Chemical Formula 156>
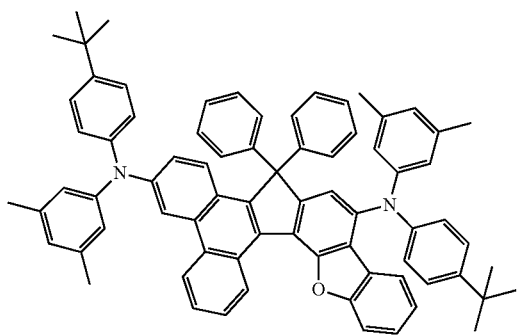
<Chemical Formula 157>
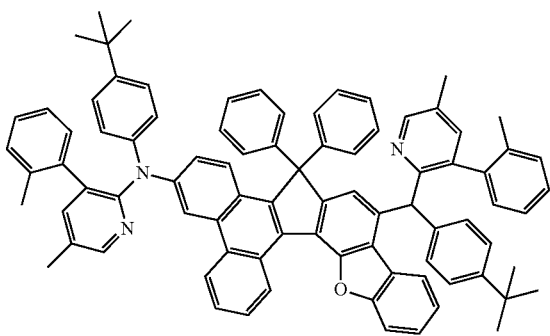

-continued
<Chemical Formula 158>
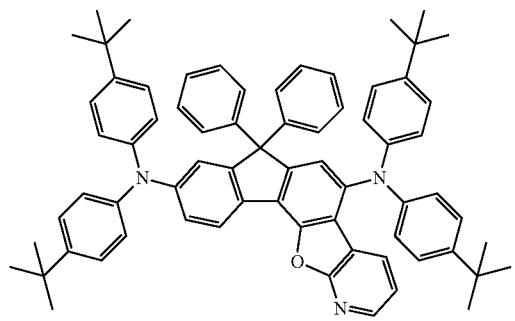
<Chemical Formula 159>
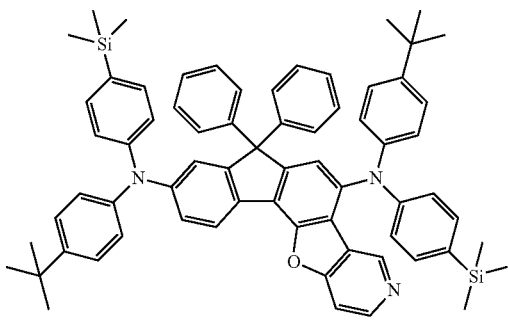
<Chemical Formula 160>
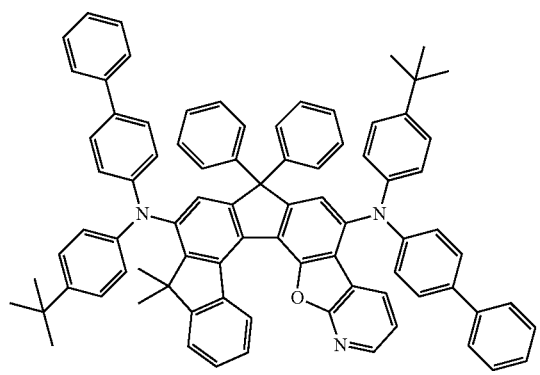
<Chemical Formula 161>
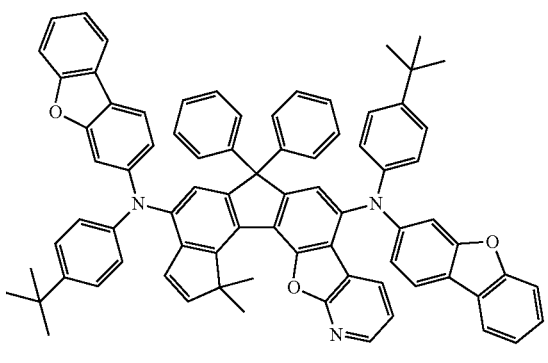
<Chemical Formula 162>
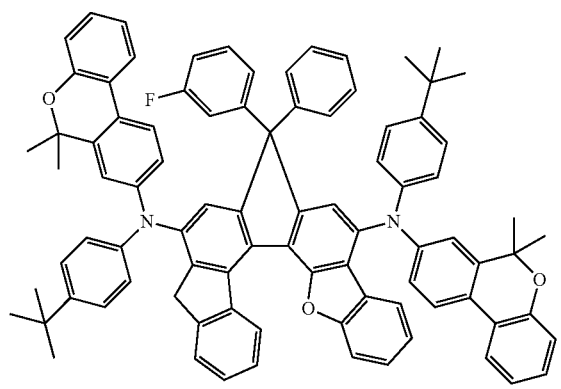
<Chemical Formula 163>
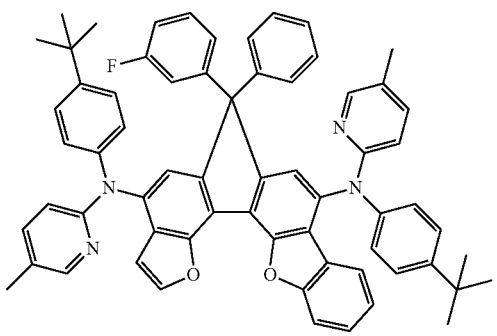
<Chemical Formula 164>
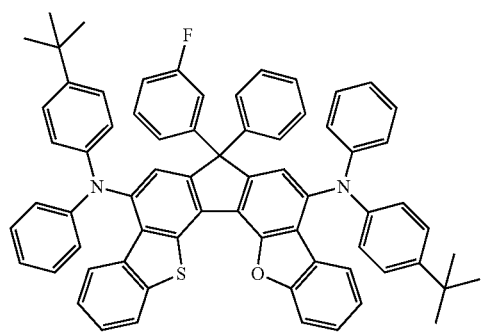
<Chemical Formula 165>
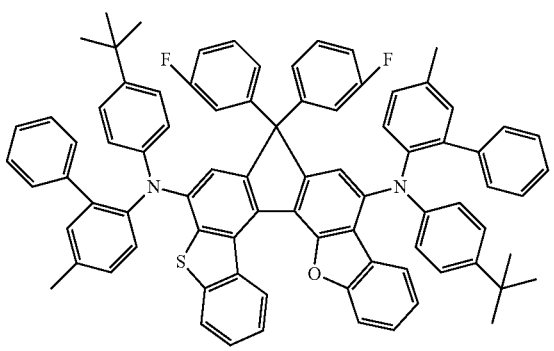

-continued
<Chemical Formula 166>
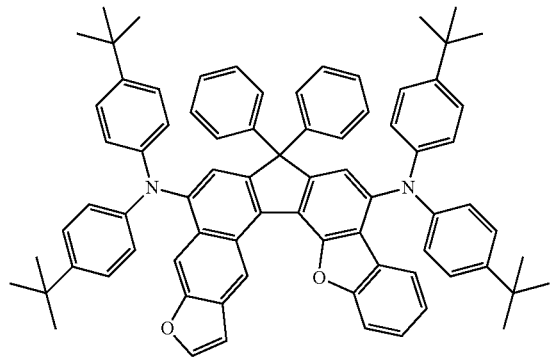
<Chemical Formula 167>
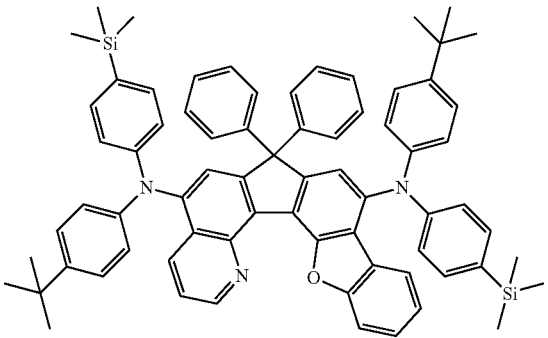
<Chemical Formula 168>
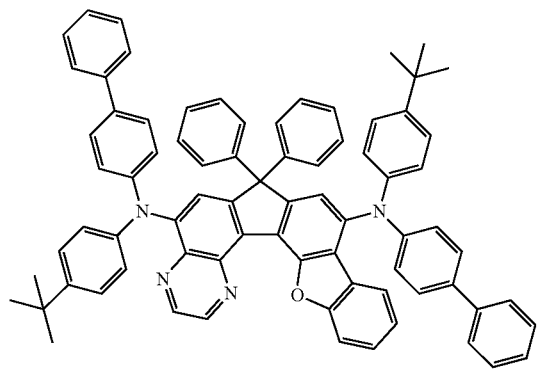
<Chemical Formula 169>
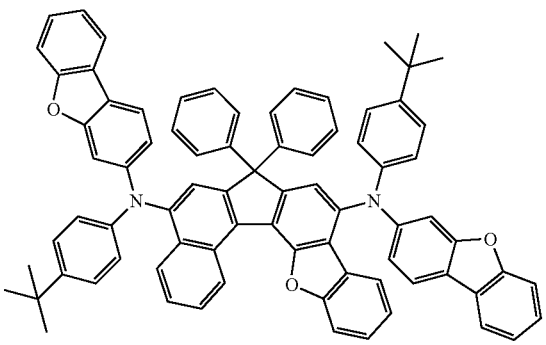
<Chemical Formula 170>
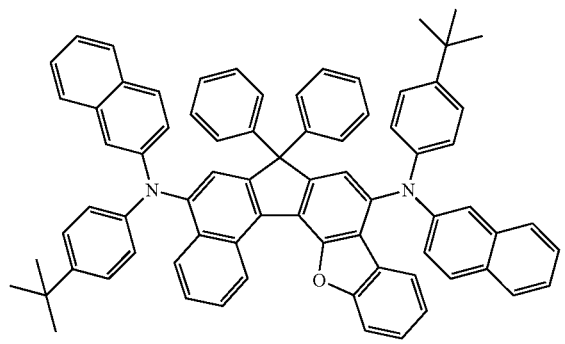
<Chemical Formula 171>
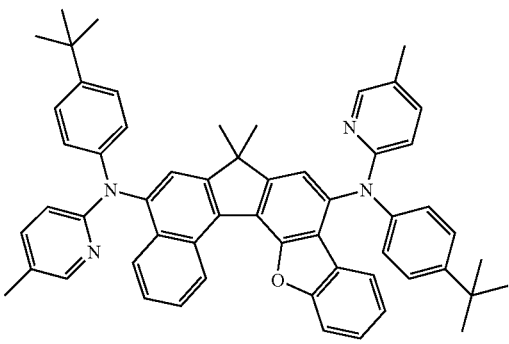
<Chemical Formula 172>
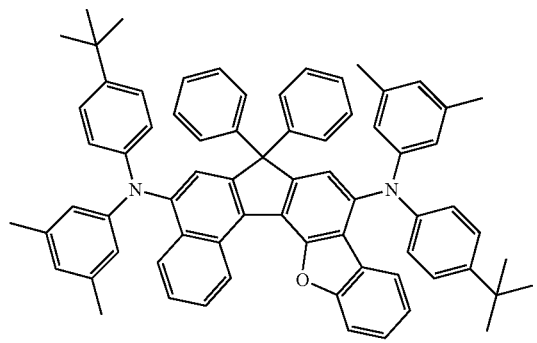
<Chemical Formula 173>
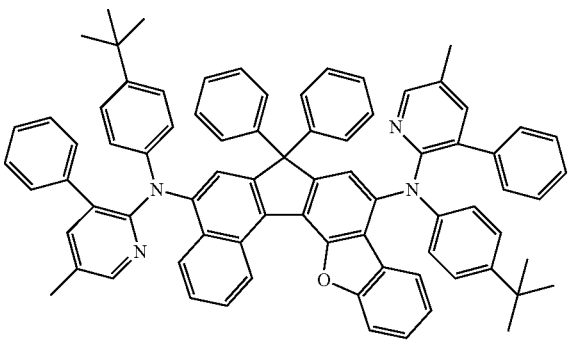

<Chemical Formula 174>
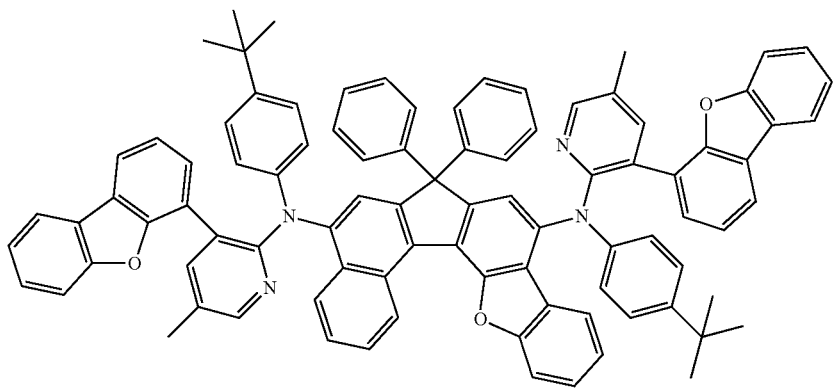
<Chemical Formula 175>
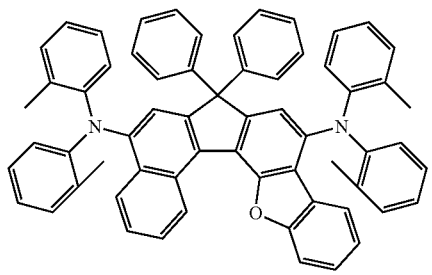
<Chemical Formula 176>
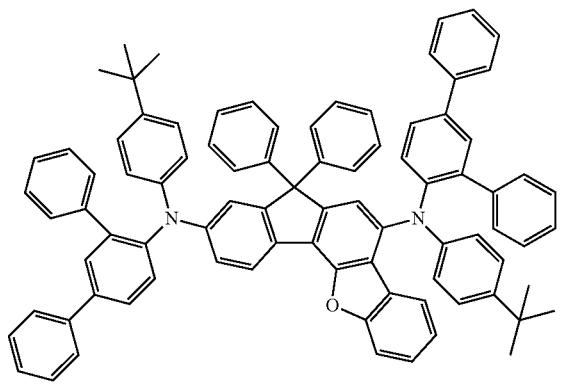
<Chemical Formula 177>
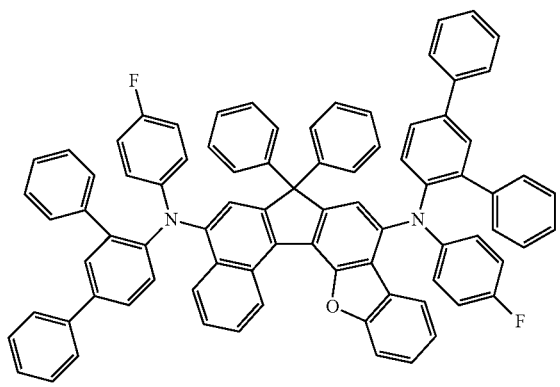
<Chemical Formula 178>
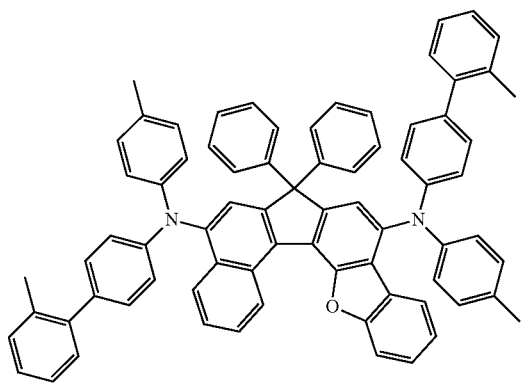
<Chemical Formula 179>
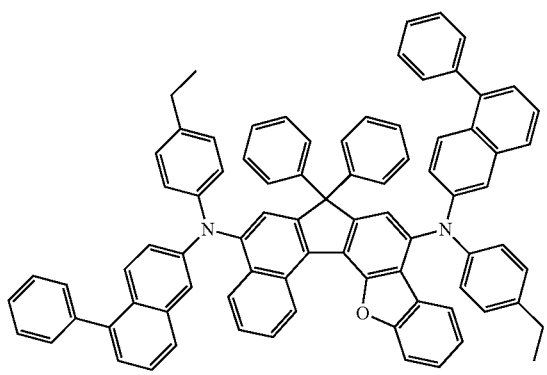
<Chemical Formula 180>
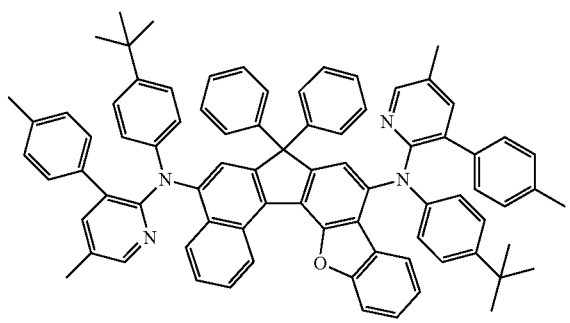

<Chemical Formula 181>
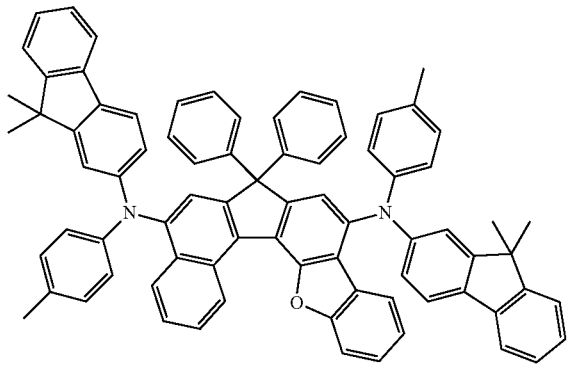
<Chemical Formula 182>
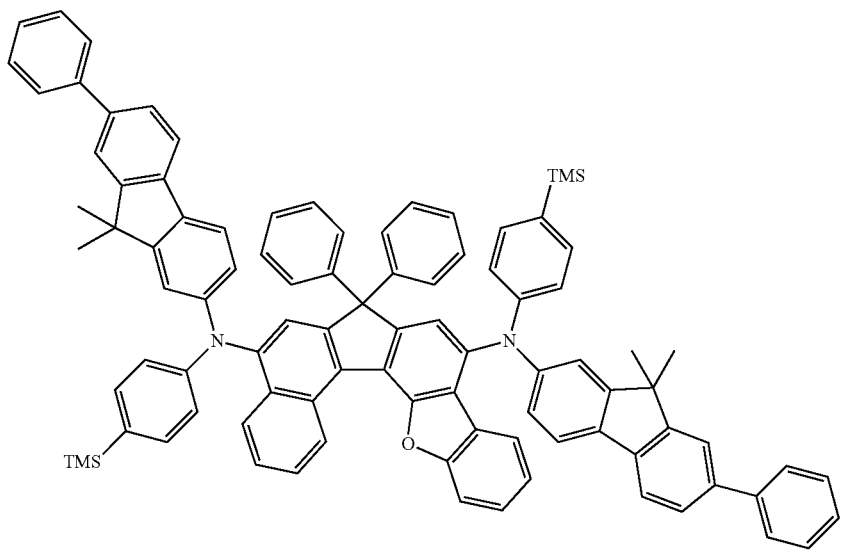
<Chemical Formula 183>
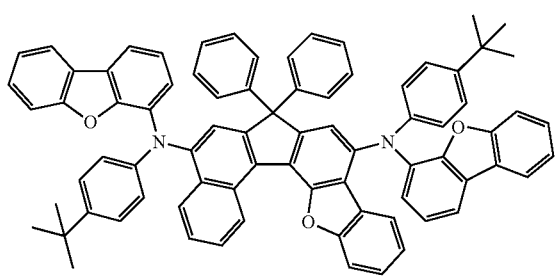
<Chemical Formula 184>
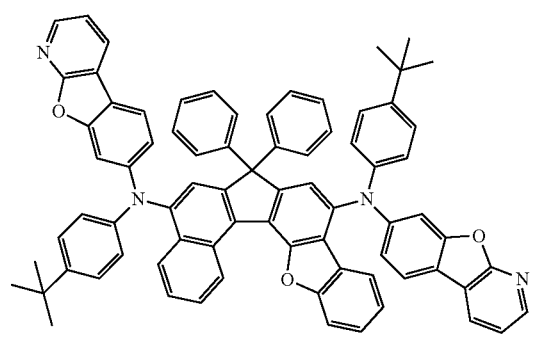

<Chemical Formula 185>
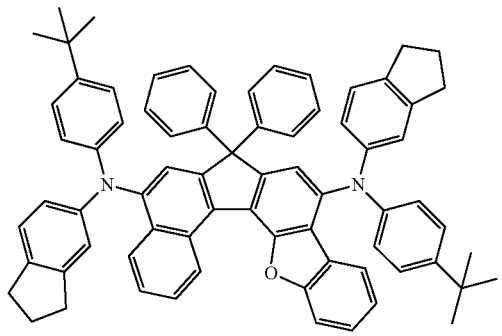
<Chemical Formula 186>
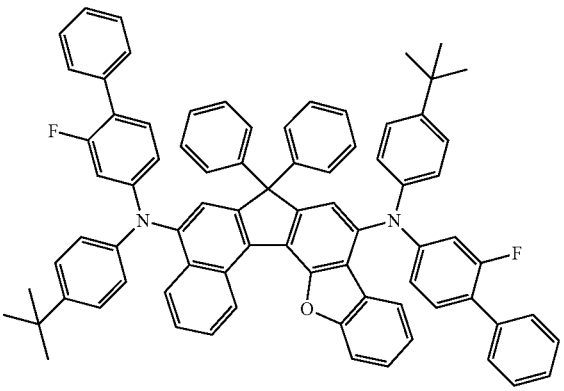
<Chemical Formula 187>
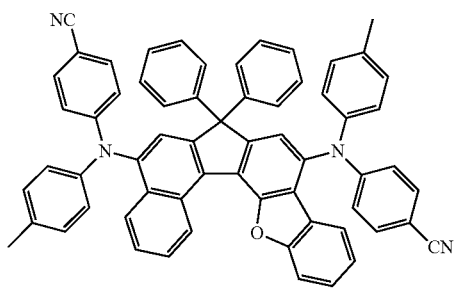
<Chemical Formula 188>
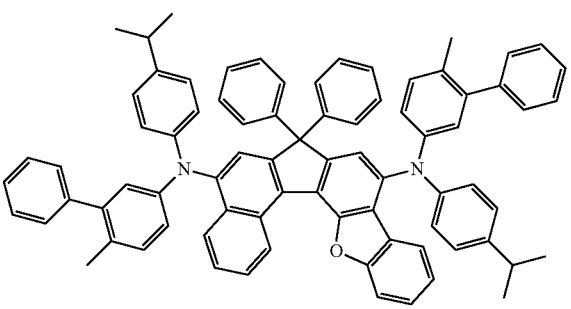
<Chemical Formula 189>
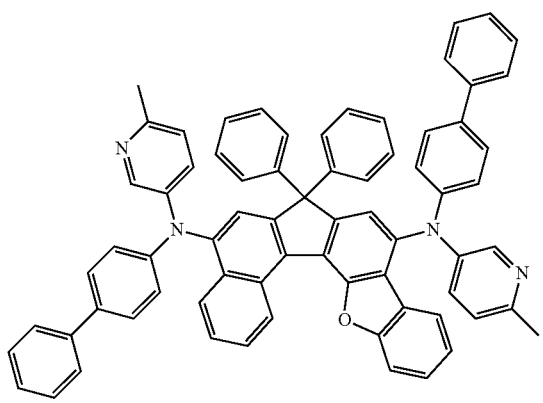
<Chemical Formula 190>
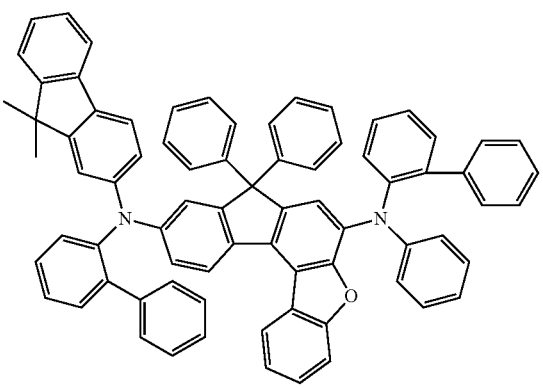
<Chemical Formula 191>
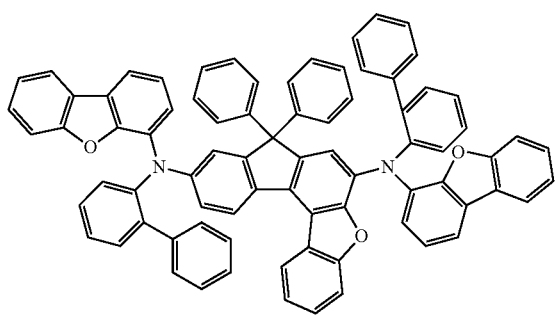
<Chemical Formula 192>
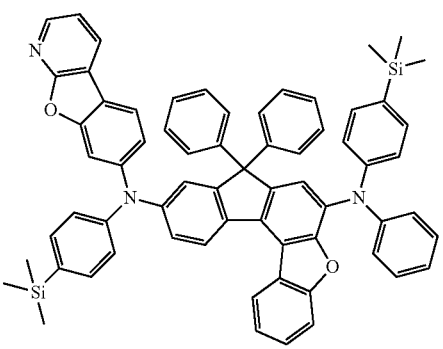

-continued
<Chemical Formula 193>
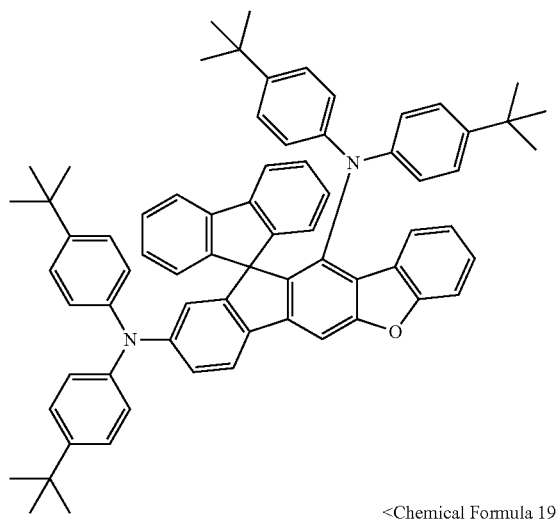
<Chemical Formula 194>
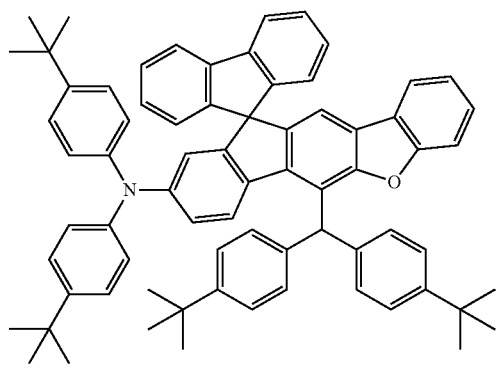
<Chemical Formula 195>
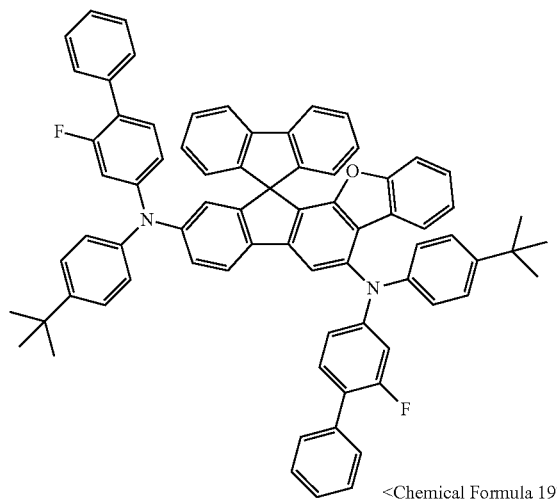
<Chemical Formula 196>
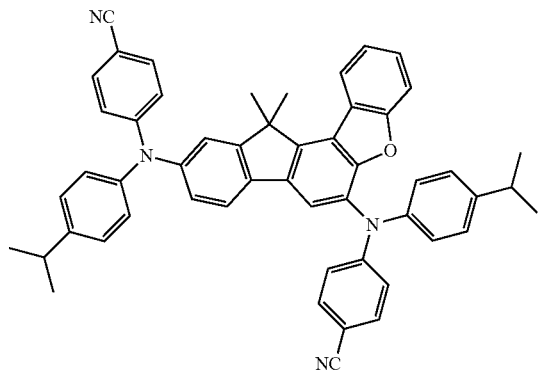
<Chemical Formula 197>
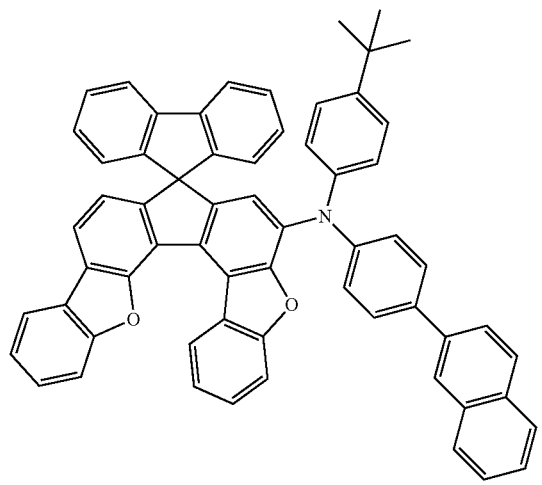
<Chemical Formula 198>
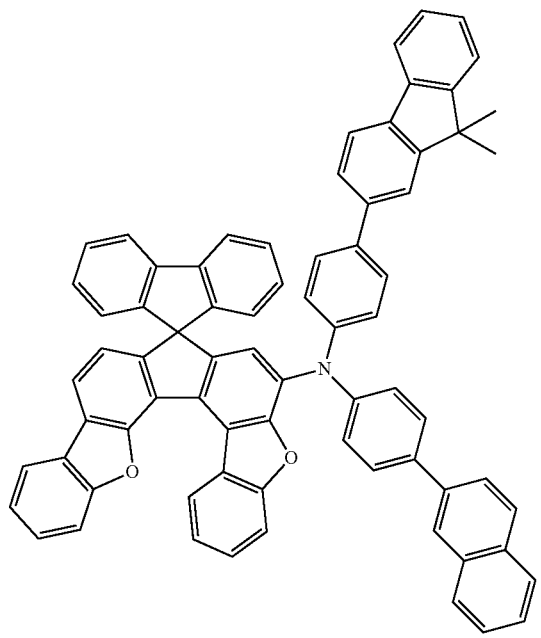

-continued
<Chemical Formula 199>
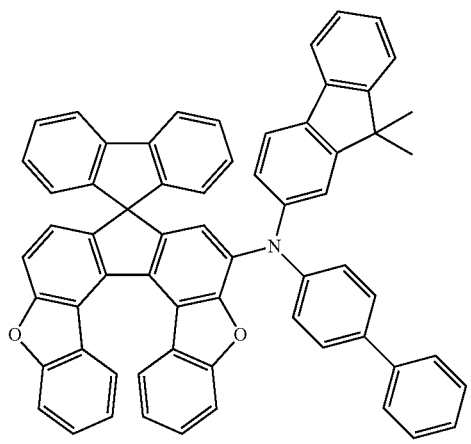
<Chemical Formula 200>
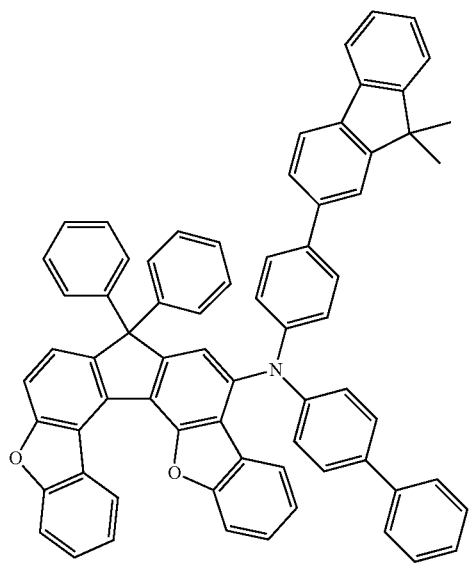
<Chemical Formula 201>
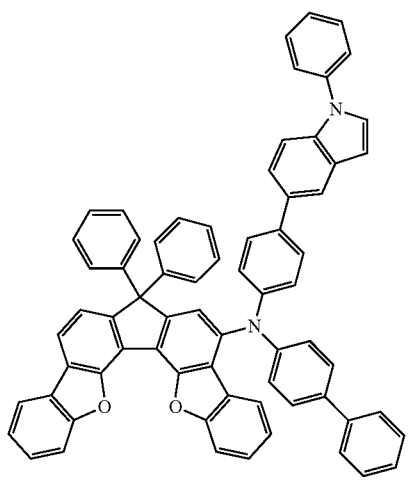
<Chemical Formula 202>
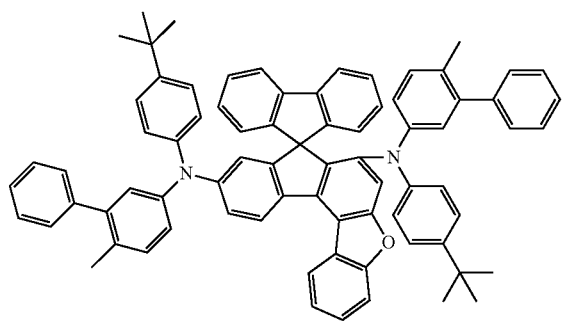
<Chemical Formula 203>
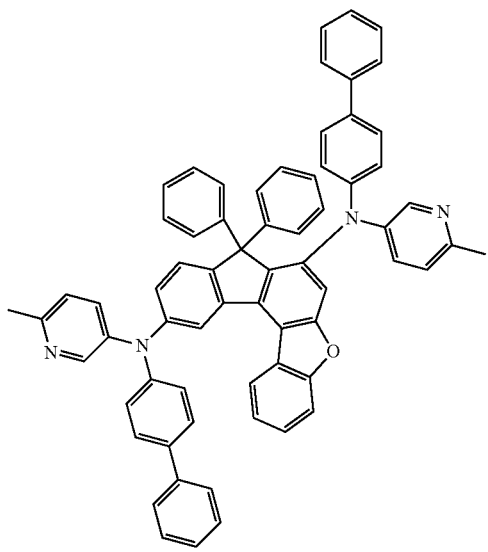
<Chemical Formula 204>
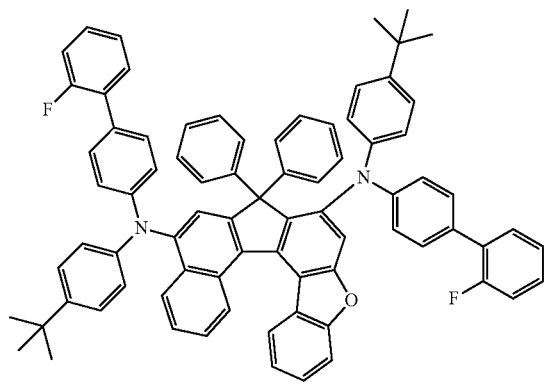

-continued
<Chemical Formula 205>
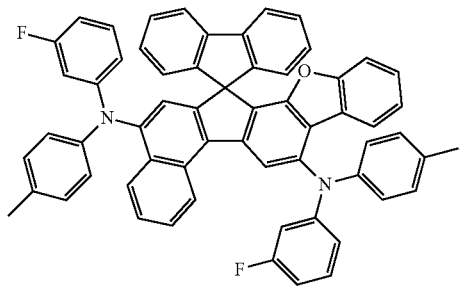
<Chemical Formula 206>
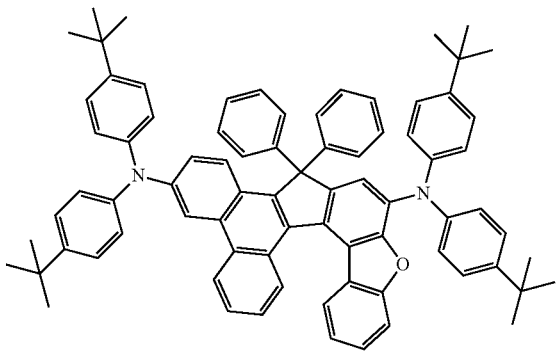
<Chemical Formula 207>
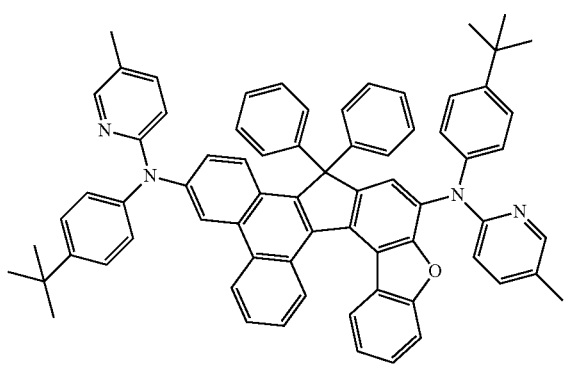
<Chemical Formula 208>
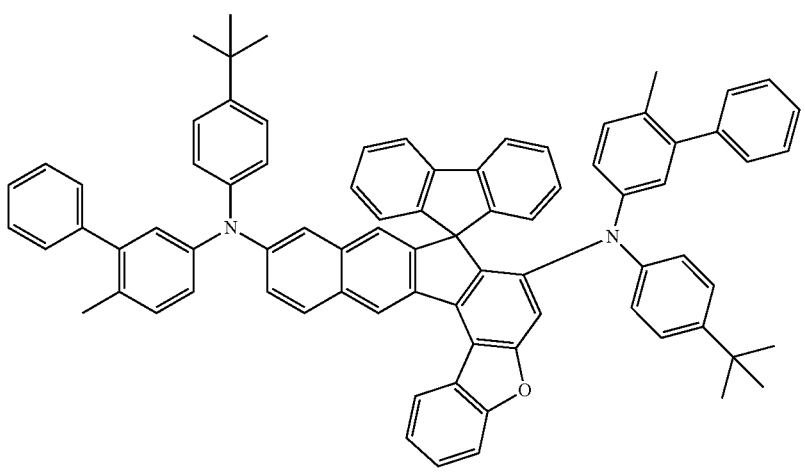
<Chemical Formula 209>
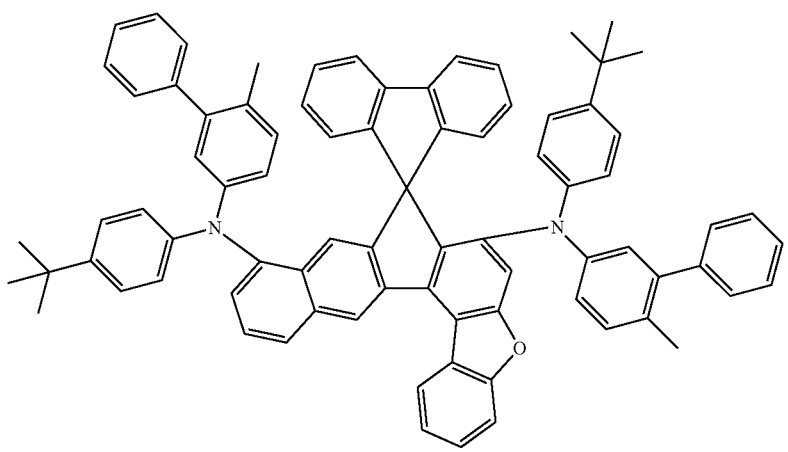

-continued
<Chemical Fomula 210>
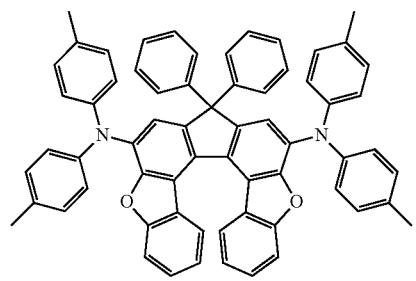
<Chemical Formula 211>
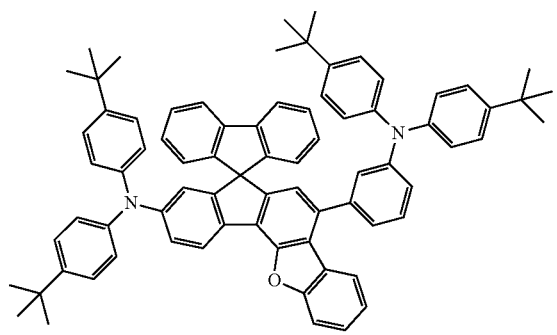
<Chemical Formula 212>
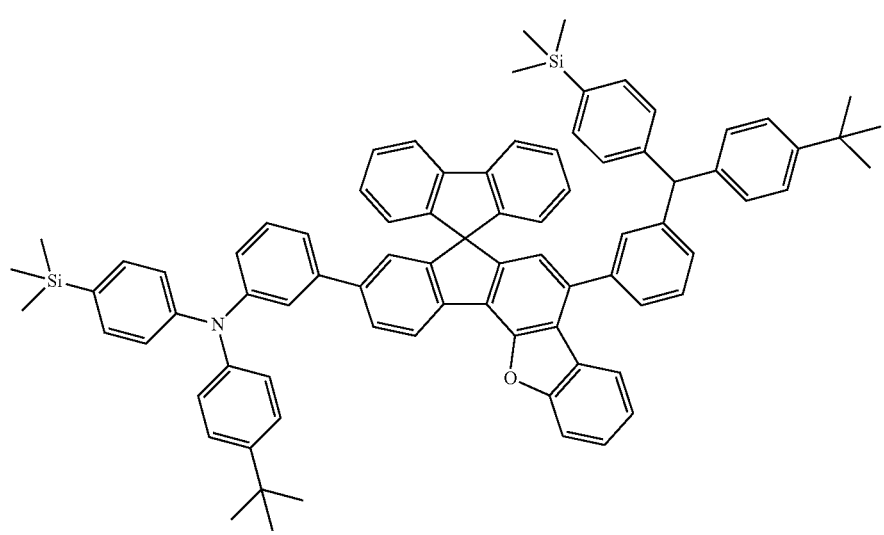
<Chemical Formula 213>
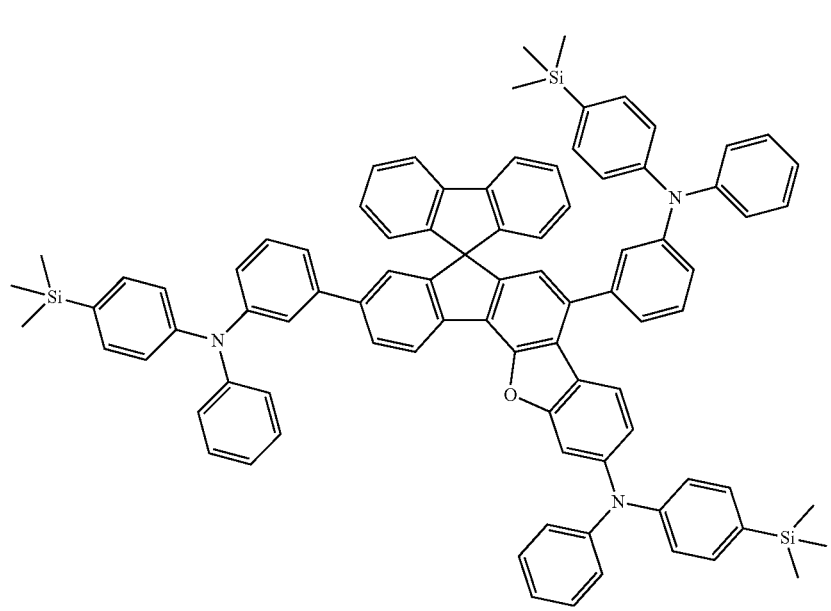

-continued
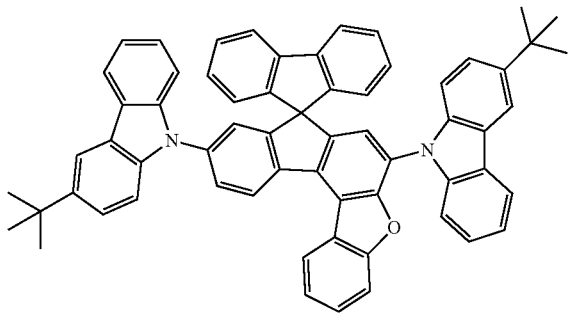
<Chemical Formula 214>
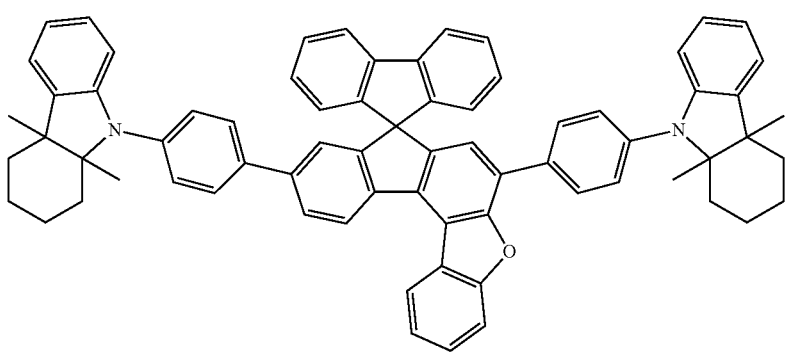
<Chemical Formula 215>
<Chemical Formula 216>
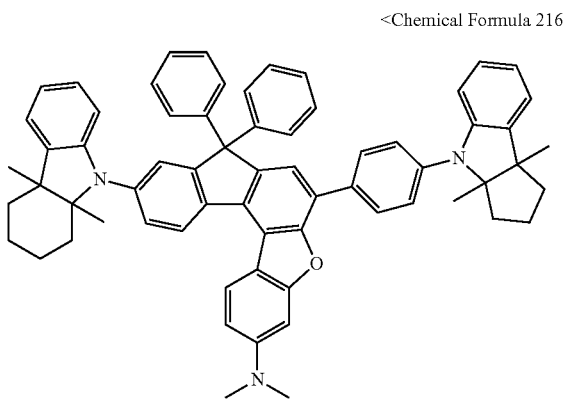
<Chemical Formula 217>
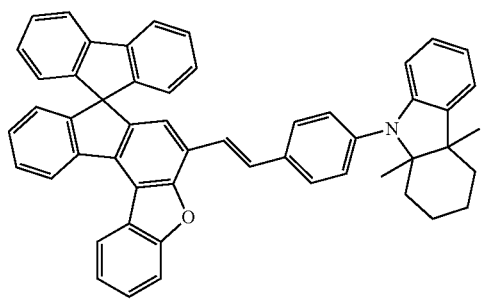
<Chemical Formula 218>
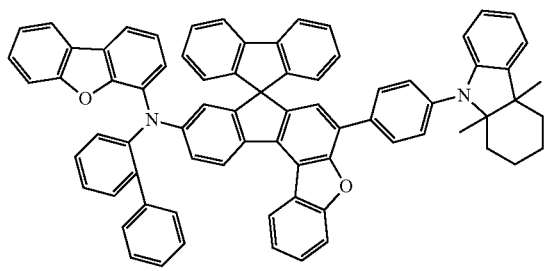
<Chemical Formula 219>
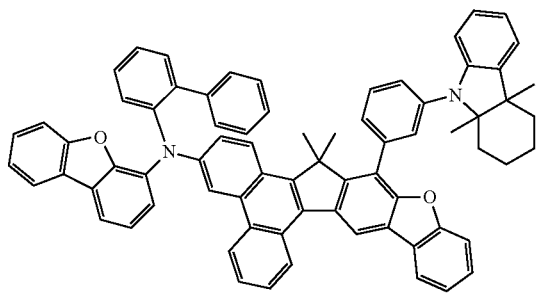

-continued
<Chemical Formula 220>
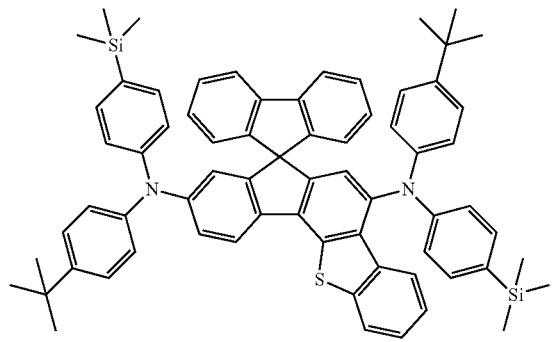
<Chemical Formula 221>
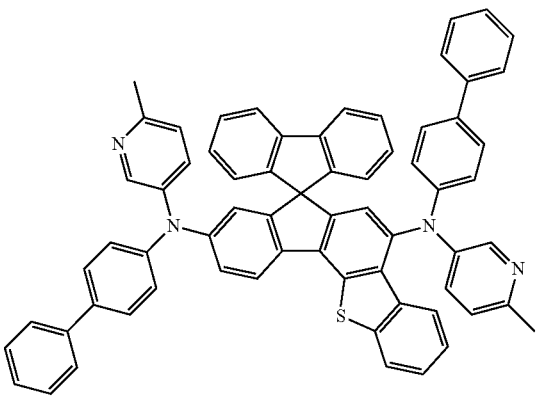
<Chemical Formula 222>
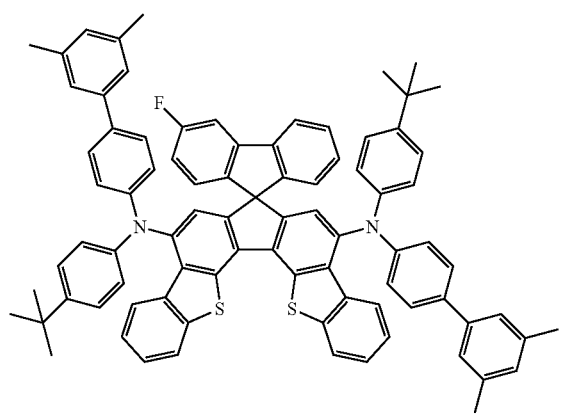
<Chemical Formula 223>
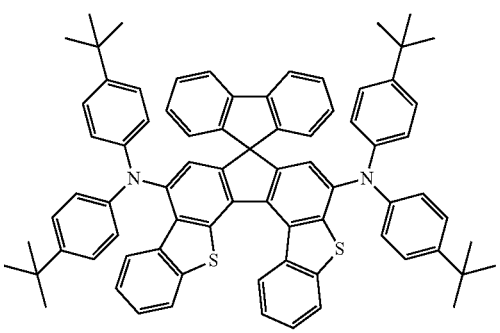
<Chemical Formula 224>
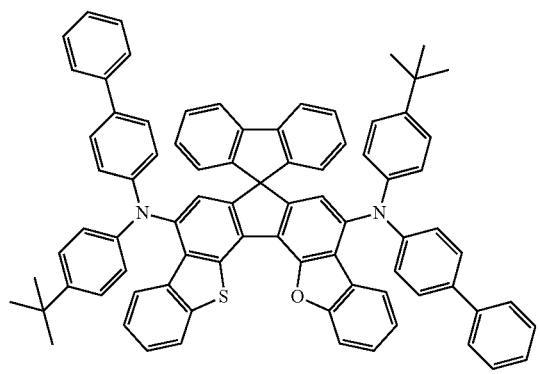
<Chemical Formula 225>
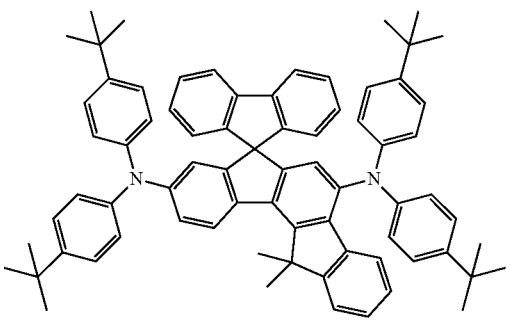
<Chemical Formula 226>
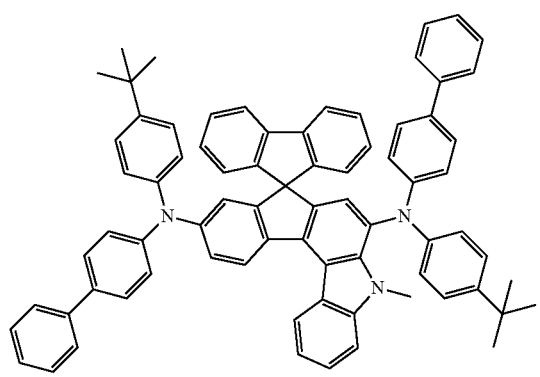
<Chemical Formula 227>
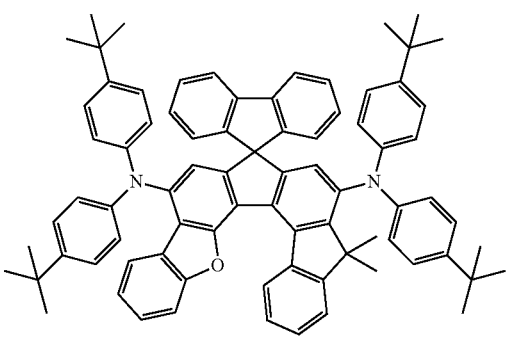

<Chemical Formula 228>
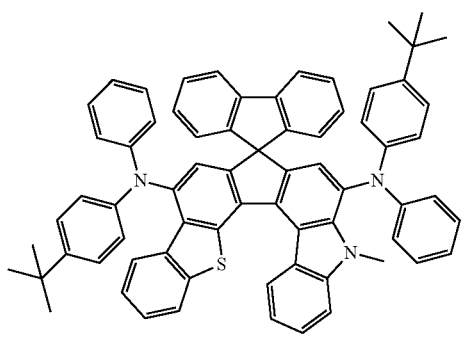
<Chemical Formula 229>
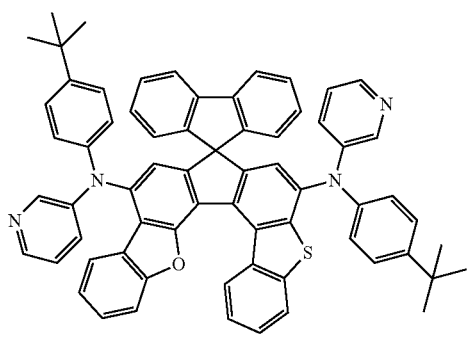
<Chemical Formula 230>
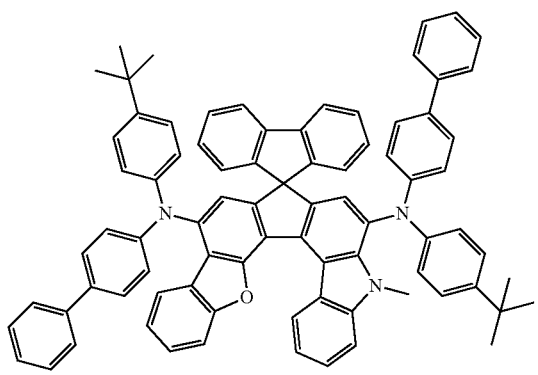
<Chemical Formula 231>
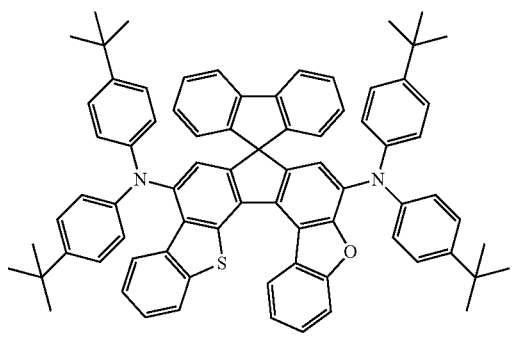
<Chemical Formula 232>
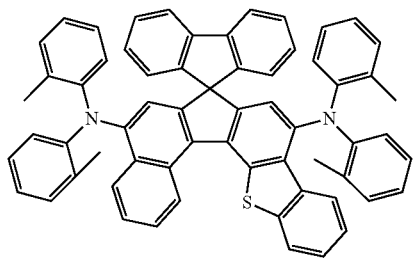
<Chemical Formula 233>
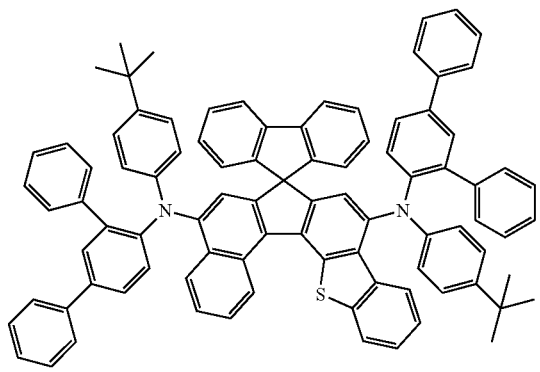
<Chemical Formula 234>
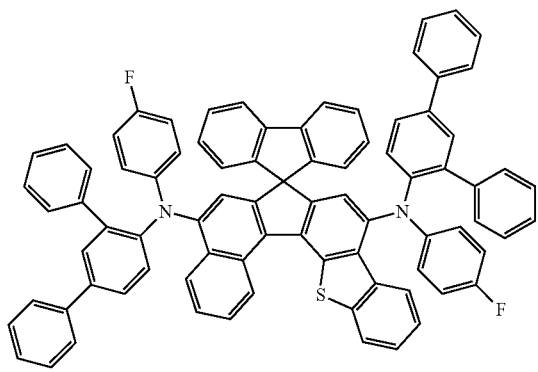
<Chemical Formula 235>
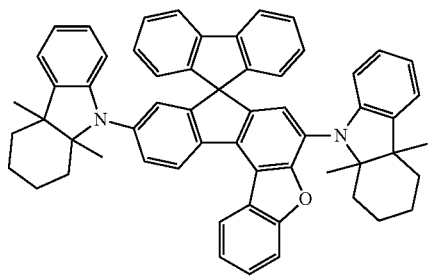

<Chemical Formula 236>

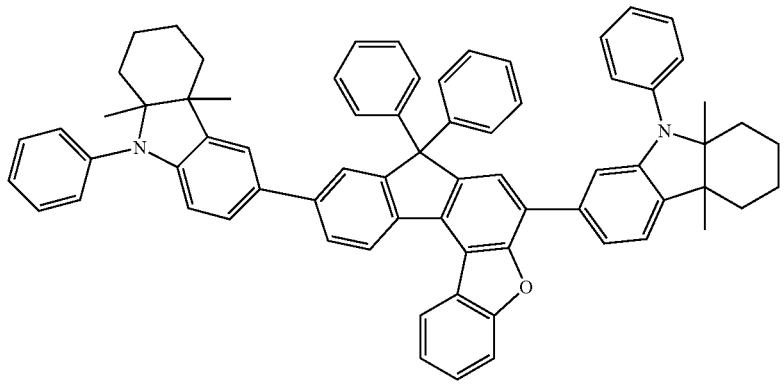

<Chemical Formula 237>

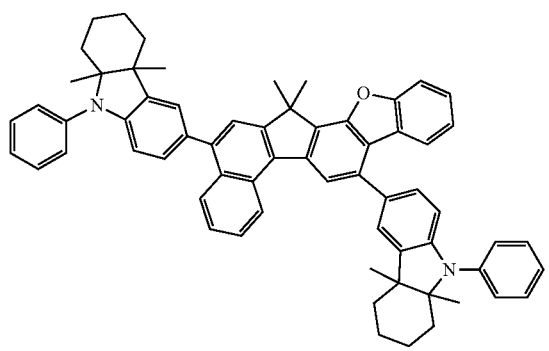

<Chemical Formula 238>

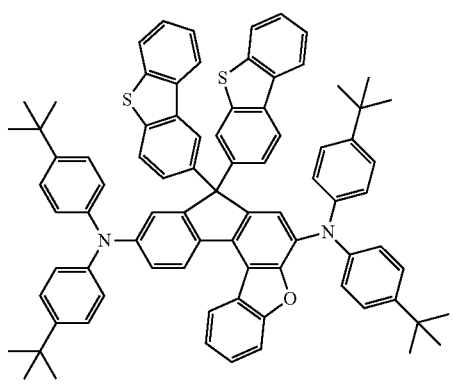

<Chemical Formula 239>

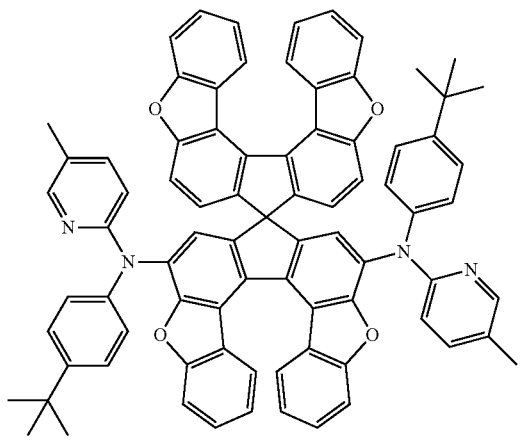

In accordance with another aspect thereof, the present disclosure addresses an organic light-emitting diode, comprising a first electrode; a second electrode facing the first electrode; an organic layer interposed between the first electrode and the second electrode, wherein the organic layer comprises at least one of the organic luminescent compounds of the present disclosure.

As used herein, the expression "(the organic layer) . . . comprising at least one organic compound" is construed to mean that the organic layer may comprise one or two or more different compounds that fall within the scope of the present disclosure.

In addition, the organic layer comprising the organic luminescent compound of the present disclosure may further comprise at least one of a hole injection layer, a hole transport layer, a functional layer capable of both hole injection and hole transport, a light-emitting layer, an electron transport layer, and an electron injection layer in addition to the light-emitting layer.

The organic layer interposed between the first electrode and the second electrode may include a light-emitting layer that comprises a host and a dopant, the organic luminescent compound of the present disclosure serving as the dopant.

In the light-emitting layer, a host material may be employed in addition to the dopant. When the light-emitting layer comprises a host and a dopant, the amount of the dopant may range from about 0.01 to about 20 weight parts, based on 100 weight parts of the host, but is not limited thereto.

The material used in the electron transport layer functions to stably carry the electrons injected from the electron injection electrode (cathode), and may be an electron transport material known in the art. Examples of the electron transport material known in the art include quinoline derivatives, particularly, tris(8-quinolinorate)aluminum(Alq3), TAZ, Balq, beryllium bis(benzoquinolin-10-olate (BebQ$_2$), ADN, Compound 201, Compound 202, BCP, and oxadiazole derivatives such as PBD, BMD, BND, etc., but are not limited thereto.

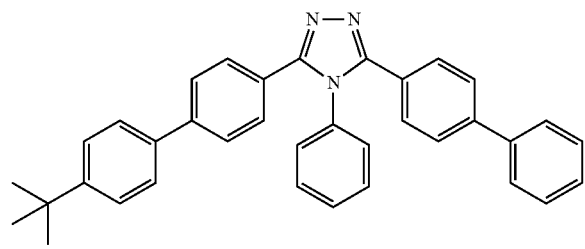

TAZ

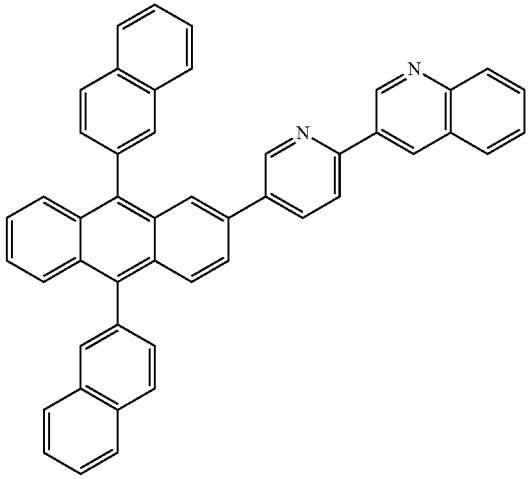

<Cpd. 202>

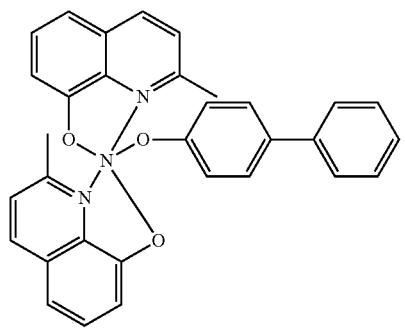

BAlq

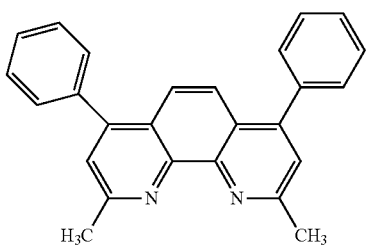

BCP

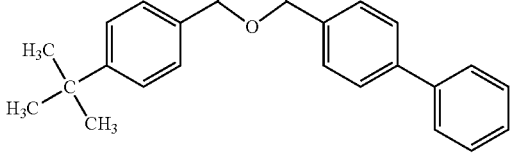

PBD

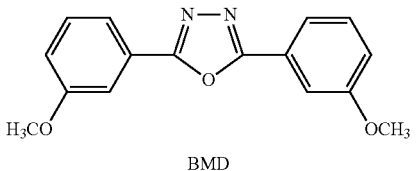

BMD

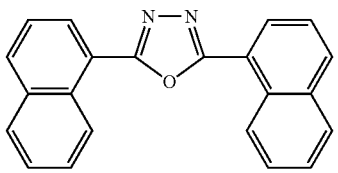

BND

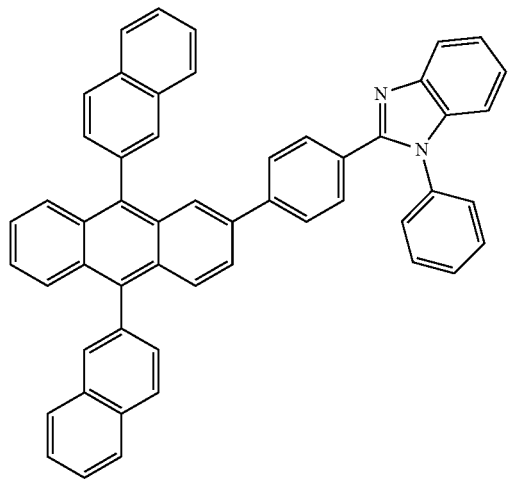

<Cpd. 201>

In addition, the electron transport layer may be made of the organic metal compound represented by Chemical Formula C, either alone or in combination with the aforementioned material.

$$Y_m\text{-M-}(OA)_n \qquad \text{[Chemical Formula C]}$$

wherein,

Y is a ligand that contains two moieties respectively responsible for forming a single bond with M through a direct bond M and for forming a coordinate bond with M, each moiety being selected from among C, N, O and S, and which is chelated by the single bond and the coordinate bond;

M is an alkali metal, an alkaline earth metal, aluminum (Al), or a boron (B) atom, with the proviso that:

when M is an alkali metal, m=1, n=0 when M is an alkaline earth metal, m=1, n=1, or m=2, n=0, or when M is aluminum or a boron, m is an integer of 1 to 3 and n is an integer of 0 to 2, satisfying the relationship m+n=3;

OA is a monodentate ligand capable of forming a single bond or a coordinate bond with M, wherein O is oxygen, and A is selected from among a substituted or unsubstituted alkyl of 1 to 30 carbon atoms, a substituted or unsubstituted aryl of 5 to 50 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, and a substituted or unsubstituted heteroaryl of 2 to 50 carbon atoms containing as a heteroatom at least one selected from among O, N, S and Si.

The term 'substituted' in the expression 'substituted or unsubstituted' means having at least one substituent selected from the group consisting of a deuterium atom, a cyano, a halogen, a hydroxy, a nitro, an alkyl, an alkoxy, an alkylamino, an arylamino, a hetero arylamino, an alkylsilyl, an arylsilyl, an aryloxy, an aryl, a heteroaryl, germanium, phosphorus, and boron.

In the present disclosure, the Y's may be the same or different and are each independently selected from among the following Structural Formula s C1 to C39, but are not limited thereto:

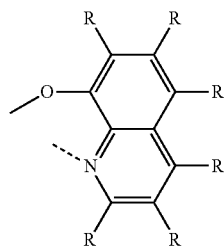

[Structural Formula C1]

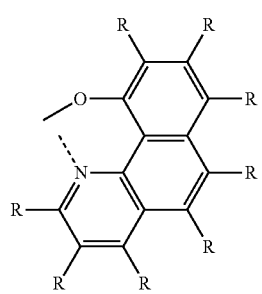

[Structural Formula C2]

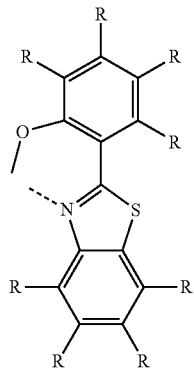

[Structural Formula C3]

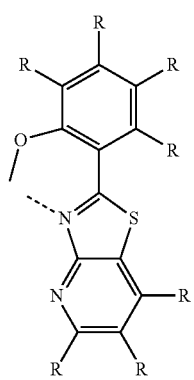

[Structural Formula C4]

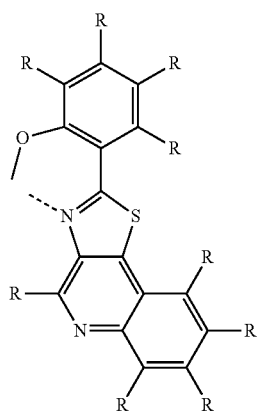

[Structural Formula C5]

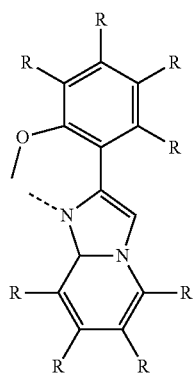

[Structural Formula C6]

[Structural Formula C7]
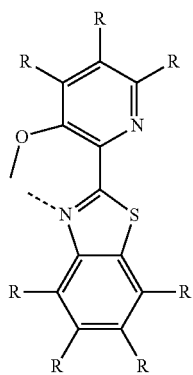
[Structural Formula C8]
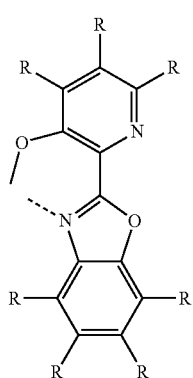
[Structural Formula C9]
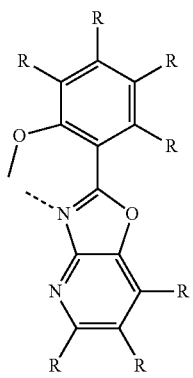
[Structural Formula C10]
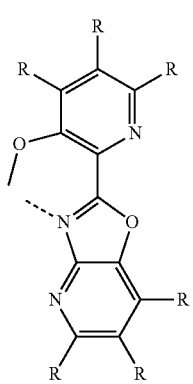
[Structural Formula C11]
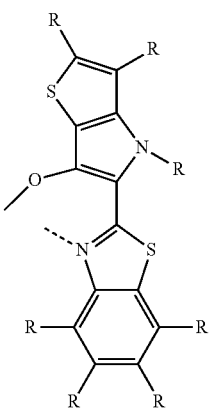
[Structural Formula C12]
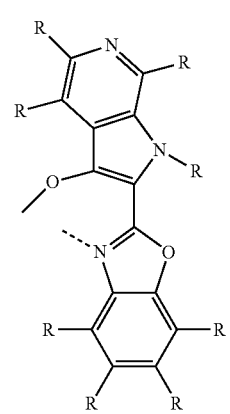
[Structural Formula C13]
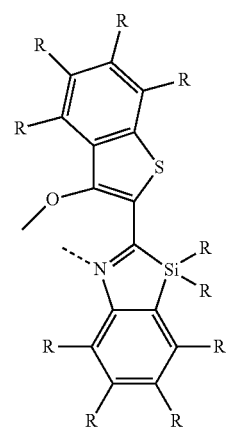
[Structural Formula C14]
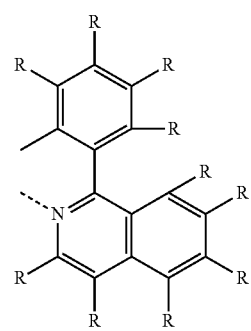

[Structural Formula C15]
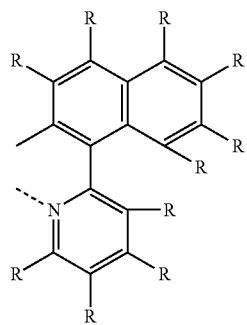
[Structural Formula C16]
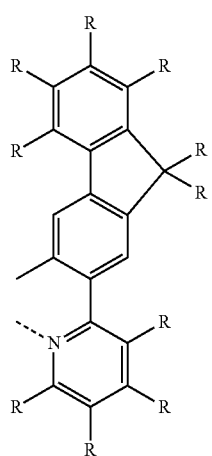
[Structural Formula C17]
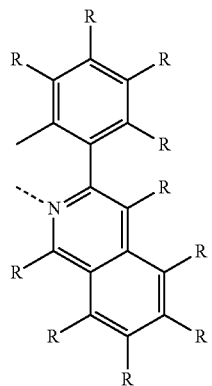
[Structural Formula C18]
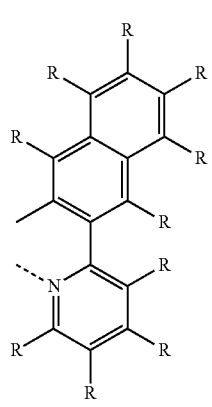
[Structural Formula C19]
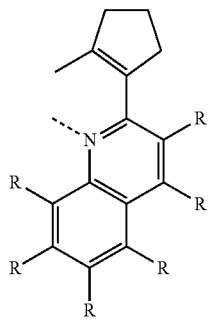
[Structural Formula C20]
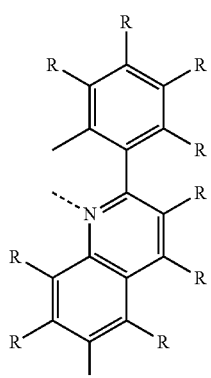
[Structural Formula C21]
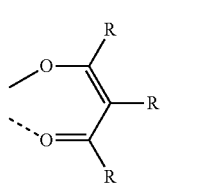
[Structural Formula C22]
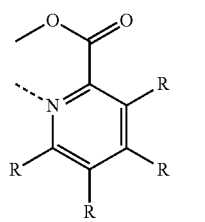
[Structural Formula C23]
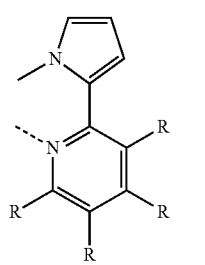
[Structural Formula C24]
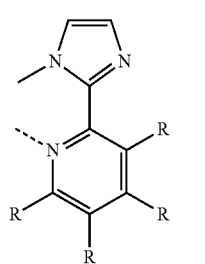

[Structural Formula C25]
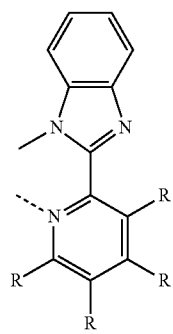
[Structural Formula C26]
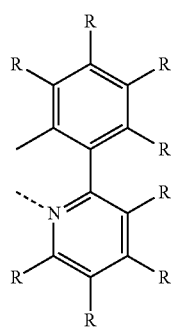
[Structural Formula C27]
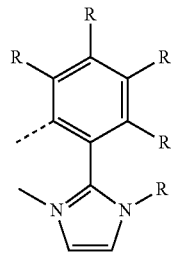
[Structural Formula C28]
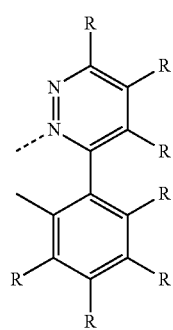
[Structural Formula C29]
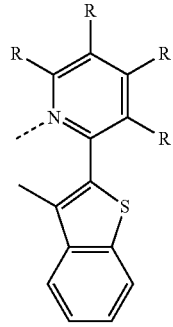
[Structural Formula C30]
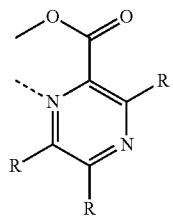
[Structural Formula C31]
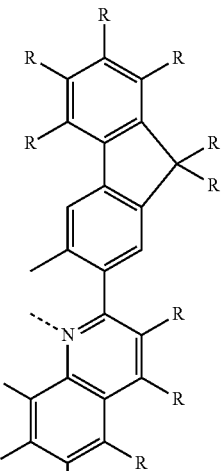
[Structural Formula C32]
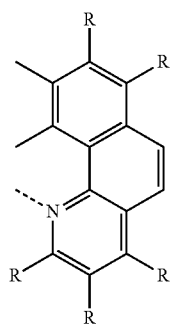
[Structural Formula C33]
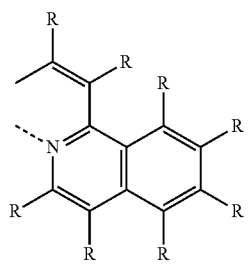
[Structural Formula C34]
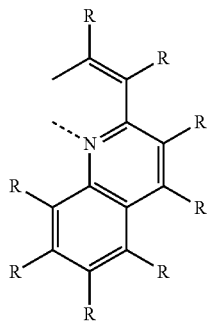

-continued

[Structural Formula C35]
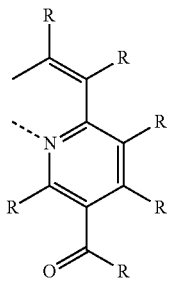

[Structural Formula C36]
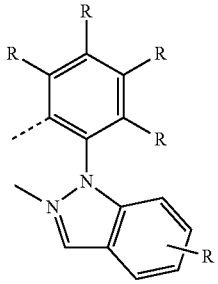

[Structural Formula C37]
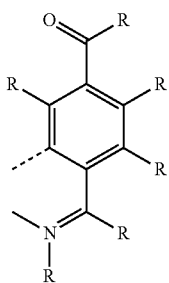

[Structural Formula C38]
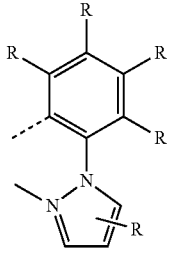

[Structural Formula C39]
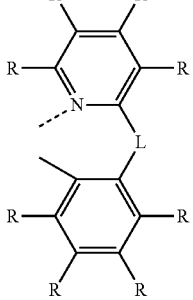

wherein,
R's, which may be the same or different, are each independently selected from among halogen, deuterium, halogen, cyano, a substituted or unsubstituted alkyl of 1 to 30 carbon atoms, a substituted or unsubstituted aryl of 6 to 60 carbon atoms, a substituted or unsubstituted heteroaryl of 3 to 30 carbon atoms, a substituted or unsubstituted alkoxy of 1 to 30 carbon atoms, a substituted or unsubstituted cycloalkyl of 3 to 30 carbon atoms, a substituted or unsubstituted alkenyl of 2 to 30 carbon atoms, a substituted or unsubstituted alkylamino of 1 to 30 carbon atoms, a substituted or unsubstituted alkylsilyl of 1 to 30 carbon atoms, a substituted or unsubstituted arylamino of 6 to 60 carbon atoms, and a substituted or unsubstituted arylsilyl of 6 to 60 carbon atoms, and may form a spiro or fused ring with an adjacent substituent via an alkylene or alkenylene linker.

Below, a description will be given of the organic light-emitting diode of the present disclosure, with reference to FIG. 1.

FIG. 1 is a schematic cross-sectional view of the structure of an organic light-emitting diode according to some embodiments of the present disclosure. The organic light-emitting diode comprises an anode 20, a hole transport layer 40, an organic light-emitting layer 50, an electron transport layer 60, and a cathode 80, and optionally a hole injection layer 30 and an electron injection layer 70. In addition, one or two intermediate layers may be further formed in the organic light-emitting diode, or a hole barrier layer or an electron barrier layer may also be employed.

Reference is made to FIG. 1 with regard to the fabrication of the organic light-emitting diode of the present disclosure. First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, and handleability. As the anode electrode material, indium tin oxide (ITO), indium zinc oxide (IZO), tin oxide ($SnO_2$), or zinc oxide (ZnO) may be used.

A hole injection layer material is applied on the anode electrode 20 by thermal deposition in a vacuum or by spin coating to form a hole injection layer 30. Subsequently, thermal deposition in a vacuum or by spin coating may also be conducted to form a hole transport layer 40 with a hole transport layer material on the hole injection layer 30.

No particular limitations are imposed on the hole injection layer material, as long as it is one that is typically used in the art. For example, mention may be made of 2-TNATA [4,4',4"-tris(2-naphthylphenyl-phenylamino)-triphenylamine], NPD [N,N'-di(1-naphthyl)-N,N'-diphenylbenzidine)], TPD [N,N'-diphenyl-N,N'-bis(3-methylphenyl)-1,1'-biphenyl-4,4'-diamine], or DNTPD [N,N'-diphenyl-N,N'-bis-[4-(phenyl-m-tolyl-amino)-phenyl]-biphenyl-4,4'-diamine].

So long as it is typically used in the art, any material for the hole transport layer may be selected without particular limitation. Examples include, but are not limited to, N,N'-bis(3-methylphenyl)-N,N'-diphenyl-[1,1-biphenyl]-4,4'-diamine(TPD) or N,N'-di(naphthalen-1-yl)-N,N'-diphenylbenzidine (α-NPD).

Then, an organic light-emitting layer 50 is deposited on the hole transport layer 40, optionally followed by the formation of a hole barrier layer (not shown) on the organic light-emitting layer 50 by deposition in a vacuum or by spin coating. When holes traverse the organic light-emitting layer and are introduced into the cathode, the diode becomes poor in efficiency and lifetime. Formed of a material with a low HOMO (Highest Occupied Molecular Orbital) level, the hole barrier layer serves to prevent the introduction of holes into the cathode. Any material that has a higher ionization potential than the light-emitting compound and is also able to carry electrons may be used for the hole barrier layer without limitation. Representative among hole barrier materials are BAlq, BCP, and TPBI.

Using a vacuum deposition method or a spin-coating method, an electron transport layer 60 may be deposited on the hole barrier layer and may then be overlaid with an electron injection layer 70.

A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

In addition, the light-emitting layer may consist of a host and a dopant.

In some embodiments of the present disclosure, the light-emitting layer particularly ranges in thickness from 50 to 2,000 Å.

The host available for use in the light-emitting layer may be selected from among the compounds represented by the following Chemical Formula 1A to Chemical Formula 1D.

[Chemical Formula 1A]

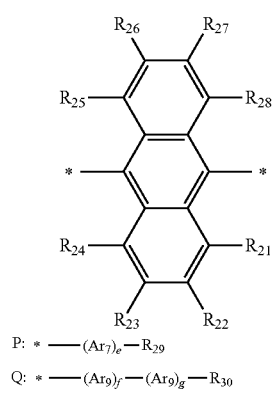

P: *──(Ar$_7$)$_e$──R$_{29}$

Q: *──(Ar$_9$)$_f$──(Ar$_9$)$_g$──R$_{30}$ wherein,

Ar$_7$, Ar$_8$ and Ar$_9$, which may be the same or different, are each independently a single bond, a substituted or unsubstituted C$_5$-C$_{60}$ aromatic linking group, or a substituted or unsubstituted C$_2$-C$_{60}$ heteroaromatic linking group;

R$_{21}$ to R$_{30}$, which may be the same or different, are each independently selected from among a hydrogen atom, a deuterium atom, a halogen atom, a hydroxyl, a cyano, a nitro, an amino, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms, a substituted or unsubstituted aryl)amino of 6 to 60 carbon atoms, a (substituted or unsubstituted aryl)amino of 6 to 60 carbon atoms, a substituted or unsubstituted alkylsilyl of 1 to 40 carbon atoms, a substituted or unsubstituted arylsilyl of 6 to 30 carbon atoms, geramanium, phosphorous, and boron, wherein the substitutents may form a fused ring with adjacent groups;

e, f, and g, which may be the same or different, are each independently an integer of 0 to 4;

the two sites represented by in the antracene compound, which may be the same or different, each may be independently connected to the P or Q moiety to form an antracene derivative selected from among compounds represented by the following Chemical Formula 1Aa-1 to 1Aa-3:

[Chemical Formula 1Aa-1]

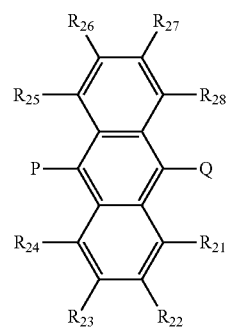

[Chemical Formula 1Aa-2]

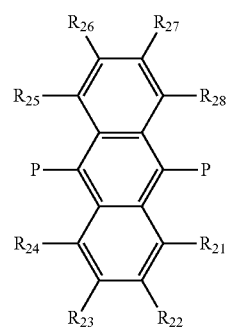

[Chemical Formula 1Aa-3]

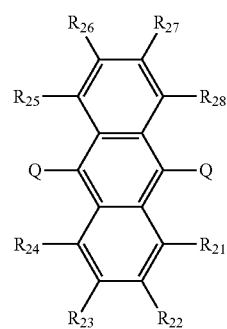

wherein the term 'substituted' in the expression 'substituted or unsubstituted' means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 1 to 24 carbon atoms, a hetero arylamino of 1 to 24 carbon atoms, an alkylsilyl of 1 to 24 carbon atoms, an arylsilyl of 1 to 24 carbon atoms, and an aryloxy of 1 to 24 carbon atoms.

[Chemical Formula 1B]

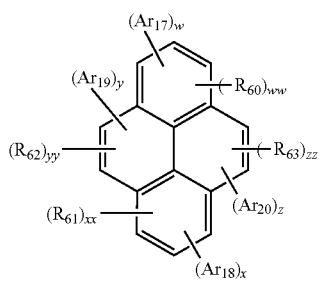

wherein,

Ar$_{17}$ to Ar$_{20}$, which may be the same or different, are each independently selected from among the substituents defined for Ar$_7$ to Ar$_8$ in Chemical Formula 1A, and R$_{60}$ to R$_{63}$ are each independently selected from among the substituents defined for R$_{21}$ to R$_{30}$ in Chemical Formula 1A; and w and ww, which may be the same or different, x and xx, which may be the same or different, are each independently an integer of 0 to 3, with the proviso that the value of w+ww may be identical to or different from that of x+xx; and y and yy, which may be the same or different, and z and zz, which may be the same or different, are each independently an integer of 0 to 2, with the proviso that the value of y+yy or z+zz are 2 or less.

[Chemical Formula 1C]

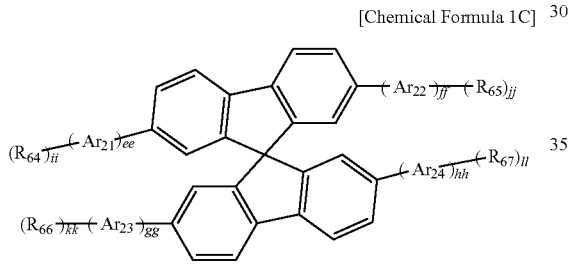

wherein,

Ar$_{21}$ to Ar$_{24}$, which may be the same or different, are each independently selected from among the substituents defined for Ar$_7$ to Ar$_8$ in Chemical Formula 1A;

R$_{64}$ to R$_{67}$, which may be the same or different, are each independently selected from among the substituents defined for R$_{21}$ to R$_{30}$ in Chemical Formula 1A; and ee to hh, which may be the same or different, are each independently an integer of 1 to 4, and ii to 11, which may be the same or different, are each independently an integer of 0 to 4.

[Chemical Formula 1D]

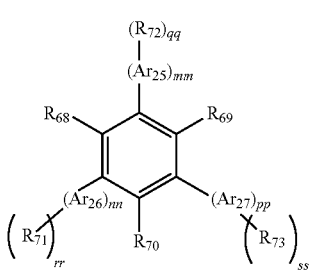

wherein,

Ar$_{25}$ to Ar$_{27}$, which may be the same or different, are each independently selected from among the substituents defined for Ar$_7$ to Ar$_8$ in Chemical Formula 1A, and R$_{68}$ to R$_{73}$, which may be the same or different, are each independently selected from the substituents defined for R$_{21}$ to R$_{30}$ in Chemical Formula 1A, with the proviso that adjacent substitutes may form a saturated or unsaturated cyclic structure; and mm to ss, which may be the same or different, are each independently an integer of 0 to 4.

By way of example, the host may be selected from among compounds represented by the following [Host 1] to [Host 56], but is not limited thereto.

[Host 1]

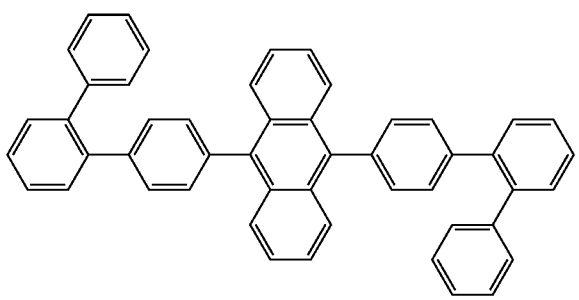

[Host 2]

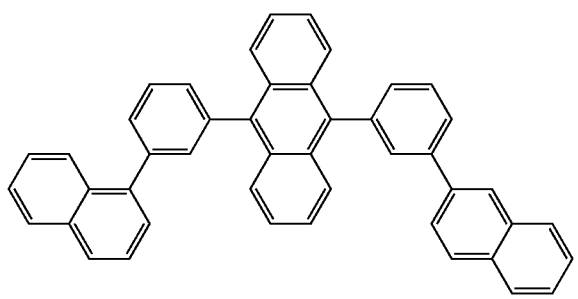

[Host 3]

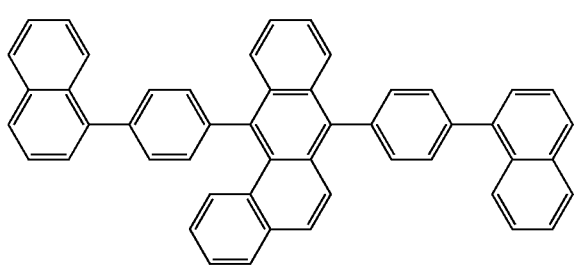

[Host 4]

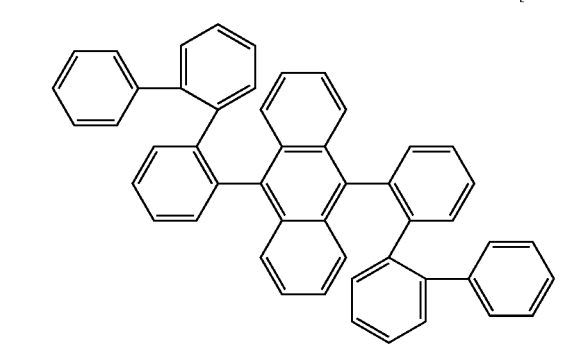

[Host 5]
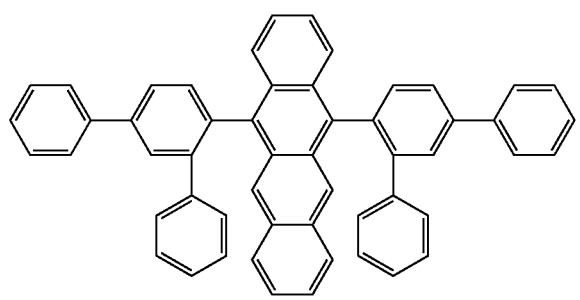
[Host 9]
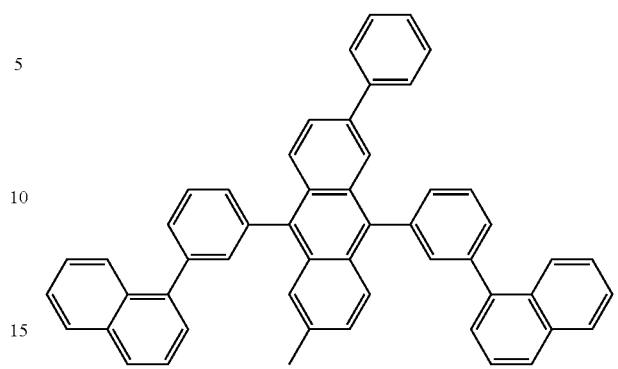
[Host 6]
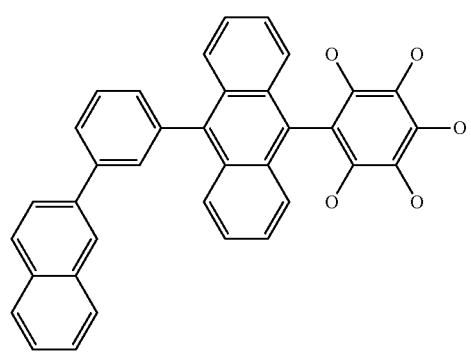
[Host 10]
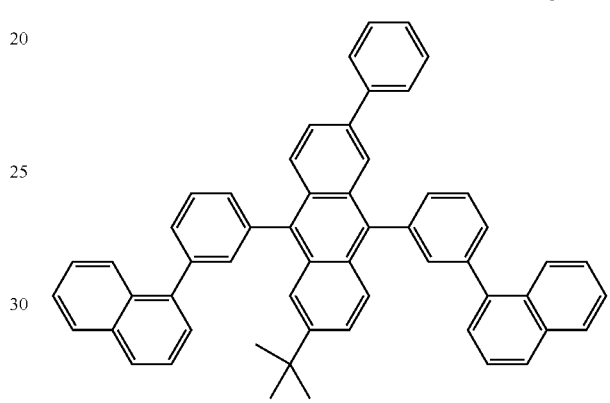
[Host 7]
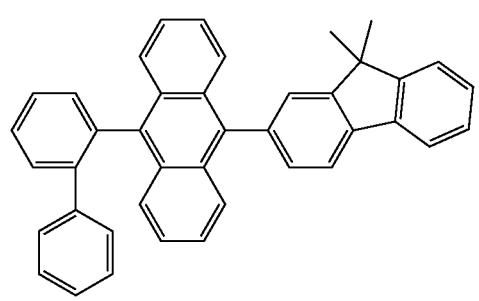
[Host 11]
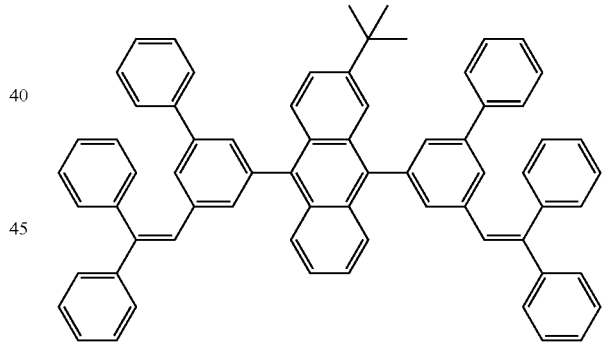
[Host 8]
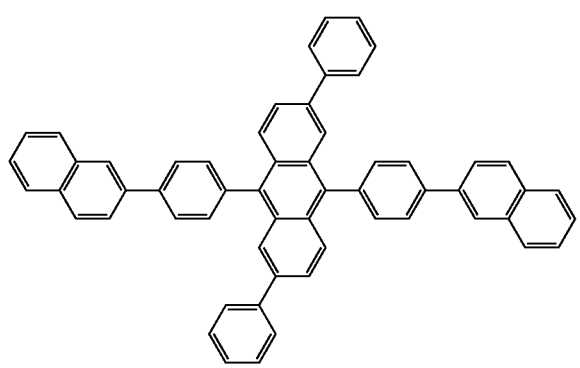
[Host 12]
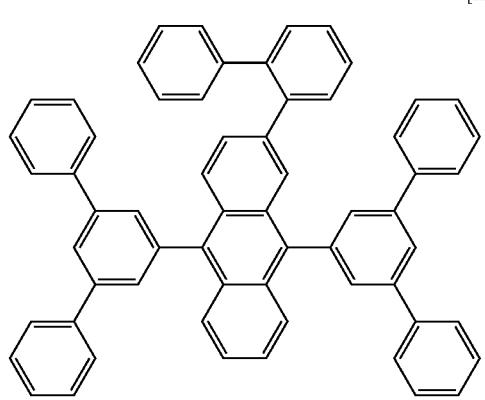

[Host 13]
[Host 14]
[Host 15]
[Host 16]
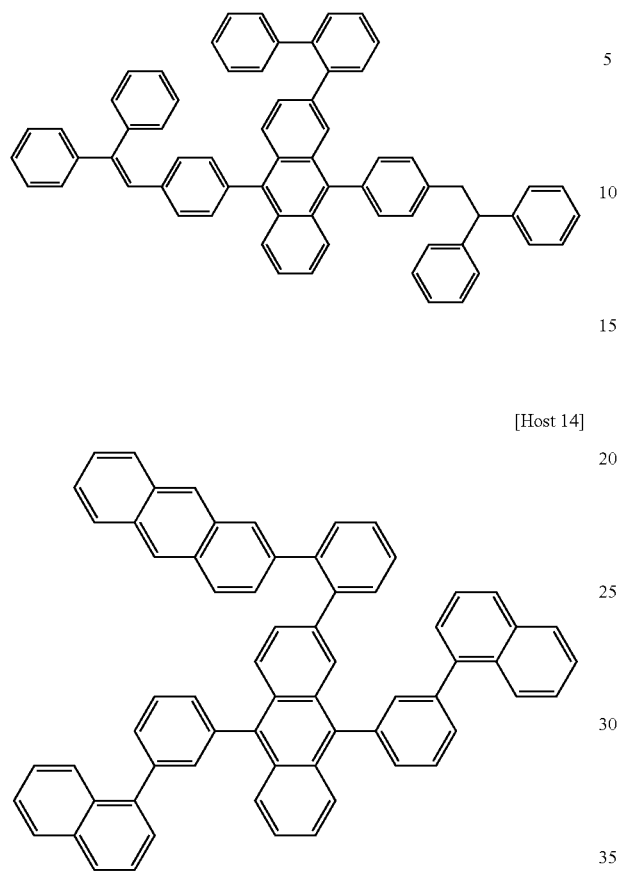
[Host 17]
[Host 18]
[Host 19]
[Host 20]
[Host 21]
[Host 22]
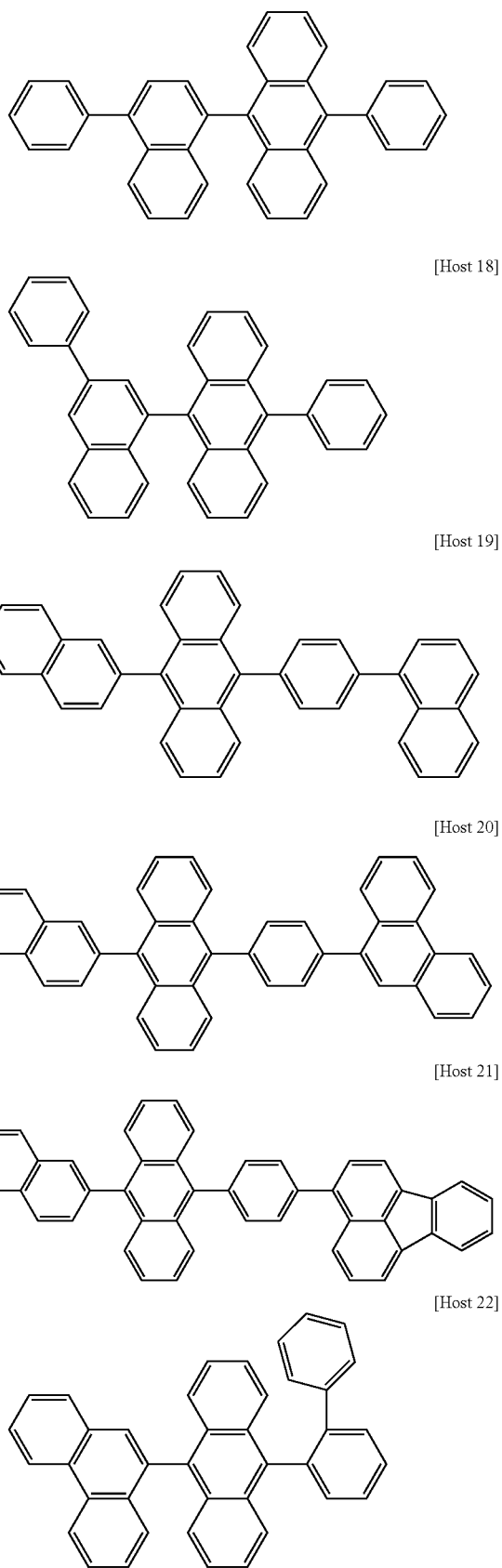

[Host 23]
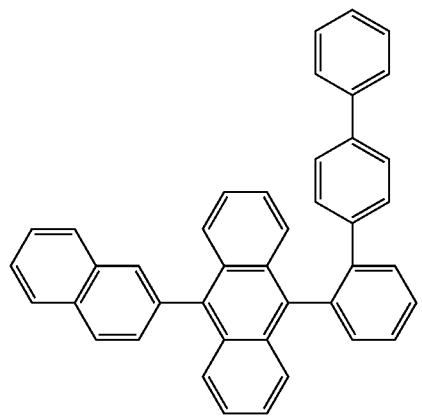
[Host 28]
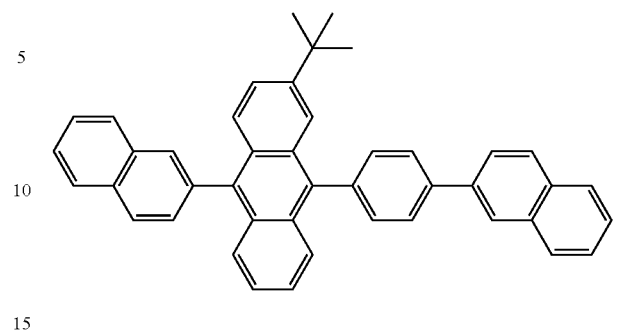
[Host 24]
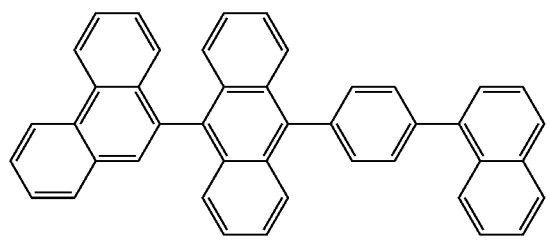
[Host 29]
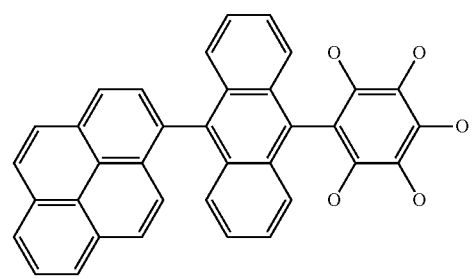
[Host 25]
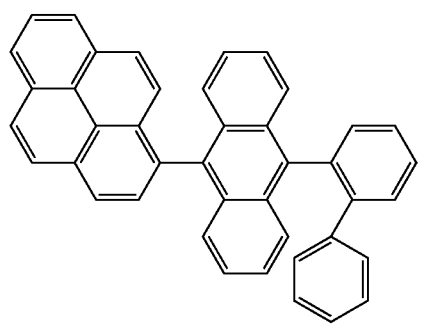
[Host 30]
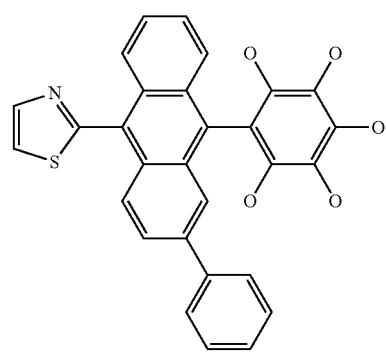
[Host 26]
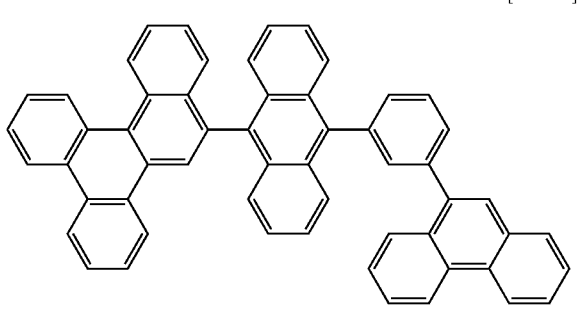
[Host 27]
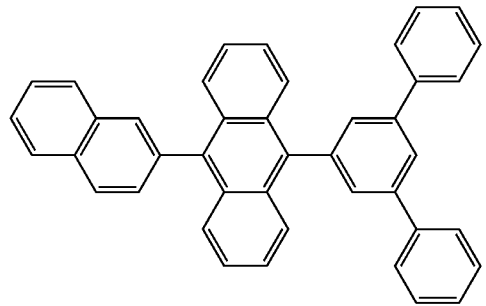
[Host 31]
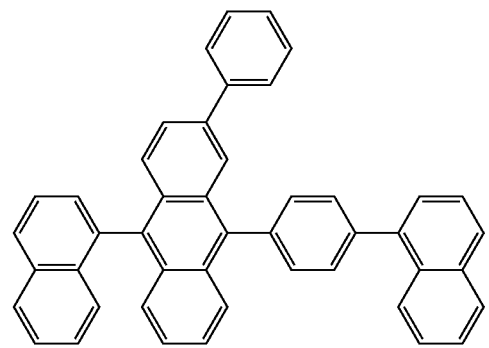

-continued
[Host 32]
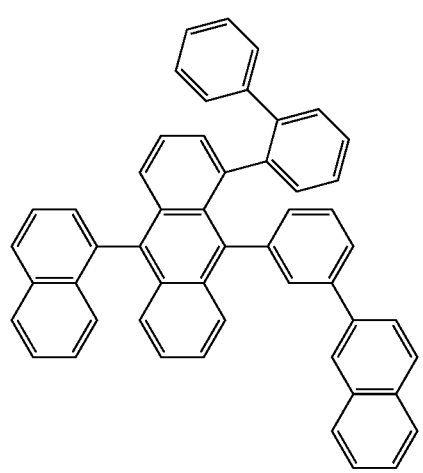
[Host 37]
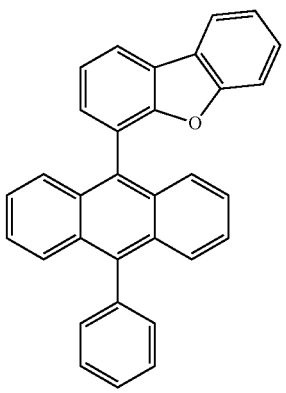
[Host 33]
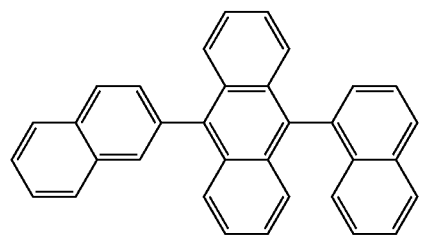
[Host 34]
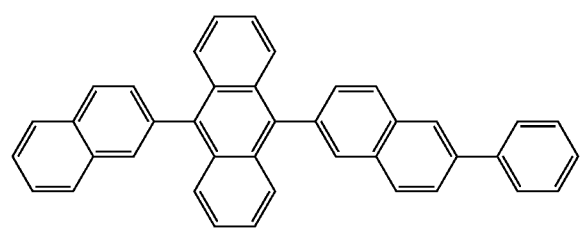
[Host 38]
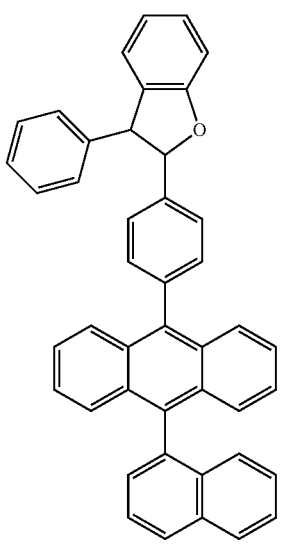
[Host 35]
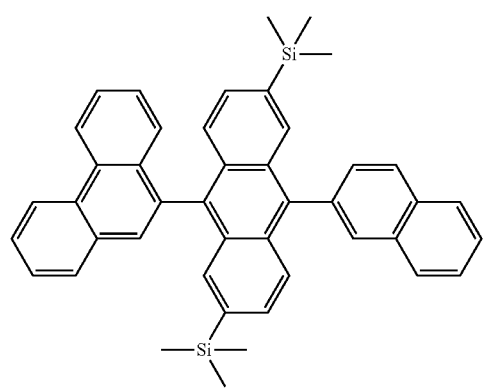
[Host 39]
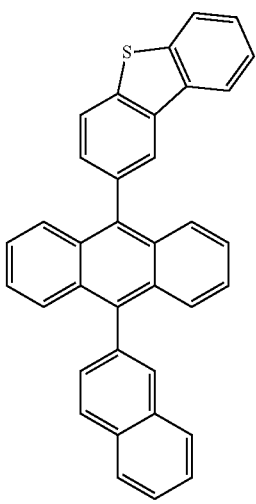
[Host 36]
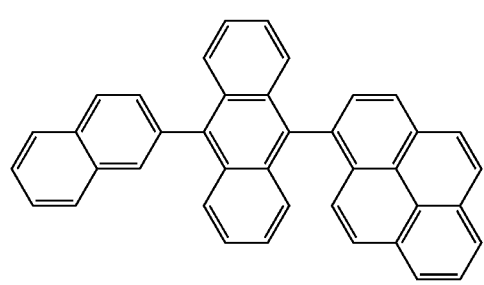

[Host 40]
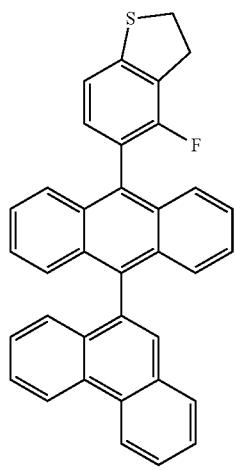
[Host 43]
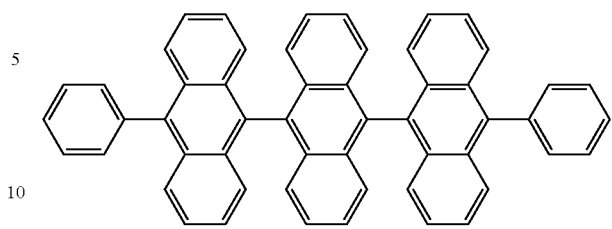
[Host 44]
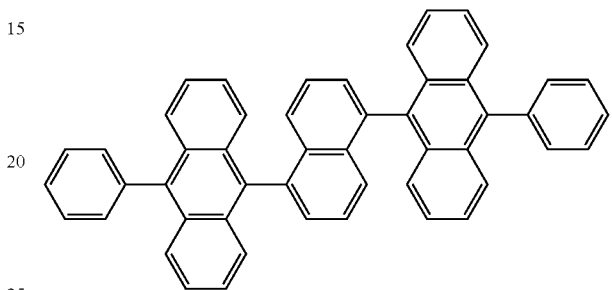
[Host 41]
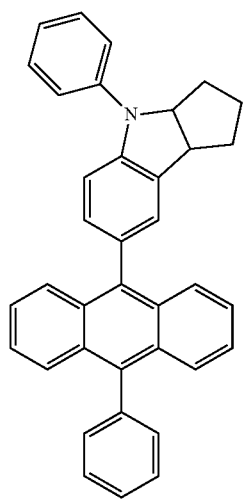
[Host 45]
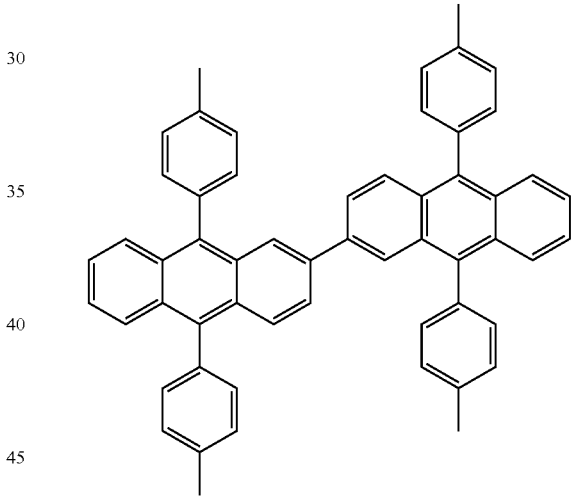
[Host 42]
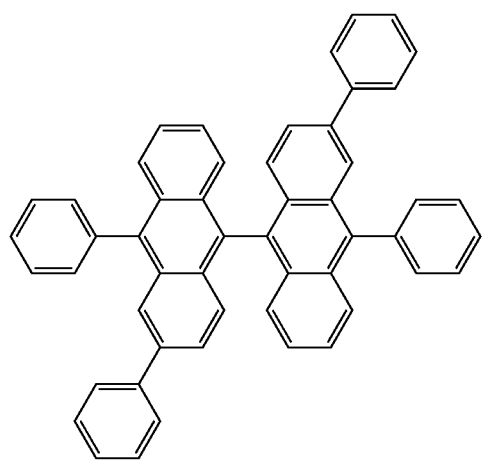
[Host 46]
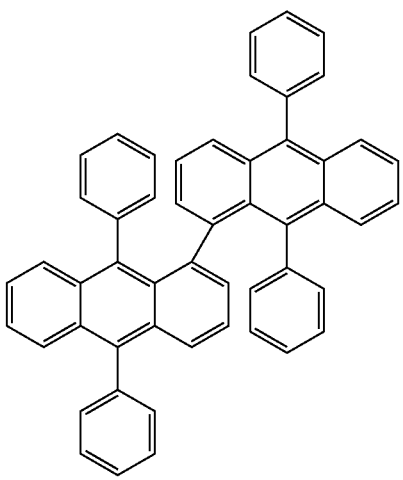

[Host 47]
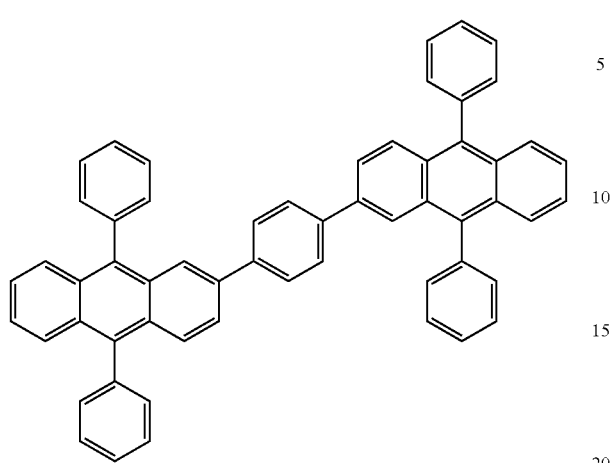
[Host 48]
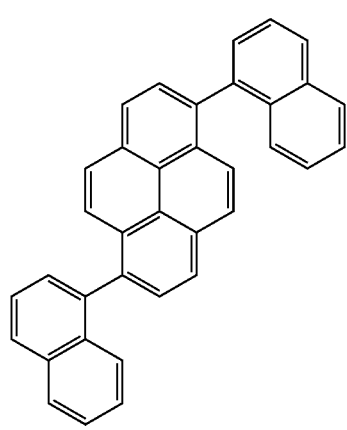
[Host 49]
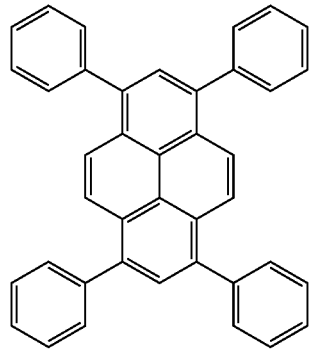
[Host 50]
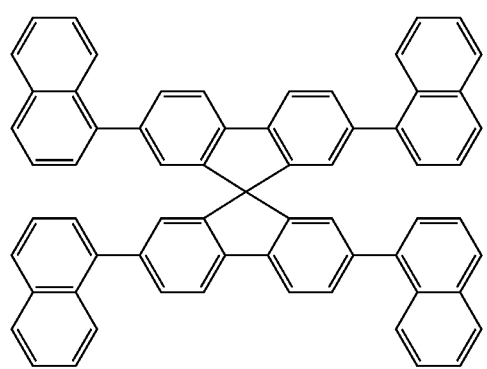
[Host 51]
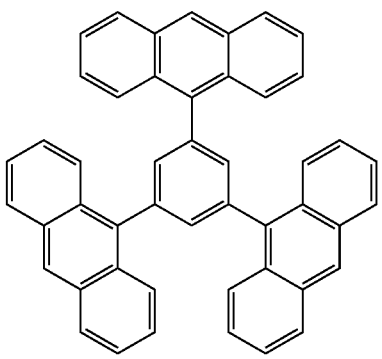
[Host 52]
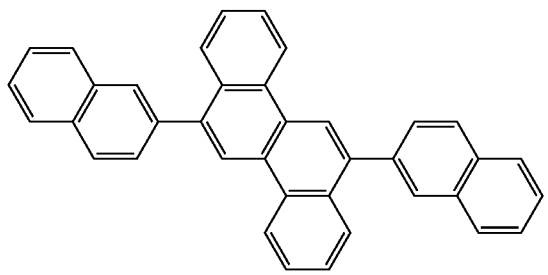
[Host 53]
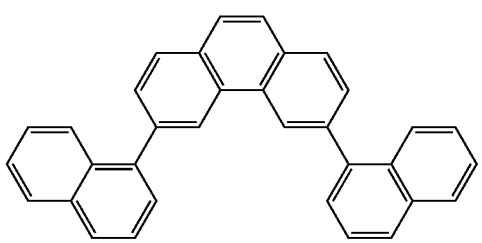
[Host 54]
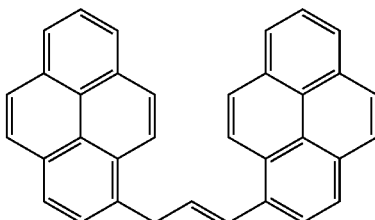
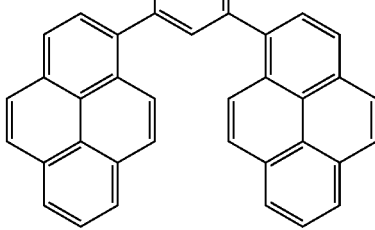

117
-continued

[Host 55]

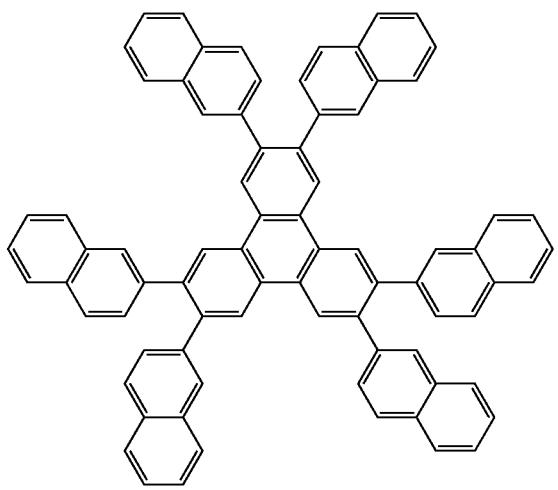

[Host 56]

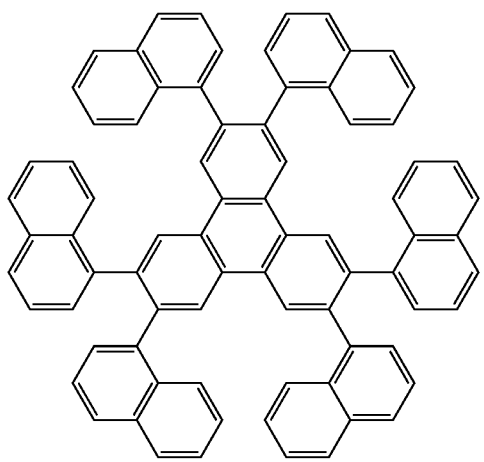

In addition to the above-mentioned dopants and hosts, the light-emitting layer may further include various hosts and dopant materials.

Further, one or more layers selected from among a hole injection layer, a hole transport layer, an electron barrier layer, a light-emitting layer, a hole barrier layer, an electron transport layer, and an electron injection layer may be deposited using a single molecule deposition process or a solution process. Here, the deposition process refers to a process by which a material is vaporized in a vacuum or at a low pressure and deposited to form a layer, and the solution process means a method in which a material is dissolved in a solvent and applied for the formation of a thin film by means of inkjet printing, roll-to-roll coating, screen printing, spray coating, dip coating, spin coating, etc.

Also, the organic light-emitting device of the present disclosure may be applied to a device selected from among flat display devices; flexible display devices; monochrome or white flat illumination devices; and monochrome or white flexible illumination devices.

A better understanding of the present disclosure may be obtained through the following examples which are set forth to illustrate, but are not to be construed as the limit of the present disclosure.

118

EXAMPLES

Synthesis Example 1: Synthesis of Compound of Chemical Formula 1

Synthesis Example 1-(1): Synthesis of [Intermediate 1-a]

[Intermediate 1-a] was synthesized as illustrated in the following Reaction Scheme 1.

<Reaction Scheme 1>

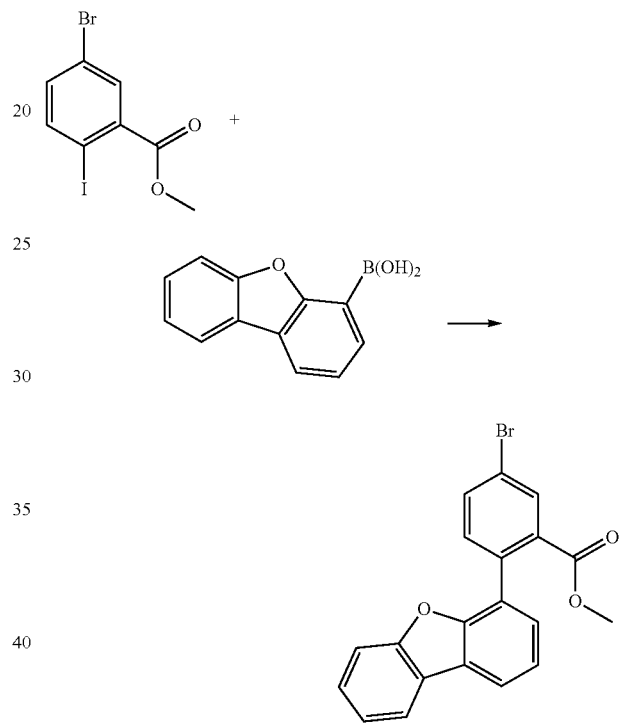

<Intermediate 1-a>

In a 500-mL round-bottom flask reactor, methyl 5-bromo-2-iodobenzoate (25.0 g, 73 mmol), 4-dibenzofuran boronic acid (18.7 g, 88 mmol), tetrakis (triphenylphosphine)palladium (1.7 g, 0.15 mmol), and potassium carbonate (20.2 g, 146.7 mmol) were stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 1-a>. (75.0 g, 60.1%).

Synthesis Example 1-(2)

Synthesis of Intermediate 1-b

Intermediate 1-b was synthesized as illustrated in the following Reaction Scheme 2:

Reaction Scheme 2

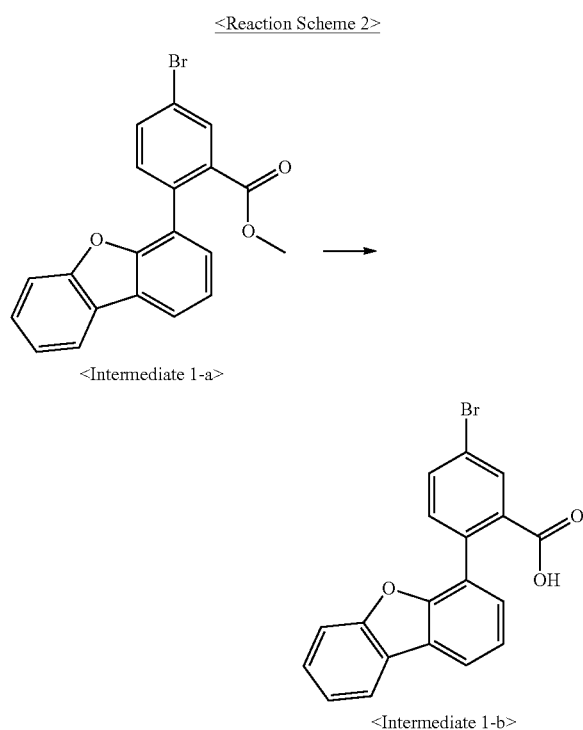

<Intermediate 1-a>

<Intermediate 1-b>

In a 500-mL round-bottom flask reactor, <Intermediate 1-a> (17.0 g, 45 mmol), sodium hydroxide (2.14 g, 54 mmol) and ethanol (170 ml) were stirred together for 48 hrs under reflux. After the completion of the reaction was confirmed using thin-layer chromatography, the reaction mixture was cooled to room temperature. The chilled solution was acidified with drops of 2-N HCl, followed by stirring for 30 min. The solid thus formed was filtered and then recrystallized in dichloromethane and n-hexane to afford <Intermediate 1-b>. (14.5 g, 88.6%)

Synthesis Example 1-(3)

Synthesis of Intermediate 1-c

Intermediate 1-c was synthesized as illustrated in the following Reaction Scheme 3:

Reaction Scheme 3

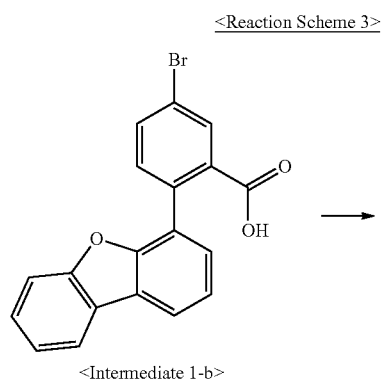

<Intermediate 1-b>

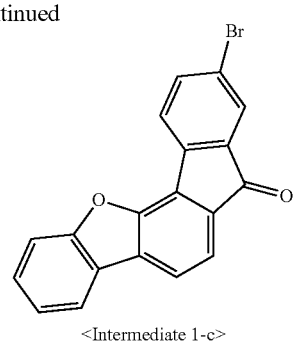

<Intermediate 1-c>

In a 250-mL round-bottom flask reactor, <Intermediate 1-b> (14.5 g, 39 mmol) and methanesulfonic acid (145 ml) were stirred together for 3 hrs at 80° C. After the completion of the reaction was confirmed using thin-layer chromatography, the reaction mixture was cooled to room temperature and dropwise added to ice water (150 ml). After stirring for 30 min, the solid thus formed was filtered and washed with water and methanol to afford <Intermediate 1-c>. (11.50 g, 83.4%)

Synthesis Example 1-(4)

Synthesis of Intermediate 1-d

Intermediate 1-d was synthesized as illustrated in the following Reaction Scheme 4:

Reaction Scheme 4

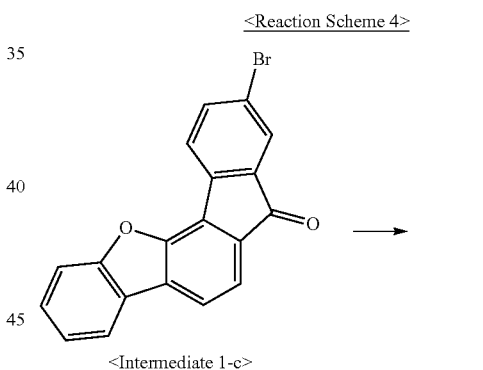

<Intermediate 1-c>

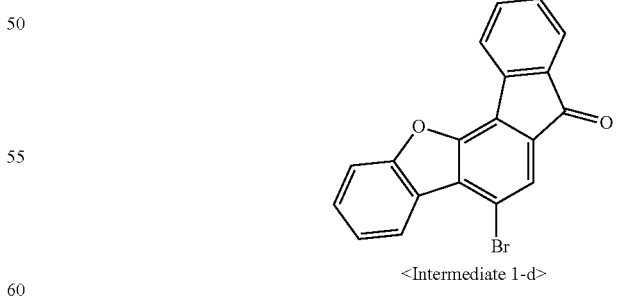

<Intermediate 1-d>

In a 1-L round-bottom flask reactor, <Intermediate 1-c> (11.5 g, 33 mmol> and dichloromethane (300 ml) were stirred together at room temperature. A dilution of bromine (3.4 ml, 66 mmol) in dichloromethane (50 ml) was dropwise added, followed by stirring at room temperature for 8 hrs. After completion of the reaction, the reaction mixture was stirred together with acetone (100 ml). The solid thus formed was filtered and washed with acetone. Recrystallization in monochlorobenzene afforded <Intermediate 1-d>. (11.0 g, 78%)

Synthesis Example 1-(5): Synthesis of Intermediate 1-e

Intermediate 1-e was synthesized as illustrated in the following Reaction Scheme 5:

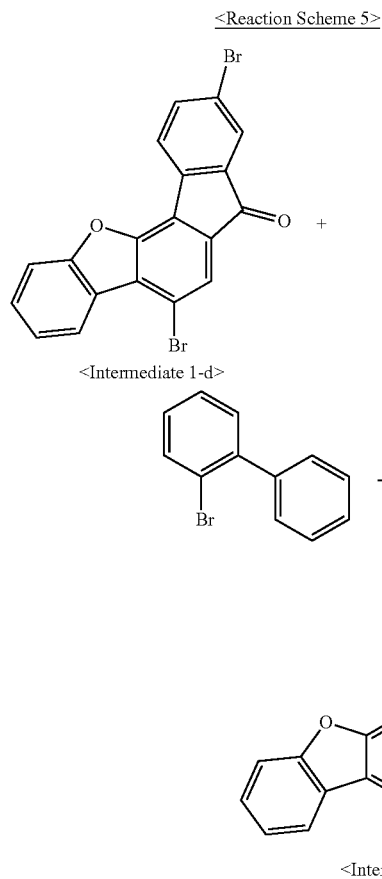

<Reaction Scheme 5>

<Intermediate 1-d>

<Intermediate 1-e>

In a 250-ml round-bottom flask reactor, 2-bromobiphenyl (8.4 g, 0.036 mol) and tetrahydrofuran (110 ml) were frozen at −78° C. in a nitrogen atmosphere. At the same temperature, n-butyl lithium (19.3 ml, 0.031 mol) was dropwise added to the reaction solution, which was then stirred for 2 hrs. Thereafter, <Intermediate 1-d> (11.0 g, 0.026 mol) was added little by little to the reaction solution and stirred at room temperature. When the reaction mixture started to change color, the reaction was monitored via thin-layer chromatography. After the reaction was stopped with $H_2O$ (50 ml), extraction was conducted with ethyl acetate and water. The organic layer was separated, concentrated in a vacuum, and recrystallized in acetonitrile to afford <Intermediate 1-e> as a solid. (12.2 g, 81.5%)

Synthesis Example 1-(6): Synthesis of Intermediate 1-f

Intermediate 1-f was synthesized as illustrated in the following Reaction Scheme 6:

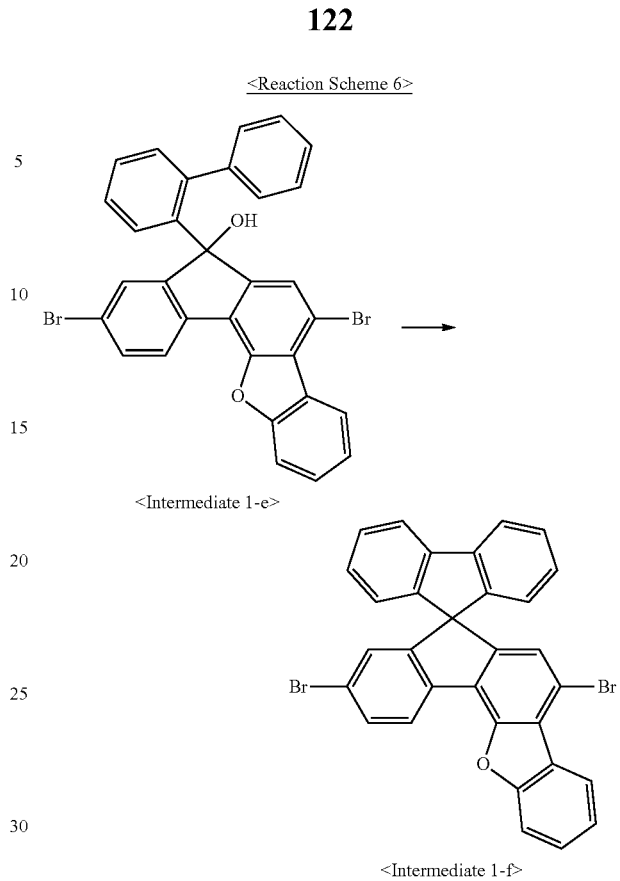

<Reaction Scheme 6>

<Intermediate 1-e>

<Intermediate 1-f>

In a 250-ml round-bottom flask reactor, a mixture of <Intermediate 1-e> (12.0 g, 0.021 mol), acetic acid (120 ml), and sulfuric acid (2 ml) was stirred for 5 hrs under reflux. When a precipitate was formed, the completion of the reaction was monitored using thin-layer chromatography. The reaction mixture was then cooled to room temperature and filtered. The filtrate was washed with $H_2O$ and methanol and dissolved in monochlorobenzene. Following silica gel chromatography, the fraction was concentrated and cooled to room temperature to give <Intermediate 1-f>. (10.7 g, 90%)

Synthesis Example 1-(7): Synthesis of Compound of Chemical Formula 1

The compound of Chemical Formula 1 was synthesized as illustrated in the following Reaction Scheme 7:

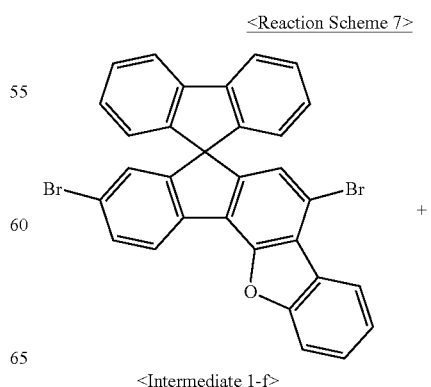

<Reaction Scheme 7>

<Intermediate 1-f>

-continued

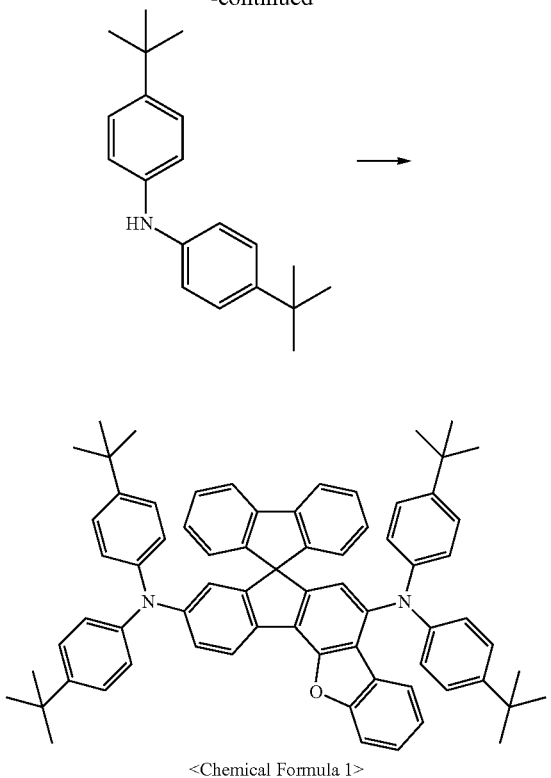

<Chemical Formula 1>

In a 250-ml round-bottom flask reactor, a mixture of <Intermediate 1-f> (5.0 g, 0.009 mol), bis(4-tert-butylphenyl)amine (6.0 g, 0.021 mol), palladium (II) acetate (0.08 g, 0.4 mmol), sodium tert-butoxide (3.4 g, 0.035 mol), tri-tert-butyl phosphine (0.07 g, 0.4 mmol), and toluene (60 ml) was stirred for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield the compound of Chemical Formula 1 as a solid (3.1 g, 38%).

MS (MALDI-TOF): m/z 964.5 [M$^+$]

Synthesis Example 2

Synthesis of Compound of Chemical Formula 33

Synthesis Example 2-(1)

Synthesis of Intermediate 2-a

Intermediate 2-a was synthesized as illustrated in the following Reaction Scheme 8:

<Reaction Scheme 8>

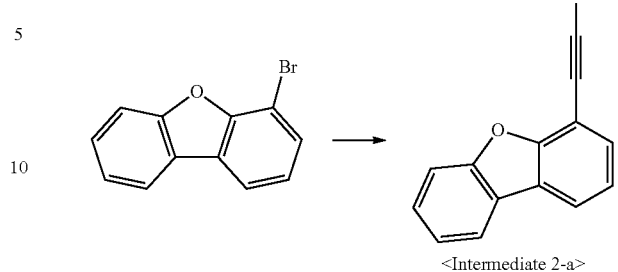

<Intermediate 2-a>

In a 2-L round bottom flask, 4-bromodibenzofuran (100.0 g, 0.405 mol), ethynyl trimethylsilane (47.7 g, 0.486 mol), [1,1'-bis(diphenylphosphino)ferrocene]dichloropalladium (9.92 g, 0.012 mol), copper iodide (2.31 g, 0.012 mol), triphenylphosphine (10.6 g, 0.040 mol), and triethylamine (700 ml) were stirred for 5 hrs under reflux in a nitrogen atmosphere. After completion of the reaction, the reaction mixture was cooled to room temperature and added with heptane (500 ml) to terminate the reaction. Filtration was conducted through a silica gel pad topped with celite. The filtrate was concentrated in a vacuum to afford <Intermediate 2-a> (130 g, 84%).

Synthesis Example 2-(2)

Synthesis of Intermediate 2-b

Intermediate 2-b was synthesized as illustrated in the following Reaction Scheme 9:

<Reaction Scheme 9>

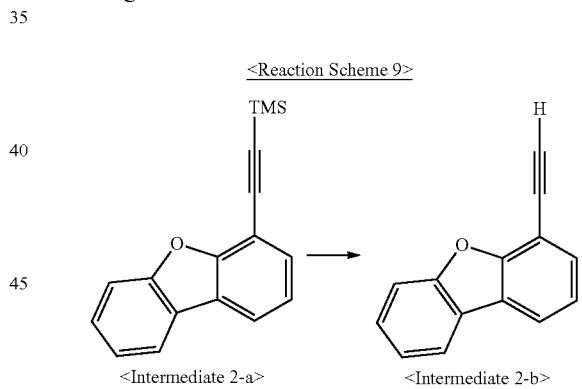

<Intermediate 2-a>   <Intermediate 2-b>

In a 2-L round-bottom flask reactor, <Intermediate 2-a> (130 g, 0.492 mol), potassium carbonate (101.9 g, 0.738 mol), methanol (650 ml), and tetrahydrofuran (650 ml) were stirred together for 2 hrs at room temperature. After completion of the reaction, heptane (500 ml) was added to terminate the reaction. The reaction mixture was filtered and the filtrate was extracted with ethyl acetate and water. The organic layer thus formed was isolated and dried over magnesium sulfate. Filtration and vacuum concentration afforded <Intermediate 2-b> as an oil (82 g, 84%).

Synthesis Example 2-(3)

Synthesis of Intermediate 2-c

Intermediate 2-c was synthesized as illustrated in the following Reaction Scheme 10:

Reaction Scheme 10

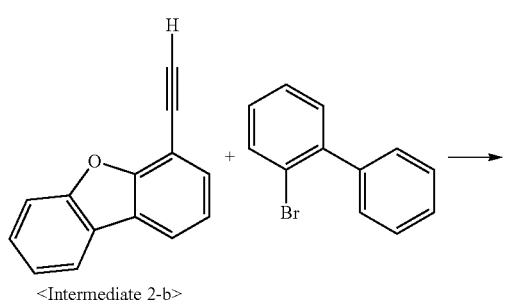

<Intermediate 2-b>

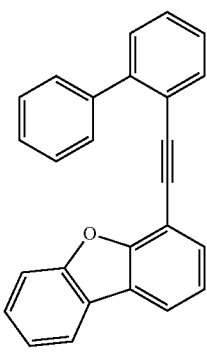

<Intermediate 2-c>

In a 2-L round-bottom flask reactor, 2-bromobiphenyl (66.0 g, 0.283 mol), <Intermediate 2-b> (65.3 g, 0.340 mol), [1,1'-bis(diphenylphosphino)ferrocene]dichloropalladium (6.94 g, 0.008 mol), copper iodide (1.62 g, 0.008 mol), triphenylphosphine (7.4 g, 0.028 mol), and triethylamine (500 ml) were stirred for 5 hrs under reflux in a nitrogen atmosphere. After completion of the reaction, the reaction mixture was cooled to room temperature and added with heptane (500 ml) to terminate the reaction. Filtration was conducted through a silica gel pad topped with celite. The filtrate was concentrated in a vacuum to afford <Intermediate 2-c> (80 g, 82%).

Synthesis Example 2-(4)

Synthesis of Intermediate 2-d

Intermediate 2-d was synthesized as illustrated in the following Reaction Scheme 11:

Reaction Scheme 11

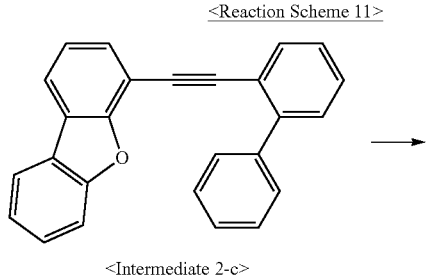

<Intermediate 2-c>

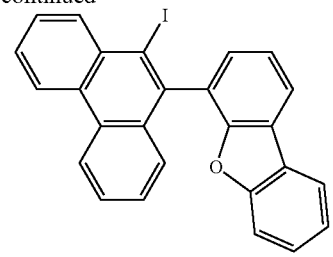

<Intermediate 2-d>

In a 2-L round-bottom flask reactor, a solution of <Intermediate 2-c> (80.0 g, 0.232 mol) in dichloromethane (960 ml) was cooled to −78° C. under a nitrogen atmosphere. Iodine monochloride (278.4 ml, 0.279 mol) was dropwise added to the chilled solution, which was then stirred at room temperature for 12 hrs. After completion of the reaction, the reaction mixture was stirred together with an aqueous saturated sodium thiosulfate solution. Following extraction with dichloromethane and water, the organic layer was isolated, concentrated in a vacuum, and washed with methanol to afford <Intermediate 2-d> as a crystal (67 g, 61.3%).

Synthesis Example 2-(5): Synthesis of Intermediate 2-e

Intermediate 2-e was synthesized as illustrated in the following Reaction Scheme 12:

Reaction Scheme 12

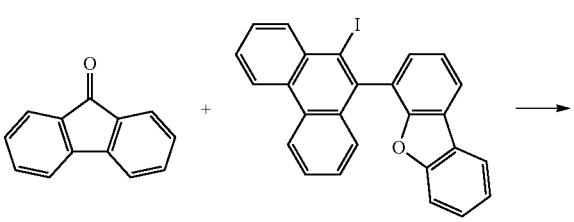

<Intermediate 2-d>

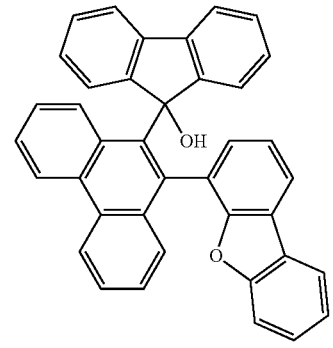

<Intermediate 2-e>

In a 500-mL round-bottom flask reactor, a solution of <Intermediate 2-d> (54.8 g, 0.117 mol) in tetrahydrofuran (150 ml) was cooled to −78° C. under a nitrogen atmosphere. At the same temperature, 1.6 M n-butyl lithium (62.4 ml, 0.1 mol) was dropwise added to the chilled solution and stirred for 1 hr. Then, a solution of 9-fluorenone (15.0 g, 0.083 mol) in tetrahydrofuran (50 ml) was dropwise added before stirring at room temperature for 8 hrs. After completion of the reaction, extraction was performed with ethyl acetate and water. The organic layer thus formed was isolated and dried over magnesium sulfate. Vacuum concentration subsequent to filtration afforded <Intermediate 2-e> as an oil (33.2 g, 76%).

Synthesis Example 2-(6)

Synthesis of Intermediate 2-f

Intermediate 2-f was synthesized as illustrated in the following Reaction Scheme 13:

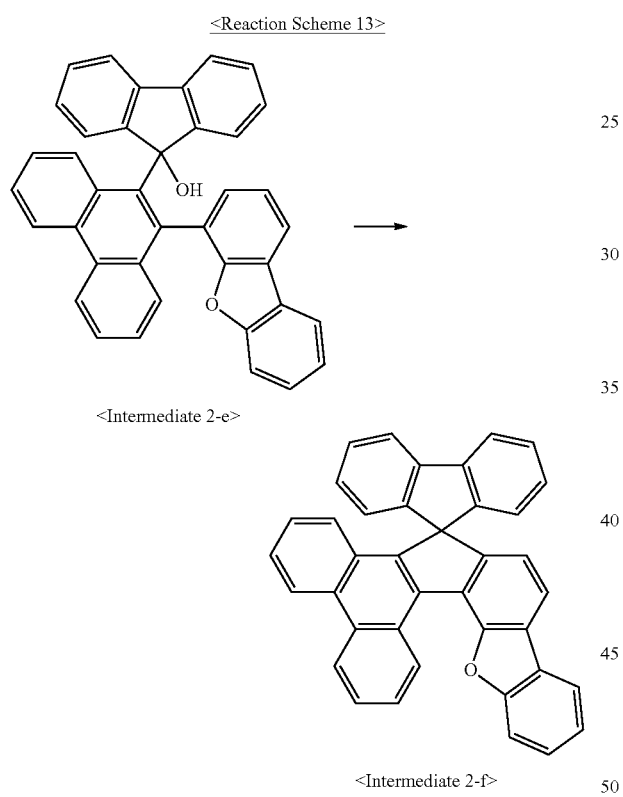

<Intermediate 2-e>

<Intermediate 2-f>

In a 1-L round-bottom flask reactor, <Intermediate 2-e> (33.3 g, 0.063 mol), acetic acid (330 ml), and sulfuric acid (3 ml) were stirred together for 3 hrs under reflux. After the completion of the reaction was confirmed using thin-layer chromatography, the reaction mixture was cooled to room temperature. The precipitates thus formed were filtered and washed with H₂O and methanol to afford <Intermediate 2-f> (28.6 g, 88%>.

Synthesis Example 2-(7)

Synthesis of Intermediate 2-g

Intermediate 2-g was synthesized as illustrated in the following Reaction Scheme 14:

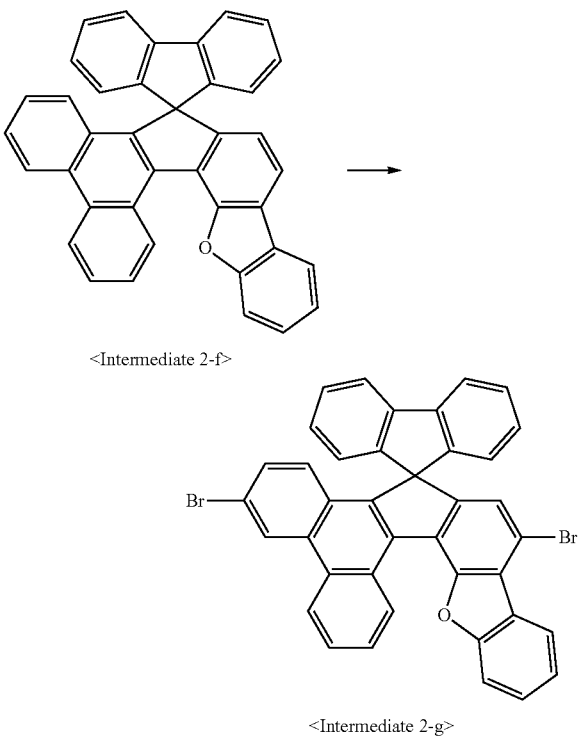

<Intermediate 2-f>

<Intermediate 2-g>

In a 1-L round-bottom flask reactor, a solution of <Intermediate 2-f> (20.0 g, 0.039 mol) in dichloromethane (200 ml) was added with drops of a dilution of bromine (6 ml, 0.118 mol) in dichloromethane (40 ml) while stirring. After completion of the reaction for 12 hrs of stirring at room temperature, the addition of methanol (100 ml) produced precipitates which were then washed with methanol. Recrystallization in 1,2-dichlorobenzene and acetone afforded <Intermediate 2-g> (16 g, 60%).

Synthesis Example 2-(8)

Synthesis of Compound of Chemical Formula 33

The compound of Chemical Formula 33 was synthesized as illustrated in the following Reaction Scheme 15:

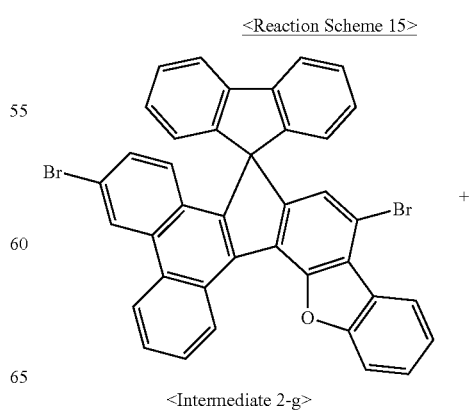

<Intermediate 2-g>

-continued

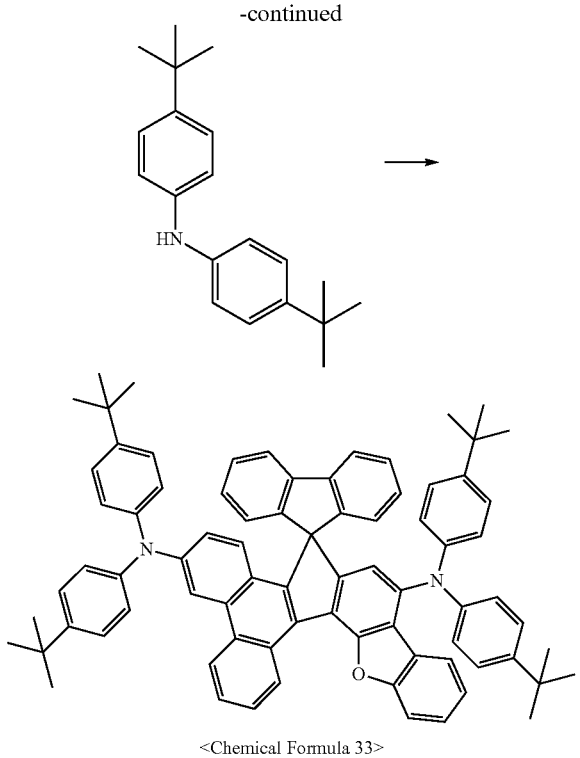

<Chemical Formula 33>

The same procedure as in Synthesis Example 1-(7), with the exception of using <Intermediate 2-g> instead of <Intermediate 1-f>, was conducted to synthesize the compound of <Chemical Formula 33> (2.5 g, 31%).

MS (MALDI-TOF): m/z 1064.5 [M$^+$]

SYNTHESIS EXAMPLE 3: Synthesis of Compound of Chemical Formula 49

Synthesis Example 3-(1): Synthesis of Intermediate 3-a

Intermediate 3-a was synthesized as illustrated in the following Reaction Scheme 16:

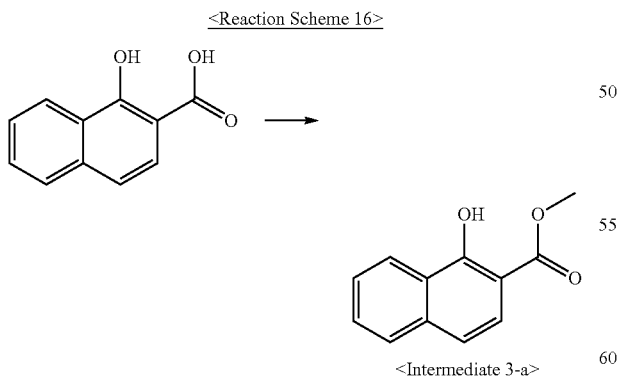

In a 2-L round-bottom flask reactor, 1-hydroxy 2-naphthalic acid (50 g, 266 mmol), methanol (1000 ml), and sulfuric acid (100 ml) were stirred together for 100 hrs under reflux. The completion of the reaction was confirmed by TLC before the reaction mixture was cooled to room temperature. The mixture was concentrated in a vacuum and extracted with dichloromethane and water. The organic layer was isolated, dried over magnesium sulfate, and filtered. The filtrate was concentrated at a reduced pressure and crystallized in an excess of heptane to afford <Intermediate 3-a> (39 g, 72.6%).

Synthesis Example 3-(2)

Synthesis of Intermediate 3-b

Intermediate 3-b was synthesized as illustrated in the following Reaction Scheme 17:

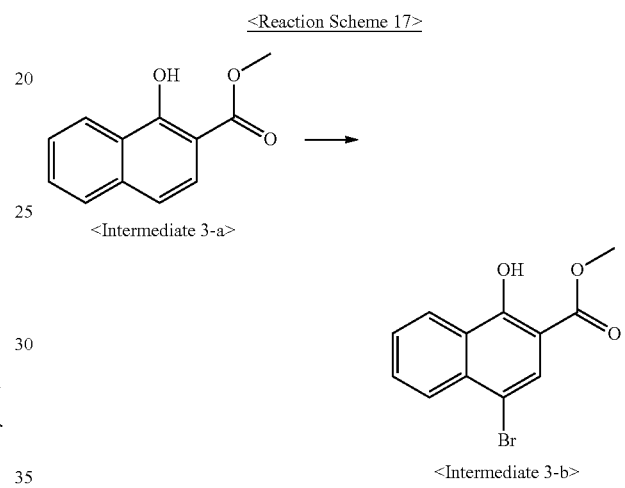

In a 1-L round-bottom flask reactor, <Intermediate 3-a> (39.0 g, 193 mmol) was stirred together with acetic acid (390 ml) at room temperature. A dilution of acetic acid (80 ml) in bromine (11.8 ml, 231 mmol) was added dropwise thereto. The resulting reaction solution was stirred for 5 hrs at room temperature. After completion of the reaction, the precipitates thus formed were filtered and slurried in heptane to afford <Intermediate 3-b> (50 g, 90%).

Synthesis Example 3-(3)

Synthesis of Intermediate 3-c

Intermediate 3-c was synthesized as illustrated in the following Reaction Scheme 18:

<Reaction Scheme 18>

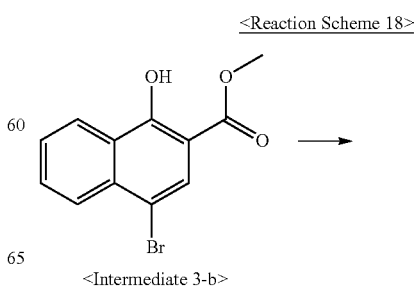

<Intermediate 3-b>

-continued

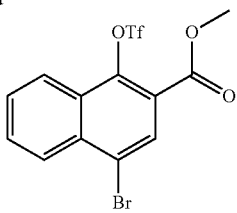
<Intermediate 3-c>

In a 2-L round-bottom flask reactor, <Intermediate 3-b> (50 g, 178 mmol) was stirred together with dichloromethane. Under a nitrogen atmosphere, pyridine (28.1 g, 356 mmol) was added and stirred at room temperature for 20 min. The resulting solution was cooled to 0° C. and then added with drops of trifluoromethanesulfonic anhydride (65.24 g, 231 mmol) under a nitrogen atmosphere. After 3 hrs of stirring, the completion of the reaction was confirmed by TLC. Water (20 ml) was added, and the mixture was stirred for 10 min. The reaction mixture was concentrated in a vacuum, followed by purification through column chromatography to afford <Intermediate 3-c> (45 g, 61%).

Synthesis Example 3-(4): Synthesis of Intermediate 3-d

Intermediate 3-d was synthesized as illustrated in the following Reaction Scheme 19:

<Reaction Scheme 19>

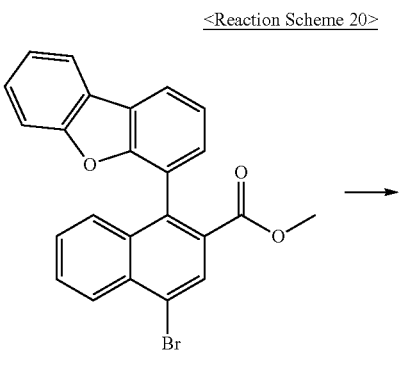

In a 1-L round-bottom flask reactor, a mixture of <Intermediate 3-c> (45.0 g, 0.109 mol), 4-dibenzoboronic acid (25.4 g, 0.120 mol), tetrakis (triphenylphosphine)palladium (2.5 g, 0.22 mmol), and potassium carbonate (30.1 g, 0.218 mol) was stirred together with toluene (300 mL), ethanol (130 mL) and water (90 mL) at 80° C. for 5 hrs. After completion of the reaction, the reaction mixture was cooled to room temperature and extracted with ethyl acetate. The organic layer was isolated and concentrated in a vacuum. Purification through column chromatography afforded Intermediate 3-d. (22.0 g, 46.1%)

Synthesis Example 3-(5)

Synthesis of Intermediate 3-e

Intermediate 3-e was synthesized as illustrated in the following Reaction Scheme 20:

<Reaction Scheme 20>

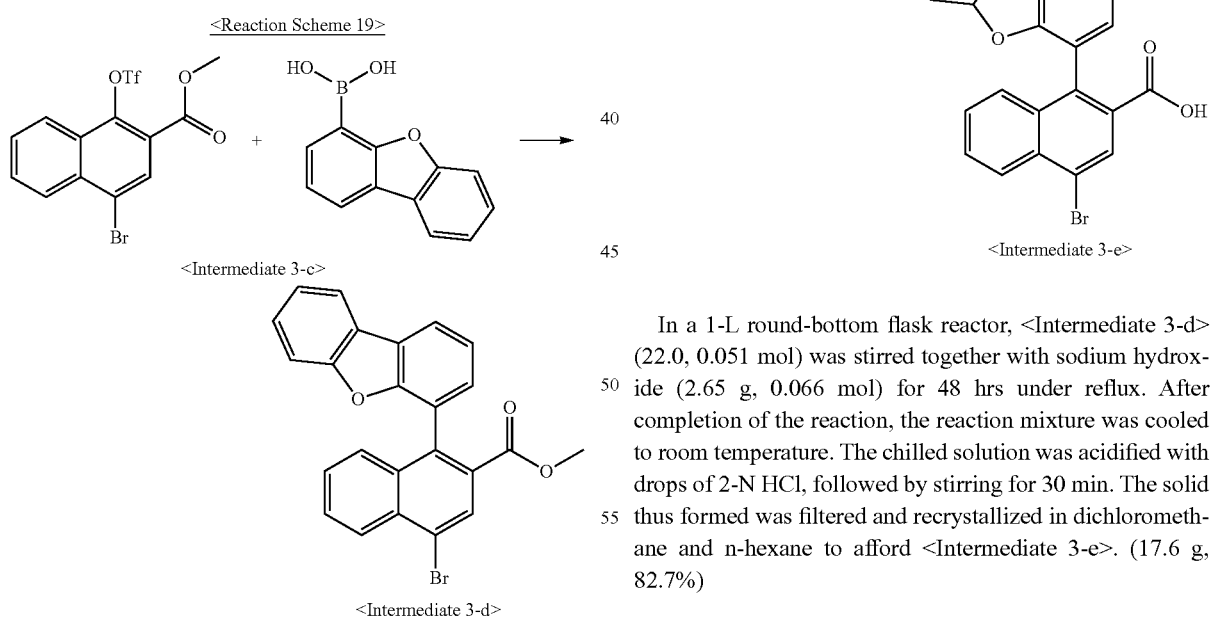

In a 1-L round-bottom flask reactor, <Intermediate 3-d> (22.0, 0.051 mol) was stirred together with sodium hydroxide (2.65 g, 0.066 mol) for 48 hrs under reflux. After completion of the reaction, the reaction mixture was cooled to room temperature. The chilled solution was acidified with drops of 2-N HCl, followed by stirring for 30 min. The solid thus formed was filtered and recrystallized in dichloromethane and n-hexane to afford <Intermediate 3-e>. (17.6 g, 82.7%)

Synthesis Example 3-(6)

Synthesis of Intermediate 3-f

Intermediate 3-f was synthesized as illustrated in the following Reaction Scheme 21:

<Reaction Scheme 21>

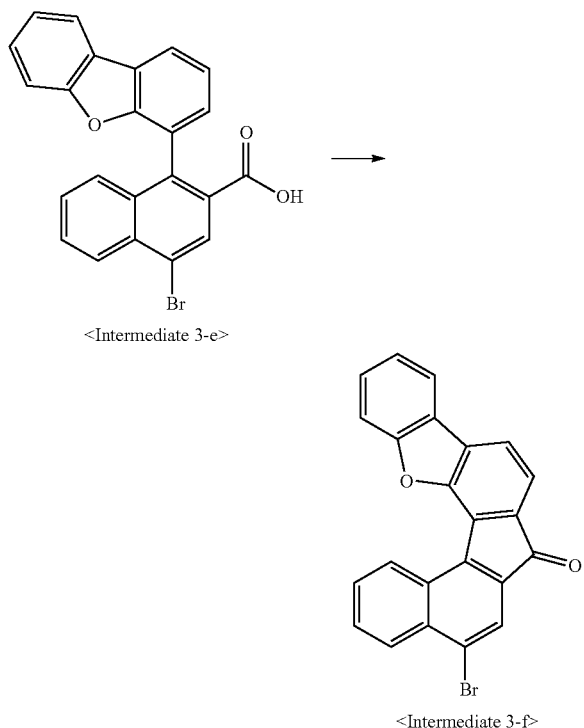

<Intermediate 3-e>

In a 500-mL round-bottom flask reactor, <Intermediate 3-e> (17.6 g, 0.042 mol) and methanesulfonic acid (170 ml) were stirred together for 3 hrs at 80° C. After the completion of the reaction was confirmed using thin-layer chromatography, the reaction mixture was cooled to room temperature and dropwise added to ice water (150 ml). After stirring for 30 min, the precipitates thus formed were filtered and washed with water and methanol. They were dissolved in monochlorobenzene and filtered through a silica gel pad. The filtrate was concentrated by heating and recrystallized in acetone to afford <Intermediate 3-f>. (12 g, 71%)

Synthesis Example 3-(7)

Synthesis of Intermediate 3-g

Intermediate 3-g was synthesized as illustrated in the following Reaction Scheme 22:

<Reaction Scheme 22>

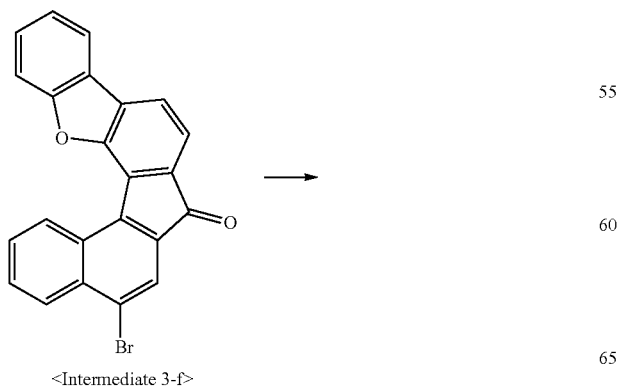

<Intermediate 3-f>

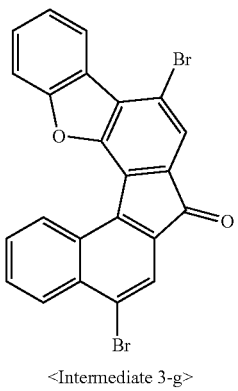

<Intermediate 3-g>

In a 1-L round-bottom flask reactor, <Intermediate 3-f> (12.0 g, 0.030 mol) and dichloromethane (360 ml) were stirred together at room temperature. A dilution of bromine (3.1 ml, 0.06 mol) in dichloromethane (40 ml) was dropwise added, followed by stirring at room temperature for 12 hrs. After completion of the reaction, methanol (100 ml) was added to induce the formation of precipitates. They were then filtered and washed with methanol. Recrystallization in 1,2-dichlorobenzene and acetone afforded <Intermediate 3-g> (10.3 g, 71.7%).

Synthesis Example 3-(8): Synthesis of Intermediate 3-h

Intermediate 3-h was synthesized as illustrated in the following Reaction Scheme 23:

<Reaction Scheme 23>

The same procedure as in Synthesis Example 1-(5), with the exception of using <Intermediate 3-g> instead of <Intermediate 1-g>, was conducted to synthesize <Intermediate 3-h> (10.0 g, 73.4%).

Synthesis Example 3-(9): Synthesis of Intermediate 3-i

Intermediate 3-i was synthesized as illustrated in the following Reaction Scheme 24:

<Reaction Scheme 24>

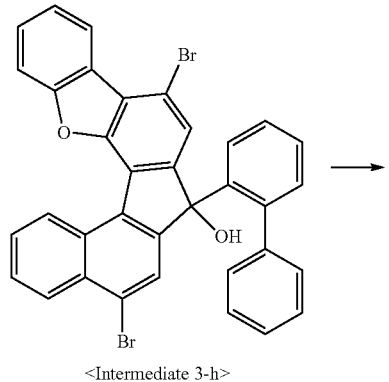

<Intermediate 3-h>

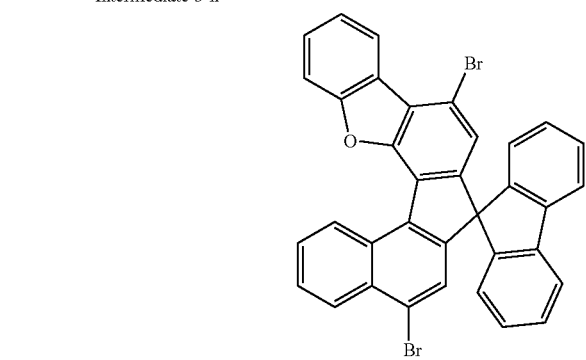

<Intermediate 3-i>

The same procedure as in Synthesis Example 1-(6), with the exception of using <Intermediate 3-h> instead of <Intermediate 1-e>, was conducted to synthesize <Intermediate 3-i> (6.3 g, 64.8%)

Synthesis Example 3-(10): Synthesis of Compound of Chemical Formula 49

The compound of Chemical Formula 49 was synthesized as illustrated in the following Reaction Scheme 25:

<Reaction Scheme 25>

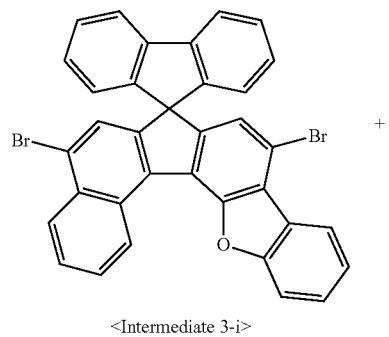

<Intermediate 3-i>

+

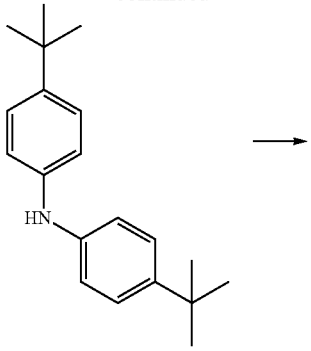

-continued

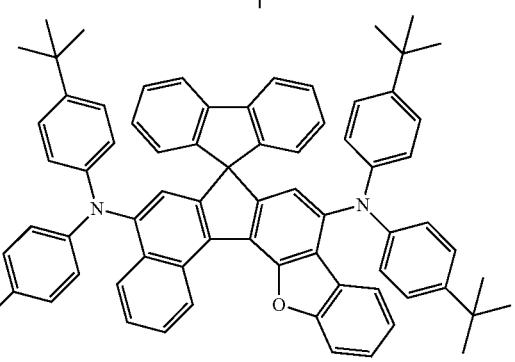

<Chemical Formula 49>

The same procedure as in Synthesis Example 1-(7), with the exception of using <Intermediate 3-i> instead of <Intermediate 1-f>, was conducted to synthesize the compound of <Chemical Formula 49> (3.0 g, 36.1%).

MS (MALDI-TOF): m/z 1014.5 [M$^+$]

SYNTHESIS EXAMPLE 4: Synthesis of Compound of Chemical Formula 76

Synthesis Example 4-(1): Synthesis of Intermediate 4-a

Intermediate 4-a was synthesized as illustrated in the following Reaction Scheme 26:

<Reaction Scheme 26>

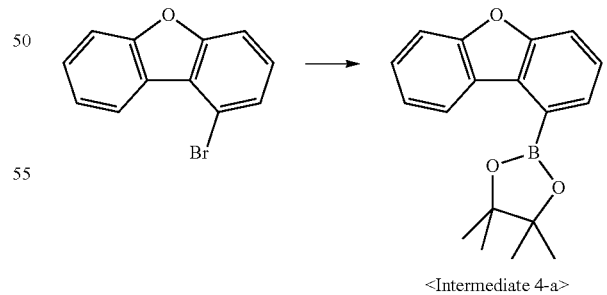

<Intermediate 4-a>

In a 500-mL round-bottom flask reactor, 1-bromodibenzofuran (20.0 g, 0.081 mmol), bis(pinacolato)diboron (26.7 g, 0.105 mol), [1,1'-bis(diphenylphosphino)ferrocene]dichloropalladium (1.3 g, 0.002 mol), potassium acetate (19.9 g, 0.202 mol), and 1,4-dioxane (200 ml) were stirred together for 10 hrs under reflux.

137

After completion of the reaction, filtration was performed through a celite pad. The filtrate was concentrated in a vacuum, purified by column chromatography, and recrystallized in dichloromethane and heptane to afford <Intermediate 4-a> (17.0 g, 70%).

Synthesis Example 4-(2)

Synthesis of Intermediate 4-b

Intermediate 4-b was synthesized as illustrated in the following Reaction Scheme 27:

<Reaction Scheme 27>

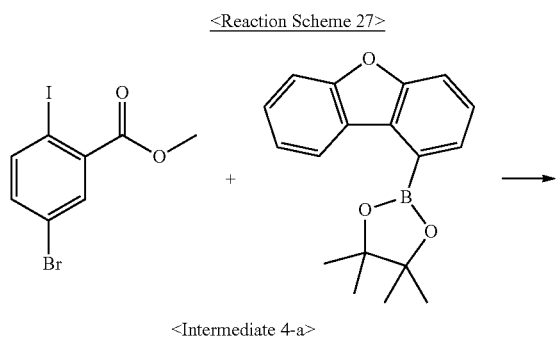

<Intermediate 4-a>

<Intermediate 4-b>

The same procedure as in Synthesis Example 1-(1), with the exception of using <Intermediate 4-a> instead of 4-dibenzobronic acid, was conducted to synthesize <Intermediate 4-b> (13.1 g, 68.9%).

Synthesis Example 4-(3)

Synthesis of Intermediate 4-c

Intermediate 4-c was synthesized as illustrated in the following Reaction Scheme 28:

<Reaction Scheme 28>

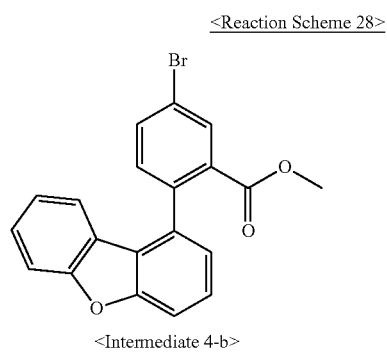

<Intermediate 4-b>

138

-continued

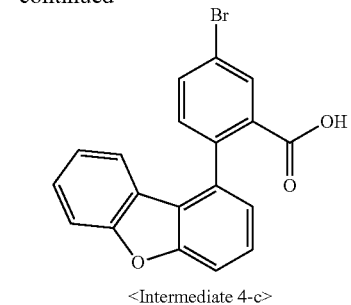

<Intermediate 4-c>

The same procedure as in Synthesis Example 1-(2), with the exception of using <Intermediate 4-b> instead of <Intermediate 1-a>, was conducted to synthesize <Intermediate 4-c> (11 g, 87%).

Synthesis Example 4-(4)

Synthesis of Intermediate 4-d

Intermediate 4-d was synthesized as illustrated in the following Reaction Scheme 29:

<Reaction Scheme 29>

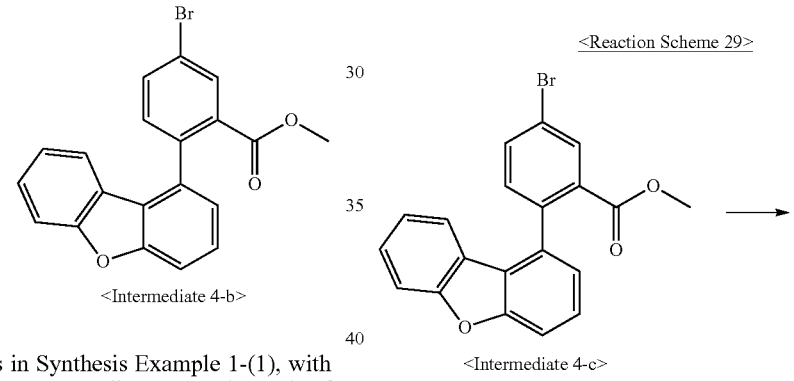

<Intermediate 4-c>

<Intermediate 4-d>

The same procedure as in Synthesis Example 1-(3), with the exception of using <Intermediate 4-c> instead of <Intermediate 1-b>, was conducted to synthesize <Intermediate 4-d> (9.0 g, 86%).

Synthesis Example 4-(5)

Synthesis of Intermediate 4-e

Intermediate 4-e was synthesized as illustrated in the following Reaction Scheme 30:

<Reaction Scheme 30>

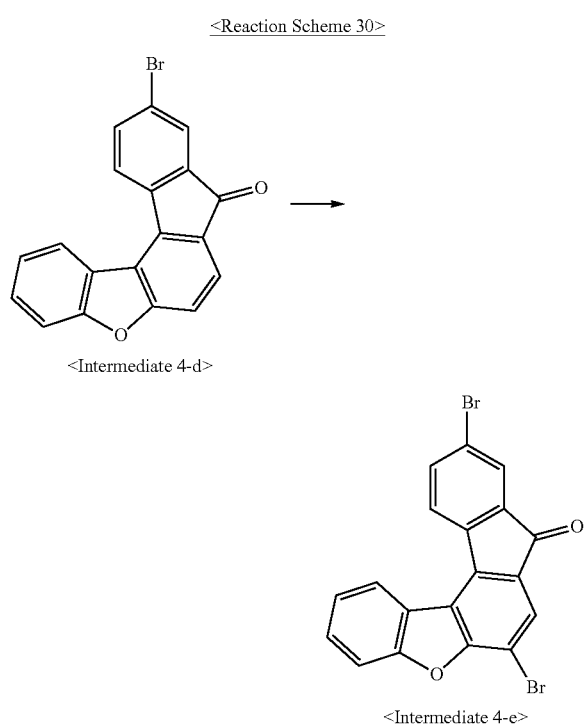

<Intermediate 4-d>

<Intermediate 4-e>

The same procedure as in Synthesis Example 1-(4), with the exception of using <Intermediate 4-d>, instead of <Intermediate 1-c>, was conducted to synthesize <Intermediate 4-e> (6.7 g, 60.7%).

Synthesis Example 4-(6): Synthesis of Intermediate 4-f

Intermediate 4-f was synthesized as illustrated in the following Reaction Scheme 31:

<Reaction Scheme 31>

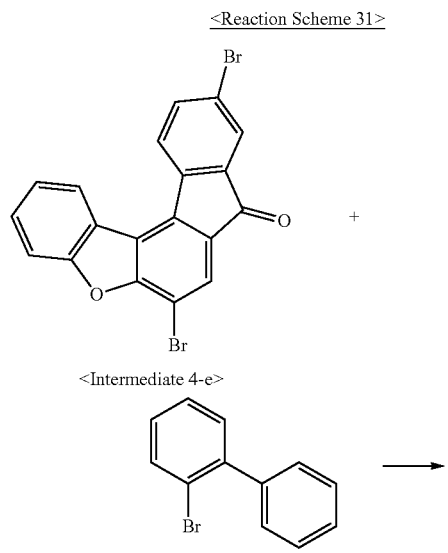

<Intermediate 4-e>

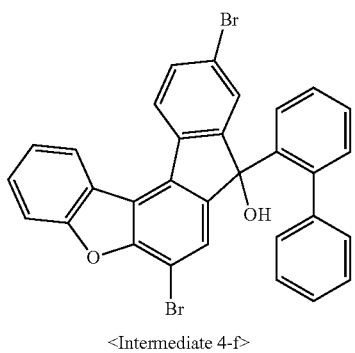

<Intermediate 4-f>

The same procedure as in Synthesis Example 1-(5), with the exception of using <Intermediate 4-e> instead of <Intermediate 1-d>, was conducted to synthesize <Intermediate 4-f> (5.2 g, 55%).

Synthesis Example 4-(7): Synthesis of Intermediate 4-g

Intermediate 4-g was synthesized as illustrated in the following Reaction Scheme:

<Reaction Scheme 32>

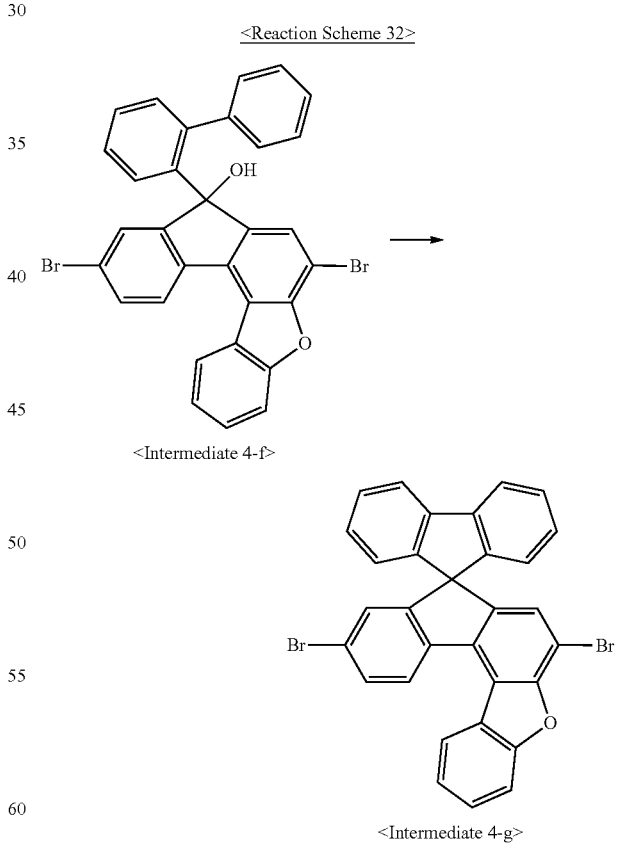

<Intermediate 4-f>

<Intermediate 4-g>

The same procedure as in Synthesis Example 1-(6), with the exception of using <Intermediate 4-f> instead of <Intermediate 1-e>, was conducted to synthesize <Intermediate 4-g> (4.3 g, 85.3%).

Synthesis Example 4-(8): Synthesis of Compound of Chemical Formula 76

The compound of Chemical Formula 76 was synthesized as illustrated in the following Reaction Scheme:

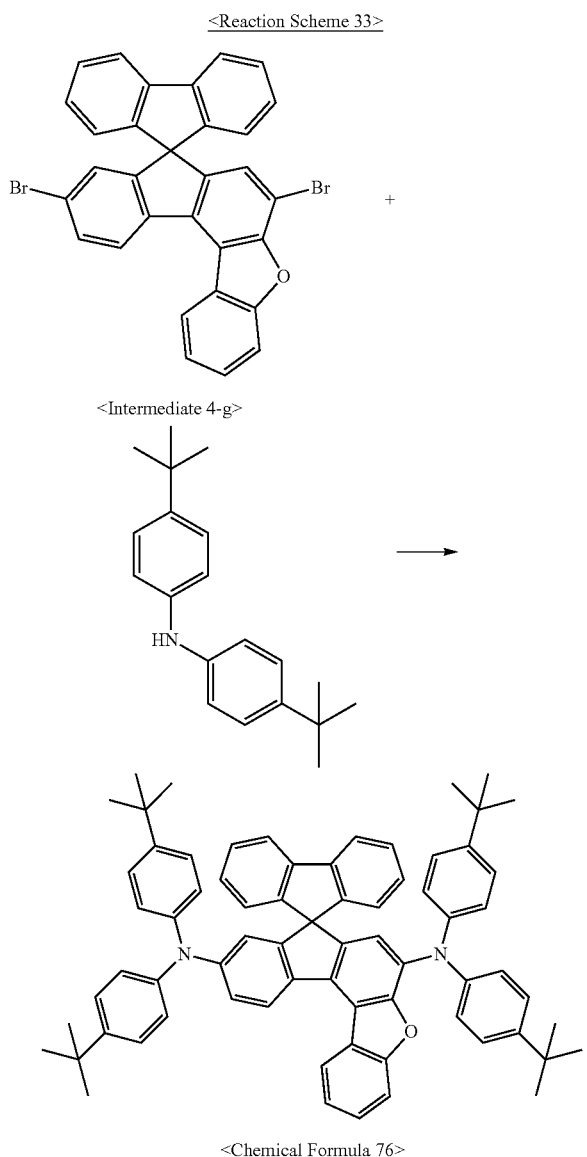

<Reaction Scheme 33>

<Intermediate 4-g>

<Chemical Formula 76>

The same procedure as in Synthesis Example 1-(7), with the exception of using <Intermediate 4-g> instead of <Intermediate 1-f>, was conducted to synthesize the compound of <Chemical Formula 76> (2.5 g, 34%).

MS (MALDI-TOF): m/z 964.5 [M$^+$]

SYNTHESIS EXAMPLE 5: Synthesis of Compound of Chemical Formula 89

Synthesis Example 5-(1): Synthesis of Intermediate 5-a

Intermediate 5-a was synthesized as illustrated in the following Reaction Scheme:

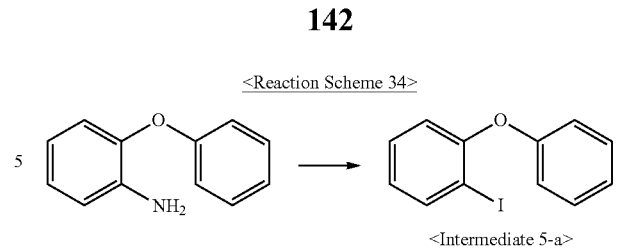

<Reaction Scheme 34>

<Intermediate 5-a>

In a 1-L round-bottom flask reactor, a mixture of 2-phenoxyaniline (25.0, 0.135 mol), HCl (30 ml), and water (150 ml) was cooled to 0° C. and stirred for 1 hr. At the same temperature, an aqueous solution (75 ml) of sodium nitrite (11.2 g, 0.162 mol) was added and then stirred for 1 hr. An aqueous solution (75 ml) of potassium iodide (44.8 g, 0.270 mol) was dropwise added, with care not to increase the temperature of the reaction solution above 5° C. Stirring was continued for 5 hrs at room temperature, and after completion of the reaction, the reaction mixture was washed with an aqueous sodium thiosulfate solution and extracted with ethyl acetate and water. The organic layer was separated and concentrated in a vacuum. Purification through column chromatography gave <Intermediate 5-a> (22.6 g, 56.5%).

Synthesis Example 5-(2): Synthesis of Intermediate 5-b

Intermediate 5-b was synthesized as illustrated in the following Reaction Scheme:

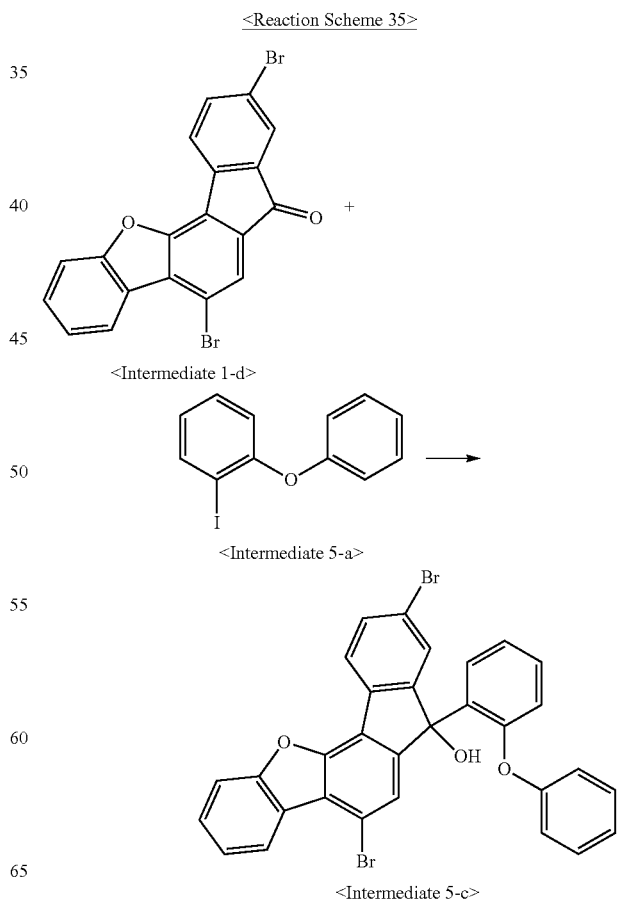

<Reaction Scheme 35>

<Intermediate 1-d>

<Intermediate 5-a>

<Intermediate 5-c>

The same procedure as in Synthesis Example 1-(5), with the exception of using <Intermediate 3-g> instead of <Intermediate 1-d>, was conducted to synthesize <Intermediate 5-b> (19.6 g, 70.4%).

Synthesis Example 5-(3): Synthesis of Intermediate 5-c

Intermediate 5-c was synthesized as illustrated in the following Reaction Scheme:

<Reaction Scheme 36>

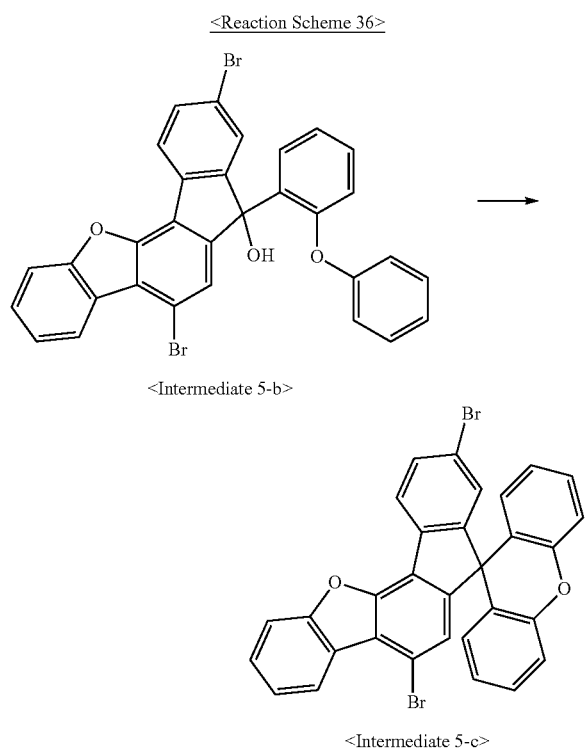

<Intermediate 5-b>

<Intermediate 5-c>

The same procedure as in Synthesis Example 1-6), with the exception of using <Intermediate 5-b> instead of <Intermediate 1-e>, was conducted to synthesize <Intermediate 5-c> (14.2 g, 74.7%).

Synthesis Example 5-(4): Synthesis of Compound of Chemical Formula 89

The compound of Chemical Formula 89 was synthesized as illustrated in the following Reaction Scheme 37:

<Reaction Scheme 37>

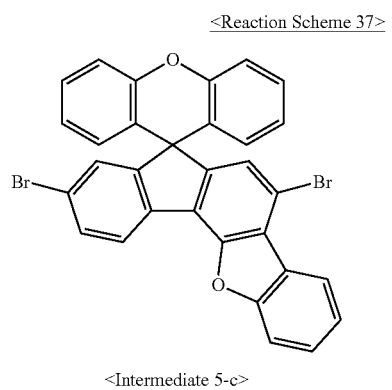

<Intermediate 5-c>

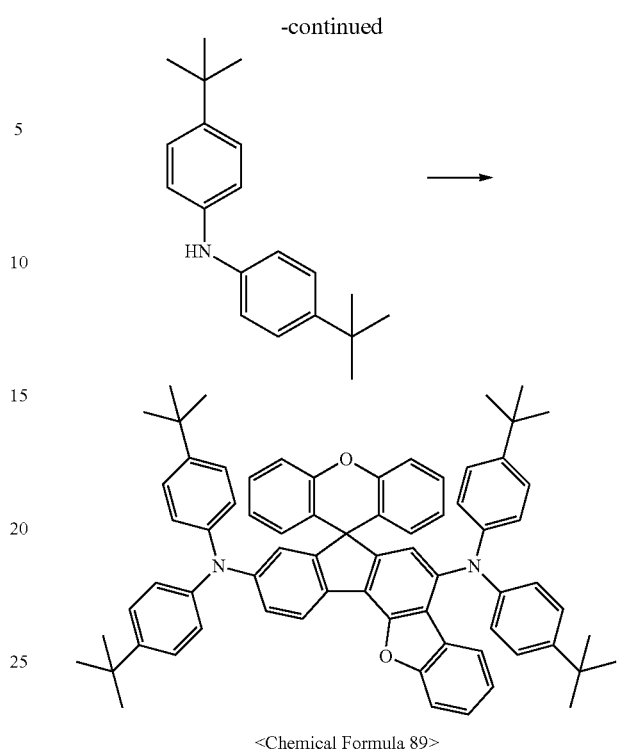

<Chemical Formula 89>

The same procedure as in Synthesis Example 1-(7), with the exception of using <Intermediate 5-c> and 1,1'-(4-methylphenyl-4-tert-butylphenyl)amine respectively instead of <Intermediate 1-f> and bis(4-tert-butylphenyl)amine, was conducted to synthesize the compound of <Chemical Formula 89> (2.4 g, 28%).

MS (MALDI-TOF): m/z 980.5 [M+]

Synthesis Example 6

Synthesis of Compound of Chemical Formula 97

Synthesis Example 6-(1)

Synthesis of Intermediate 6-a

Intermediate 6-a was synthesized as illustrated in the following Reaction Scheme:

<Reaction Scheme 38>

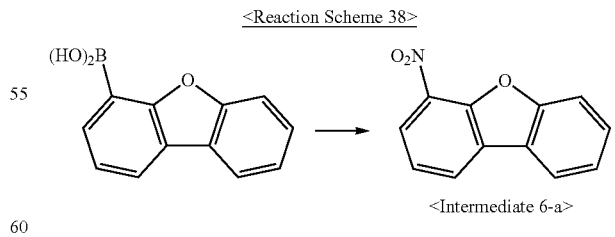

<Intermediate 6-a>

In a 2-L round-bottom flask reactor, 4-dibenzoboronic acid (85.0 g, 0.401 mol), bismuth (III) nitrate pentahydrate (99.2 g, 0.200 mol), and toluene (400 ml) were stirred together at 70° C. for 3 hrs under a nitrogen atmosphere. After completion of the reaction, the reaction mixture was cooled to room temperature, and the precipitates thus Synthesis Example 6-(2)

Synthesis of Intermediate 6-b

Intermediate 6-b was synthesized as illustrated in the following Reaction Scheme 39:

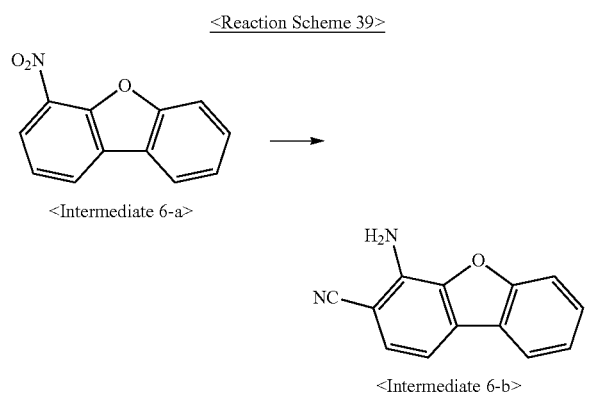

<Reaction Scheme 39>

<Intermediate 6-a>

<Intermediate 6-b>

In a 2-L round-bottom flask reactor, ethylcyanoacetate (202.9 g, 1.794 mol) and dimethylformamide (500 ml) were placed. Potassium hydroxide (67.10 g, 1.196 mol) and potassium cyanide (38.95 g, 0.598 mol) were added thereto, followed by dimethyl formamide (200 ml). The reaction solution was stirred at room temperature. <Intermediate 6-a> (127.5 g, 0.737 mol) was added little by little to the reaction solution, followed by stirring at 50° C. for 72 hrs. After completion of the reaction, an aqueous sodium hydroxide solution (25%, 200 ml) was added to the reaction solution, which was then stirred for 3 hrs under reflux and cooled to room temperature. Extraction was performed using ethyl acetate and water. The organic layer was isolated and concentrated in a vacuum. Purification through column chromatography afforded <Intermediate 6-b> (20.0 g, 16%).

Synthesis Example 6-(3)

Synthesis of Intermediate 6-c

Intermediate 6-c was synthesized as illustrated in the following Reaction Scheme 40:

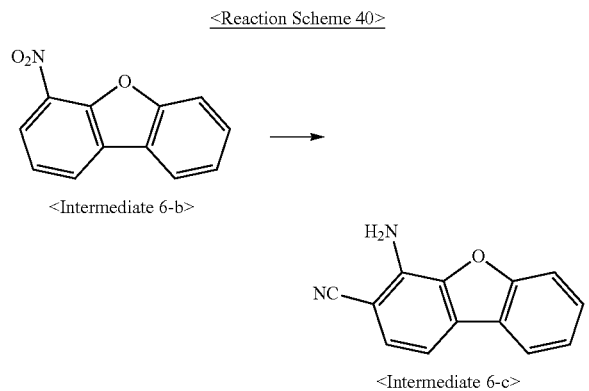

<Reaction Scheme 40>

<Intermediate 6-b>

<Intermediate 6-c>

In a 2-L round-bottom flask reactor, <Intermediate 6-b> (20.0 g, 0.096 mol), ethanol (600 ml), and an aqueous potassium hydroxide solution (142.26 g, 2.53 mol, 170 ml) were stirred together for 12 hrs under reflux. After completion of the reaction, the reaction mixture was cooled to room temperature and acidified with 6-N HCl (400 ml). The solid thus formed was stirred for 20 min and filtered. The filtrate was washed with ethanol to afford <Intermediate 6-c> (17.0 g, 88.5%).

Synthesis Example 6-(4)

Intermediate 6-d

Intermediate 6-d was synthesized as illustrated in the following Reaction Scheme 41:

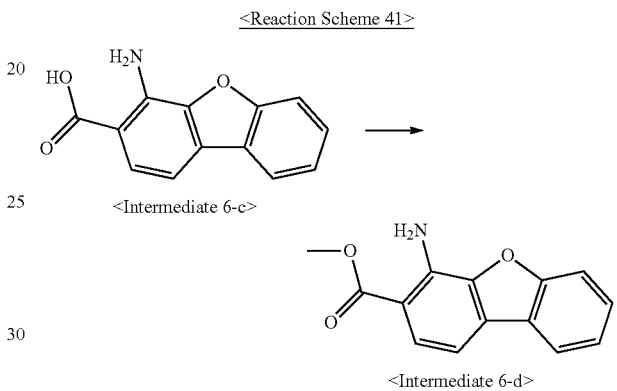

<Reaction Scheme 41>

<Intermediate 6-c>

<Intermediate 6-d>

In a 2-L round-bottom flask reactor, <Intermediate 6-c> (17.0 g, 0.075 mol) and sulfuric acid (15 ml) were stirred together for 72 hrs under reflux. After completion of the reaction, the reaction mixture was cooled to room temperature and then extracted with ethyl acetate and water. The organic layer was isolated and washed with an aqueous sodium hydrogen carbonate, followed by concentration in a vacuum. The concentrate was crystallized in an excess of methanol and filtered to afford <Intermediate 6-d> (14.0 77.6%).

Synthesis Example 6-(5) Synthesis of Intermediate 6-e

Intermediate 6-d was synthesized as illustrated in the following Reaction Scheme 42:

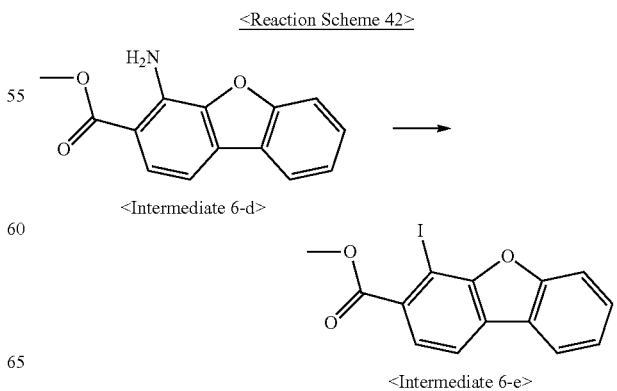

<Reaction Scheme 42>

<Intermediate 6-d>

<Intermediate 6-e>

The same procedure as in Synthesis Example 5-(1), with the exception of using <Intermediate 6-d> instead of 2-phenoxyaniline, was conducted to synthesize <Intermediate 6-e> (9.1 g, 48%).

Synthesis Example 6-(6): Synthesis of Intermediate 6-f

Intermediate 6-f was synthesized as illustrated in the following Reaction Scheme 43:

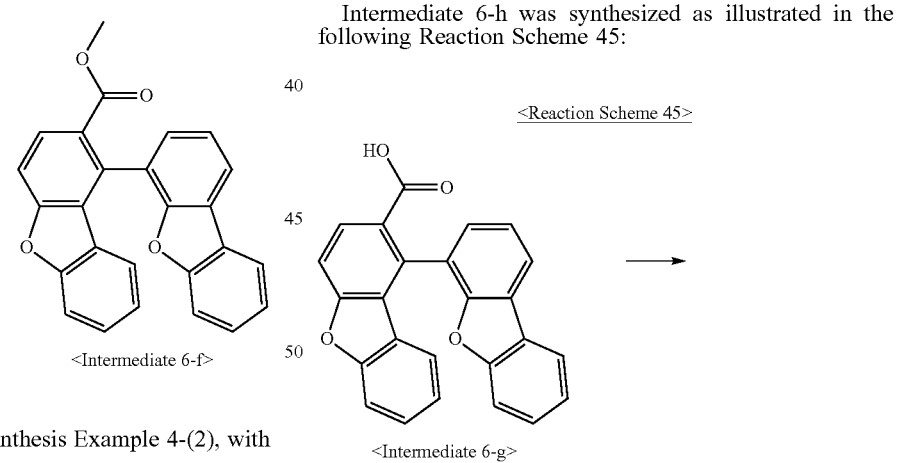

<Reaction Scheme 43>

<Intermediate 6-e>

<Intermediate 4-a>

<Intermediate 6-f>

The same procedure as in Synthesis Example 4-(2), with the exception of using <Intermediate 6-e> instead of methyl 5-bromo-2-iodobenzoate, was conducted to synthesize <Intermediate 6-f> (5.3 g, 52.3%).

Synthesis Example 6-(7)

Synthesis of Intermediate 6-g

Intermediate 6-g was synthesized as illustrated in the following Reaction Scheme 44:

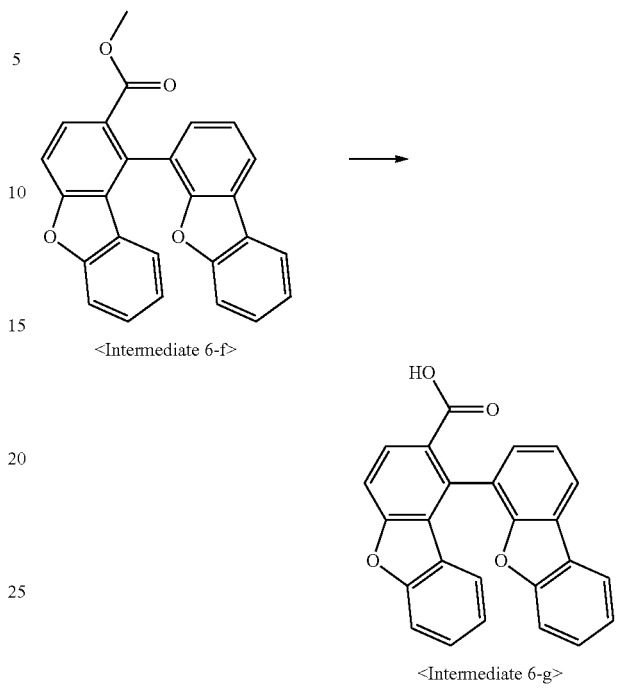

<Reaction Scheme 44>

<Intermediate 6-f>

<Intermediate 6-g>

The same procedure as in Synthesis Example 1-(2), with the exception of using <Intermediate 6-f> instead of <Intermediate 1-a>, was conducted to synthesize <Intermediate 6-g> (4.5 g, 88.1%).

Synthesis Example 6-(8)

Synthesis of Intermediate 6-h

Intermediate 6-h was synthesized as illustrated in the following Reaction Scheme 45:

<Reaction Scheme 45>

<Intermediate 6-g>

<Intermediate 6-h>

The same procedure as in Synthesis Example 1-(3), with the exception of using <Intermediate 6-g> instead of <Intermediate 1-b>, was conducted to synthesize <Intermediate 6-h> (3.8 g, 88.8%).

Synthesis Example 6-(9): Synthesis of Intermediate 6-i

Intermediate 6-i was synthesized as illustrated in the following Reaction Scheme 46:

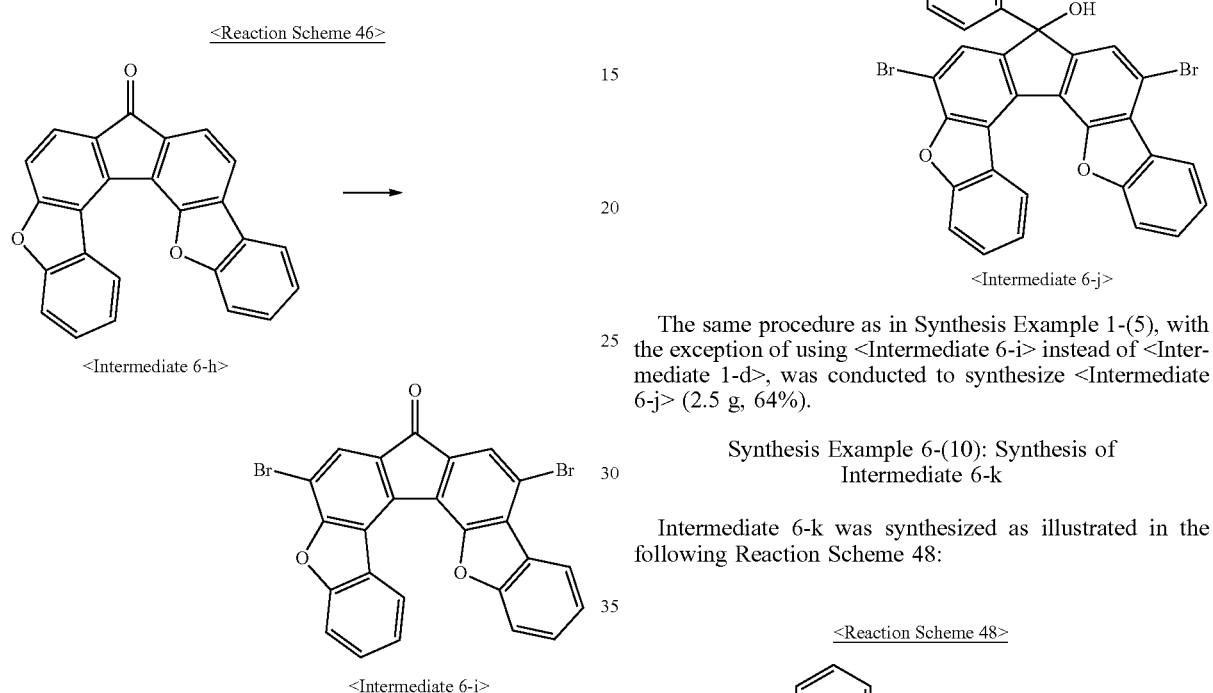

The same procedure as in Synthesis Example 1-(4), with the exception of using <Intermediate 6-h> instead of <Intermediate 1-c>, was conducted to synthesize <Intermediate 6-i> (3 g, 55%).

Synthesis Example 6-(10): Synthesis of Intermediate 6-j

Intermediate 6-j was synthesized as illustrated in the following Reaction Scheme 47:

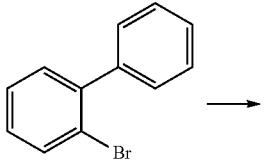

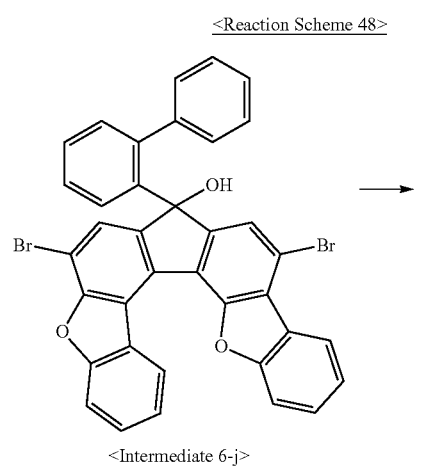

The same procedure as in Synthesis Example 1-(5), with the exception of using <Intermediate 6-i> instead of <Intermediate 1-d>, was conducted to synthesize <Intermediate 6-j> (2.5 g, 64%).

Synthesis Example 6-(10): Synthesis of Intermediate 6-k

Intermediate 6-k was synthesized as illustrated in the following Reaction Scheme 48:

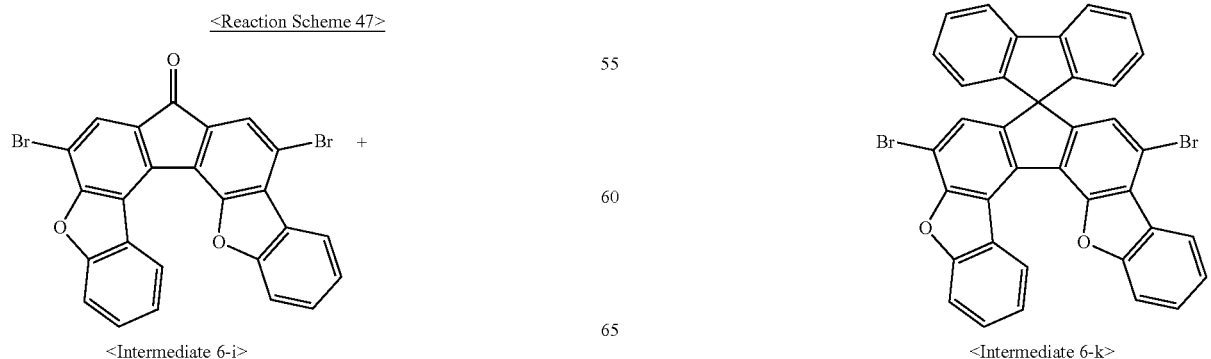

The same procedure as in Synthesis Example 1-(6), with the exception of using <Intermediate 6-j> instead of <Intermediate 1-e>, was conducted to synthesize <Intermediate 6-k> (2.2 g, 90.4%).

Synthesis Example 6-(11): Synthesis of Intermediate 6-1

Intermediate 6-1 was synthesized as illustrated in the following Reaction Scheme 49:

<Reaction Scheme 49>

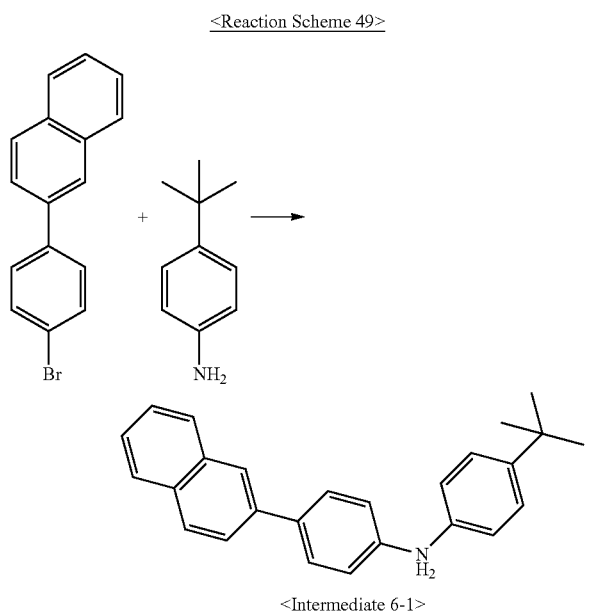

<Intermediate 6-1>

In a 250-ml round-bottom flask reactor, 1-bromo-4-(2-naphthyl)benzene (10.0 g, 0.035 mol), 4-tert-butyl aniline (5.8 g, 0.039 mol), tris(dibenzylidne acetone)dipalladium(0) (0.65 g, 0.0007 mol), sodium tert-butoxide (6.79 g, 0.0706 mol), 2,2'-bis(diphenylphosphino)-1,1'-binaphthalene (0.44 g, 0.0007 mol), and toluene (100 ml) were stirred together for 3 hrs under reflux. After completion of the reaction, the reaction mixture was cooled to room temperature and extracted with ethyl acetate and water. The organic layer was isolated, dried over magnesium sulfate, and concentrated in a vacuum. Purification through column chromatography gave <Intermediate 6-1> (10 g, 80%).

Synthesis Example 6-(12): Synthesis of Compound of Chemical Formula 97

The compound of Chemical Formula 97 was synthesized as illustrated in the following Reaction Scheme 50:

<Reaction Scheme 50>

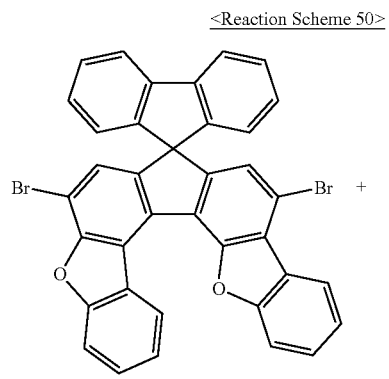

-continued

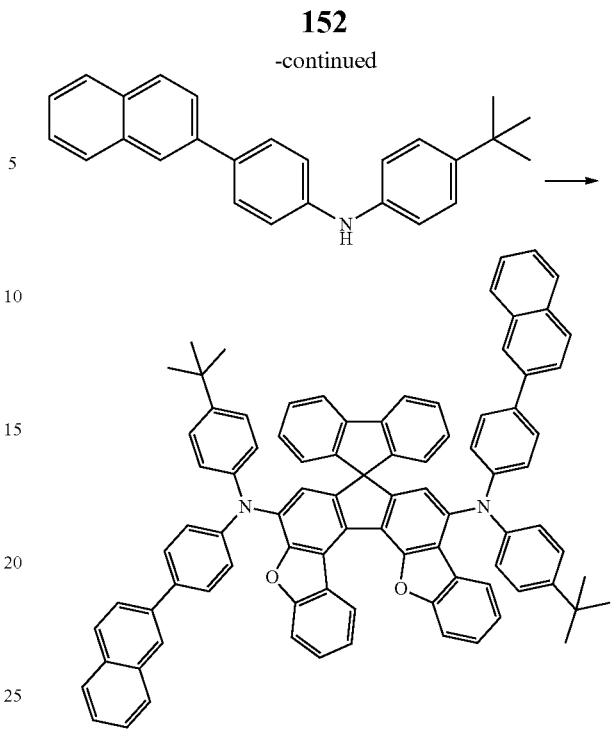

<Intermediate 6-k><Intermediate 6-1><Chemical Formula 97>

The same procedure as in Synthesis Example 1-(7), with the exception of using <Intermediate 6-k> and <Intermediate 6-1> respectively instead of <Intermediate 1-f> and bis(4-tert-butylphenyl)amin, was conducted to synthesize <Chemical Formula 97> (1.6 g, 38%).

MS (MALDI-TOF): m/z 1194.5 [M$^+$]

SYNTHESIS EXAMPLE 7: Synthesis of Compound of Chemical Formula

Synthesis Example 7-(1): Synthesis of Intermediate 7-a

Intermediate 7-a was synthesized as illustrated in the following Reaction Scheme 51:

<Reaction Scheme 51>

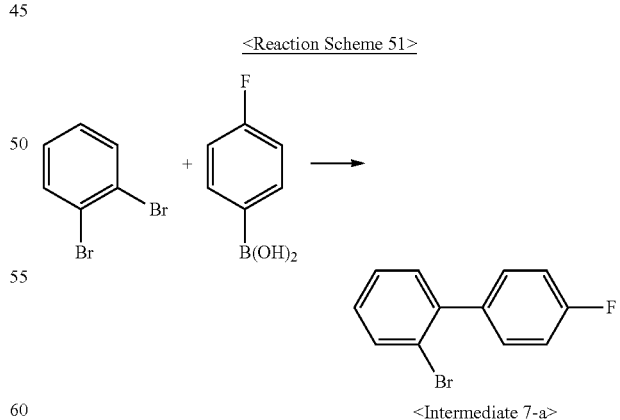

<Intermediate 7-a>

In a 500-mL round-bottom flask reactor, 1,2-dibromobenzene (20.0 g, 0.085 mol), 4-fluorobenzobronic acid (14.2 g, 0.102 mol), tetrakis (triphenylphosphine)palladium (2.9 g, 0.0025 mmol), and potassium carbonate (23.4 g, 0.169 mol) were placed, followed by toluene (100 mL), tetrahydrofuran (100 mL) and water (40 mL). The reaction mixture was heated to 80° C. and stirred for 10 hrs. After completion of the reaction, the reaction mixture was cooled to room temperature and extracted with ethyl acetate. The organic layer was isolated and concentrated in a vacuum. Purification through column chromatography afforded Intermediate 7-a (14.1 g, 66.2%)

Synthesis Example 7-(2): Synthesis of Intermediate 7-b

Intermediate 7-b was synthesized as illustrated in the following Reaction Scheme 52:

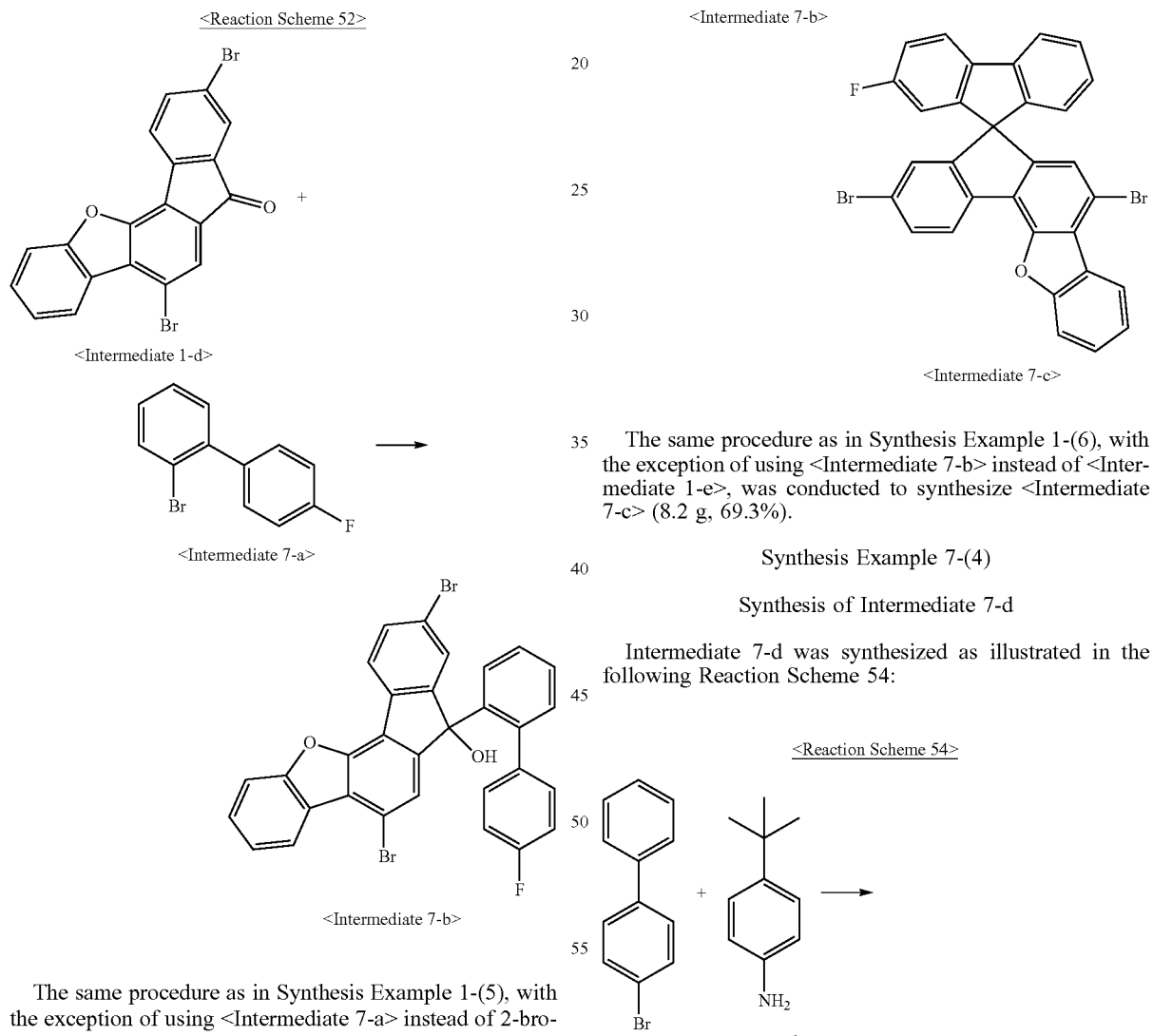

The same procedure as in Synthesis Example 1-(5), with the exception of using <Intermediate 7-a> instead of 2-bromobiphenyl, was conducted to synthesize <Intermediate 7-b> (12.2 g, 79%).

Synthesis Example 7-(3): Synthesis of Intermediate 7-c

Intermediate 7-c was synthesized as illustrated in the following Reaction Scheme 53:

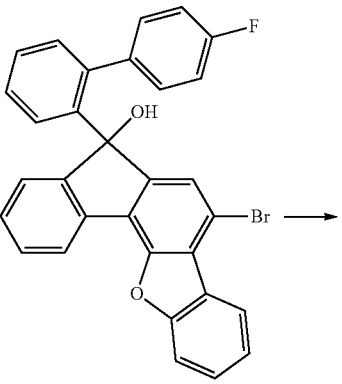

The same procedure as in Synthesis Example 1-(6), with the exception of using <Intermediate 7-b> instead of <Intermediate 1-e>, was conducted to synthesize <Intermediate 7-c> (8.2 g, 69.3%).

Synthesis Example 7-(4)

Synthesis of Intermediate 7-d

Intermediate 7-d was synthesized as illustrated in the following Reaction Scheme 54:

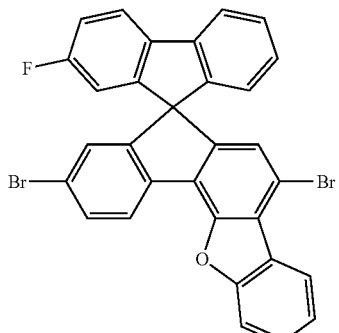

The same procedure as in Synthesis Example 6-(11), with the exception of using 4-bromobiphenyl instead of 1-bromo 4-(2-naphthyl)benzene, was conducted to synthesize <Intermediate 7-d> (14.0 g, 72%).

Synthesis Example 7-(5)

Synthesis of Compound of Chemical Formula 45

The compound of Chemical Formula 45 was synthesized as illustrated in the following Reaction Scheme 55:

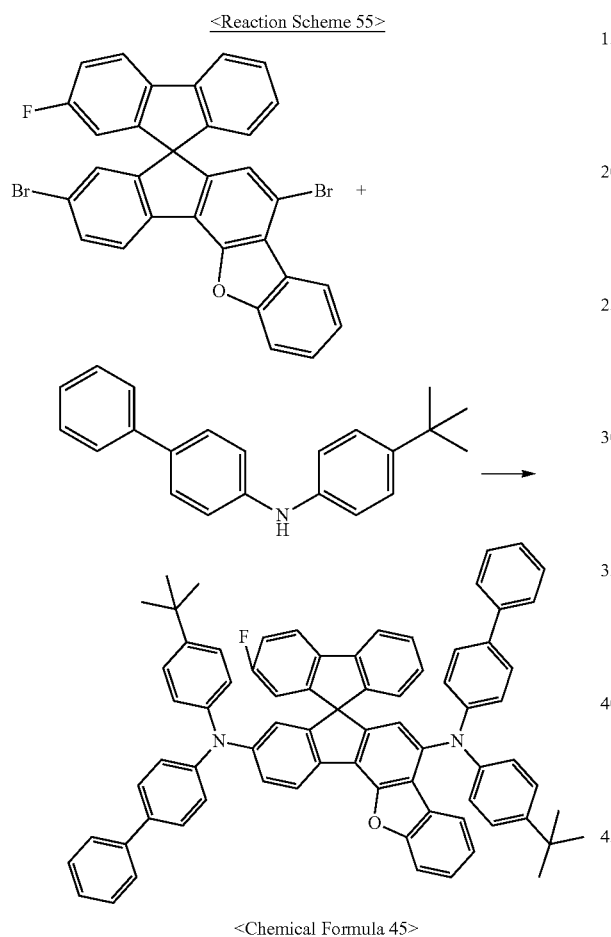

The same procedure as in Synthesis Example 1-(7), with the exception of using <Intermediate 7-c> and <Intermediate 7-d> respectively instead of <Intermediate 1-f> and bis(4-tert-butylphenyl)amine, was conducted to synthesize the compound of <Chemical Formula 45> (2.4 g, 28%).

MS (MALDI-TOF): m/z 1022.4 [M$^+$]

Synthesis Example 8

Synthesis of Compound of Chemical Formula

Synthesis Example 8-(1): Synthesis of Intermediate 8-a

Intermediate 8-a was synthesized as illustrated in the following Reaction Scheme 56:

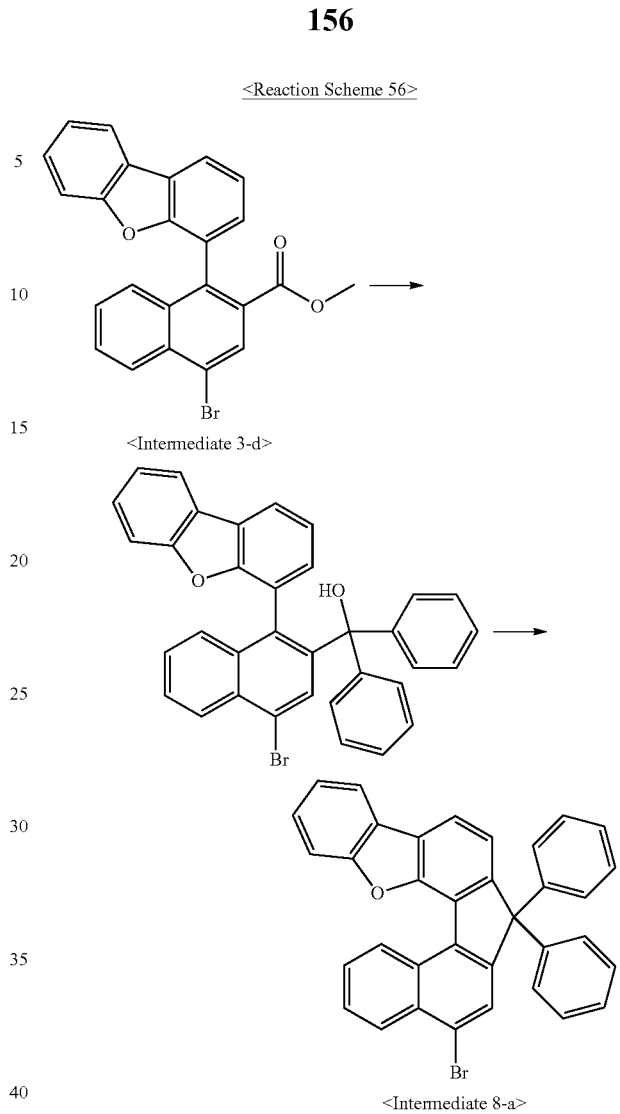

In a 500-mL round-bottom flask reactor, a mixture of bromobenzene (25.46 g, 0.163 mol) and tetrahydrofuran (170 ml) was cooled to −78° C. under a nitrogen atmosphere. N-butyl lithium (1.6 M)(95.6 ml, 0.153 mol) was dropwise added to the chilled solution, which was then stirred at the same temperature for 1 hr. <Intermediate 3-d> (22.0 g, 0.051 mol) was added, followed by stirring at room temperature for 3 hrs. After completion of the reaction, the reaction mixture was stirred together with water (50 ml) for 30 min. Extraction was made with ethyl acetate and water. The organic layer was isolated and concentrated in a vacuum. The concentrate was stirred together with acetic acid (200 ml) and HCl (1 ml) at 80° C. After the reaction was completed, the precipitate thus formed was filtered and washed with methanol to afford <Intermediate 8-a> (20.0 g, 73%).

Synthesis Example 8-(2): Synthesis of Intermediate

Intermediate 8-b was synthesized as illustrated in the following Reaction Scheme 57:

<Reaction Scheme 57>

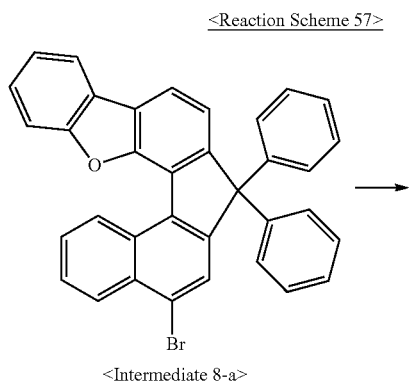

<Intermediate 8-a>

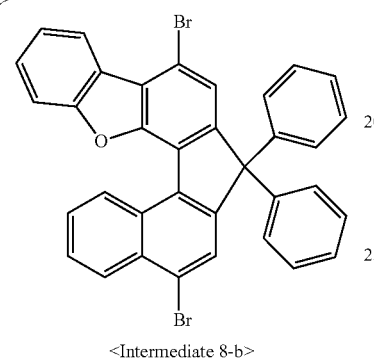

<Intermediate 8-b>

In a 1-L round-bottom flask reactor, a mixture of <Intermediate 8-a> (20.0 g, 0.037 mol) and chloroform (600 ml) was added with drops of a dilution of bromine (5.7 ml, 0.112 mol) in chloroform (40 ml) while stirring at room temperature for 12 hrs. After completion of the reaction, methanol (100 ml) was added to produce precipitates which were then washed with methanol. They were recrystallized in 1,2-dichlorobenzene and acetone to afford <Intermediate 8-b> (14.0 g, 61.7%).

Synthesis Example 8-(3): Synthesis of Intermediate 8-c

Intermediate 8-c was synthesized as illustrated in the following Reaction Scheme 58:

<Reaction Scheme 58>

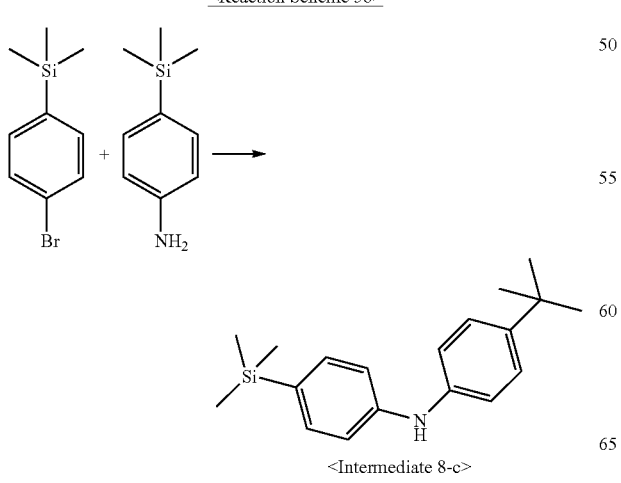

<Intermediate 8-c>

Synthesis of Intermediate 8-a

The same procedure as in Synthesis Example 6-(11), with the exception of using 1-bromo-4-(trimethylsilyl)benzene instead of 1-bromo 4-(2-naphthyl)benzene, was conducted to synthesize <Intermediate 8-c> (13.1 g, 72.1%).

Synthesis Example 8-(4)

Synthesis of Compound of Chemical Formula 105

The compound of Chemical Formula 105 was synthesized as illustrated in the following Reaction Scheme 59:

<Reaction Scheme 59>

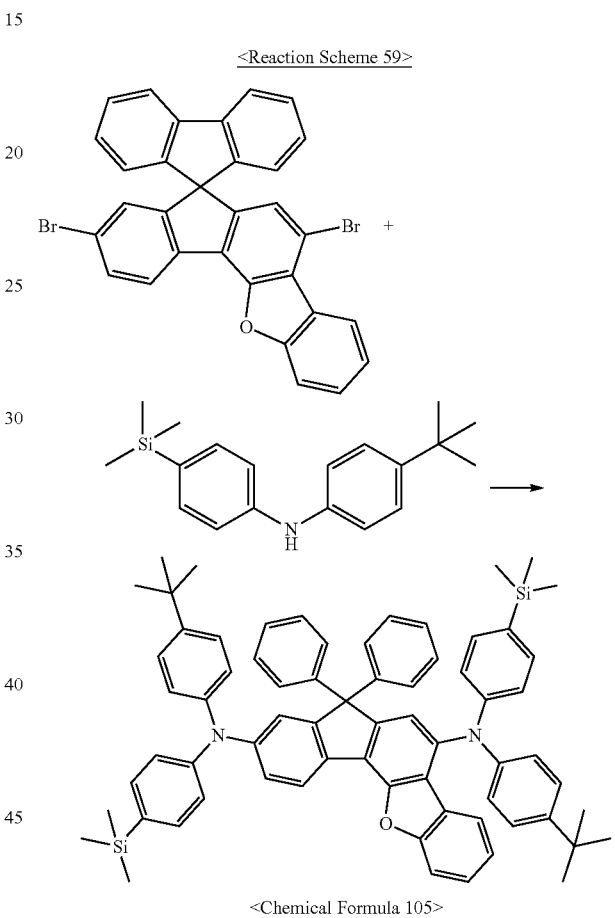

<Chemical Formula 105>

The same procedure as in Synthesis Example 1-(7), with the exception of using <Intermediate 8-b> and <Intermediate 8-c> respectively instead of <Intermediate 1-f> and bis(4-tert-butylphenyl)amine, was conducted to synthesize the compound of <Chemical Formula 105> (3.0 g, 35%).
MS (MALDI-TOF): m/z 1048.5 [M$^+$]

Synthesis Example 9

Synthesis of Compound of Chemical Formula 220

Synthesis Example 9-(1)

Synthesis of Intermediate 9-a

Intermediate 9-a was synthesized as illustrated in the following Reaction Scheme 60:

<Reaction Scheme 60>

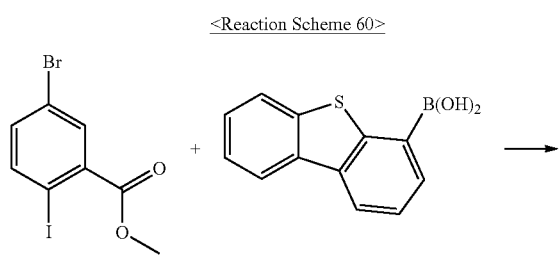

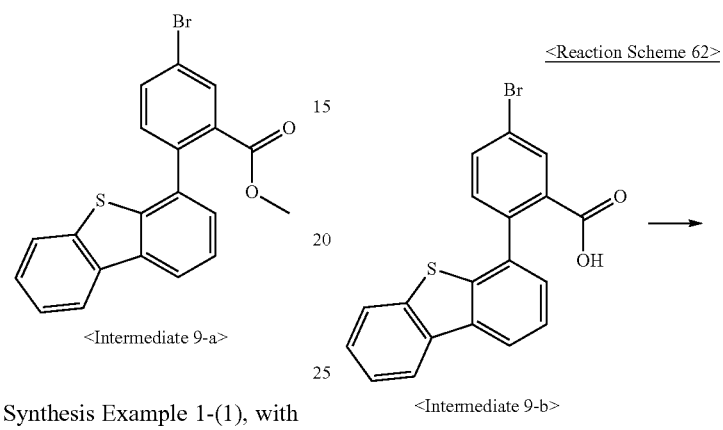

The same procedure as in Synthesis Example 1-(1), with the exception of using 4-dibenzothiophene boronic acid instead of 4-dibenzofuran boronic acid, was conducted to synthesize <Intermediate 9-a> (18.0 g, 61.8%).

Synthesis Example 9-(2): Synthesis of Intermediate 9-b

Intermediate 9-b was synthesized as illustrated in the following Reaction Scheme 61:

<Reaction Scheme 61>

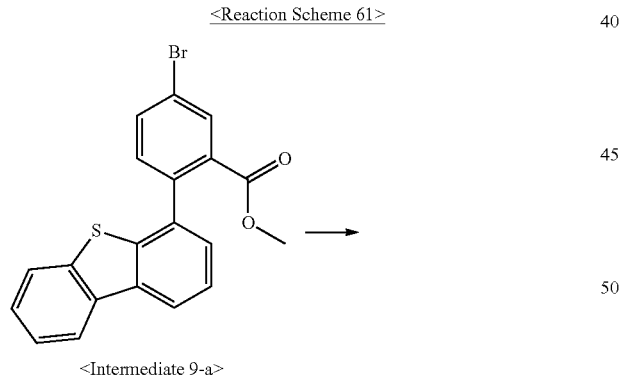

The same procedure as in Synthesis Example 1-(2), with the exception of using <Intermediate 9-a> instead of <Intermediate 1-a>, was conducted to synthesize <Intermediate 9-b> (15.0 g, 86.5%).

Synthesis Example 9-(3)

Synthesis of Intermediate 9-c

Intermediate 9-c was synthesized as illustrated in the following Reaction Scheme 62:

The same procedure as in Synthesis Example 1-(3), with the exception of using <Intermediate 9-b> instead of <Intermediate 1-b>, was conducted to synthesize <Intermediate 9-c> (12.0 g, 83.9%).

Synthesis Example 9-(4)

Synthesis of Intermediate 9-d

Intermediate 9-d was synthesized as illustrated in the following Reaction Scheme 63:

<Reaction Scheme 63>

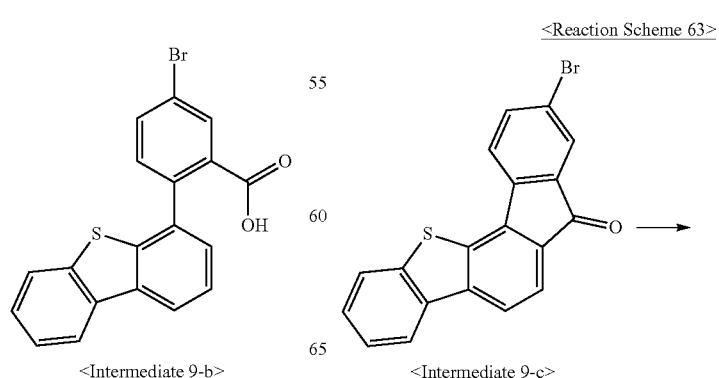

161
-continued

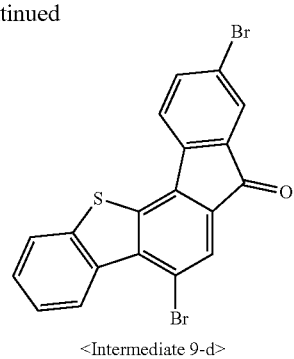
<Intermediate 9-d>

The same procedure as in Synthesis Example 1-(4), with the exception of using <Intermediate 9-c> instead of <Intermediate 1-c>, was conducted to synthesize <Intermediate 9-d> (11.0 g, 75.4%).

Synthesis Example 9-(5)

Synthesis of Intermediate 9-e

Intermediate 9-e was synthesized as illustrated in the following Reaction Scheme 64:

<Reaction Scheme 64>

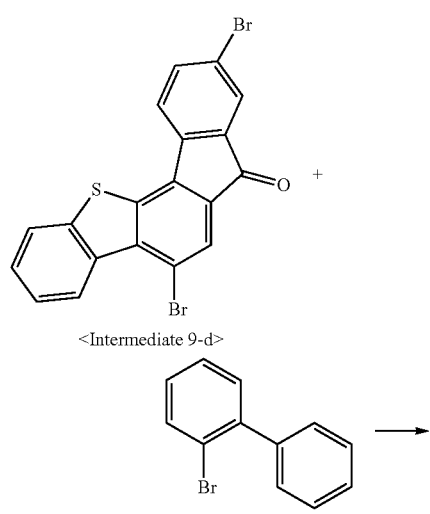
<Intermediate 9-d>

<Intermediate 9-e>

The same procedure as in Synthesis Example 1-(5), with the exception of using <Intermediate 9-d> instead of <Intermediate 1-d>, was conducted to synthesize <Intermediate 9-e> (11.2 g, 75.6%).

162

Synthesis Example 9-(6): Synthesis of Intermediate 9-f

Intermediate 9-f was synthesized as illustrated in the following Reaction Scheme 65:

<Reaction Scheme 65>

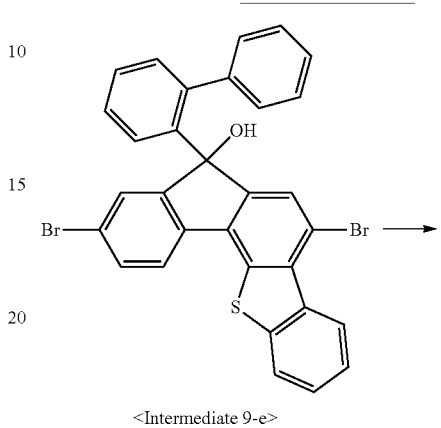
<Intermediate 9-e>

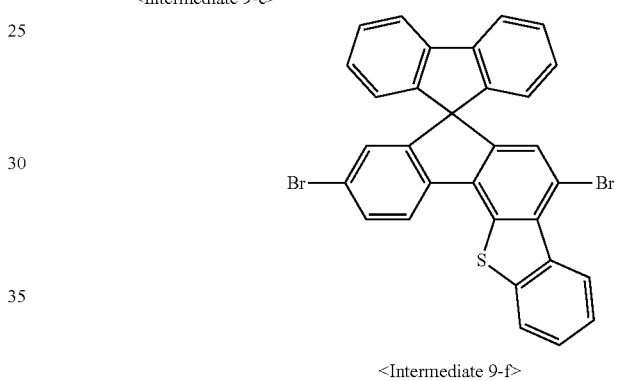
<Intermediate 9-f>

The same procedure as in Synthesis Example 1-(6), with the exception of using <Intermediate 9-e> instead of <Intermediate 1-e>, was conducted to synthesize <Intermediate 9-f> (8.7 g, 80.1%).

Synthesis Example 9-(7): Synthesis of Compound of Chemical Formula 220

The compound of Chemical Formula 220 was synthesized as illustrated in the following Reaction Scheme 66:

<Reaction Scheme 66>

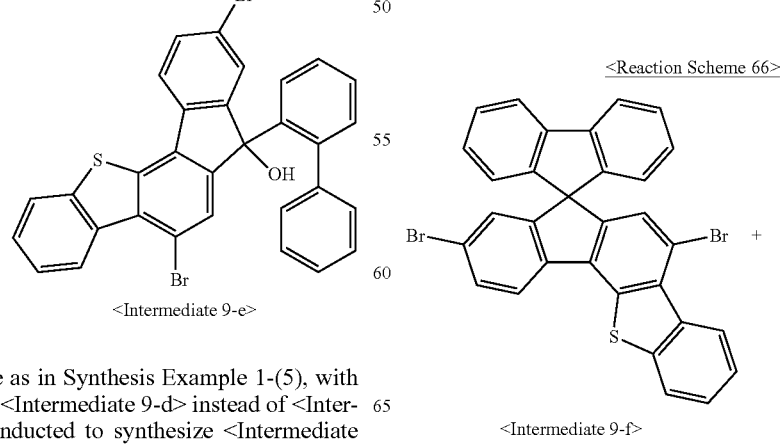
<Intermediate 9-f>

-continued

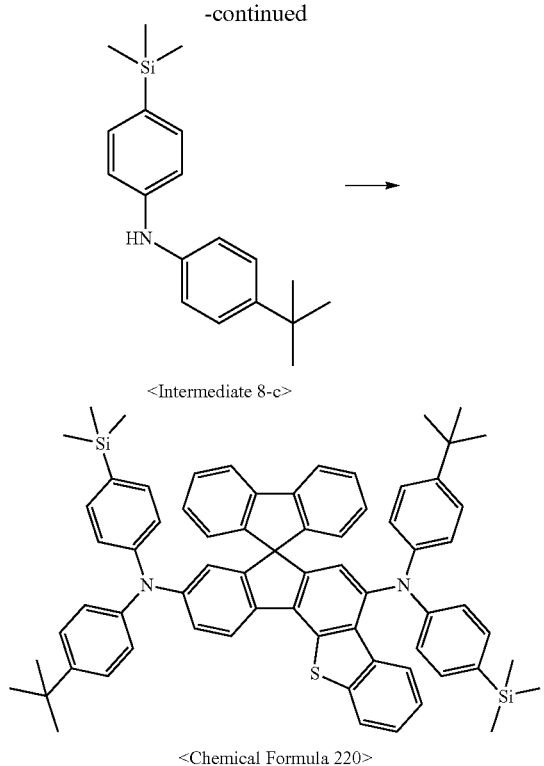

<Intermediate 8-c>

<Chemical Formula 220>

The same procedure as in Synthesis Example 1-(7), with the exception of using <Intermediate 9-f> instead of <Intermediate 1-f>, was conducted to synthesize the compound of <Chemical Formula 220> (3.2 g, 36.6%).

SYNTHESIS EXAMPLE 10: Synthesis of Compound of Chemical Formula 224

Synthesis Example 10-(1): Synthesis of Intermediate 10-a

Intermediate 10-a was synthesized as illustrated in the following Reaction Scheme 67:

<Reaction Scheme 67>

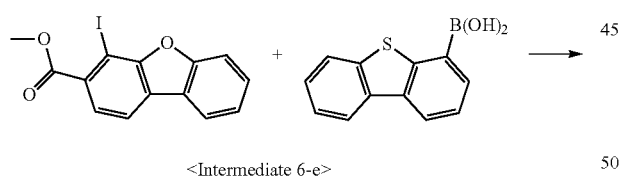

<Intermediate 6-e>

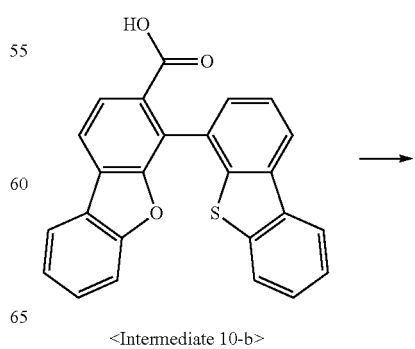

<Intermediate 10-a>

The same procedure as in Synthesis Example 4-(2), with the exception of using <Intermediate 6-e> and 4-dibenzo-thiophene boronic acid respectively instead of methyl 5-bromo-2-iodobenzoate and <Intermediate 4-a>, was conducted to synthesize <Intermediate 10-a> (20.2 g, 84.3%).

Synthesis Example 10-(2)

Synthesis of Intermediate 10-b

Intermediate 10-b was synthesized as illustrated in the following Reaction Scheme 68:

<Reaction Scheme 68>

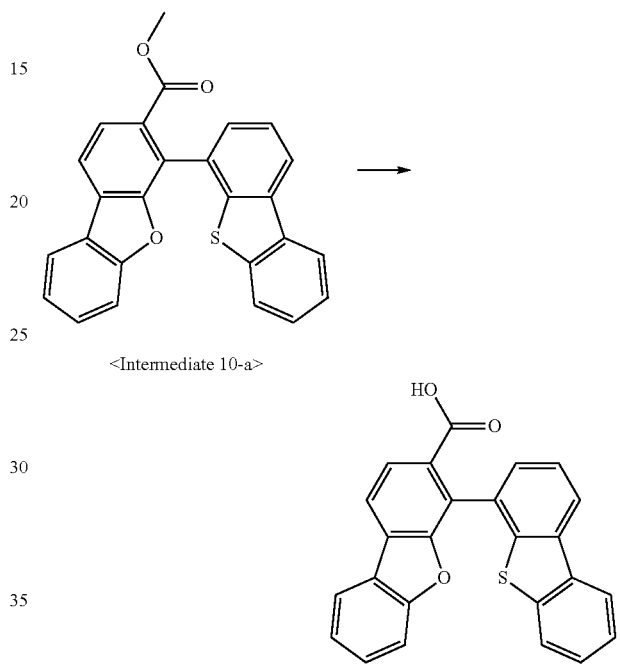

<Intermediate 10-a>

<Intermediate 10-b>

The same procedure as in Synthesis Example 1-(2), with the exception of using <Intermediate 10-a> instead of <Intermediate 1-a>, was conducted to synthesize <Intermediate 10-b> (16.5 g, 84.6%).

Synthesis Example 10-(3)

Synthesis of Intermediate 10-c

Intermediate 10-c was synthesized as illustrated in the following Reaction Scheme 69:

<Reaction Scheme 69>

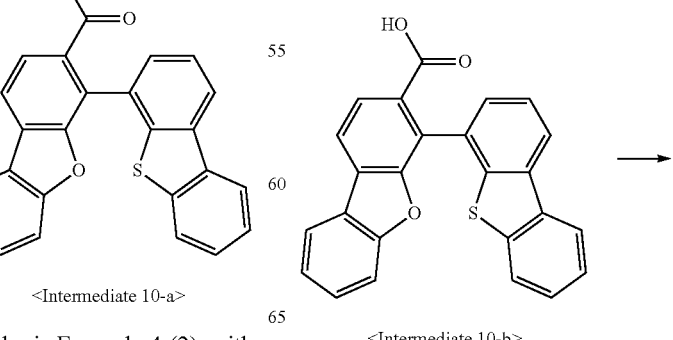

<Intermediate 10-b>

-continued

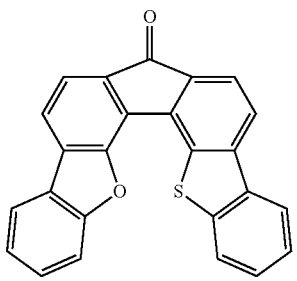

<Intermediate 10-c>

The same procedure as in Synthesis Example 1-(3), with the exception of using <Intermediate 10-b> instead of <Intermediate 1-b>, was conducted to synthesize <Intermediate 10-c> (12.4 g, 78.7%).

Synthesis Example 10-(4)

Synthesis of Intermediate 10-d

Intermediate 10-d was synthesized as illustrated in the following Reaction Scheme 70:

<Reaction Scheme 70>

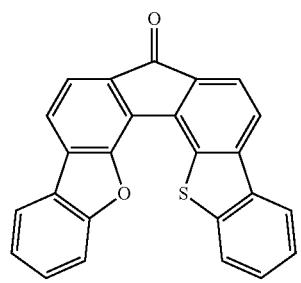

<Intermediate 10-c>

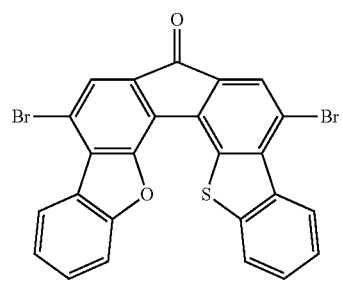

<Intermediate 10-d>

The same procedure as in Synthesis Example 1-(4), with the exception of using <Intermediate 10-c> instead of <Intermediate 1-c>, was conducted to synthesize <Intermediate 10-d> (3 g, 62.5%).

Synthesis Example 10-(5)

Synthesis of Intermediate 10-e

Intermediate 10-e was synthesized as illustrated in the following Reaction Scheme 71:

<Reaction Scheme 71>

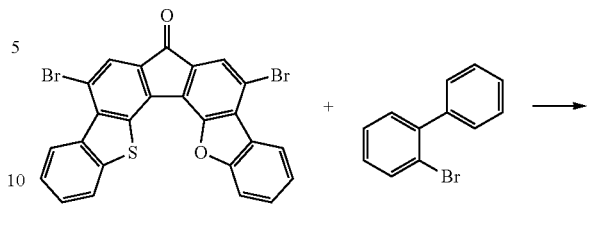

<Intermediate 10-d>

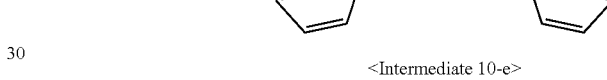

<Intermediate 10-e>

The same procedure as in Synthesis Example 1-(5), with the exception of using <Intermediate 10-d> instead of <Intermediate 1-d>, was conducted to synthesize <Intermediate 10-e> (10.2 g, 72.0%).

Synthesis Example 10-(6)

Synthesis of Intermediate 10-f

Intermediate 10-f was synthesized as illustrated in the following Reaction Scheme 72:

<Reaction Scheme 72>

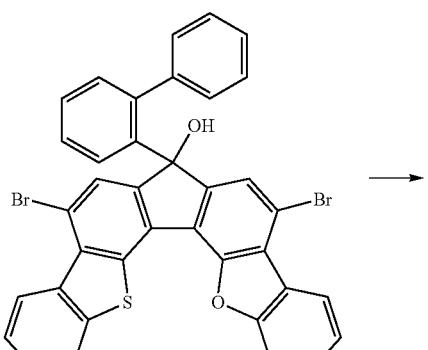

<Intermediate 10-e>

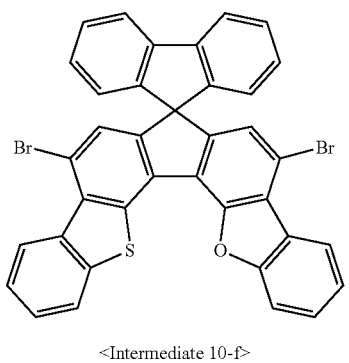

<Intermediate 10-f>

The same procedure as in Synthesis Example 1-(6), with the exception of using <Intermediate 10-e> instead of <Intermediate 1-e>, was conducted to synthesize <Intermediate 10-f> (8.7 g, 87.6%).

Synthesis Example 10-(7): Synthesis of Compound of Chemical Formula 224

The compound of Chemical Formula 224 was synthesized as illustrated in the following Reaction Scheme 73:

<Reaction Scheme 73>

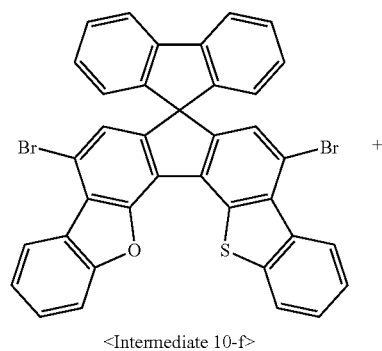

<Intermediate 10-f>

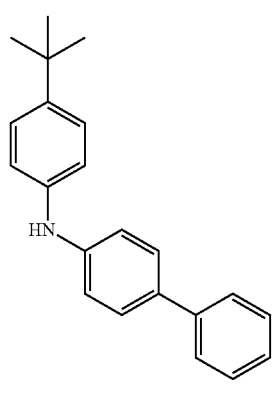

<Intermediate 7-d>

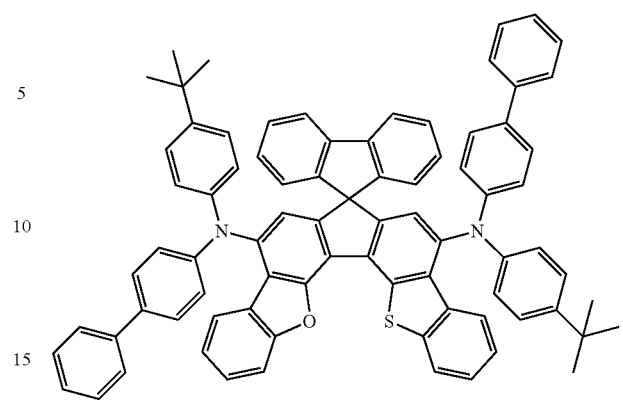

<Chemical Formula 224>

The same procedure as in Synthesis Example 1-(7), with the exception of using <Intermediate 10-f> and <Intermediate 7-d> respectively instead of <Intermediate 1-f> and bis(4-tert-butylphenyl)amine, was conducted to synthesize <Chemical Formula 224> (2.8 g, 33.8%).

SYNTHESIS EXAMPLE 11: Synthesis of Compound of Chemical Formula 225

Synthesis Example 11-(1): Synthesis of Intermediate 11-a

Intermediate 11-a was synthesized as illustrated in the following Reaction Scheme 74:

<Reaction Scheme 74>

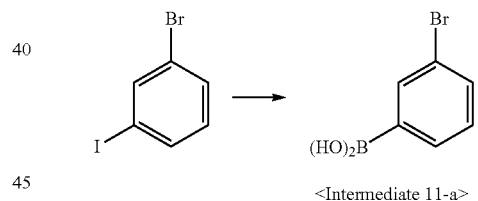

<Intermediate 11-a>

In a 500-ml round-bottom flask reactor, 1-bromo-3-iodo-benzene (25.0 g, 88 mmol) was dissolved in tetrahydrofuran (200 ml). This solution was cooled to −78° C. and slowly added with drops of N-butyl lithium (60.75 ml, 97 mmol) over 30 min while stirring for 1 hr. At the same temperature, trimethyl borate (11 g, 106 mmol) was dropwise added to the reaction mixture, which was then stirred overnight at room temperature. Acidification with drops of 2-N HCl was performed, followed by stirring for 1 hr. Extraction with ethyl acetate formed an organic layer which was then isolated and concentrated in a vacuum. Crystallization in chilled normal hexane afforded <Intermediate 11-a>. (12 g, 67.6%)

Synthesis Example 11-(2): Synthesis of Intermediate 11-b

Intermediate 11-b was synthesized as illustrated in the following Reaction Scheme 75:

<Reaction Scheme 75>

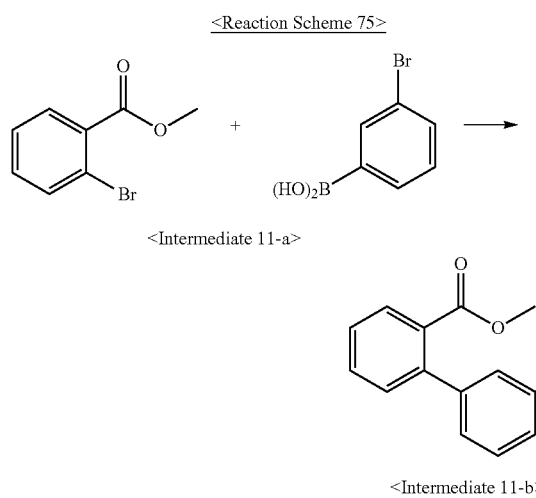

<Intermediate 11-a>

<Intermediate 11-b>

The same procedure as in Synthesis Example 4-(2), with the exception of using methyl 2-bromobenzoate and <Intermediate 11-a> respectively instead of methyl 5-bromo-2-iodobenzoate and <Intermediate 4-a>, was conducted to synthesize <Intermediate 11-b> (10.2 g, 68.5%).

Synthesis Example 11-(3): Synthesis of Intermediate 11-c

Intermediate 11-c was synthesized as illustrated in the following Reaction Scheme 76:

<Reaction Scheme 76>

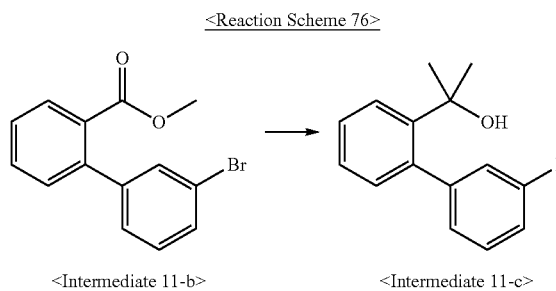

<Intermediate 11-b>    <Intermediate 11-c>

In a 250-ml round-bottom flask, a mixture of <Intermediate 11-b> (10.2 g, 35 mmol) and tetrahydrofuran (100 ml) was cooled to 0° C. in a nitrogen atmosphere. After methyl magnesium bromide (17.5 ml, 53 mmol) was dropwise added to the chilled reaction solution, it was stirred for 2 hrs at room temperature and for 2 hrs under reflux and cooled to room temperature. The reaction mixture was acidified with drops of 0.2 N HCl and extracted with ethyl acetate and water. The organic layer was isolated, concentrated in a vacuum, and purified through a column to afford <Intermediate 11-c> (7.6 g, 74.5%).

Synthesis Example 11-(4): Synthesis of Intermediate 11-d

Intermediate 11-d was synthesized as illustrated in the following Reaction Scheme 7:

<Reaction Scheme 77>

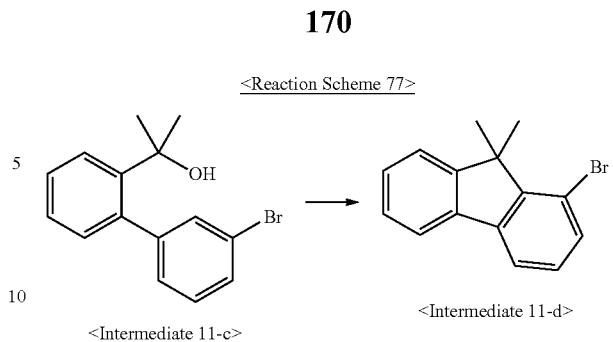

<Intermediate 11-c>    <Intermediate 11-d>

In a 500-ml round-bottom flask, <Intermediate11-c> (20.0 g, 69 mmol), acetic acid (300 ml), and HCl (1 ml) were stirred together under reflux. After completion of the reaction was confirmed using thin-layer chromatography, the reaction mixture was cooled to room temperature. Extraction was conducted with methylene chloride and water. The organic layer was isolated and concentrated in a vacuum. Purification through column chromatography afforded <Intermediate 11-d> (8.2 g, 43.7%).

Synthesis Example 11-(5): Synthesis of Intermediate 11-e

Intermediate 11-e was synthesized as illustrated in the following Reaction Scheme 78:

<Reaction Scheme 78>

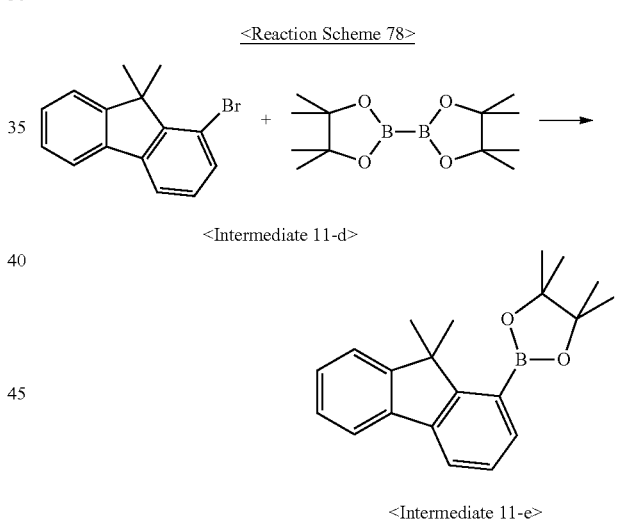

<Intermediate 11-d>

<Intermediate 11-e>

In a 250-ml round-bottom flask reactor, <Intermediate 11-d> (8.2 g, 30 mmol), bis(pinacolato)diboron (9.9 g, 39 mmol), [1,1'-bis(diphenylphosphino)ferrocene]dichloropalladium (0.5 g, 0.001 mol), potassium acetate (7.4 g, 75 mmol), and 1,4-dioxane (80 ml) were stirred together for 10 hrs under reflux. After completion of the reaction, filtration through a celite pad was conducted. The filtrate was concentrated in a vacuum, purified through a column, and recrystallized in dichloromethane and heptane to afford <Intermediate 11-e> (7.0 g, 72.8%).

Synthesis Example 11-(6): Synthesis of Intermediate 11-f

Intermediate 11-f was synthesized as illustrated in the following Reaction Scheme 79:

<Reaction Scheme 79>

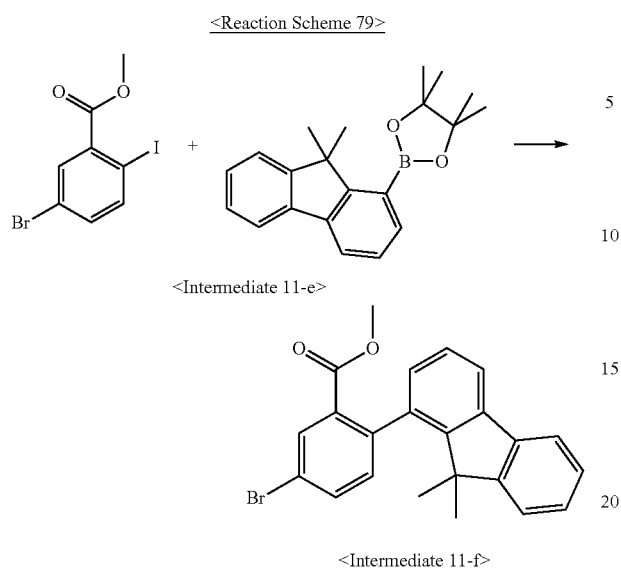

<Intermediate 11-e>

<Intermediate 11-f>

The same procedure as in Synthesis Example 1-(6), with the exception of using <Intermediate 11-e> instead of 4-dibenzofuran boronic acid, was conducted to synthesize <Intermediate 11-f> (8.2 g, 68.6%).

Synthesis Example 11-(7): Synthesis of Intermediate 11-g

Intermediate 11-g was synthesized as illustrated in the following Reaction Scheme 80:

<Reaction Scheme 80>

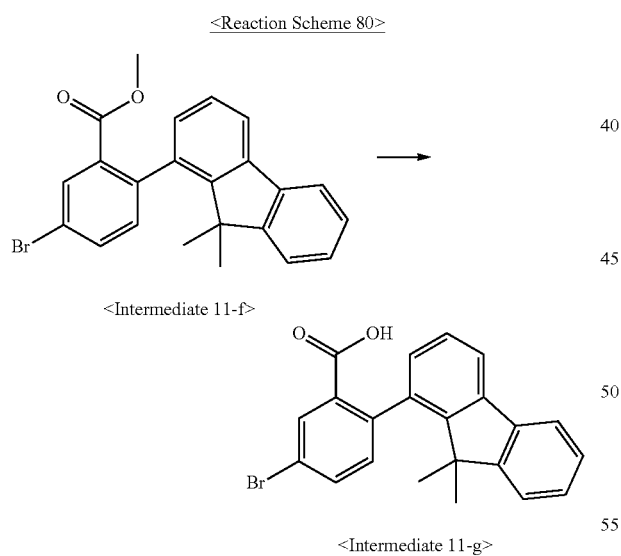

<Intermediate 11-f>

<Intermediate 11-g>

The same procedure as in Synthesis Example 1-(2), with the exception of using <Intermediate 11-f> instead of <Intermediate 1-a>, was conducted to synthesize <Intermediate 11-g> (6.5 g, 82.1%).

Synthesis Example 11-(8): Synthesis of Intermediate 11-h

Intermediate 11-h was synthesized as illustrated in the following Reaction Scheme 81:

<Reaction Scheme 81>

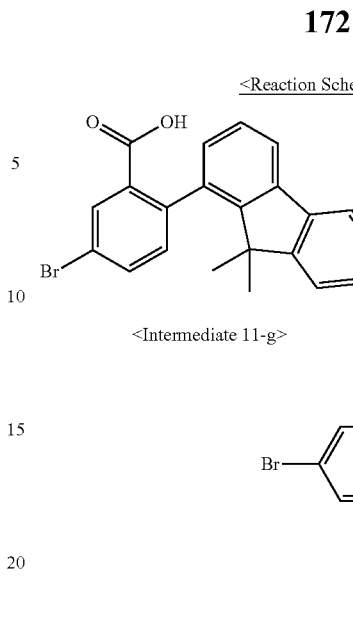

<Intermediate 11-g>

<Intermediate 11-h>

The same procedure as in Synthesis Example 1-(3), with the exception of using <Intermediate 11-g> instead of <Intermediate 1-b>, was conducted to synthesize <Intermediate 11-h> (5.0 g, 80.6%).

Synthesis Example 11-(9): Synthesis of Intermediate 11-i

Intermediate 11-i was synthesized as illustrated in the following Reaction Scheme 82:

<Reaction Scheme 82>

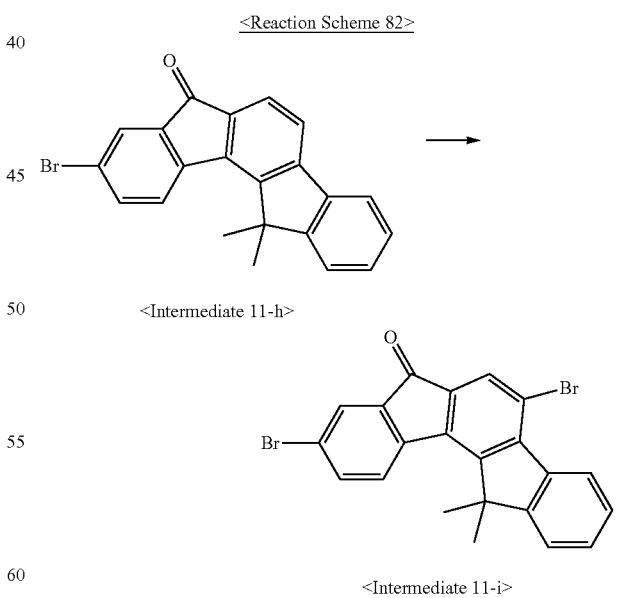

<Intermediate 11-h>

<Intermediate 11-i>

The same procedure as in Synthesis Example 1-(4), with the exception of using <Intermediate 11-h> instead of <Intermediate 1-c>, was conducted to synthesize <Intermediate 11-i> (3.5 g, 57.8%).

Synthesis Example 11-(10): Synthesis of Intermediate 11-j

Intermediate 11-j was synthesized as illustrated in the following Reaction Scheme 83:

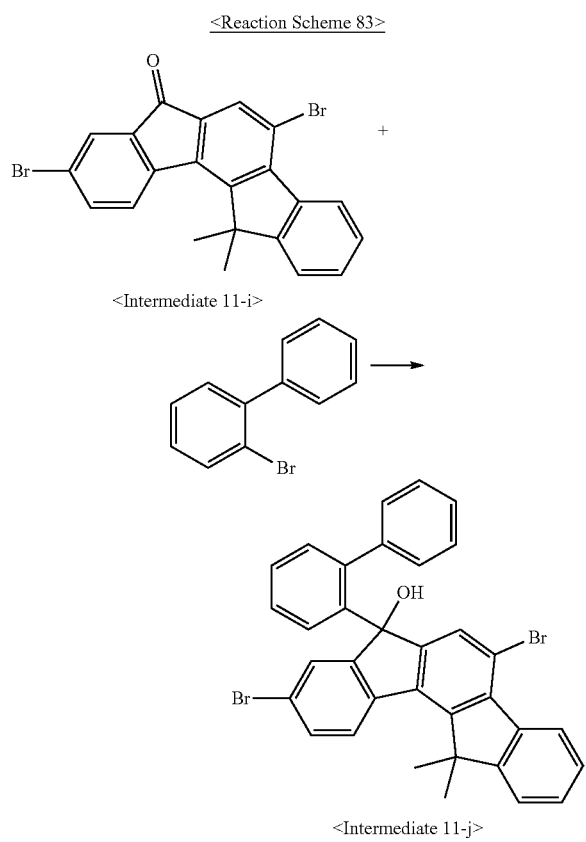

<Reaction Scheme 83>

<Intermediate 11-i>

<Intermediate 11-j>

The same procedure as in Synthesis Example 1-(5), with the exception of using <Intermediate 11-i> instead of <Intermediate 1-d>, was conducted to synthesize <Intermediate 11-j> (3.0 g, 64%).

Synthesis Example 11-(11): Synthesis of Intermediate 11-k

Intermediate 11-k was synthesized as illustrated in the following Reaction Scheme 84:

<Reaction Scheme 84>

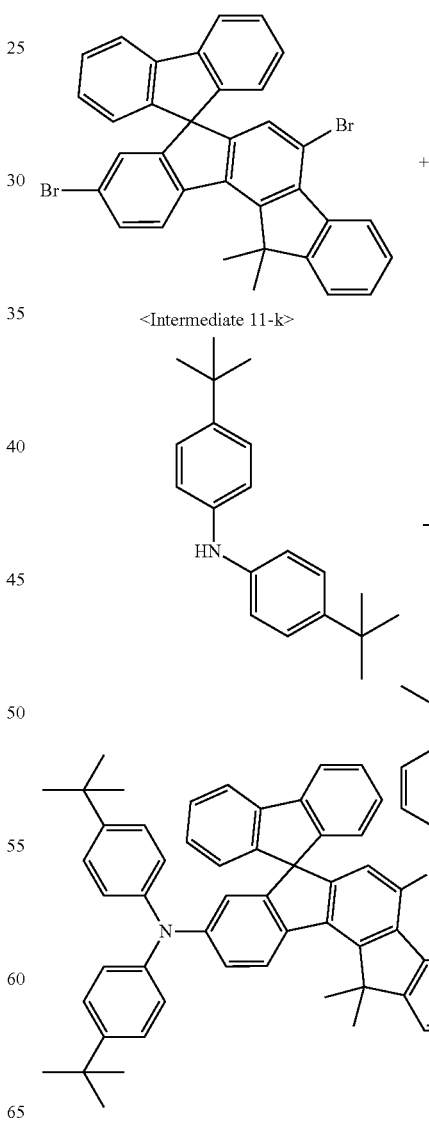

<Intermediate 11-j>

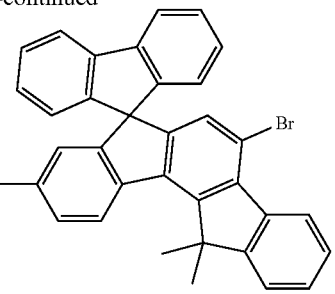

<Intermediate 11-k>

The same procedure as in Synthesis Example 1-(6), with the exception of using <Intermediate 11-j> instead of <Intermediate 1-e>, was conducted to synthesize <Intermediate 11-k> (2.2 g, 75.6%).

Synthesis Example 11-(12): Synthesis of Compound of Chemical Formula 225

The compound of Chemical Formula 225 was synthesized as illustrated in the following Reaction Scheme 85:

<Reaction Scheme 85>

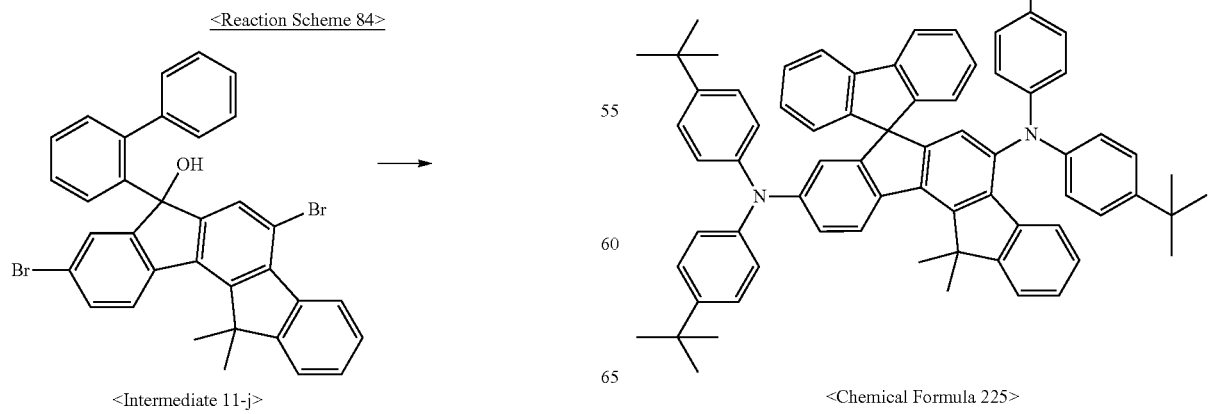

<Chemical Formula 225>

The same procedure as in Synthesis Example 1-(7), with the exception of using <Intermediate 11-k> instead of <Intermediate 1-f>, was conducted to synthesize the compound of <Chemical Formula 225> (1.8 g, 48.7%).

SYNTHESIS EXAMPLE 12: Synthesis of Compound of Chemical Formula 226

Synthesis Example 12-(1): Synthesis of Intermediate 12-a

Intermediate 12-a was synthesized as illustrated in the following Reaction Scheme 86:

<Reaction Scheme 86>

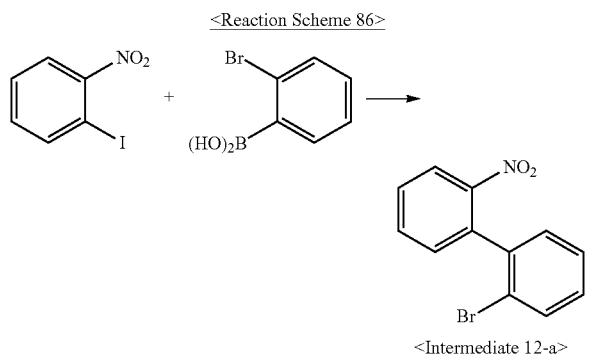

<Intermediate 12-a>

In a 1-L round-bottom flask reactor, 2-iodonitrobenzene (15.0 g, 0.060 mol), 2-bromophenyl boronic acid (13.3 g, 0.066 mol), palladium acetate (0.67 g, 0.003 mol), potassium carbonate (16.6 g, 0.120 mol), and triphenylphosphine (2.37 g, 0.009 mol) were placed, followed by toluene (525 mL), ethanol (60 ml), and water (60 mL). The reaction mixture was heated to 100° C. and stirred for 18 hrs. After completion of the reaction, the reaction mixture was cooled to room temperature and extracted with ethyl acetate. The organic layer was isolated, concentrated in a vacuum, and purified through column chromatography to afford <Intermediate 12-a>. (14.0 g, 83.6%)

Synthesis Example 12-(2): Synthesis of Intermediate 12-b

Intermediate 12-b was synthesized as illustrated in the following Reaction Scheme 87:

<Reaction Scheme 87>

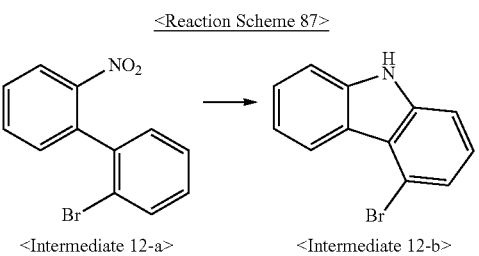 [SMILES: O=[N+]([O-])c1ccccc1-c1ccccc1Br ; Brc1cccc2[nH]c3ccccc3c12]

<Intermediate 12-a>   <Intermediate 12-b>

In a 250-ml round-bottom flask, <Intermediate 12-a> (14.0 g, 0.050 mol), triphenylphosphine (33.01 g, 0.126 mol), and N,N-dimethyl acetamide (100 ml) were stirred together at 180° C. for 14 hrs. After completion of the reaction, the reaction mixture was cooled to room temperature and stirred together with water (200 ml). Extraction with ethyl acetate gave an organic layer which was then isolated, concentrated in a vacuum, and purified through a column to afford <Intermediate 12-b> (7.0 g, 56.5%).

Synthesis Example 12-(3): Synthesis of Intermediate 12-c

Intermediate 12-c was synthesized as illustrated in the following Reaction Scheme 88:

<Reaction Scheme 88>

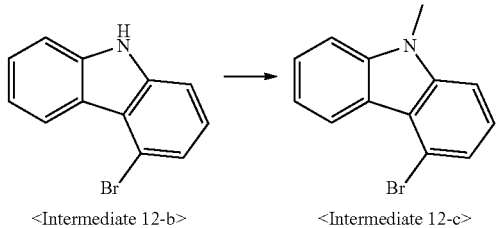

<Intermediate 12-b>   <Intermediate 12-c>

In a 250-ml round-bottom flask, <Intermediate 12-b> (7.0 g, 0.028 mol), tetrahydrofuran (140 ml), and sodium hydride (60%) (1.19 g, 0.029 mol) were stirred together for 30 min at room temperature and then at 0° C. Drops of iodomethane (3.5 ml, 0.057 mol) were added to the chilled solution, followed by stirring at room temperature for 18 hrs. After completion of the reaction, water (100 ml) was added, and extraction was conducted with ethyl acetate. The organic layer was isolated, dried over anhydrous magnesium sulfate, filtered, and concentrated in a vacuum. Purification through column chromatography afforded <Intermediate 12-c> (7.2 g, 92.7%).

Synthesis Example 12-(4): Synthesis of Intermediate 12-d

Intermediate 12-d was synthesized as illustrated in the following Reaction Scheme 89:

<Reaction Scheme 89>

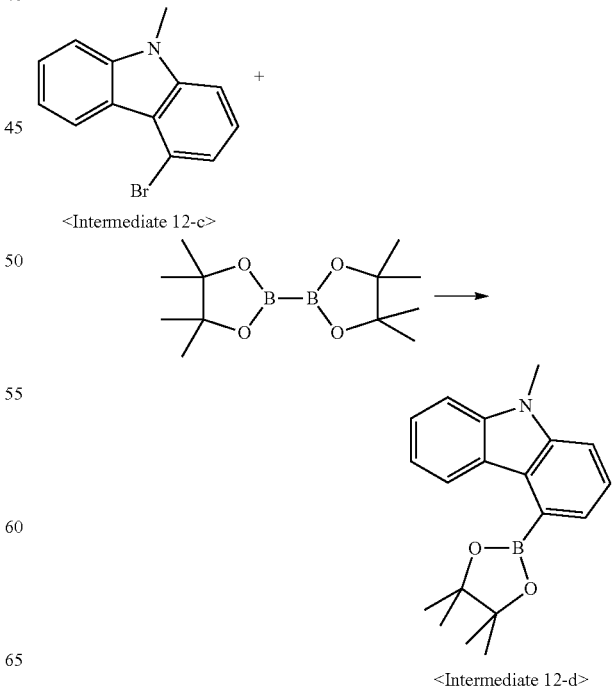

<Intermediate 12-d>

The same procedure as in Synthesis Example 4-(1), with the exception of using <Intermediate 12-c> instead of 1-bromodibenzofuran, was conducted to synthesize <Intermediate 12-d> (6.1 g, 71.7%).

Synthesis Example 12-(5): Synthesis of Intermediate 12-e

Intermediate 12-e was synthesized as illustrated in the following Reaction Scheme 90:

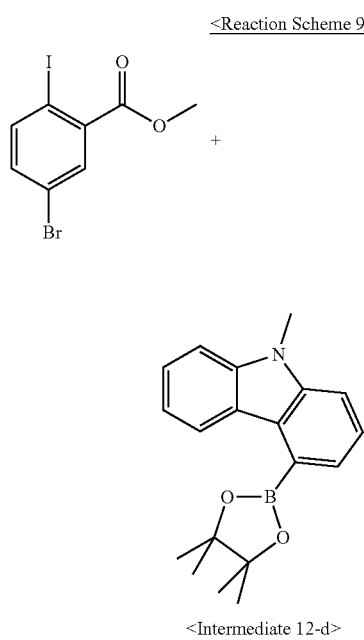

The same procedure as in Synthesis Example 1-(1), with the exception of using <Intermediate 12-d> instead of 4-dibenzofuran boronic acid, was conducted to synthesize <Intermediate 12-e> (5.2 g, 73.7%)

Synthesis Example 12-(6): Synthesis of Intermediate 12-f

Intermediate 12-f was synthesized as illustrated in the following Reaction Scheme 91:

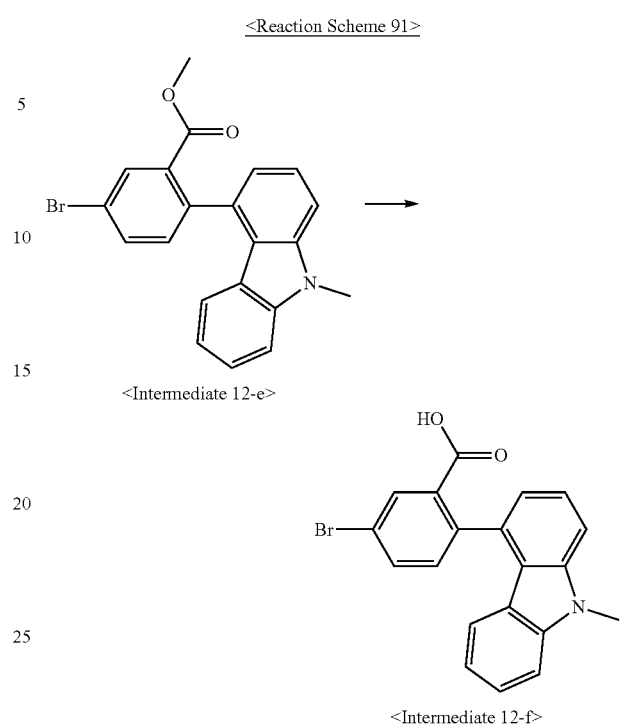

The same procedure as in Synthesis Example 1-(2), with the exception of using <Intermediate 12-e> instead of <Intermediate 1-a>, was conducted to synthesize <Intermediate 12-f> (8.2 g, 85%).

Synthesis Example 12-(7): Synthesis of Intermediate 12-g

Intermediate 12-g was synthesized as illustrated in the following Reaction Scheme 92:

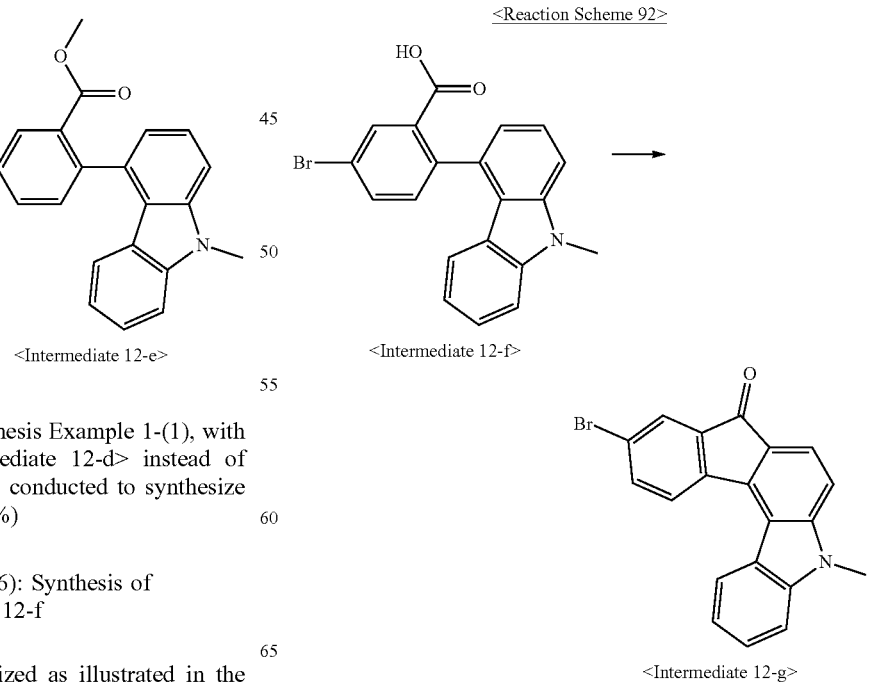

The same procedure as in Synthesis Example 1-(3), with the exception of using <Intermediate 12-f> instead of <Intermediate 1-b>, was conducted to synthesize <Intermediate 12-g> (6.7 g, 85.8%).

Synthesis Example 12-(8): Synthesis of Intermediate 12-h

Intermediate 12-h was synthesized as illustrated in the following Reaction Scheme 93:

<Reaction Scheme 93>

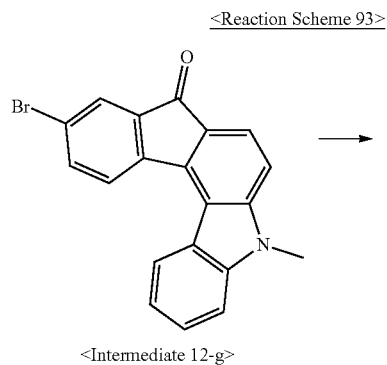

<Intermediate 12-g>

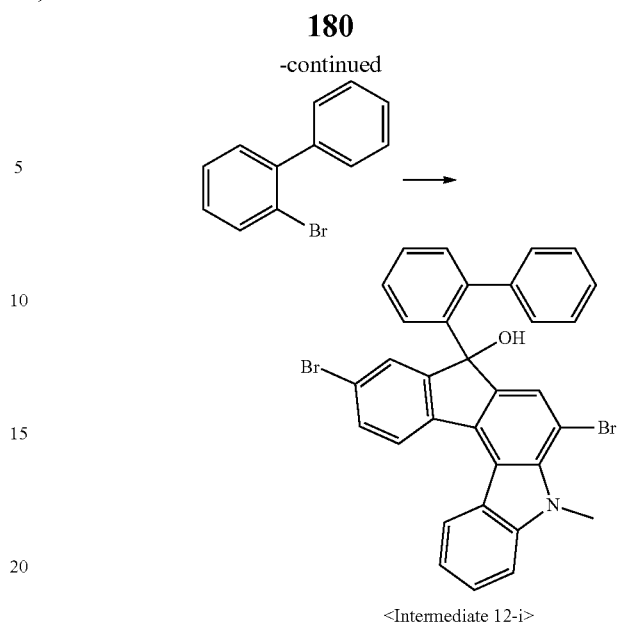

<Intermediate 12-h>

The same procedure as in Synthesis Example 1-(4), with the exception of using <Intermediate 12-g> instead of <Intermediate 1-c>, was conducted to synthesize <Intermediate 12-h> (4.3 g, 52.7%).

Synthesis Example 12-(9): Synthesis of Intermediate 12-i

Intermediate 12-i was synthesized as illustrated in the following Reaction Scheme 94:

<Reaction Scheme 94>

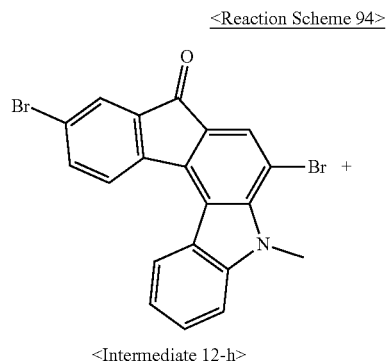

<Intermediate 12-h>

<Intermediate 12-i>

The same procedure as in Synthesis Example 1-(5), with the exception of using <Intermediate 12-h> instead of <Intermediate 1-d>, was conducted to synthesize <Intermediate 12-i> (4.0 g, 68.9%).

Synthesis Example 12-(10): Synthesis of Intermediate 12-j

Intermediate 12-j was synthesized as illustrated in the following Reaction Scheme 95:

<Reaction Scheme 95>

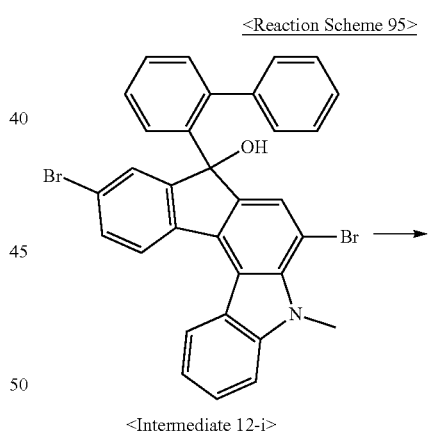

<Intermediate 12-i>

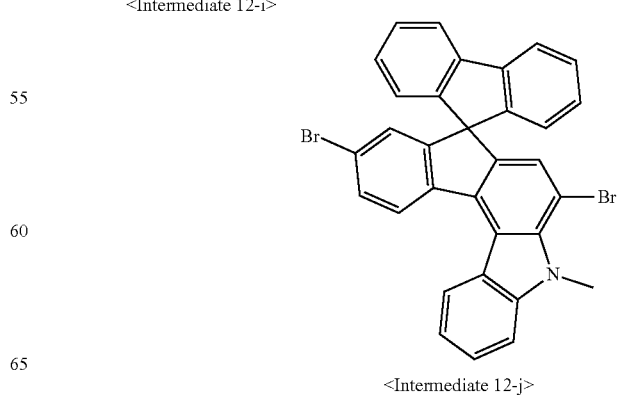

<Intermediate 12-j>

The same procedure as in Synthesis Example 1-(6), with the exception of using <Intermediate 12-i> instead of <Intermediate 1-e>, was conducted to synthesize <Intermediate 12-j> (3.2 g, 82.5%).

Synthesis Example 12-(11): Synthesis of Compound of Chemical Formula 226

Chemical Formula 226 was synthesized as illustrated in the following Reaction Scheme 96:

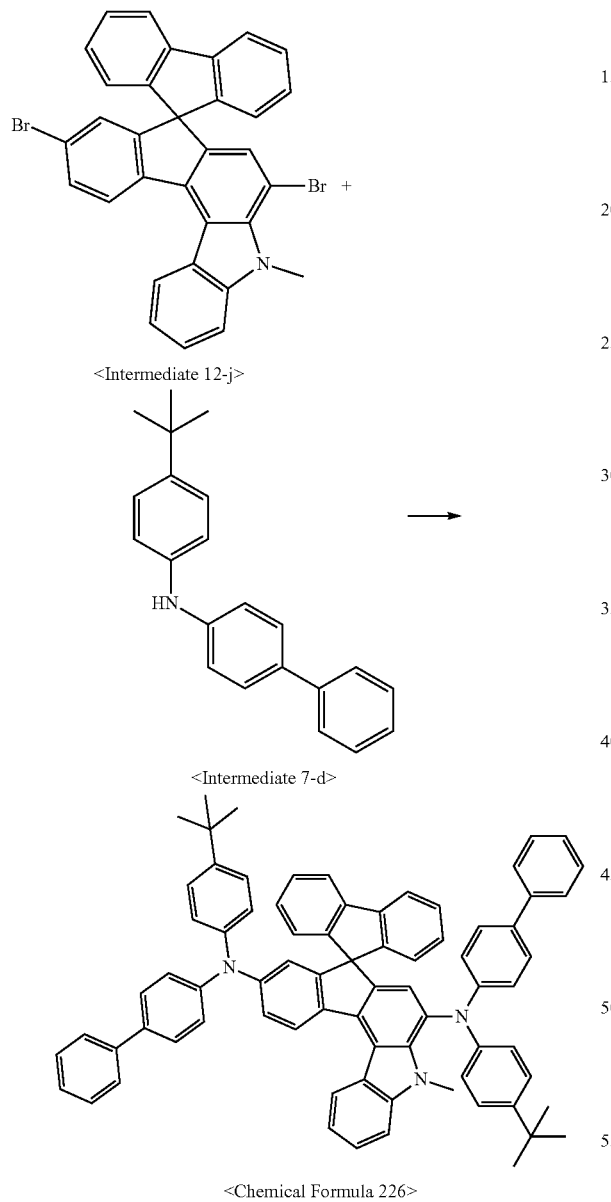

The same procedure as in Synthesis Example 1-(7), with the exception of using <Intermediate 12-j> and <Intermediate 7-d> respectively instead of <Intermediate 1-f> and bis(4-tert-butylphenyl)amine, was conducted to synthesize the compound of <Chemical Formula 226> (2.3 g, 40.7%).

EXAMPLES 1 TO 11: Fabrication of Organic Light-Emitting Diode

An ITO glass substrate was patterned to have a translucent area of 2 mm×2 mm and cleansed. The ITO glass was mounted in a vacuum chamber that was then set to have a base pressure of $1\times10^{-7}$ torr. On the ITO glass substrate, films were formed of DNTPD(700 Å) and α-NPD (300 Å) in that order. A light-emitting layer (250 Å) was formed of a mixture including [BH1] and 3% of each of the compounds shown in Table 1 according to the present disclosure. Then, [Chemical Formula E-1] and [Chemical Formula E-2] were deposited at a ratio of 1:1 to form an electron transport layer 300 Å thick, on which an electron injection layer of [Chemical Formula E-1] (5 Å thick) was formed and then covered with an Al layer (1000 Å) to fabricate an organic light-emitting diode. The organic light-emitting diodes thus obtained were measured at 0.4 mA for luminescence properties.

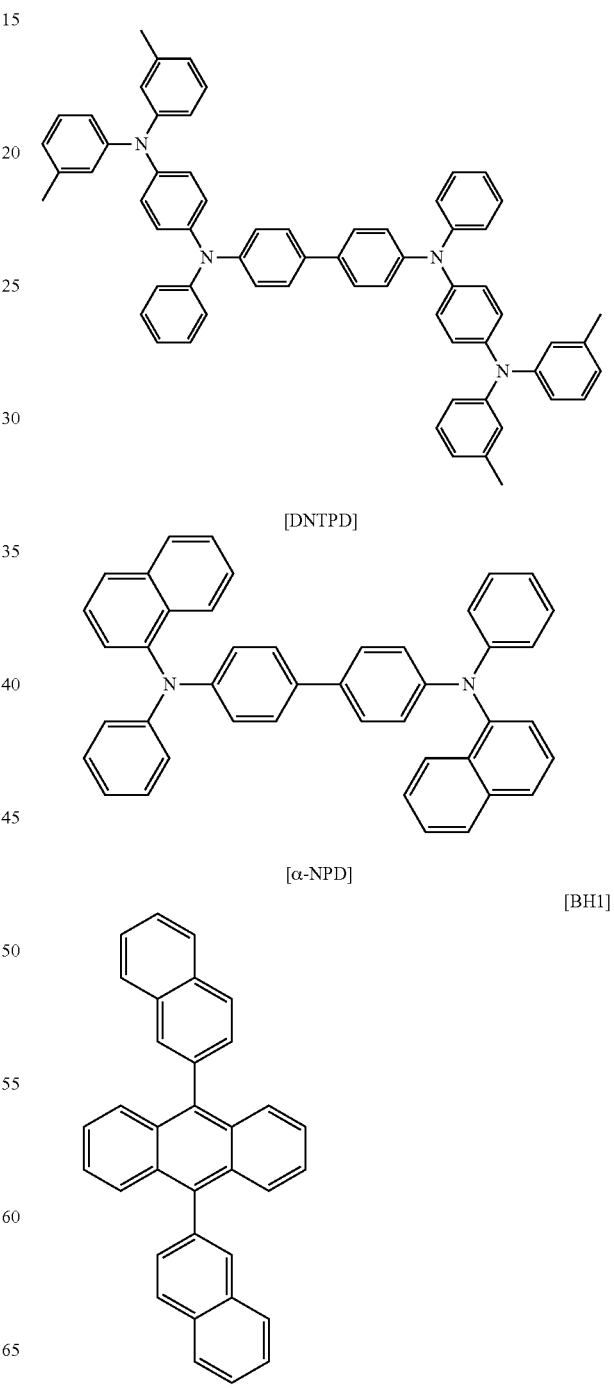

[Chemical Formula E-1]

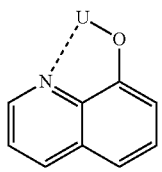

[Chemical Formula E-2]

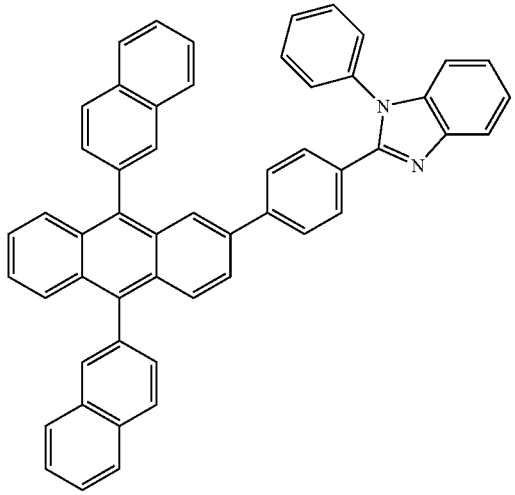

Comparative Examples 1 and 2

Organic light-emitting diodes were fabricated in the same manner as in Examples 1 to 11, with the exception that [BD1] and [BD2] were used, instead of the compounds used in Examples 1 to 11. The luminescence of the organic light-emitting diodes was measured at 0.4 mA. The structures of [BD1] and [BD2] are as follows.

[BD1]

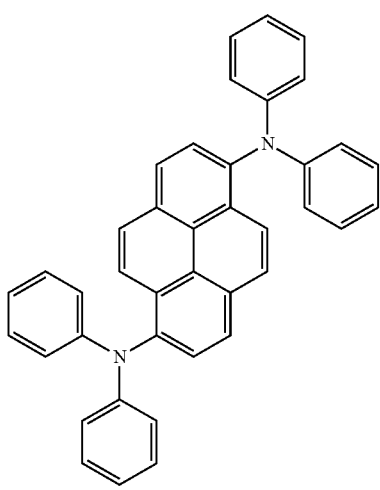

[BD2]

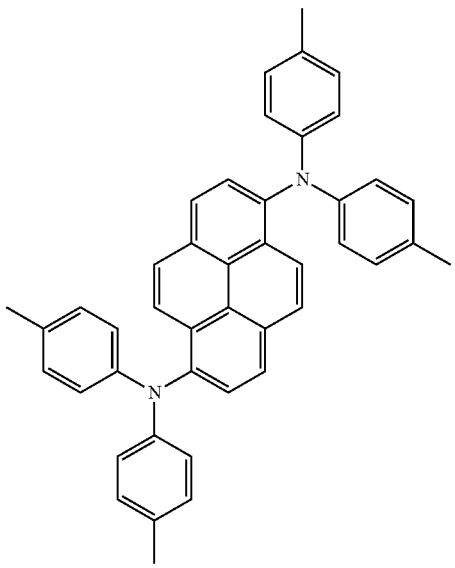

The organic light-emitting diodes fabricated in Examples 1 to and Comparative Examples 1 and 2 were measured for voltage, current, luminance, color coordinates, and lifetime, and the results are summarized in Table 1, below. In Table 1, T97 refers to the time taken for the initial luminance to decrease by 3%.

TABLE 1

| Ex. No. | Volt. | Current Density (mA/cm$^2$) | Luminance (cd/m$^2$) | CIEx | CIEy | T97 |
|---|---|---|---|---|---|---|
| C. 1 [BD1] | 4.1 | 10 | 515 | 0.143 | 0.150 | 42 |
| C. 2 [BD2] | 4.0 | 10 | 550 | 0.141 | 0.154 | 40 |
| 1 [Cpd. 1] | 3.8 | 10 | 750 | 0.130 | 0.133 | 98 |
| 2 [Cpd. 33] | 3.8 | 10 | 880 | 0.136 | 0.133 | 110 |
| 3 [Cpd. 24] | 3.8 | 10 | 667 | 0.133 | 0.117 | 125 |
| 4 [Cpd. 45] | 3.8 | 10 | 650 | 0.133 | 0.115 | 113 |
| 5 [Cpd. 49] | 3.8 | 10 | 980 | 0.132 | 0.181 | 110 |
| 6 [Cpd. 76] | 3.8 | 10 | 679 | 0.141 | 0.116 | 121 |
| 7 [Cpd. 89] | 3.8 | 10 | 801 | 0.138 | 0.110 | 120 |
| 8 [Cpd. 96] | 3.8 | 10 | 780 | 0.134 | 0.120 | 100 |
| 9 [Cpd. 97] | 3.8 | 10 | 816 | 0.134 | 0.121 | 120 |
| 10 [Cpd. 101] | 3.8 | 10 | 710 | 0.133 | 0.120 | 105 |
| 11 [Cpd. 105] | 3.8 | 10 | 850 | 0.130 | 0.164 | 118 |

As is understood from the data of Table 1, the amine compounds of the present disclosure exhibited far higher luminance and light emission efficiency and a longer lifetime than the compounds of Comparative Examples 1 to 4, thereby demonstrating their high applicability to organic electroluminescence devices.

INDUSTRIAL APPLICABILITY

Available for use in organic light-emitting devices having excellent properties, such as high luminance, high light emission efficiency, and long lifetime, the present disclosure is industrially applicable.

The invention claimed is:
1. An amine compound represented by the following:

[Chemical Formula B]

$$\left[\begin{array}{c}Ar_3\\ \diagdown\\ (L_4)_{p2}\\ N-(L_6)_{s2}\\ (L_5)_{r2}\\ \diagup\\ Ar_4\end{array}\right]_y \left[\begin{array}{c}Ar_1\\ \diagdown\\ (L_1)_{p1}\\ R_2\quad N-(L_2)_{r1}-Ar_2\\ R_1\quad (L_3)_{s1}\\ A_1\quad A_2\quad Q_1\\ Q_2\end{array}\right]_x$$

$$\left[\begin{array}{c}Ar_6\\ \diagdown\\ (L_7)_{p3}\\ N-(L_8)_{r3}-Ar_6\\ (L_9)_{s1}\\ M\\ *\underbrace{\phantom{xxx}}_{E}\end{array}\right]_z \left[\begin{array}{c}Ar_7\\ \diagdown\\ (L_{10})_{p4}\\ N-(L_{11})_{r4}-Ar_8\\ (L_{12})_{s4}\\ M\\ *\underbrace{\phantom{xxx}}_{F}\end{array}\right]_z$$

$Q_1: *\underbrace{\phantom{xxx}}_{E}$  $Q_2: *\underbrace{\phantom{xxx}}_{F}$ wherein,
$A_1$, $A_2$, E, and F are same or different, and are each independently a substituted or unsubstituted aromatic hydrocarbon ring of 6 to 50 carbon atoms, or a substituted or unsubstituted heteroaromatic ring of 2 to 40 carbon atoms, wherein,
two adjacent carbon atoms of the aromatic ring $A_1$ and two adjacent carbon atoms of the aromatic ring $A_2$ form a 5-membered fused ring together with a carbon atom to which substituents $R_1$ and $R_2$ are bonded;
linkers $L_1$ to $L_{12}$ are same or different, and are each independently selected from among a direct bond and a substituted or unsubstituted arylene of 6 to 60 carbon atoms;
M is any one selected from among N—$R_3$, $CR_4R_5$, O, and S;
$R_1$ to $R_5$ and $Ar_1$ to $Ar_8$ are same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkylsilyl of 1 to 30 carbon atoms, a substituted or unsubstituted arylsilyl of 6 to 30 carbon atoms,
in the alternative for $R_1$ and $R_2$, $R_1$ and $R_2$ together form a mono- or polycyclic aliphatic or aromatic ring, and
in the alternative for $Ar_1$ to $Ar_8$, $Ar_1$ forms a ring with $Ar_2$, $Ar_3$ forms a ring with $Ar_4$, $Ar_5$ forms a ring with $Ar_6$, and/or $Ar_7$ forms a ring with $Ar_8$,
p1 to p4, $r_1$ to $r_4$, and s1 to s4 are each independently an integer of 1 to 3, with the proviso that when any of them is 2 or greater, the corresponding linkers are same or different, and
x is 1 with an amine radical having substituents $Ar_1$ and $Ar_2$ being bonded to the $A_2$ ring moiety,
y is 0 or 1 and z is 0 or 1, with a proviso that:
an amine radical having substituents $Ar_3$ and $Ar_4$ is bonded to the $A_1$ ring moiety, or an amine radical having substituents $Ar_5$ and $Ar_6$ is bonded to the E ring moiety, or an amine radical having substituents $Ar_7$ and $Ar_8$ is bonded to the F ring moiety; and
two adjacent carbon atoms of the $A_2$ ring moiety occupy respective positions * of Structural Formula $Q_1$ to form a fused ring, and
two adjacent carbon atoms of the $A_1$ ring moiety occupy respective positions * of structural Formula $Q_2$ to form a fused ring,
wherein the term "substituted" in the expression "substituted or unsubstituted" means having at least one substituent selected from the group consisting of a deuterium, a cyano, a halogen, a nitro, an alkyl of 1 to 24 carbon atoms, a halogenated alkyl of 1 to 24 carbon atoms, an aryl of 6 to 24 carbon atoms, an arylalkyl of 7 to 24 carbon atoms, a heteroaryl of 2 to 24 carbon atoms, a heteroarylalkyl of 2 to 24 carbon atoms, an alkylsilyl of 1 to 24 carbon atoms, and an arylsilyl of 6 to 24 carbon atoms.

2. The amine compound of claim 1, wherein $A_1$, $A_2$, E, and F, which are same or different, are each independently a substituted or unsubstituted aromatic hydrocarbon ring of 6 to 50 carbon atoms.

3. The amine compound of claim 2, wherein the aromatic hydrocarbon ring is selected from among [Structural Formula 10] to [Structural Formula 21]:

[Structural Formula 10]

[Structural Formula 11]

[Structural Formula 12]

[Structural Formula 13]

[Structural Formula 14]

[Structural Formula 15]

[Structural Formula 16]

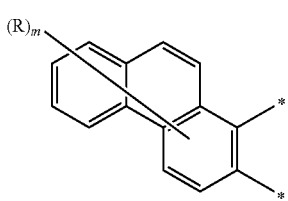

[Structural Formula 17]

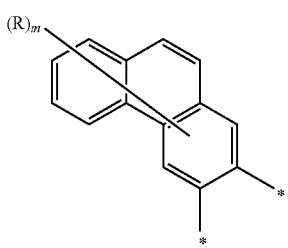

[Structural Formula 18]

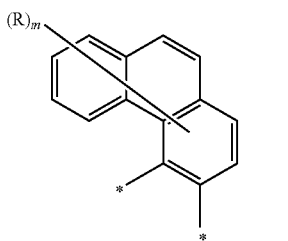

[Structural Formula 19]

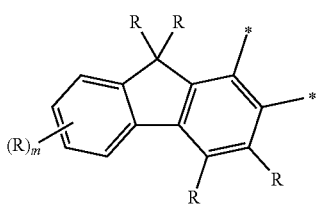

[Structural Formula 20]

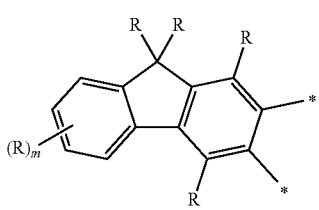

[Structural Formula 21]

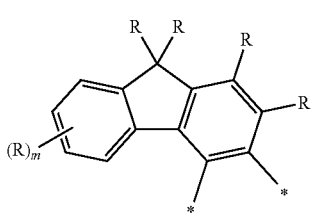

wherein,

"-*" denotes a bonding site for forming a 5-membered ring containing the carbon atom connected to both the substituents $R_1$ and $R_2$, or a bonding site for forming a 5-membered ring containing M of the structural Formula $Q_1$ and $Q_2$ with moiety $A_1$ or $A_2$, when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring; and R's are the same as defined above for $R_1$ and $R_2$, and m is an integer of 1 to 8, with the proviso that when m is 2 or greater or two or more R's exist, the corresponding R's are the same or different.

4. The amine compound of claim 1, wherein the linkers $L_1$ to $L_{12}$ are each selected from among a single bond and a substituted or unsubstituted arylene of 6 to 20 carbon atoms.

5. The amine compound of claim 4, wherein the linkers $L_1$ to $L_{12}$ each is a single bond, or any one selected from the following [Structural Formula 22], [Structural Formula 23], [Structural Formula 25], [Structural Formula 27], [Structural Formula 28], and [Structural Formula 30], wherein each of the unsubstituted carbon atoms of the aromatic ring moiety is bound with a hydrogen atom or a deuterium atom; and p1 to p4, $r_1$ to $r_4$, and s1 to s4 are each 1 or 2;

[Structure Formula 22]

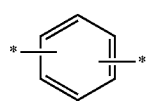

[Structure Formula 23]

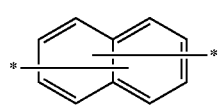

[Structure Formula 24]

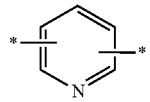

[Structure Formula 25]

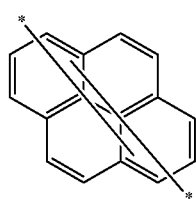

[Structure Formula 26]

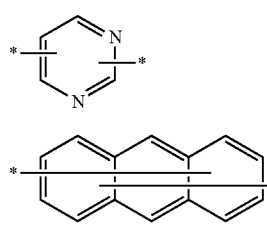

[Structure Formula 27]

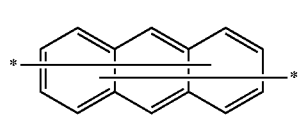

-continued

[Structure Formula 28]
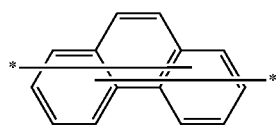

[Structure Formula 29]
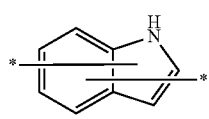

[Structure Formula 30]
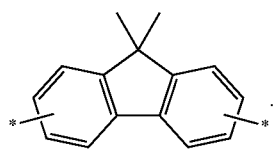

6. The amine compound of claim 5, wherein y is 1 and z is 0 in Chemical Formula B.

7. The amine compound of claim 1, wherein the substituents $R_1$ and $R_2$, which are same or different, are each independently a substituted or unsubstituted aryl of 6 to 24 carbon atoms, and are connected to each other to form a ring.

8. The amine compound of claim 1, wherein the substituents $R_1$ and $R_2$, which are same or different, are each independently a substituted or unsubstituted aryl of 6 to 24 carbon atoms, and are disconnected to form no rings.

9. The amine compound of claim 1, wherein $R_1$ to $R_5$, and $Ar_1$ to $Ar_8$ are same or different and are each independently any one selected from among a substituted or unsubstituted aryl of 6 to 20 carbon atoms and a substituted or unsubstituted cycloalkyl of 3 to 30 carbon atoms.

10. The amine compound of claim 1, wherein an substituent on each of the substituted $A_1$, $A_2$, E, F, $Ar_1$ to $Ar_8$, $L_1$ to $L_{12}$, and $R_1$ to $R_9$ is any one selected from the group consisting of a cyano, a halogen, an alkyl of 1 to 6 carbon atoms, an aryl of 6 to 18 carbon atoms, an arylalkyl of 6 to 18 carbon atoms, a heteroaryl of 3 to 18 carbon atoms, an alkylsilyl of 1 to 12 carbon atoms, and an arylsilyl of 6 to 18 carbon atoms.

11. The amine compound of claim 1, being selected from among compounds represented by the following Compounds:

<Chemical Formula 25>

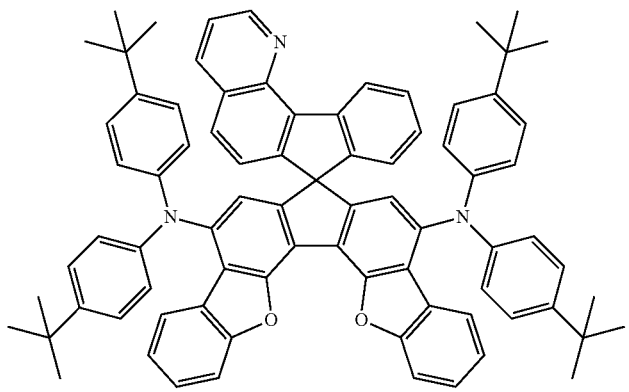

<Chemical Formula 26>

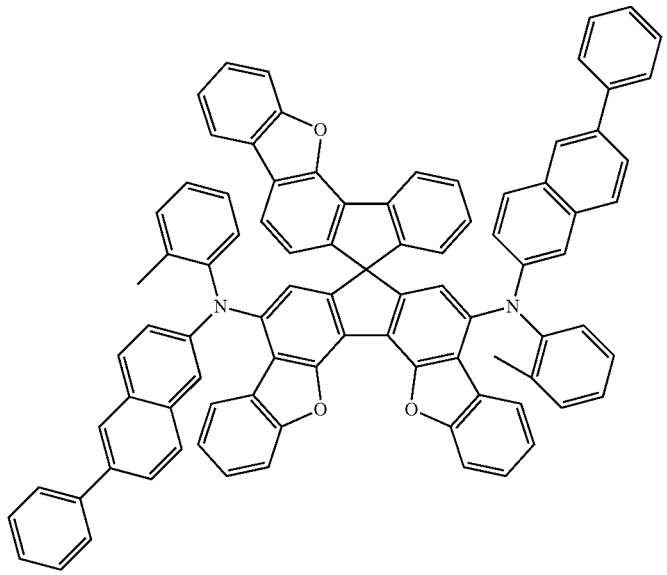

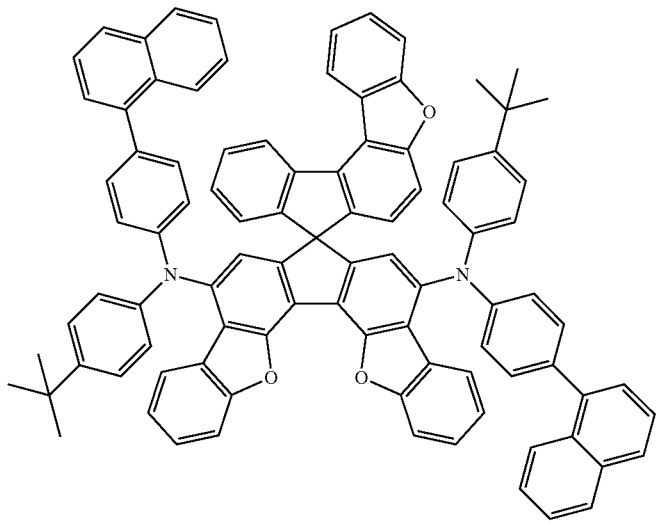
<Chemical Formula 27>
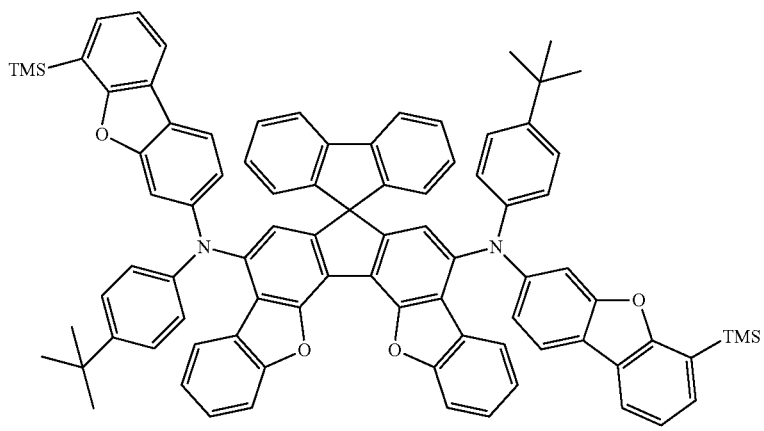
<Chemical Formula 28>
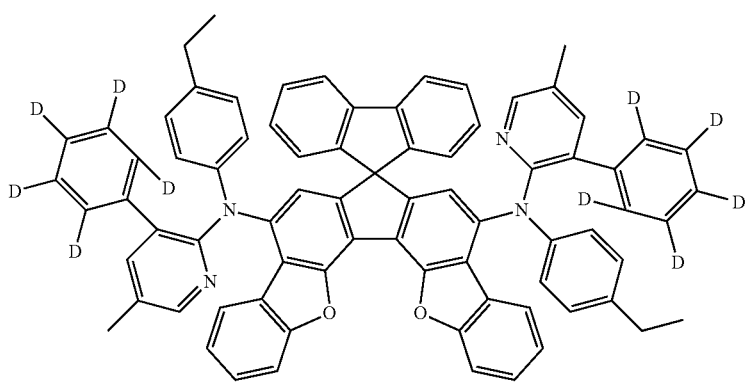
<Chemical Formula 29>

-continued
<Chemical Formula 30>
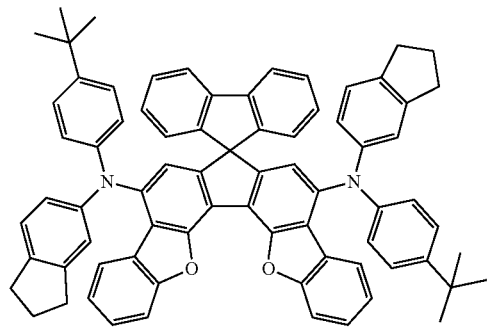
<Chemical Formula 31>
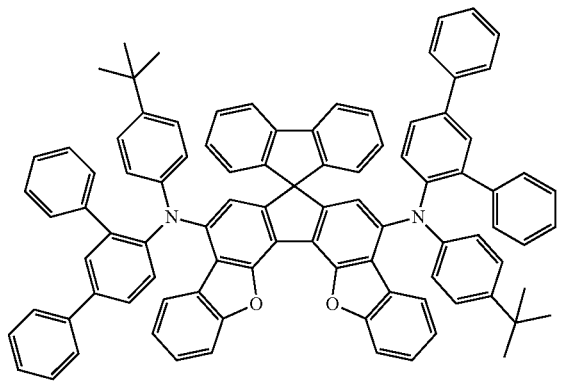
<Chemical Formula 32>
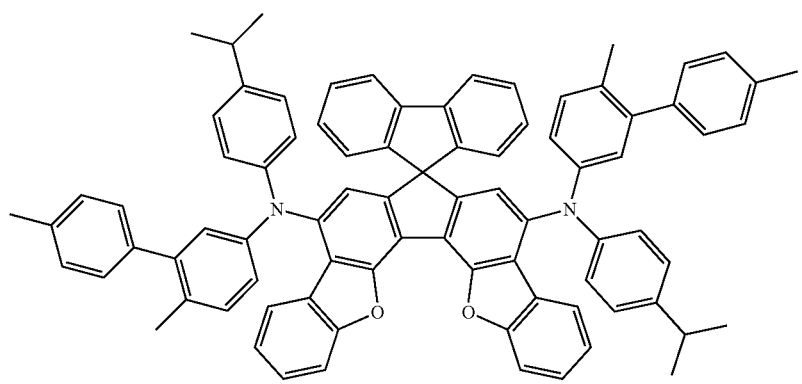
<Chemical Formula 85>
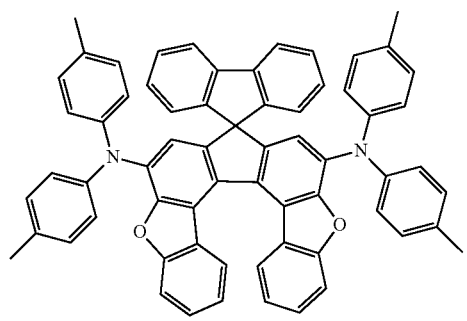
<Chemical Formula 91>
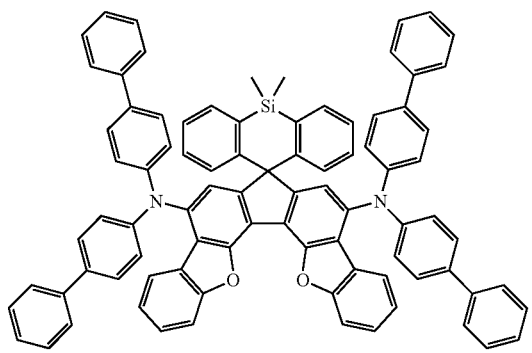

<Chemical Formula 92>
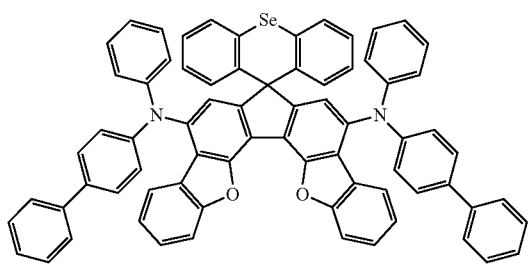
<Chemical Formula 97>
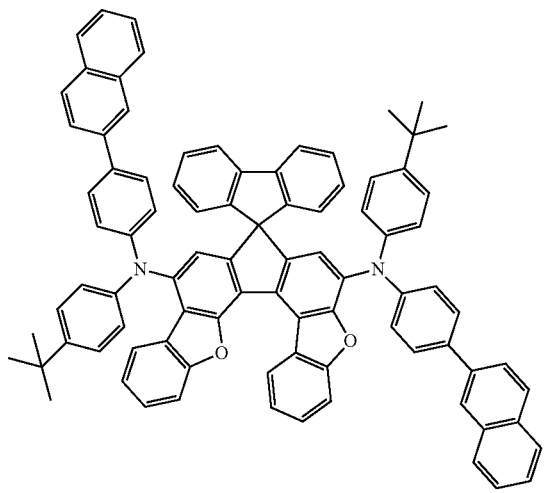
<Chemical Formula 98>
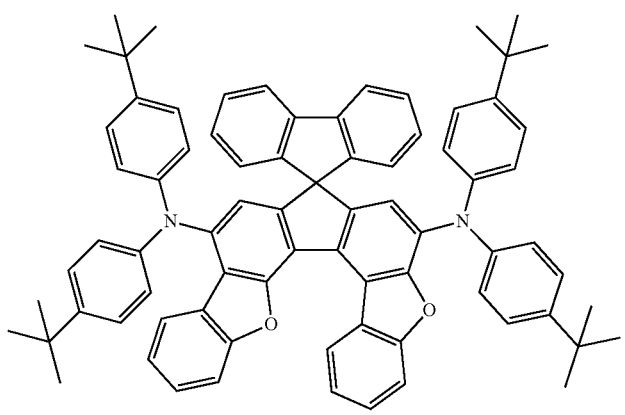
<Chemical Formula 102>
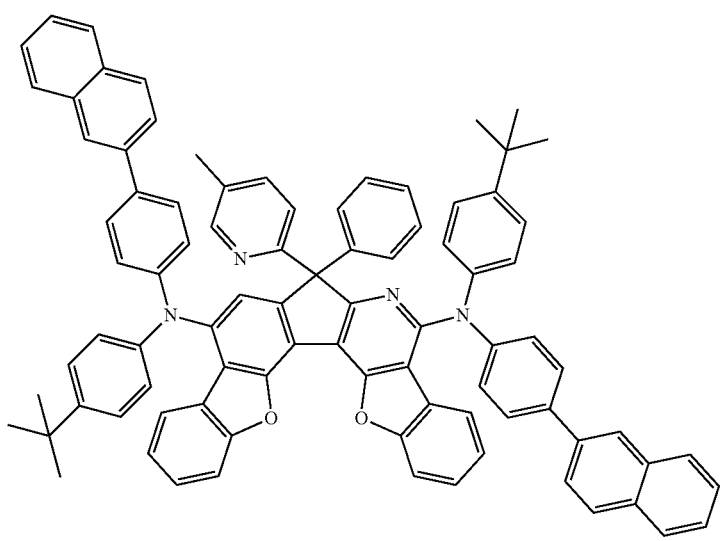

<Chemical Formula 117>
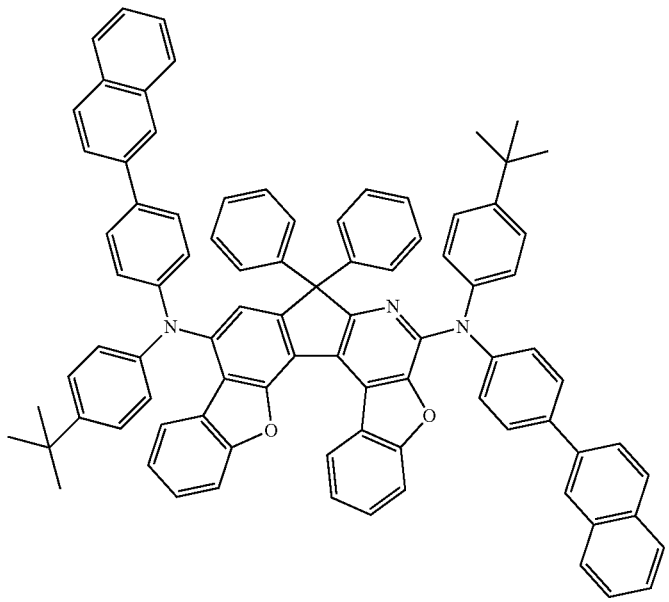
<Chemical Formula 142>
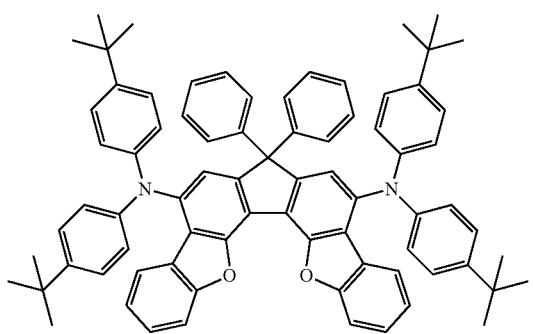
<Chemical Formula 143>
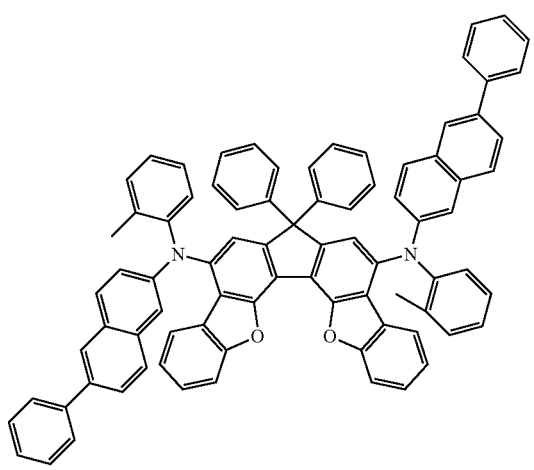
<Chemical Formula 144>
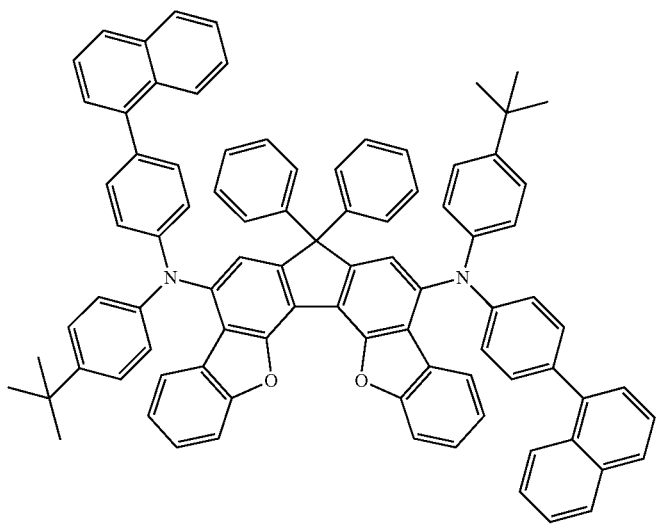

-continued
<Chemical Formula 145>
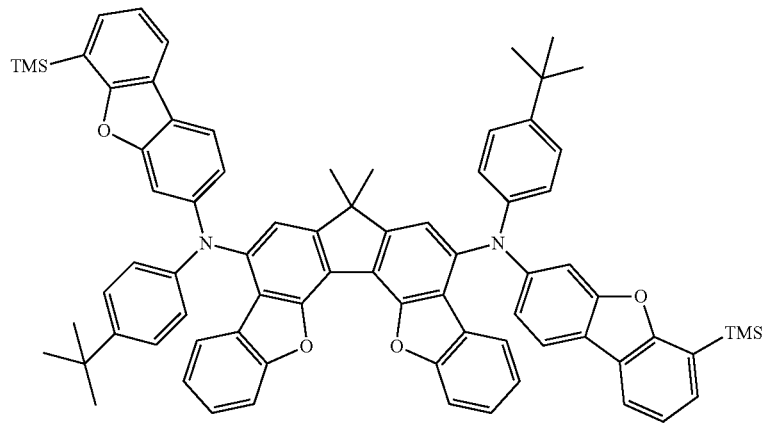
<Chemical Formula 146>
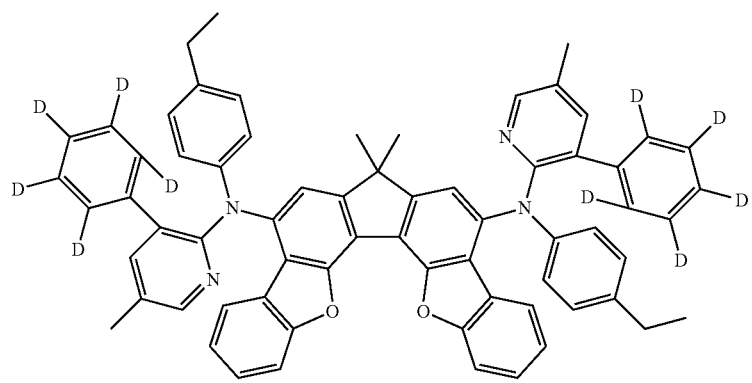
<Chemical Formula 147>
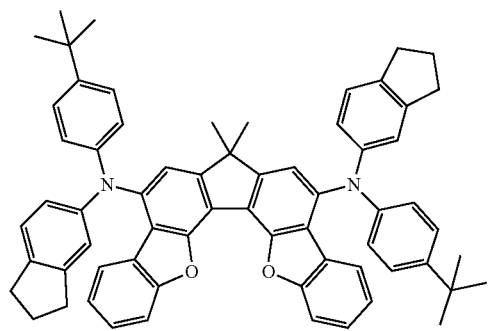
<Chemical Formula 148>
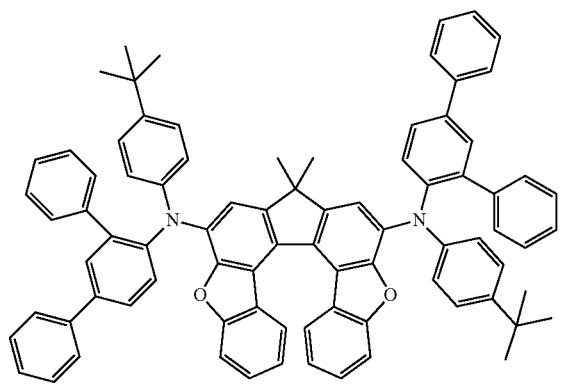
<Chemical Formula 149>
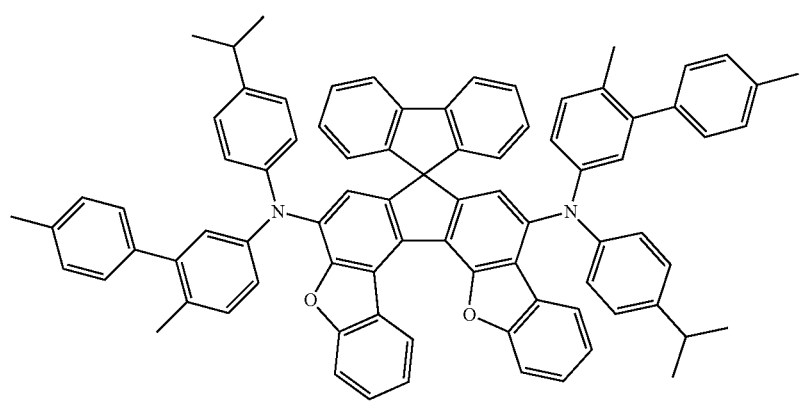

<Chemical Formula 160>
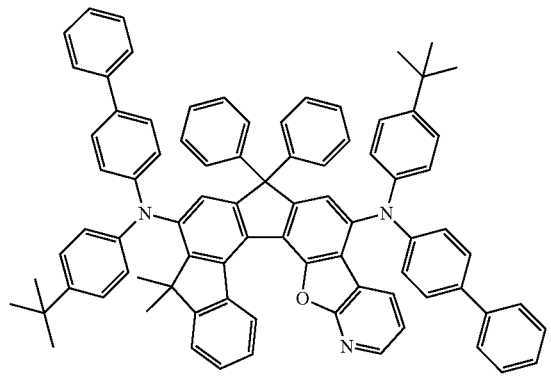
<Chemical Formula 162>
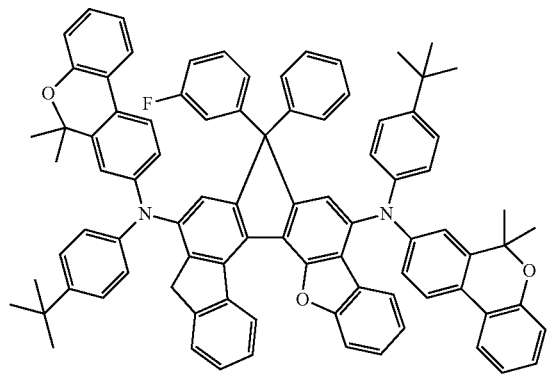
<Chemical Formula 164>
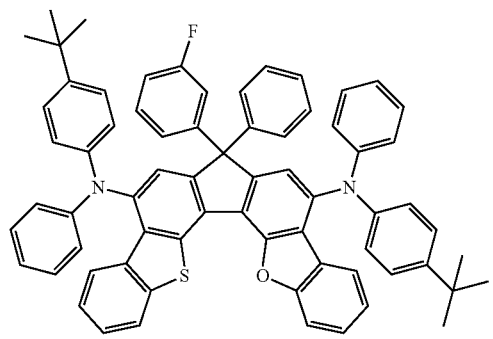
<Chemical Formula 165>
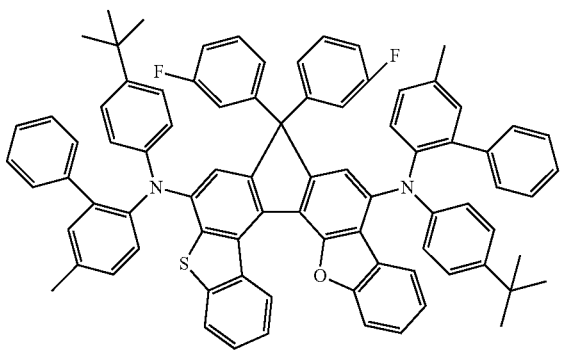
<Chemical Formula 210>
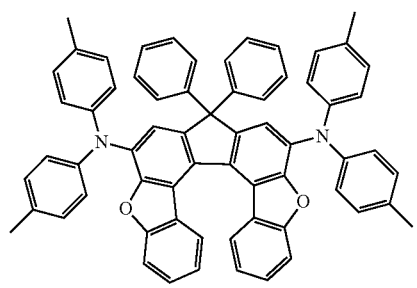
<Chemical Formula 222>
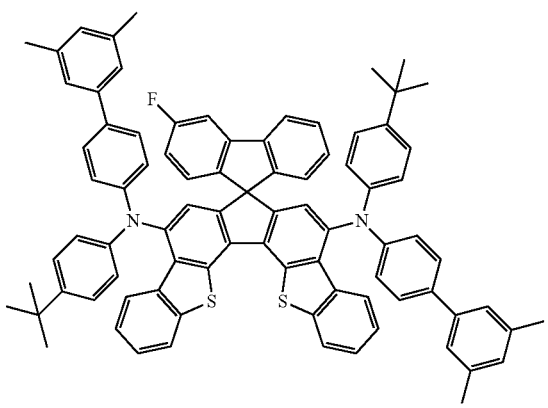

<Chemical Formula 223>
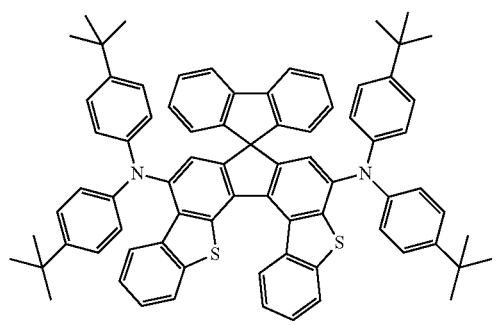
<Chemical Formula 224>
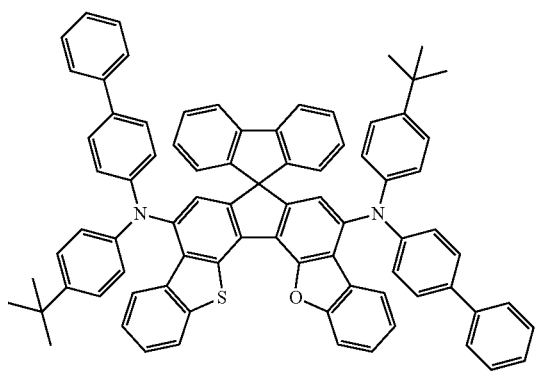
<Chemical Formula 227>
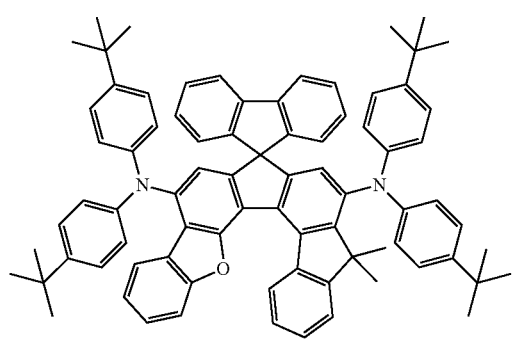
<Chemical Formula 228>
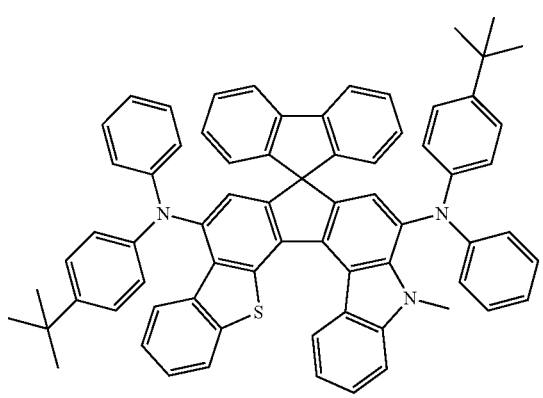
<Chemical Formula 229>
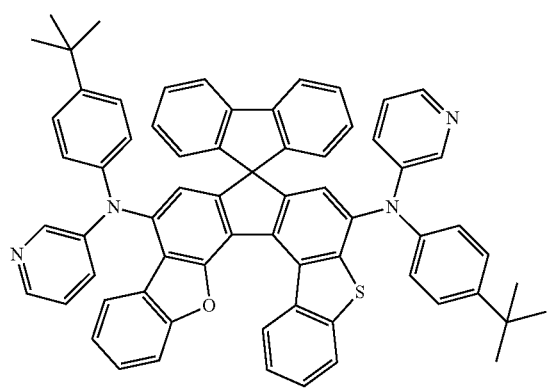
<Chemical Formula 230>
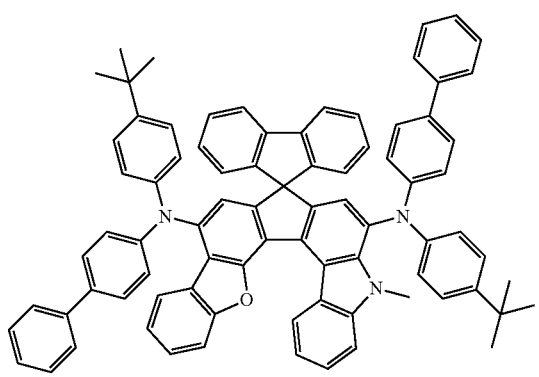

-continued

<Chemical Formula 231>

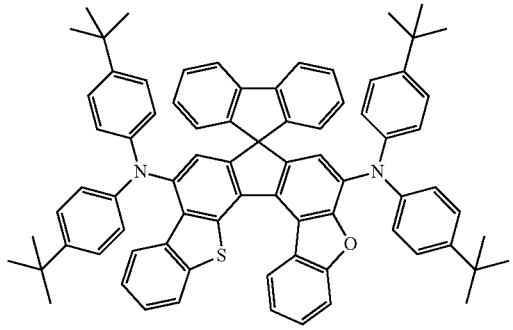

<Chemical Formula 239>

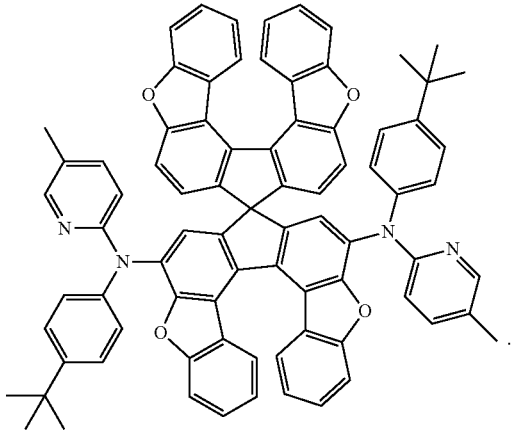

12. An organic light-emitting diode, comprising:
a first electrode;
a second electrode facing the first electrode; and
an organic layer interposed between the first electrode and the second electrode,
wherein the organic layer comprises at least one of the compounds of claim 1.

13. The organic light-emitting diode of claim 12, wherein the organic layer comprises at least one of a hole injection layer, a hole transport layer, a functional layer capable of both hole injection and hole transport, a light-emitting layer, an electron transport layer, and an electron injection layer.

14. The organic light-emitting diode of claim 13, wherein the organic layer interposed between the first electrode and the second electrode comprises a light-emitting layer wherein the light-emitting layer is composed of a host and a dopant, the at least one of the compounds of claim 1 serving as the dopant.

15. The organic light-emitting diode of claim 13, wherein at least one of the layers is formed using a deposition process or a solution process.

16. The organic light-emitting diode of claim 12, wherein the organic light-emitting diode is used for a device selected from among a flat display device, a flexible display device, a monochrome or white flat illumination device, and a monochrome or white flexible illumination device.

17. The organic light-emitting diode of claim 1, wherein $R_1$ and $R_2$ together form the mono- or polycyclic aliphatic or aromatic ring, and the mono- or polycyclic aliphatic or aromatic ring is a heterocyclic ring containing a heteroatom selected from the group consisting of N, O, P, Si, S, Ge, Se, and Te as a ring member.

* * * * *